US011248044B2

(12) United States Patent
Donahue et al.

(10) Patent No.: US 11,248,044 B2
(45) Date of Patent: Feb. 15, 2022

(54) METHODS FOR ALTERING BODY COMPOSITION BY ADMINISTERING A GDF8 INHIBITOR AND AN ACTIVIN A INHIBITOR

(71) Applicant: Regeneran Pharmaceuticals, Inc., Tarrytown, NY (US)

(72) Inventors: Stephen Donahue, Princeton, NJ (US); Robert C. Pordy, Ardsley, NY (US); Gary Herman, Princeton, NJ (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/290,287

(22) Filed: Mar. 1, 2019

(65) Prior Publication Data

US 2019/0276527 A1 Sep. 12, 2019

Related U.S. Application Data

(60) Provisional application No. 62/637,017, filed on Mar. 1, 2018.

(51) Int. Cl.

| | |
|---|---|
| ***A61K 39/395*** | (2006.01) |
| ***A61P 3/04*** | (2006.01) |
| ***A61P 21/06*** | (2006.01) |
| ***C07K 16/22*** | (2006.01) |
| ***A61P 21/00*** | (2006.01) |
| *A61K 9/00* | (2006.01) |
| *A61K 39/00* | (2006.01) |

(52) U.S. Cl.

CPC .......... *C07K 16/22* (2013.01); *A61K 39/3955* (2013.01); *A61P 3/04* (2018.01); *A61P 21/00* (2018.01); *A61P 21/06* (2018.01); *A61K 9/0019* (2013.01); *A61K 9/0053* (2013.01); *A61K 2039/505* (2013.01); *A61K 2039/507* (2013.01); *A61K 2039/54* (2013.01); *A61K 2039/545* (2013.01); *A61K 2300/00* (2013.01); *C07K 2317/76* (2013.01)

(58) Field of Classification Search

CPC ... C07K 16/22; A61K 39/395; A61K 39/3955

See application file for complete search history.

(56) References Cited

U.S. PATENT DOCUMENTS

| | | | |
|---|---|---|---|
| 5,500,362 | A | 3/1996 | Robinson et al. |
| 5,821,337 | A | 10/1998 | Carter et al. |
| 6,096,506 | A | 8/2000 | Lee et al. |
| 6,368,597 | B1 | 4/2002 | Strassmann et al. |
| 6,468,535 | B1 | 10/2002 | Lee et al. |
| 6,858,208 | B2 | 2/2005 | Lee et al. |
| 6,927,044 | B2 | 8/2005 | Stahl et al. |
| 7,056,512 | B1 | 6/2006 | Klysner et al. |
| 7,063,954 | B2 | 6/2006 | Isfort et al. |
| 7,070,784 | B1 | 7/2006 | Halkier et al. |
| 7,241,444 | B2 | 7/2007 | Goetsch et al. |
| 7,261,893 | B2 | 8/2007 | Veldman et al. |
| 7,320,789 | B2 | 1/2008 | Aghajanian et al. |
| 7,531,637 | B2 | 5/2009 | Siadak et al. |
| 7,534,432 | B2 | 5/2009 | Lee et al. |
| 7,582,298 | B2 | 9/2009 | Stevens et al. |
| 7,598,227 | B2 | 10/2009 | Crooke et al. |
| 7,632,499 | B2 | 12/2009 | Davies et al. |
| 7,635,760 | B2 | 12/2009 | Han et al. |
| 7,655,763 | B2 | 2/2010 | Veldman et al. |
| 7,731,961 | B1 | 6/2010 | Aghajanian et al. |
| 7,745,583 | B2 | 6/2010 | Han et al. |
| 7,750,141 | B2 | 7/2010 | Crooke et al. |
| 7,785,587 | B2 | 8/2010 | Whittemore et al. |
| 7,807,159 | B2 | 10/2010 | Chin et al. |
| 7,807,631 | B2 | 10/2010 | Knopf et al. |
| 7,888,486 | B2 | 2/2011 | Walsh et al. |
| 7,892,561 | B2 | 2/2011 | Junker et al. |
| 7,910,107 | B2 | 3/2011 | Walsh et al. |
| 8,063,188 | B2 | 11/2011 | Sayers et al. |
| 8,309,082 | B2 | 11/2012 | Han et al. |
| 8,415,459 | B2 | 4/2013 | LaVallie et al. |
| 8,496,934 | B2 | 7/2013 | Walsh et al. |
| 8,530,439 | B2 | 9/2013 | Crooke et al. |

(Continued)

FOREIGN PATENT DOCUMENTS

| | | |
|---|---|---|
| CN | 101522707 A | 9/2009 |
| EP | 1 773 041 A1 | 4/2007 |

(Continued)

OTHER PUBLICATIONS

Aagaard et al., "RNAi therapeutics: Principles, prospects and challenges," Advanced Drug Delivery Reviews, 59:75-86 (2007).

Abbott et al., "Current approaches to fine mapping of antigen-antibody interactions," Immunology.; 142(4):526-535 (Aug. 2014).

Al-Lazikani et al., "Standard Conformations for the Canonical Structures of Immunoglobulins," J Mol Biol, 273(4):927-948 (1997).

Allen et al., "Skeletal Muscle Fatigue: Cellular Mechanisms," Physiol. Rev., 88:287-332 (2008).

Allen et al., "Expression and Function of Myostatin in Obesity, Diabetes, and Exercise Adaptation," Medicine and Science in Sports and Exercise, vol. 43, No. 10, pp. 1828-1835 (Oct. 1, 2011).

(Continued)

*Primary Examiner* — Zachary C Howard

(74) *Attorney, Agent, or Firm* — Merchant & Gould P.C.

(57) ABSTRACT

The present invention relates to compositions and methods for altering body composition in a subject, wherein the alteration of body composition is an increase in muscle mass and a reduction of fat mass simultaneously. The present invention also relates to compositions and methods for reducing fat mass in a subject. The compositions and methods also increase muscle volume and lean body mass in the subject. The present invention also relates to compositions that comprise a GDF8 inhibitor and an Activin A inhibitor and the use of such compositions to treat diseases and disorders characterized by increased fat mass, and/or decreased muscle volume.

27 Claims, 18 Drawing Sheets

Specification includes a Sequence Listing.

(56) References Cited

U.S. PATENT DOCUMENTS

| | | | |
|---|---|---|---|
| 8,586,713 | B2 | 11/2013 | Davis et al. |
| 8,840,894 | B2 | 9/2014 | Stitt et al. |
| 8,871,209 | B2 | 10/2014 | Stitt et al. |
| 8,940,874 | B2 | 1/2015 | Veldman et al. |
| 8,992,913 | B2 | 3/2015 | Mader et al. |
| 8,999,343 | B2 | 4/2015 | Han et al. |
| 9,260,515 | B2 | 2/2016 | Stitt et al. |
| 9,718,881 | B2 | 8/2017 | Gromada et al. |
| 9,890,212 | B2 | 2/2018 | Stitt et al. |
| 10,400,036 | B2 | 9/2019 | Stitt et al. |
| 10,526,403 | B2 | 1/2020 | Gromada et al. |
| 2004/0101920 | A1 | 5/2004 | Radziejewski et al. |
| 2004/0142382 | A1 | 7/2004 | Veldman et al. |
| 2005/0175612 | A1 | 8/2005 | Lee et al. |
| 2006/0034831 | A1 | 2/2006 | Tobin |
| 2006/0263354 | A1 | 11/2006 | Chin et al. |
| 2007/0087000 | A1 | 4/2007 | Walsh et al. |
| 2007/0178095 | A1 | 8/2007 | Smith et al. |
| 2007/0280945 | A1 | 12/2007 | Stevens et al. |
| 2008/0187543 | A1 | 8/2008 | Kambadur et al. |
| 2008/0299126 | A1 | 12/2008 | Han et al. |
| 2009/0136481 | A1 | 5/2009 | Kambadur et al. |
| 2009/0148436 | A1 | 6/2009 | Lavallie et al. |
| 2009/0227497 | A1 | 9/2009 | Sun et al. |
| 2009/0234106 | A1 | 9/2009 | Han et al. |
| 2009/0311252 | A1 | 12/2009 | Knopf et al. |
| 2010/0080811 | A1 | 4/2010 | Davies et al. |
| 2010/0166764 | A1 | 7/2010 | Sayers et al. |
| 2010/0183624 | A1 | 7/2010 | Seehra et al. |
| 2010/0272734 | A1 | 10/2010 | Berger et al. |
| 2010/0322942 | A1 | 12/2010 | Whittemore et al. |
| 2011/0008375 | A1 | 1/2011 | Hq et al. |
| 2011/0020330 | A1 | 1/2011 | Aghajanian et al. |
| 2011/0256132 | A1 | 10/2011 | Ashman et al. |
| 2011/0293630 | A1 | 12/2011 | Stitt et al. |
| 2012/0015877 | A1 | 1/2012 | Seehra et al. |
| 2012/0237521 | A1 | 9/2012 | Berger et al. |
| 2013/0122007 | A1 | 5/2013 | Stitt et al. |
| 2013/0142788 | A1 | 6/2013 | Ashman et al. |
| 2013/0209489 | A1 | 8/2013 | Han et al. |
| 2013/0336982 | A1 | 12/2013 | Mader et al. |
| 2015/0010568 | A1 | 1/2015 | Stitt et al. |
| 2015/0037339 | A1 | 2/2015 | Gromada et al. |
| 2015/0203591 | A1 | 7/2015 | Yancopoulos et al. |
| 2016/0304595 | A1 | 10/2016 | Pordy et al. |
| 2016/0340421 | A1 | 11/2016 | Stitt et al. |
| 2017/0008956 | A1 | 1/2017 | Stitt et al. |
| 2017/0226197 | A1 | 8/2017 | Stitt et al. |
| 2018/0008672 | A1 | 1/2018 | Chalothorn et al. |
| 2018/0155416 | A1 | 6/2018 | Gromada et al. |
| 2018/0171006 | A1 | 6/2018 | Stitt et al. |
| 2019/0023777 | A1 | 1/2019 | Stitt et al. |
| 2020/0010540 | A1 | 1/2020 | Stitt et al. |

FOREIGN PATENT DOCUMENTS

| | | | |
|---|---|---|---|
| EP | 2 594 280 | A1 | 5/2013 |
| WO | 2004/037861 | A2 | 5/2004 |
| WO | 2005/094446 | A2 | 10/2005 |
| WO | 2005/103081 | A2 | 11/2005 |
| WO | 2006/116269 | A2 | 11/2006 |
| WO | 2007/044411 | A2 | 4/2007 |
| WO | 2007/047112 | A2 | 4/2007 |
| WO | 2008/031061 | A2 | 3/2008 |
| WO | 2009/058346 | A1 | 5/2009 |
| WO | 2009/059943 | A1 | 5/2009 |
| WO | 2010/070094 | A1 | 6/2010 |
| WO | 2011/063018 | A1 | 5/2011 |
| WO | 2011/150008 | A1 | 12/2011 |
| WO | 2012/064771 | A1 | 5/2012 |
| WO | 2013/074557 | A1 | 5/2013 |
| WO | 2013/186719 | A1 | 12/2013 |
| WO | 2014/121221 | A1 | 8/2014 |
| WO | 2015/022658 | A2 | 2/2015 |
| WO | 2016/039796 | A2 | 3/2016 |
| WO | 2016/168613 | A1 | 10/2016 |

OTHER PUBLICATIONS

Altschul et al., "Basic local alignment search tool," J Mol Biol, 215(3):403-410 (1990).

Altschul et al., "Gapped BLAST and PSI-BLAST: a new generation of protein database search programs," Nucleic Acids Research, 25(17):3389-33402 (1997).

Angal et al., "A single amino acid substitution abolishes the heterogeneity of chimeric mouse/human (IgG4) antibody," Molecular Immunology, 30(1):105-108 (Jan. 1993).

Boder et al., "Directed evolution of antibody fragments with monovalent femtomolar antigen-binding affinity," Proc Natl Acad SCi USA, 97(20):10701-10705 (Sep. 26, 2000).

Bogdanovich et al., "Myostatin blockade improves function but not histopathology in a murine model of limb-girdle musclar dystrophy 2C," Muscle Nerve, 37(30):308-316 (Mar. 2008).

Bowie et al., "Deciphering the Message in Protein Sequences: Tolerance to Amino Acid Substitutions," Science, 247:1306-1310 (Mar. 16, 1990).

Britton et al., "Body Fat Distribution, Incident Cardiovascular Disease, Cancer, and All-Cause Mortality," JACC, vol. 62, No. 10, pp. 921-9215 (Sep. 3, 2013).

Brown et al., "Tolerance to Single, but Not Multiple, Amino Acid Replacements in Antibody VH CDR2: A Means of Minimizing B Cell Wastage from Somatic Hypermutation?," The Journal of Immunology, 156(9):3285-3291 (May 1, 1996).

Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," J. Cell Biol., vol. 111, pp. 2129-2138 (Nov. 1, 1990).

Cacia et al., "Isomerization of an Aspartic Acid Residue in the Cmoplemetnarity—Determining Regions of a Recombinant Antibody to Humn IgE: Identification and Effect on Binding Affinity," Biochemistry, vol. 35, No. 6, pp. 1897-1903 (1996).

Cadena et al., "Administration of a soluble activin type IIB receptor promotes muscle growth independent of fiber type," Journal of Applied Physiology, vol. 109, pp. 635-642 (2010).

Canziani et al., "Characterization of neutralizing affinity-matured human respiratory syncytial virus F binding antibodies in the sub-picomolar affinity range," J of Molecular Recognition, 25(3):136-146 (Mar. 28, 2012).

Casset at al., "A peptide mimetic of an anti-CD4 monoclonal antibody by rational design," Biochemical and Biophysical Research Communications, vol. 307, pp. 198-205 (2003).

Chen et al., "Selection and Analysis of an Optimized Anti-VEGF Antibody: Crystal Structure of an Affinity-matured Fab in Complex with Antigen," Journal of Molecular Biology, vol. 293, pp. 865-881 (1999).

Chilean Substantive Report dated Oct. 10, 2014, in corresponding Chilean Patent Application 3283-2012.

Clark et al., "Discovery and Development of Janus Kinase (JAK) Inhibitors for Inflammatory Diseases," Journal of Medicinal Chemistry, vol. 57, No. 12, pp. 5023-5038 (2014).

Clynes et al., "Fc receptors are required in passive and active immunity to melanoma," Immunology, Proc. Nat'l. Acad. Sci. USA; 95:652-656 (Jan. 1998).

Cochrane et al., "Renal Structural and Functional Repair in a Mouse Model of Reversal of Ureteral Obstruction," J Am Soc Nephrol, 16(12):3623-3630 (Dec. 1, 2005).

Colombian Office Action dated Aug. 19, 2014 for related Colombian patent application 12233131.

Cook et al., "Structural Basis for a Functional Antagonist in the Transforming Growth Factor β Superfamily," J Biol Chem. 280(48): 40177-40186 (Epub Sep. 26, 2005) (Dec. 2, 2005).

Cooper et al., "Variable: Domain-identical antibodies exhibit IgG subclass-related differences in affinity and kinetic constants as

(56) References Cited

OTHER PUBLICATIONS determined by surface plasmon resonance," Molecular Immunology, vol. 31, No. 8, pp. 577-584 (1984).
Davies et al., Affinity improvement of single antibody VH domains: residues in all three hypervariable regions affect antigen binding, Immunotechnology, 2(3):169-179 (Sep. 1996).
Dufner et al., "Harnessing phage and ribosome display for antibody optimisation," Trends in Biotechnology, 24(11):523-529 (Nov. 1, 2006).
Ehring, "Hydrogen Exchange/Electrospray Ionizatino Mass Spectrometry Sudies of Structural Features of Proteins and Protein/Protein Interactions," Analytical Biochemistry; 267(2):252-259 (Feb. 15, 1999).
Engen et al., "Investigating protein structure and dynamics by hydrogen exchange MS," Anal. Chem., 73(9):256A-265A (May 1, 2001).
Giusti et al., "Somatic diversification of S107 from an antiphosphocholine to an anti-DNA autoantibody is due to a single base change in its heavy chain variable region," Proc. Natl. Acad. Sci. USA, 84(9):2926-2930 (May 1987).
Gonnet et al., "Exhaustive Matching of the Entire Protein Sequence Database," Science, 256(5062):1443-1445 (Jun. 5, 1992).
Goodson, "Dental applications," Medical Applications of Controlled Release, 2:115-138 (1984).
Grobet et al., "A deletion in the bovine myostatin gene causes the double-muscled phenotype in cattle," Nature Genetics, 17:71-74 (Sep. 1997).
Guido et al., "Virtual Screening and its Integration with Modern Drug Design Technologies," Current Medicinal Chemistry, vol. 15, No. 1, pp. 37-46 (2008).
Hanes et al., "Picomolar affinity antibodies from a fully synthetic naïve library selected and evolved by ribosome display," Nature Biotechnology, 18(12):1287-1292 (Dec. 2000).
He et al., "Activin A inhibits formation of skeletal muscle during chick development," Anat. Embryol (Berl); 209(5):401-407 (Jun. 2005).
Heineke et al., "Genetic Deltion of Myostatin from the Heart Prevents Skeletal Muscle Atrophy in Heart Failure," Circulation, vol. 121, pp. 419-4215 (2010).
Hochleitner et al., "Characterization of a discontinuous epitope of the human immunodeficiency virus (HIV) core protein p24 by epitope excision and differential chemical modification followed by mass spectrometric peptide mapping analysis," Protein Science, 9:487-496 (2000).
Holm et al., "Functional mapping and single chain construction of the anti-cytokeratin 8 monoclonal antibody TS1," Molecular Immunology, Vvol. 44, pp. 1075-1084 (2007).
Holt et al., "Domain antibodies: proteins for therapy," Trends in Biotechnology, 21(11):484-490 (Nov. 2003).
Holzbaur et al., "Myostatiin inhibition slows muscle atrophy in rodent models of amyotrophic lateral sclerosis," Neurobiol. Dis., 23(3):697-707 (Sep. 2006) Epub Jul. 11, 2006.
Hoogenboom, "Selecting and screening recombinant antibody libraries," Nature Biotechnology, 23(9):1105-1116 (Sep. 2005).
Indian Office Action dated Apr. 25, 2018 in Indian Patent Application No. 10677/CHENP/2012, 7 pages total.
International Search Report for Application No. PCT/US2011/037837 dated Sep. 21, 2011.
International Search Report for Application No. PCT/US2012/064911 dated Jan. 17, 2013.
International Search Report for Application No. PCT/US2014/048957 dated Jan. 8, 2015.
International Search Report and Written Opinion for Application No. PCT/US2016/027774 dated Jun. 30, 2016, 22 pages total.
Junghans et al., "Anti-Tac-H, a Humanized Antibody to the Interleukin 2 Receptor with New Features for Immunotherapy in Malignant and Immune Disorders," Cancer Research, 50:1495-1502 (Mar. 1, 1990).
Kabat et al., "Sequences of Proteins of Immunological Interest," National Institutes of Health (U.S.), 6 pages (1991).
PCT International Search Report and Written Opinion in International Application PCT/US2019/020330, dated May 16, 2019, 19 pages.
Ester Latres, et al., "Activin A more prominently regulates muscle mass in primates that does GDF8", Jul. 28, 2017, pp. 1-13, retrieved from the internet: https://www.ncbi.nlm.nih.gov/PMC/articles/PMC5414365/.
Singapore Search Report and Written Opinion dated Mar. 1, 2017 in corresponding application SG 11201600731W, 11 pages total.
Smith et al., "Myostatin inhibitors as therapies for muscle wasting associated with cancer and other disorders," Curr Opin Support Palliat Care, vol. 7, No. 4, pp. 352-360 (Dec. 2013).
Souza et al., "Proteomic identification and Functional Validation of Activins and Bone Morphogenetic Protein 11 as Candidate Novel Muscle Mass Regulators," Molecular Endocrinology, 22(12):2689-2702 (Dec. 2008).
Sozzani et al., "The yin and yang of Activin A," Blood, 117(19):5013-5015 (May 12, 2011).
Sutcliffe et al., "Antibodies that React with Predetermined Sites on Proteins," Science, 219:660-666 (Feb. 11, 1983).
Taylor et al., "A Transgenic mouse that expresses a diversity of human sequence heavy and light chain immunoglobulins," Nucleic Acids Research, 20(23):6287-6295 (1992).
Thompson et al., "Structures of an ActRIIB:activin A complex reveal a novel binding mode for TGF-β ligand:receptor interactions" The EMBO Journal, 22(7):1555-1566 (Apr. 1, 2003).
Thornton et at. "Prediction of progress at last," Nature, vol. 354, pp. 105-106 (Nov. 14, 1991).
Tornetta et al., "Antibody Fab display and selection through fusion to the pIX coat protein of filamentous phage," Journal of Immunological Methods, 360(1-2):39-46 (Aug. 31, 2010).
Tsuchida et al., "Activin signaling as an emerging target for therapeutic interventions," Cell Communication and Signaling, 7:15, 11 pages (Jun. 18, 2009).
Tutt et al., "Trispecific F(ab')3 derivatives that use cooperative signaling via the TCR/CD3 complex and CD2 to activiate and redirect resting cytotoxic T cells," Journal of Immunology, 147(1):60-69 (Jul. 1, 1991).
Vajdos et al., "Comprehensive Functional Maps of the Antigen-binding Site of an Anti-ErbB2 Antibody Obtained with Shotgun Scanning Mutagenesis," J. Mol Biol., 320(2):415-428 (Jul. 2002).
Wagner et al., "A Phase I/II trial of MYO-29 in Adult Subjects with Muscular Dystrophy," Annals of Neurology, vol. 63, No. 5, pp. 561-571 (May 2008).
Wark et al., "Latest technologies for the enhancement of antibody affinity," Advanced Drug Delivery Reviews, 58(5-6):657-670 (Aug. 7, 2006).
Warzocha et al , "Antisense Strategy: Biological Utility and Prospects in the Treatment of Hematological Malignancies," Leukemia and Lymphoma, vol. 24, pp. 267-281 (1997).
Whittemore et al., "Inhibition of myostatin in adult mice increases skeletal muscle mass and strength," Biochem, Biophys. Res. Commun., 300:965-971 (2003).
Willis et al., "Effects of aerobic and/or resistance training on body mass and fat mass in overweight or obese adults," Journal of Applied Physiology, 113(12):1831-1837 (2012).
Wu et al., "Receptor-mediated in Vitro Gene Transformation by a Soluble DNA Carrier System," Journal of Biological Chemistry, 262(10):4429-4432 (Apr. 5, 1987).
Wu et al., "Humanization of a Murine Monoclonal Antibody by Simultaneous Optimization of Framework and CDR Residues," J. Mol. Biol., 294(1): 151-162 (Nov. 19, 1999).
Xia et al., "The biology of activing: recent advances in structure, regulation and function," Journal of Endocrinology, 202(1):1-12 (Jul. 2009) (Epub Mar. 9, 2009).
Xiang et al., "Study of B72.3 combining sites by molecular modeling and site-directed mutagenesis," Protein Engineering, 13(5):339-344 (May 2000).
Zhou et al., "Reversal of Cancer Cachexia and Muscle Wasting by ActRIIB Antagonism Leads to Prolonged Survival," Cell, 142(4):531-543 (Aug. 20, 2010).

(56) References Cited

OTHER PUBLICATIONS

Kazane et al., “Self-Assembled Antibody Multimers through Peptide Nucleic Acid Conjugation,” J Am Chem Soc., 135(1):340-346 (Jan. 9, 2013).
Khurana et al., “Pharmacological Strategies for Muscular Dystrophy,” Nature Reviews/Druq Discovery, 2.379-390 (May 2003).
Klein et al., “Progress in overcoming the chain association issue in bispecific heterodimeric IgG antibodies,” mAbs 4(6):653-663 (Nov./Dec. 2012).
Kufer et al., “A revival of bispecific antibodies,” Trends Biotechnol, 22(5):238-244 (May 2004).
Kussie et al., “A Single Engineered Amino Acid Substitution Changes Antibody Fine Specificity,” Journal of Immunology, 152:146-152 (1994).
Langer, “New Methods of Drug Delivery,” Science, 249:1527-1533 (Sep. 23, 1990).
Lazar et al., “Transforming Growth Factor α: Mutation of Aspartic Acid 47 and Leucine 48 Results in Different Biological Activities,” Mol. Cell. Biol., 8(3):1247-1252 (Mar. 1988).
LeBrasseur et al., “Myostatin Inhibition Enhances the Effects of Exercise on Performance and Metabolic Outcomes in Aged Mice,” J Gerontol A Biol Sci Med Sci, vol. 64A, No. 9, pp. 940-948 (2009).
Lee, “Extracellular Regulation of Myostatin: A Molecular Rheostat for Muscle Mass,” Immun. Endoc. & Metab. Agents in Med. Chem., 10(4):183-194 (2010).
Lee et al., “Regulation of muscle growth by multiple ligands signaling through Activin type II receptors,” PNAS USA, 102(50):18117-18122 (Dec. 13, 2005) (Epub Dec. 5, 2005).
Lee et al., “Regulation of GDF-11 and myostatin activity by GASP-1 and GASP-2,” PNAS USA, 110(3):E3713-E3722 (Sep. 9, 2013).
Lin et al., “The structural basis of TGF-β, bone morphogenetic protein, and activing ligand binding.” Reproduction, 132(2): 179-190 (Aug. 2006).
Liu et al., “Fine mapping of the antigen-antibody interaction of scFv215, a recombinant antibody inhibiting RNA polymerase II from *Drosophila melanogaster*,” Journal of Molecular Recognition, 12(2):103-111 (1999).
MacCallum et al., “Antibody-Antigen Interactions: Contact Analysis and Binding Site Topography,” J. Mol. Biol., 262(5):732-745 (Oct. 11, 1996).
Martin et al., “Modeling antibody bypervariable loops: A combined algorithm,” Proc. Natl. Acad. Sci. USA, 86(23):9268-9272 (Dec. 1989).
Maynard et al., “Antibody Engineering,” Annu. Rev. Biomed. Eng., 2:339-376 (2000).
McKeague et al., “Challenges and Opportunities for Small Molecule Aptamer Development,” Journal of Nucleic Acids, vol. 212, Article ID 748913, 20 pages (2012) (Epub Oct. 24, 2012).
McPherron, “Metaboloic Functions of Myostatin and GDF11,” Immunol. Endocr Metab Agents Med Chem, 10(4):217-231 (Dec. 2010).
McPherron et al., “Regulation of skeletal muscle mass in mice by a new TGF-β superfamily member,” Nature, 387(6628):83-90 (May 1997).
McPherron et al., “Redundancy of myostatin and growth/differentiation factor 11 function,” BMC Developmental Biology, 9:24, 9 pages (Mar. 19, 2009).
Mordenti et al., “Interspecies Scaling of Clearance and Volume of Distribution Data for Five Therapeutic Proteins,” Pharmaceutical Research, 8(11):1351-1359 (Nov. 1991).
Mosher et al., “A Mutation in the Myostatin Gene Increases Muscle Mass and Enhances Racing Performance in Heterozygote Dogs,” PLoS Genet, vol. 3, No. 5, e79, pp. 779-786 (May 2007).
Munoz et al., “Biologicals Targeting Myostatin/GDF-11/Activins Prevent Burn-Induced Muscle Loss in Mice,” Journal of Surgical Research, 186(2)(abstract 34.6):591-592 (Feb. 2014).
Musculoskeletal Diseases, in MESH Database, National Center for Biotechnology Information, Bethesda, Maryland, USA [online], [retrieved on Jan. 9, 2017]. Retrieved from the Internet: <URL: https://www.ncbi.nlm.nih.gov/mesh/?term=musculoskeletal+diseases>. 4 pages total.
Noguera-Troise et al., “Abstract #4650: Development of human blocking antibodies to \#916;-like ligand-4 (DII4) in VelocImmune mice for anti-angiogenesis therapy,” Cancer Research, vol. 69, Abstract No. 4650 (May 2009).
Office Action for Chilean Patent Application No. 201600251 (dated May 5, 2018).
Office Action for Chilean Patent Application No. 201600251 (dated Aug. 27, 2018).
Office Action for Japanese Patent Application No. 2016-531870 (dated Jul. 24, 2018).
Office Action for Taiwanese Patent Application No. 103125622 (dated Aug. 23, 2018).
Office Action for Moroccan Patent Application No. 38807 (dated May 8, 2018).
Orcutt et al., “Engineering an antibody with picomolar affinity to DOTA chelates of multiple radionuclides for pretargeted radioimmunotherapy and imaging,” Nuclear Medicine and Biology, 38(2):223-233 (2011).
Padhi et al., “Pharmacological Inhibition of Myostatin and Changes in Lean Body Mass and Lower Extremity Muscle Size in Patients Receiving Androgen Deprivation Therapy for Prostate Cancer,” J Clin Endocrinol Metab, vol. 99, No. 10, pp. E1967-E1975 (Oct. 2014).
Pascalis et al., “Grafting of “Abbreviated” Complentarity-Determining Regions Containing Specificity-Determining Residues Essential for Ligand Contact to Engineer a Less Immunogenic Humanized Monoclonal Antibody,” Journal of Immunology, vol. 169, pp. 3076-3084 (2002).
Paul, “Fundamental Immunology,” Third Edition, Raven Press, New York, pp. 292-295 (1993).
Pearson, “Using the FASTA Program to Search Protein and DNA Sequence Databases,” Methods in Molecular Biology, 24(Ch 26): 307-331 (1994).
Pearson, “Flexible sequence similarity searching with the FASTA3 program package,” Methods in Molecular Biology, 132:185-219 (2000).
Pini et al., “Design and Use of a Phage Display Library: Human Antibodies with Subnanomolar Affinity Against a Marker of Angiogenesis Eluted from a Two-Dimentional Gel,” The Journal of Biological Chemistry, 273(34):21769-21776 (Aug. 21, 1998).
Powell et al., “Compendium of Excipients for Parenteral Formulations,” Journal of Pharmaceutical Science & Technology, 52(5):238-311 (Sep.-Oct. 1998).
Rajpal et al., “A general method for greatly improving the affinity of antibodies by using combinatorial libraries,” Proc. Natl. Acad. Sci. USA, 102(24)8466-8471 (Jun. 14, 2005).
Record for Clinical Trial NCT01910220, version dated Feb. 12, 2014, available at https://clinicaltrials.gov/archive/NCT01910220/2014_02_12, 3 pages as printed.
Reddy et al., “Elimination of Fc Receptor-Dependent Effector Functions of a Modified IgG4 Monoclonal Antibody to Human CD4,” Journal of Immunology, 164:1925-1933 (2000).
Reineke, “Antibody Epitope Mapping Using Arrays of Synthetic Peptides,” Methods in Molecular Biology, 248(26):443-463 (2004).
Rudikoff et al., “Single amino acid substitution altering antigen-binding specificity,” Proc. Natl. Acad. Sci. USA, 79:1979-1983 (Mar. 1982).
Schildbach et al., “Heavy Chain Position 50 Is a Determinant of Affinity and Specificity for the Anti-digoxin Antibody 26-10,” The Journal of Biological Chemistry, 268(29):21739-21747 (Oct. 15, 1993).
Schildbach et al., “Contribution of a single heavy chain residue to specificity of an anti-digoxin monoclonal antibody,” Protein Science, 3(5):737-749 (1994).
Schuelke et al., “Myostatin Mutation Associatedwith Gross Muscle Hypertrophy in a Child,” N Engl J Med, 350:2682-2688 (Jun. 24, 2004).
Sefton, “Implantable Pumps”; CRC Critical Reviews in Biomedical Engineering, 14(3):201-240 (1987).

(56) References Cited

OTHER PUBLICATIONS

Sharp et al., "The effects of a myostatin inhibitor on lean body mass, strength, and power in resistance trained males," Journal of the International Society of Sports Nutrition, 11(Suppl 1:P42 (Dec. 1, 2014).
Shepherd et al., "The design of the humanized antibody," Monoclonal Antibodies: A Practical Approach, Oxford University Press, GB, pp. 58-66 (Jan. 2000).
Shields et al., "Lack of Fucose on Human IgG1 N-Linked Oligosaccharide Improves Binding to Human FcγRIII and Antibody-dependent Cellular Toxicity," J. Biol. Chem., 277(30):26733-26740 (Jul. 26, 2002).
European Communication pursuantto Article 94(3) EPC for European Patent Application No. 16718831.7 (dated May 7, 2020).
European Extended Search Report for European Patent Application No. 20176858.7, dated Sep. 30, 2020, 11 pages total.
Gould et al., "Cancer cachexia prevention via physical exercise: molecular mechanisms," Journal of Cachexia, Sarcopenia and Muscle, vol. 4(2): 111-124 (2013).
Kim et. al. "Impact of resistance loading on myostatin expression and cell cycle regulation in young and older men and women", Am Physiol Endocrinol Metab 288: E1110-1119, 2005.
Lowe et al., "Animal Models for Inducing Muscle Hypertrophy: Are They Relevant for Clinical Applications in Humans?," Journal of Orthopaedic & Sports Physical Therapy, vol. 32, pp. 36-43 (2002).
Mosler et al., "Combinatory effects of siRNA-induced myostatin inhibition and exercise on skeletal muscle homeostasis and body composition," Physiological Reports, vol. 2, No. 3, 13 pages (2014).
Korean Office Action dated Jun. 28, 2019 in corresponding application KR 10-2014-7016067 and English language translation, 6 pages total.
Japanese Office Action for Japanese Patent Application No. 2017-553974 (dated Mar. 31, 2020).
Eurasian Office Action dated Nov. 18, 2020 in Eurasian Patent Application No. 201792298 and English translation thereof, 5 pages total.
Saremi et al., "Effects of oral creatine and resistance training on serum myostatin and GASP-1," Molecular and Cellular Endocrinology, vol. 317, pp. 25-30 (2010).
Saremi et al., "Twelve-week resistance training decreases myostatin level and improves insulin sensitivity in overweight-obese woman," Int. J. Diabetes & Metab. vol. 19, pp. 63-68 (2011).
Siparsky et al., "Muscle Changes in Aging: Understanding Sarcopenia," Sports Health, vol. 6, No. 1, pp. 36-40 (Jan.-Feb. 2014).

| Low<br>Panel A<br>N=8 (6:2) | Mid<br>Panel B<br>N=8 (6:2) | High<br>Panel C<br>N=8 (6:2) | Panel D<br>N=24 (6:6:6:6) |
|---|---|---|---|
| 1mg/kg anti-activin A +<br>6mg/kg anti-GDF8 | 3mg/kg anti-activin A +<br>6mg/kg anti-GDF8 | 10mg/kg anti-activin A +<br>6mg/kg anti-GDF8 | 10mg/kg anti-activin A +<br>6mg/kg anti-GDF8 |
| Placebo | Placebo | Placebo | Placebo |
| - | - | - | 6mg/kg anti-GDF8 |
| - | - | - | 10mg/kg anti-activin A |

N = 12 High dose combo
vs.
N = 12 Pooled Placebo

Figure 2A

% Change in Thigh Muscle Volume
Least Square Mean (+SE)
20
15
10
5
0
+2.0
+3.7
+2.6
+5.3
+6.9
α-Act A : - 10 - 1 3 10
α-GDF8 : - - 6 6 6 6
n : 12 6 6 6 6 12

% Change in Total Fat Mass (DXA)
10
5
0
-5
-10
-0.7
-2.1
-0.2
-2.1
-3.9
α-Act A : - 10 - 1 3 10
α-GDF8 : - - 6 6 6 6
n : 12 6 6 6 6 12

Percent Change from Baseline in Thigh Muscle Volume
Placebo
R1033
R2477 high
R1033+R2477 low
R1033+R2477 med
R1033+R2477 high
Percent Change in Thigh Muscle Volume (%)
Week
15
10
5
0
0
4
8

```
                         SEQUENCE LISTING


<160> NUMBER OF SEQ ID NOS: 648

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1

caggtgcagc tggtgcagtc tgggggaggc ttggtccagc ctggggggtc cctgagactc      60

tcctgtgcag cctctggatt cacctttaac acctatgcca taagctgggt ccgccaggct     120

ccagggaagg ggctggaatg ggtctcaact attactggta gtggttataa cacatactac     180

gcagactccg tgaagggccg gttcaccatc tccagagaca attccaagaa cacactgtat     240

ctacagatga gcagcctgag agccgaggac acggccgtat tttactgtgc gaaagactct     300

cggtataact ggaattacgg aatttttgac tactggggcc agggaaccac ggtcaccgtc     360

tcctca                                                                366


<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Ile Ser Trp Val Arg Gln Ala Pro Gly Lys Gly Leu Glu Trp Val
        35                  40                  45

Ser Thr Ile Thr Gly Ser Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Phe Tyr Cys
                85                  90                  95

Ala Lys Asp Ser Arg Tyr Asn Trp Asn Tyr Gly Ile Phe Asp Tyr Trp
            100                 105                 110

Gly Gln Gly Thr Thr Val Thr Val Ser Ser
        115                 120


<210> SEQ ID NO 3
```

<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct ttaacaccta tgcc 24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asn Thr Tyr Ala
1 5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attactggta gtggttataa caca 24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Thr Gly Ser Gly Tyr Asn Thr
1 5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgaaagact ctcggtataa ctggaattac ggaatttttg actac 45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Lys Asp Ser Arg Tyr Asn Trp Asn Tyr Gly Ile Phe Asp Tyr
1 5 10 15

<210> SEQ ID NO 9
<211> LENGTH: 324
<212> TYPE: DNA
<213> ORGANISM: Artificial Sequence
<220> FEATURE:

<223> OTHER INFORMATION: Synthetic

<400> SEQUENCE: 9

```
gacatccaga tgacccagtc tccagccacc ctgtctgtgt ctccagggga aagagccacc     60

ctctcctgca gggccagtca gagtgttagc agcaacttag cctggtacca tcagaaacct    120

ggccaggctc ccaggctcct catctatggt gtatccacca gggccactgg tatcccagcc    180

aggttcagtg gcaatgggtc tgggacagag ttcactctca ccatcagcag cctgcagtct    240

gaagattttg cagtttatta ctgtcagcag cataataact ggccgctcac tttcggcgga    300

gggaccaagg tggagatcaa acga                                           324
```

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Val Ser Thr Arg Ala Thr Gly Ile Pro Ala Arg Phe Ser Gly
    50                  55                  60

Asn Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Asn Trp Pro Leu
                85                  90                  95

Thr Phe Gly Gly Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagagtgtta gcagcaac                                                   18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Asn
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgtatcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Val Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcagcata ataactggcc gctcact 27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln His Asn Asn Trp Pro Leu Thr
1 5

<210> SEQ ID NO 17
<211> LENGTH: 375
<212> TYPE: DNA
<213> ORGANISM: Artificial Sequence
<220> FEATURE:
<223> OTHER INFORMATION: Synthetic

<400> SEQUENCE: 17
caggtgcagc tggtgcagtc gggcccagga ctggtgaagc cttcggagac cctgtccctc 60
acctgcactg tctctggtgg ctccatcagc aatagtaatt actactgggg ctggatccgc 120
cagcccccag ggaaggggct ggagtggatt gggactacct attatagtgg gaccacctac 180
tacaacccgt ccctcaagag tcgagtcacc atatccgtag acacgtccaa gaaccagttc 240
tccctgaagc tgagctctgt gaccgccgca gacacggctg tgtattactg tgcgagagat 300
tattatgata gtagtggtta ttattacaac tggttcgatc cctggggcca gggaaccacg 360
gtcaccgtct cctca 375

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Pro Gly Leu Val Lys Pro Ser Glu
1 5 10 15

```
Thr Leu Ser Leu Thr Cys Thr Val Ser Gly Gly Ser Ile Ser Asn Ser
            20                  25                  30

Asn Tyr Tyr Trp Gly Trp Ile Arg Gln Pro Pro Gly Lys Gly Leu Glu
        35                  40                  45

Trp Ile Gly Thr Thr Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Thr Val Thr Val Ser Ser
        115                 120                 125


<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19

ggtggctcca tcagcaatag taattactac                                      30


<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly Gly Ser Ile Ser Asn Ser Asn Tyr Tyr
1               5                   10


<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21

acctattata gtgggaccac c                                               21


<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Thr Tyr Tyr Ser Gly Thr Thr
1               5


<210> SEQ ID NO 23
<211> LENGTH: 51
<212> TYPE: DNA
<213> ORGANISM: Artificial Sequence
<220> FEATURE:
<223> OTHER INFORMATION: Synthetic
```

<400> SEQUENCE: 23
gcgagagatt attatgatag tagtggttat tattacaact ggttcgatcc c 51

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Ala Arg Asp Tyr Tyr Asp Ser Ser Gly Tyr Tyr Tyr Asn Trp Phe Asp
1 5 10 15

Pro

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25
gacatccagt tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcagtctca cactcagcag cctgcagcct 240
gaagattttg caacttattt ctgtctacag catcatattt acccgtggac gttcggccaa 300
gggaccaagc tggagatcaa acga 324

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Ser Leu Thr Leu Ser Ser Leu Gln Pro
65 70 75 80

Glu Asp Phe Ala Thr Tyr Phe Cys Leu Gln His His Ile Tyr Pro Trp
85 90 95

Thr Phe Gly Gln Gly Thr Lys Leu Glu Ile Lys Arg
100 105

<210> SEQ ID NO 27
<211> LENGTH: 18
<212> TYPE: DNA
<213> ORGANISM: Artificial Sequence
<220> FEATURE:

<223> OTHER INFORMATION: Synthetic

<400> SEQUENCE: 27
caggacatta gaaatgat 18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Asp Ile Arg Asn Asp
1 5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ctacagcatc atatttaccc gtggacg 27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Gln His His Ile Tyr Pro Trp Thr
1 5

<210> SEQ ID NO 33
<211> LENGTH: 375
<212> TYPE: DNA
<213> ORGANISM: Artificial Sequence
<220> FEATURE:
<223> OTHER INFORMATION: Synthetic

<400> SEQUENCE: 33

```
caagttcagc tggtggagtc gggcccagga ctggtgaagc cttcggagac cctgtccctc      60

acctgcactg tctatggtgg ctccatcagc agtggtaatt actactgggg ctggatccgc     120

cagcccccag ggaagggact ggagtggatt gggactatct attatagtgg aagcgcctac     180

tacaacccgt ccctcaagag tcgagtcacc atgtccgtag acacgtccaa gaaccagttc     240

tccctgaaac tgagctctgt gaccgccgca gacacggctg tttattactg tgtgagagat     300

tactatgata gtagtggtca ttattacaac tggttcgacc cctggggcca gggaaccacg     360

gtcaccgtct cctca                                                      375
```

```
<210> SEQ ID NO 34
<211> LENGTH: 125
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Glu Ser Gly Pro Gly Leu Val Lys Pro Ser Glu
1               5                   10                  15

Thr Leu Ser Leu Thr Cys Thr Val Tyr Gly Gly Ser Ile Ser Ser Gly
            20                  25                  30

Asn Tyr Tyr Trp Gly Trp Ile Arg Gln Pro Pro Gly Lys Gly Leu Glu
        35                  40                  45

Trp Ile Gly Thr Ile Tyr Tyr Ser Gly Ser Ala Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Asp Tyr Tyr Asp Ser Ser Gly His Tyr Tyr Asn Trp Phe
            100                 105                 110

Asp Pro Trp Gly Gln Gly Thr Thr Val Thr Val Ser Ser
        115                 120                 125
```

```
<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35

ggtggctcca tcagcagtgg taattactac                                       30
```

```
<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Gly Gly Ser Ile Ser Ser Gly Asn Tyr Tyr
1               5                   10
```

```
<210> SEQ ID NO 37
<211> LENGTH: 21
<212> TYPE: DNA
<213> ORGANISM: Artificial Sequence
<220> FEATURE:
```

<223> OTHER INFORMATION: Synthetic

<400> SEQUENCE: 37
atctattata gtggaagcgc c 21

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ile Tyr Tyr Ser Gly Ser Ala
1 5

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39
gtgagagatt actatgatag tagtggtcat tattacaact ggttcgaccc c 51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Val Arg Asp Tyr Tyr Asp Ser Ser Gly His Tyr Tyr Asn Trp Phe Asp
1 5 10 15

Pro

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gccatccaga tgacccagtc tccatcctcc ctgtctgcat ctgtaggaga cagagtcacc 60
atcacttgcc gggcaagtca ggacattaga catgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cataatactt acccgtggac gttcggccaa 300
gggaccaagg tggagatcaa acga 324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Ala Ile Gln Met Thr Gln Ser Pro Ser Ser Leu Ser Ala Ser Val Gly

```
1               5                   10                  15

Asp Arg Val Thr Ile Thr Cys Arg Ala Ser Gln Asp Ile Arg His Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys Arg
            100                 105


<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43

caggacatta gacatgat                                                   18


<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Asp Ile Arg His Asp
1               5


<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45

gctgcatcc                                                              9


<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
1


<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
```

```
ctacagcata atacttaccc gtggacg                                          27


<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Leu Gln His Asn Thr Tyr Pro Trp Thr
1               5


<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49

caggtgcagc tggtgcagtc tgggggaggc ctggtcaagc ctggggggtc cctgagactc      60

tcctgtgcag cctctggatt caccttcagt agctatagca tgaactgggt ccgccaggct     120

ccagggaagg ggctggagtg ggtctcatcc attagtagta gtagtagtta catatactac     180

gcagactcag tgaagggccg attcaccatc tccagagaca acgccaagaa ctcactgtat     240

ctgcaaatga acagcctgag agccgaggac acggctgtgt attactgtgc gagagatcgt     300

ggatacacct ttggggttga ctactggggc cagggaacca cggtcaccgt ctcctca       357


<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Thr Phe Gly Val Asp Tyr Trp Gly Gln Gly
            100                 105                 110

Thr Thr Val Thr Val Ser Ser
        115


<210> SEQ ID NO 51
<211> LENGTH: 24
<212> TYPE: DNA
<213> ORGANISM: Artificial Sequence
<220> FEATURE:
<223> OTHER INFORMATION: Synthetic
```

<400> SEQUENCE: 51
ggattcacct tcagtagcta tagc 24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Ser
1 5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtagta gtagtagtta cata 24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Ser Ser Ser Tyr Ile
1 5

<210> SEQ ID NO 55
<211> LENGTH: 36
<212> TYPE: DNA
<213> ORGANISM: Artificial Sequence
<220> FEATURE:
<223> OTHER INFORMATION: Synthetic

<400> SEQUENCE: 55
gcgagagatc gtggatacac ctttggggtt gactac 36

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ala Arg Asp Arg Gly Tyr Thr Phe Gly Val Asp Tyr
1 5 10

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccatcctcc ctgtctgcat ctgtaggaga cagagtcacc 60

```
atcacttgcc gggcaagtca gggcattaga aatgatttag gctggtatca gcagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag cataatagtt acccgtacac ttttggccag    300

gggaccaagg tggagatcaa acga                                           324


<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Val Glu Ile Lys Arg
            100                 105


<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

cagggcatta gaaatgat                                                   18


<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Arg Asn Asp
1               5


<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61

gctgcatcc                                                              9
```

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
ctacagcata atagttaccc gtacact 27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Gln His Asn Ser Tyr Pro Tyr Thr
1 5

<210> SEQ ID NO 65
<211> LENGTH: 375
<212> TYPE: DNA
<213> ORGANISM: Artificial Sequence
<220> FEATURE:
<223> OTHER INFORMATION: Synthetic

<400> SEQUENCE: 65
caggtgcagc tggtgcagtc gggcccagga ctggtgaagc cttcggagac cctgtccctc 60
acctgcactg tctctggtgg ctccatcatc acttatagtt actactgggg ctggatccgc 120
cagcccccag ggaaggggct ggagtggatt gggactatcc atcatagtgg gagcacctac 180
tacaacccgt ccctcaagag tcgagtcacc atatccgtag acacgtccaa gaaccagttc 240
tccctgacac tgagttctgt gaccgccgca gacacggctg tgtattactg tgcgagagac 300
tactatgata gtagtggtta ttattataac tggttcgacc cctggggcca gggaaccatg 360
gtcaccgtct cctca 375

<210> SEQ ID NO 66
<211> LENGTH: 125
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Pro Gly Leu Val Lys Pro Ser Glu
1 5 10 15

Thr Leu Ser Leu Thr Cys Thr Val Ser Gly Gly Ser Ile Ile Thr Tyr
20 25 30

Ser Tyr Tyr Trp Gly Trp Ile Arg Gln Pro Pro Gly Lys Gly Leu Glu

```
        35                  40                  45

Trp Ile Gly Thr Ile His His Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Met Val Thr Val Ser Ser
        115                 120                 125


<210> SEQ ID NO 67
<211> LENGTH: 30
<212> TYPE: DNA
<213> ORGANISM: Artificial Sequence
<220> FEATURE:
<223> OTHER INFORMATION: Synthetic

<400> SEQUENCE: 67

ggtggctcca tcatcactta tagttactac                                        30


<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Gly Gly Ser Ile Ile Thr Tyr Ser Tyr Tyr
1               5                   10


<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69

atccatcata gtgggagcac c                                                 21


<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile His His Ser Gly Ser Thr
1               5


<210> SEQ ID NO 71
<211> LENGTH: 51
<212> TYPE: DNA
<213> ORGANISM: Artificial Sequence
<220> FEATURE:
<223> OTHER INFORMATION: Synthetic

<400> SEQUENCE: 71

gcgagagact actatgatag tagtggttat tattataact ggttcgaccc c                51
```

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Ala Arg Asp Tyr Tyr Asp Ser Ser Gly Tyr Tyr Tyr Asn Trp Phe Asp
1               5                   10                  15

Pro

<210> SEQ ID NO 73
<211> LENGTH: 324
<212> TYPE: DNA
<213> ORGANISM: Artificial Sequence
<220> FEATURE:
<223> OTHER INFORMATION: Synthetic

<400> SEQUENCE: 73
gccatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt ccccgtggac gttcggccaa    300
gggaccaagg tggagatcaa acga                                           324

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Ser Pro Trp
                85                  90                  95

Thr Phe Gly Gln Gly Thr Lys Val Glu Ile Lys Arg
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagggcatta gaaatgat                                                   18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Gly Ile Arg Asn Asp
1 5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
ctacagcata atagttcccc gtggacg 27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Leu Gln His Asn Ser Ser Pro Trp Thr
1 5

<210> SEQ ID NO 81
<211> LENGTH: 369
<212> TYPE: DNA
<213> ORGANISM: Artificial Sequence
<220> FEATURE:
<223> OTHER INFORMATION: Synthetic

<400> SEQUENCE: 81
caggtgcact tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaatga tgataagcgc 180

```
tacagcccat ctctgaagag caggctcacc atcaccaagg acacctccaa aaaccaggtg    240

gtccttacaa tgaccaacat ggaccctgtg gacacagcca catattactg tacacacacc    300

tcccgttata actggcacta cggcttcctt gactactggg gccagggaac cacggtcacc    360

gtctcctca                                                            369


<210> SEQ ID NO 82
<211> LENGTH: 123
<212> TYPE: PRT
<213> ORGANISM: Artificial Sequence
<220> FEATURE:
<223> OTHER INFORMATION: Synthetic

<400> SEQUENCE: 82

Gln Val His Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr His Thr Ser Arg Tyr Asn Trp His Tyr Gly Phe Leu Asp Tyr
            100                 105                 110

Trp Gly Gln Gly Thr Thr Val Thr Val Ser Ser
        115                 120


<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83

gggttctcac tcagcactag tggagtgggt                                     30


<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Gly Phe Ser Leu Ser Thr Ser Gly Val Gly
1               5                   10


<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85

atttattgga atgatgataa g                                              21
```

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Ile Tyr Trp Asn Asp Asp Lys
1               5

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
acacacacct cccgttataa ctggcactac ggcttccttg actac 45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Thr His Thr Ser Arg Tyr Asn Trp His Tyr Gly Phe Leu Asp Tyr
1               5                   10                  15

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gccatccaga tgacccagtc tccatcctca ctgtctgcat ctgtaggaga cagagtcacc 60
atcacttgtc gggcgagtca gggcattagc aattatttag cctggtttca gcagaaacca 120
gggaaagccc ctaagtccct gatctatgct gcatccagtt tgcaaagtgg ggtcccatca 180
aagttcagcg gcagtggatc tgggacagat ttcactctca ccatcagcag cctgcagcct 240
gaagattttg caacttatta ctgccaacaa tataatagtt acccgctcac tttcggcgga 300
gggaccaagg tggaaatcaa acga 324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

```
Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105


<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91

cagggcatta gcaattat                                                    18


<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Asn Tyr
1               5


<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93

gctgcatcc                                                               9


<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1


<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95

caacaatata atagttaccc gctcact                                          27


<210> SEQ ID NO 96
<211> LENGTH: 9
<212> TYPE: PRT
```

<213> ORGANISM: Artificial Sequence
<220> FEATURE:
<223> OTHER INFORMATION: Synthetic

<400> SEQUENCE: 96

Gln Gln Tyr Asn Ser Tyr Pro Leu Thr
1               5

<210> SEQ ID NO 97
<211> LENGTH: 375
<212> TYPE: DNA
<213> ORGANISM: Artificial Sequence
<220> FEATURE:
<223> OTHER INFORMATION: Synthetic

<400> SEQUENCE: 97
gaggtgcagc tggtgcagtt gggcccagga ctggtgaagc cttcggagac cctgtccctc 60
acctgcactg tctctggtgg ctccatcagc aatagtaatt actactgggg ctggatccgc 120
cagcccccag ggaaggggct ggagtggatt gggactacct attatagtgg gaccacctac 180
tacaacccgt ccctcaagag tcgagtcacc atatccgtag acacgtccaa gaaccagttc 240
tccctgaagc tgagctctgt gaccgccgca gacacggctg tgtattactg tgcgagagat 300
tattatgata gtagtggtta ttattacaac tggttcgatc cctggggcca gggaaccacg 360
gtcaccgtct cctca 375

<210> SEQ ID NO 98
<211> LENGTH: 125
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Gln Leu Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Asn Tyr Tyr Trp Gly Trp Ile Arg Gln Pro Pro Gly Lys Gly Leu Glu
        35                  40                  45

Trp Ile Gly Thr Thr Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Thr Val Thr Val Ser Ser
        115                 120                 125

<210> SEQ ID NO 99
<211> LENGTH: 30
<212> TYPE: DNA
<213> ORGANISM: Artificial Sequence
<220> FEATURE:
<223> OTHER INFORMATION: Synthetic

<400> SEQUENCE: 99
ggtggctcca tcagcaatag taattactac 30

<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Gly Gly Ser Ile Ser Asn Ser Asn Tyr Tyr
1 5 10

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
acctattata gtgggaccac c 21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Thr Tyr Tyr Ser Gly Thr Thr
1 5

<210> SEQ ID NO 103
<211> LENGTH: 51
<212> TYPE: DNA
<213> ORGANISM: Artificial Sequence
<220> FEATURE:
<223> OTHER INFORMATION: Synthetic

<400> SEQUENCE: 103
gcgagagatt attatgatag tagtggttat tattacaact ggttcgatcc c 51

<210> SEQ ID NO 104
<211> LENGTH: 17
<212> TYPE: PRT
<213> ORGANISM: Artificial Sequence
<220> FEATURE:
<223> OTHER INFORMATION: Synthetic

<400> SEQUENCE: 104

Ala Arg Asp Tyr Tyr Asp Ser Ser Gly Tyr Tyr Tyr Asn Trp Phe Asp
1 5 10 15

Pro

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gccatccaga tgacccagtc tccatcctcc ctgtctgcat ctgtaggaga cagagtcacc 60
atcacttgcc gggcaagtca ggacattaga aatgatttag gctggtatca gcagaaacca 120

```
gggaaagccc ctaagcgcct gatctatgct gcatccagtt tgcaaagtgg ggtcccatca    180

aggttcagcg gcagtggatc tgggacagaa ttcagtctca cactcagcag cctgcagcct    240

gaagattttg caacttattt ctgtctacag catcatattt acccgtggac gttcggccaa    300

gggaccaagg tggagatcaa acga                                            324


<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Leu Ser Ser Leu Gln Pro
65                  70                  75                  80

Glu Asp Phe Ala Thr Tyr Phe Cys Leu Gln His His Ile Tyr Pro Trp
                85                  90                  95

Thr Phe Gly Gln Gly Thr Lys Val Glu Ile Lys Arg
            100                 105


<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107

caggacatta gaaatgat                                                    18


<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asp Ile Arg Asn Asp
1               5


<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109

gctgcatcc                                                               9


<210> SEQ ID NO 110
<211> LENGTH: 3
```

<212> TYPE: PRT
<213> ORGANISM: Artificial Sequence
<220> FEATURE:
<223> OTHER INFORMATION: Synthetic

<400> SEQUENCE: 110

Ala Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacagcatc atatttaccc gtggacg 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln His His Ile Tyr Pro Trp Thr
1 5

<210> SEQ ID NO 113
<211> LENGTH: 355
<212> TYPE: DNA
<213> ORGANISM: Artificial Sequence
<220> FEATURE:
<223> OTHER INFORMATION: Synthetic

<400> SEQUENCE: 113
caggtgcagc tggtggagtc tgggggaggc gtggtccagc ctgggaggtc cctgagactc 60
tcctgtgcag cctctggatt caccttcagt cgctatggca ttcactgggt ccgccaggct 120
ccaggcaagg ggctggagtg ggtggctgtt atatcttatg atggaagtga tgaatactat 180
gtagactccg tgaagggccg attcagcatc tcccgagaca attccaagaa cacgctttat 240
ctacaaatga acagtctgag gcctgcggac tcggctgttt attactgtgt gaaaggagat 300
ctggaacttg gttttgacta ctggggccag ggaaccctgg tcaccgtctc ctcaa 355

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Arg Tyr
20 25 30

Gly Ile His Trp Val Arg Gln Ala Pro Gly Lys Gly Leu Glu Trp Val
35 40 45

Ala Val Ile Ser Tyr Asp Gly Ser Asp Glu Tyr Tyr Val Asp Ser Val
50 55 60

```
Lys Gly Arg Phe Ser Ile Ser Arg Asp Asn Ser Lys Asn Thr Leu Tyr
65                  70                  75                  80

Leu Gln Met Asn Ser Leu Arg Pro Ala Asp Ser Ala Val Tyr Tyr Cys
                85                  90                  95

Val Lys Gly Asp Leu Glu Leu Gly Phe Asp Tyr Trp Gly Gln Gly Thr
            100                 105                 110

Leu Val Thr Val Ser Ser
        115


<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

ggattcacct tcagtcgcta tggc                                             24


<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Arg Tyr Gly
1               5


<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117

atatcttatg atggaagtga tgaa                                             24


<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Tyr Asp Gly Ser Asp Glu
1               5


<210> SEQ ID NO 119
<211> LENGTH: 33
<212> TYPE: DNA
<213> ORGANISM: Artificial Sequence
<220> FEATURE:
<223> OTHER INFORMATION: Synthetic

<400> SEQUENCE: 119

gtgaaaggag atctggaact tggttttgac tac                                   33


<210> SEQ ID NO 120
<211> LENGTH: 11
<212> TYPE: PRT
<213> ORGANISM: Artificial Sequence
```

<220> FEATURE:
<223> OTHER INFORMATION: Synthetic

<400> SEQUENCE: 120

Val Lys Gly Asp Leu Glu Leu Gly Phe Asp Tyr
1               5                   10

<210> SEQ ID NO 121
<211> LENGTH: 337
<212> TYPE: DNA
<213> ORGANISM: Artificial Sequence
<220> FEATURE:
<223> OTHER INFORMATION: Synthetic

<400> SEQUENCE: 121
gatattgtga tgactcaggc tgcaccctct atacctgtca ttccaggaga gtcagtatcc     60
atgtcctgca ggtctagtaa gagtctcctg tacagtaatg gacatactta cgtgtattgg    120
tttgtgcaga ggccaggcca gtctcctcag ctcctgatat atcggatgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaaaatct agaatttccg    300
ctcacgttcg gtgctgggac caagctggag ctgaaac                             337

<210> SEQ ID NO 122
<211> LENGTH: 112
<212> TYPE: PRT
<213> ORGANISM: Artificial Sequence
<220> FEATURE:
<223> OTHER INFORMATION: Synthetic

<400> SEQUENCE: 122

Asp Ile Val Met Thr Gln Ala Ala Pro Ser Ile Pro Val Ile Pro Gly
1               5                   10                  15

Glu Ser Val Ser Met Ser Cys Arg Ser Ser Lys Ser Leu Leu Tyr Ser
            20                  25                  30

Asn Gly His Thr Tyr Val Tyr Trp Phe Val Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln Asn
                85                  90                  95

Leu Glu Phe Pro Leu Thr Phe Gly Ala Gly Thr Lys Leu Glu Leu Lys
            100                 105                 110

<210> SEQ ID NO 123
<211> LENGTH: 33
<212> TYPE: DNA
<213> ORGANISM: Artificial Sequence
<220> FEATURE:
<223> OTHER INFORMATION: Synthetic

<400> SEQUENCE: 123
aagagtctcc tgtacagtaa tggacatact tac                                  33

<210> SEQ ID NO 124
<211> LENGTH: 11
<212> TYPE: PRT
<213> ORGANISM: Artificial Sequence
<220> FEATURE:

<223> OTHER INFORMATION: Synthetic

<400> SEQUENCE: 124

Lys Ser Leu Leu Tyr Ser Asn Gly His Thr Tyr
1 5 10

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 cggatgtcc 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Arg Met Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
atgcaaaatc tagaatttcc gctcacg 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Met Gln Asn Leu Glu Phe Pro Leu Thr
1 5

<210> SEQ ID NO 129
<211> LENGTH: 355
<212> TYPE: DNA
<213> ORGANISM: Artificial Sequence
<220> FEATURE:
<223> OTHER INFORMATION: Synthetic

<400> SEQUENCE: 129
caggtgcagc tggtggaggc ggggggaggc gtggtccagc ctgggaggtc cctgagactc 60
tcctgtgcag cctctggatt caccttcagt cgctatggca ttcactgggt ccgccaggct 120
ccaggcaagg ggctggagtg ggtggctgtt atatcttatg atggaactga tgaatactat 180
gcagactccg tgaagggccg attcaccatc tcccgagaca attccaagaa cacgctttat 240
ctacaaatga acagtctgag acctgcggac tcggctgtat attactgtgc gaaaggagat 300
ctggaacttg gttttgacta ctggggccag ggaaccctgg tcaccgtctc ctcaa 355

<210> SEQ ID NO 130
<211> LENGTH: 118
<212> TYPE: PRT
<213> ORGANISM: Artificial Sequence
<220> FEATURE:
<223> OTHER INFORMATION: Synthetic

<400> SEQUENCE: 130

```
Gln Val Gln Leu Val Glu Ala Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Thr Asp Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Ala Asp Ser Ala Val Tyr Tyr Cys
                85                  90                  95

Ala Lys Gly Asp Leu Glu Leu Gly Phe Asp Tyr Trp Gly Gln Gly Thr
            100                 105                 110

Leu Val Thr Val Ser Ser
        115
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131

```
ggattcacct tcagtcgcta tggc                                            24
```

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

```
Gly Phe Thr Phe Ser Arg Tyr Gly
1               5
```

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133

```
atatcttatg atggaactga tgaa                                            24
```

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Tyr Asp Gly Thr Asp Glu
1 5

<210> SEQ ID NO 135
<211> LENGTH: 33
<212> TYPE: DNA
<213> ORGANISM: Artificial Sequence
<220> FEATURE:
<223> OTHER INFORMATION: Synthetic

<400> SEQUENCE: 135
gcgaaaggag atctggaact tggttttgac tac 33

<210> SEQ ID NO 136
<211> LENGTH: 11
<212> TYPE: PRT
<213> ORGANISM: Artificial Sequence
<220> FEATURE:
<223> OTHER INFORMATION: Synthetic

<400> SEQUENCE: 136

Ala Lys Gly Asp Leu Glu Leu Gly Phe Asp Tyr
1 5 10

<210> SEQ ID NO 137
<211> LENGTH: 322
<212> TYPE: DNA
<213> ORGANISM: Artificial Sequence
<220> FEATURE:
<223> OTHER INFORMATION: Synthetic

<400> SEQUENCE: 137
gccatccggt tgacccagtc tccatcttcc gtgtctgcat ctgtgggaga cagagtcacc 60
atcacttgtc gggcgagtca ggatattagt atttggttag cctggtatca gcagagtcca 120
gggaaagccc ctaaactcct gatcaatgtt gcatcccgtt tgcaaagtgg ggtcccatca 180
aggttcagcg gcagtggatc tgggacagat ttcactctca ccatcaacgg tctgcagcct 240
gaagattttg taacttacta ttgtcaacag gctaacagtt tcccgatcac cttcggccaa 300
gggacacgac tggcgaccaa ac 322

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Ala Ile Arg Leu Thr Gln Ser Pro Ser Ser Val Ser Ala Ser Val Gly
1 5 10 15

Asp Arg Val Thr Ile Thr Cys Arg Ala Ser Gln Asp Ile Ser Ile Trp
20 25 30

Leu Ala Trp Tyr Gln Gln Ser Pro Gly Lys Ala Pro Lys Leu Leu Ile
35 40 45

Asn Val Ala Ser Arg Leu Gln Ser Gly Val Pro Ser Arg Phe Ser Gly
50 55 60

Ser Gly Ser Gly Thr Asp Phe Thr Leu Thr Ile Asn Gly Leu Gln Pro
65 70 75 80

Glu Asp Phe Val Thr Tyr Tyr Cys Gln Gln Ala Asn Ser Phe Pro Ile
85 90 95

Thr Phe Gly Gln Gly Thr Arg Leu Ala Thr Lys
100 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggatatta gtatttgg 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asp Ile Ser Ile Trp
1 5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gttgcatcc 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Val Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacaggcta acagtttccc gatcacc 27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ala Asn Ser Phe Pro Ile Thr
1 5

<210> SEQ ID NO 145
<211> LENGTH: 358
<212> TYPE: DNA
<213> ORGANISM: Artificial Sequence
<220> FEATURE:
<223> OTHER INFORMATION: Synthetic

<400> SEQUENCE: 145
caggtgcagc tggtgcagtc tgggggaggc ctggtcaagc ctggggggtc cctgagactc 60
tcctgtgcag cctctggatt catcttcaat acctatacca tgaattgggt ccgccaggct 120
ccagggaagg ggctggagtg ggtctcatcc atcactagtc gtggtactta tatattctac 180
tcagactcac ttaagggccg attcaccatt tccagagaca acgccaataa ctcactgttt 240
ctgcaaatga acagcctgag agtcgaagac acggctgttt attactgttc gagagatcgt 300
ggatacacct ttggtcctga ctactggggc cagggaaccc tggtcaccgt ctcttcag 358

<210> SEQ ID NO 146
<211> LENGTH: 119
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Gly Gly Leu Val Lys Pro Gly Gly
1 5 10 15

Ser Leu Arg Leu Ser Cys Ala Ala Ser Gly Phe Ile Phe Asn Thr Tyr
20 25 30

Thr Met Asn Trp Val Arg Gln Ala Pro Gly Lys Gly Leu Glu Trp Val
35 40 45

Ser Ser Ile Thr Ser Arg Gly Thr Tyr Ile Phe Tyr Ser Asp Ser Leu
50 55 60

Lys Gly Arg Phe Thr Ile Ser Arg Asp Asn Ala Asn Asn Ser Leu Phe
65 70 75 80

Leu Gln Met Asn Ser Leu Arg Val Glu Asp Thr Ala Val Tyr Tyr Cys
85 90 95

Ser Arg Asp Arg Gly Tyr Thr Phe Gly Pro Asp Tyr Trp Gly Gln Gly
100 105 110

Thr Leu Val Thr Val Ser Ser
115

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcatct tcaataccta tacc 24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Ile Phe Asn Thr Tyr Thr 1 5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atcactagtc gtggtactta tata 24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Thr Ser Arg Gly Thr Tyr Ile
1 5

<210> SEQ ID NO 151
<211> LENGTH: 36
<212> TYPE: DNA
<213> ORGANISM: Artificial Sequence
<220> FEATURE:
<223> OTHER INFORMATION: Synthetic

<400> SEQUENCE: 151
tcgagagatc gtggatacac ctttggtcct gactac 36

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Ser Arg Asp Arg Gly Tyr Thr Phe Gly Pro Asp Tyr
1 5 10

<210> SEQ ID NO 153
<211> LENGTH: 322
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagggcct gatctatgct gcatccagtt tgcaaagtgg ggtcccatca 180
aggttcagcg gcagtggatc tgggacagaa ttcactctca caatcagcag cctgcagcct 240
gaagattttg caacttatca ctgtctacat tatgattttc atcctcggac gttcggccaa 300
gggaccaagg tggaaatcaa gc 322

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Gly Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr His Cys Leu His Tyr Asp Phe His Pro Arg
                85                  90                  95

Thr Phe Gly Gln Gly Thr Lys Val Glu Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155

```
caggacatta gaaatgat                                                    18
```

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

```
Gln Asp Ile Arg Asn Asp
1               5
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157

```
gctgcatcc                                                               9
```

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

```
Ala Ala Ser
1
```

<210> SEQ ID NO 159
<211> LENGTH: 27

```
<212> TYPE: DNA
<213> ORGANISM: Artificial Sequence
<220> FEATURE:
<223> OTHER INFORMATION: Synthetic

<400> SEQUENCE: 159

ctacattatg attttcatcc tcggacg                                          27


<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Leu His Tyr Asp Phe His Pro Arg Thr
1               5


<210> SEQ ID NO 161
<211> LENGTH: 391
<212> TYPE: DNA
<213> ORGANISM: Artificial Sequence
<220> FEATURE:
<223> OTHER INFORMATION: Synthetic

<400> SEQUENCE: 161

caggtgcaac tggtggagtc tgggggaggc gtggtccagc ctgggaggtc cctgagactc      60

tcctgtgcag cgtctggatt caccttcagt agctatgcca tgcactgggt ccgccaggct     120

ccaggcaagg ggctggagtg ggtggcagtt atatggtatg atggaactaa ttattactat     180

gcagactccg tgaagggccg attcaccatc tccagagaca attccaagaa cacgctgtat     240

ctgcaaatga acagcctgag agccgaggac acggctgtgt attactgtgc gagagatccc     300

ctatattacg atattttgac tggttattcc cccgactact actacggtat ggacgtctgg     360

ggccaaggga ccacggtcac cgtctcctca g                                    391


<210> SEQ ID NO 162
<211> LENGTH: 130
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Trp Tyr Asp Gly Thr Asn Tyr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Leu Tyr Tyr Asp Ile Leu Thr Gly Tyr Ser Pro Asp
            100                 105                 110

Tyr Tyr Tyr Gly Met Asp Val Trp Gly Gln Gly Thr Thr Val Thr Val
        115                 120                 125
```

Ser Ser
130

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct tcagtagcta tgcc 24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Ala
1 5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atatggtatg atggaactaa ttat 24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Trp Tyr Asp Gly Thr Asn Tyr
1 5

<210> SEQ ID NO 167
<211> LENGTH: 69
<212> TYPE: DNA
<213> ORGANISM: Artificial Sequence
<220> FEATURE:
<223> OTHER INFORMATION: Synthetic

<400> SEQUENCE: 167
gcgagagatc ccctatatta cgatattttg actggttatt cccccgacta ctactacggt 60
atggacgtc 69

<210> SEQ ID NO 168
<211> LENGTH: 23
<212> TYPE: PRT
<213> ORGANISM: Artificial Sequence
<220> FEATURE:
<223> OTHER INFORMATION: Synthetic

<400> SEQUENCE: 168

Ala Arg Asp Pro Leu Tyr Tyr Asp Ile Leu Thr Gly Tyr Ser Pro Asp

```
1               5                   10                  15

Tyr Tyr Tyr Gly Met Asp Val
            20


<210> SEQ ID NO 169
<211> LENGTH: 322
<212> TYPE: DNA
<213> ORGANISM: Artificial Sequence
<220> FEATURE:
<223> OTHER INFORMATION: Synthetic

<400> SEQUENCE: 169

gaaatagtga tgacgcagtc tccagccacc ctgtctgtgt ctccagggga aagagccacc     60

ctctcctgca gggccagtca gacttttagc agcaacttag cctggtacca gcagaaacct    120

ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tataataagt ggccgctcac tttcggcgga    300

gggaccaagg tggagatcaa ac                                              322


<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Phe Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Val Glu Ile Lys
            100                 105


<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

cagactttta gcagcaac                                                   18


<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172
```

Gln Thr Phe Ser Ser Asn
1 5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 ggtgcatcc 9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Gly Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
cagcagtata ataagtggcc gctcact 27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Tyr Asn Lys Trp Pro Leu Thr
1 5

<210> SEQ ID NO 177
<211> LENGTH: 367
<212> TYPE: DNA
<213> ORGANISM: Artificial Sequence
<220> FEATURE:
<223> OTHER INFORMATION: Synthetic

<400> SEQUENCE: 177
gaggtgcagc tgttggagtc tgggggaggc ttggtccagc ctggggagtc cctgagactc 60
tcctgtgcag cctctggatt cacctttagc agctatgcca tgaactgggt ccgccaggct 120
ccagggaagg ggctggagtg ggtctcaact atcagtggta gtggtggtta tatatactac 180
gcagactccg tgaagggccg gttcaccatc tccagagaca attccaagaa cacgctgtat 240
ctgcaaatga acagcctgag agccgaagac acggccgtat atttctgtgc gaaagattcc 300
aggtataact ggaactacgg caattttgac tactggggcc agggaaccct ggtcaccgtc 360
tcctcag 367

```
<210> SEQ ID NO 178
<211> LENGTH: 122
<212> TYPE: PRT
<213> ORGANISM: Artificial Sequence
<220> FEATURE:
<223> OTHER INFORMATION: Synthetic

<400> SEQUENCE: 178

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Ser Arg Tyr Asn Trp Asn Tyr Gly Asn Phe Asp Tyr Trp
            100                 105                 110

Gly Gln Gly Thr Leu Val Thr Val Ser Ser
        115                 120


<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179

ggattcacct ttagcagcta tgcc                                            24


<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Ala
1               5


<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181

atcagtggta gtggtggtta tata                                            24


<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182
```

```
Ile Ser Gly Ser Gly Gly Tyr Ile
1               5


<210> SEQ ID NO 183
<211> LENGTH: 45
<212> TYPE: DNA
<213> ORGANISM: Artificial Sequence
<220> FEATURE:
<223> OTHER INFORMATION: Synthetic

<400> SEQUENCE: 183

gcgaaagatt ccaggtataa ctggaactac ggcaattttg actac                        45


<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

Ala Lys Asp Ser Arg Tyr Asn Trp Asn Tyr Gly Asn Phe Asp Tyr
1               5                   10                  15


<210> SEQ ID NO 185
<211> LENGTH: 322
<212> TYPE: DNA
<213> ORGANISM: Artificial Sequence
<220> FEATURE:
<223> OTHER INFORMATION: Synthetic

<400> SEQUENCE: 185

gaaatagtga tgacgcagtc tccagccacc ctgtctgtgt ctccagggga aagagccacc     60

ctctcctgca gggccagtca gaatgttagc agcaacttag cctggaacaa gcagaaacct    120

ggccaggctc ccagactcct catctatgct acatccacca gggccactgg tgtcccagcc    180

aggttcagtg ccagtgggtc tgggacagac ttcgctctca ccatcaacag cctgcagtct    240

gaagattttg cagtttatta ctgtcagcag tataataact ggcctctcac tttcggcgga    300

gggaccaagg tggagatcaa ac                                             322


<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Val Ser Ser Asn
            20                  25                  30

Leu Ala Trp Asn Lys Gln Lys Pro Gly Gln Ala Pro Arg Leu Leu Ile
        35                  40                  45

Tyr Ala Thr Ser Thr Arg Ala Thr Gly Val Pro Ala Arg Phe Ser Ala
    50                  55                  60

Ser Gly Ser Gly Thr Asp Phe Ala Leu Thr Ile Asn Ser Leu Gln Ser
65                  70                  75                  80

Glu Asp Phe Ala Val Tyr Tyr Cys Gln Gln Tyr Asn Asn Trp Pro Leu
                85                  90                  95
```

```
Thr Phe Gly Gly Gly Thr Lys Val Glu Ile Lys
            100                 105


<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187

cagaatgtta gcagcaac                                                    18


<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Asn Val Ser Ser Asn
1               5


<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189

gctacatcc                                                               9


<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Thr Ser
1


<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191

cagcagtata ataactggcc tctcact                                          27


<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Asn Asn Trp Pro Leu Thr
1               5
```

<210> SEQ ID NO 193
<211> LENGTH: 367
<212> TYPE: DNA
<213> ORGANISM: Artificial Sequence
<220> FEATURE:
<223> OTHER INFORMATION: Synthetic

<400> SEQUENCE: 193
gaggtgcaac tgttggaatc tgggggaggc ttggtacagc ctggggggtc cctgagactc 60
tcctgtgtag cctctcgatt caccttcagc agcaatgcca tgagttgggt ccgccaggct 120
ccagggacgg ggctggagtg ggtctcagct attactggta gtggtagtag gacatactac 180
gcagactccg tgaagggccg gttcaccatc tccagagaca attccaagaa cacggtgtat 240
ctgcaaatga acagcctgag aggcgaggac acggccgtat attactgtgc gaaagatcaa 300
gggggtacct ggaactacgg agattttgac tactggggcc agggaaccct ggtcaccgtc 360
tcctcag 367

<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Val Ala Ser Arg Phe Thr Phe Ser Ser Asn
            20                  25                  30

Ala Met Ser Trp Val Arg Gln Ala Pro Gly Thr Gly Leu Glu Trp Val
        35                  40                  45

Ser Ala Ile Thr Gly Ser Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Gly Glu Asp Thr Ala Val Tyr Tyr Cys
                85                  90                  95

Ala Lys Asp Gln Gly Gly Thr Trp Asn Tyr Gly Asp Phe Asp Tyr Trp
            100                 105                 110

Gly Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
cgattcacct tcagcagcaa tgcc 24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Arg Phe Thr Phe Ser Ser Asn Ala
1 5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attactggta gtggtagtag gaca 24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Thr Gly Ser Gly Ser Arg Thr
1 5

<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgaaagatc aagggggtac ctggaactac ggagattttg actac 45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Lys Asp Gln Gly Gly Thr Trp Asn Tyr Gly Asp Phe Asp Tyr
1 5 10 15

<210> SEQ ID NO 201
<211> LENGTH: 322
<212> TYPE: DNA
<213> ORGANISM: Artificial Sequence
<220> FEATURE:
<223> OTHER INFORMATION: Synthetic

<400> SEQUENCE: 201
gaaatagtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tctcccagcc 180
aggttcagtg gcagtgggtc tgggacagac ttcactctca ccatcagcag cctgcagtct 240
gaagattttg cagtttatta ctgtcagcag tataataact ggcctctcac tttcggcgga 300
gggaccaagg tggagatcaa gc 322

<210> SEQ ID NO 202
<211> LENGTH: 107
<212> TYPE: PRT

<213> ORGANISM: Artificial Sequence
<220> FEATURE:
<223> OTHER INFORMATION: Synthetic

<400> SEQUENCE: 202

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Leu Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105
```

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtgtta gcagcaac 18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

```
Gln Ser Val Ser Ser Asn
1               5
```

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 ggtgcatcc 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

```
Gly Ala Ser
1
```

<210> SEQ ID NO 207

<211> LENGTH: 27
<212> TYPE: DNA
<213> ORGANISM: Artificial Sequence
<220> FEATURE:
<223> OTHER INFORMATION: Synthetic

<400> SEQUENCE: 207
cagcagtata ataactggcc tctcact 27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Asn Trp Pro Leu Thr
1 5

<210> SEQ ID NO 209
<211> LENGTH: 373
<212> TYPE: DNA
<213> ORGANISM: Artificial Sequence
<220> FEATURE:
<223> OTHER INFORMATION: Synthetic

<400> SEQUENCE: 209
caggtgcagc tggtggagtc tgggggagac gtggtccagc ctgggaggtc cctgagactc 60
tcctgtacag cctctggatt caccttcagt agttatggca tgcactgggt ccgccaggct 120
ccaggcaggg ggctggagtg ggtggcagtt atatcatttg atggaaaaaa taaatactat 180
gcagactccg tgaagggccg attcaccgtc tccagagaca attccaagaa cacgctgttt 240
ctgcaaatga acagcctgag agctgaggac acggctctat attactgtgc gaaaaggata 300
gcagcaactg gttactacta cttctacggt ttggacgtct ggggccaagg gaccacggtc 360
accgtctcct cag 373

<210> SEQ ID NO 210
<211> LENGTH: 124
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Asp Val Val Gln Pro Gly Arg
1 5 10 15

Ser Leu Arg Leu Ser Cys Thr Ala Ser Gly Phe Thr Phe Ser Ser Tyr
20 25 30

Gly Met His Trp Val Arg Gln Ala Pro Gly Arg Gly Leu Glu Trp Val
35 40 45

Ala Val Ile Ser Phe Asp Gly Lys Asn Lys Tyr Tyr Ala Asp Ser Val
50 55 60

Lys Gly Arg Phe Thr Val Ser Arg Asp Asn Ser Lys Asn Thr Leu Phe
65 70 75 80

Leu Gln Met Asn Ser Leu Arg Ala Glu Asp Thr Ala Leu Tyr Tyr Cys
85 90 95

Ala Lys Arg Ile Ala Ala Thr Gly Tyr Tyr Tyr Phe Tyr Gly Leu Asp
100 105 110

Val Trp Gly Gln Gly Thr Thr Val Thr Val Ser Ser 115 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct tcagtagtta tggc 24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Ser Tyr Gly
1 5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
atatcatttg atggaaaaaa taaa 24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Phe Asp Gly Lys Asn Lys
1 5

<210> SEQ ID NO 215
<211> LENGTH: 51
<212> TYPE: DNA
<213> ORGANISM: Artificial Sequence
<220> FEATURE:
<223> OTHER INFORMATION: Synthetic

<400> SEQUENCE: 215
gcgaaaagga tagcagcaac tggttactac tacttctacg gtttggacgt c 51

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Ala Lys Arg Ile Ala Ala Thr Gly Tyr Tyr Tyr Phe Tyr Gly Leu Asp
1 5 10 15

Val

<210> SEQ ID NO 217
<211> LENGTH: 322
<212> TYPE: DNA
<213> ORGANISM: Artificial Sequence
<220> FEATURE:
<223> OTHER INFORMATION: Synthetic

<400> SEQUENCE: 217
gaaataatga tgacgcagtc tccagccacc ctgtctgtgt ctccagggga aagaggcacc 60
ctctcctgca gggccagtca gagtgttagt agcaacttag cctggtacca gcagaaacct 120
ggccaggctc ccaggctcct catctatggt gcatccacca gggccagtgg tatcccagcc 180
aggttcagtg gcagtgggtc tgggacagag ttcactctca ccgtcagcag cctgcagtct 240
gaagattttg cagtttatta ctgtcagcag tataataact ggccgctcac tttcggcgga 300
gggaccaagg tggagatcaa ac 322

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Glu Ile Met Met Thr Gln Ser Pro Ala Thr Leu Ser Val Ser Pro Gly
1 5 10 15

Glu Arg Gly Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Ser Gly Ile Pro Ala Arg Phe Ser Gly
50 55 60

Ser Gly Ser Gly Thr Glu Phe Thr Leu Thr Val Ser Ser Leu Gln Ser
65 70 75 80

Glu Asp Phe Ala Val Tyr Tyr Cys Gln Gln Tyr Asn Asn Trp Pro Leu
85 90 95

Thr Phe Gly Gly Gly Thr Lys Val Glu Ile Lys
100 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagagtgtta gtagcaac 18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Ser Val Ser Ser Asn
1 5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 ggtgcatcc 9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Gly Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
cagcagtata ataactggcc gctcact 27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Asn Asn Trp Pro Leu Thr
1 5

<210> SEQ ID NO 225
<211> LENGTH: 367
<212> TYPE: DNA
<213> ORGANISM: Artificial Sequence
<220> FEATURE:
<223> OTHER INFORMATION: Synthetic

<400> SEQUENCE: 225
gaggttcagc tgttggagtc tgggggaggc ttggtacagc cggggggtc cctgagactc 60 tcctgtgcag cctctggatt cacctctatc acctatgcca tgagctgggt ccgccaggct 120
ccagggaagg ggctggagtg ggtctcagct attagtgtta gtggtactaa tacatactac 180
gcagactccg tgaagggccg gttcaccatc tccagagaca agtccaagaa catgctgtat 240
ctgcaaatga acagcctgag agccgaggac acggccgtgt attactgtgc gaaagatctc 300
ctacataact ggaaatacgg gacttttgat atctggggcc aagggacaat ggtcaccgtc 360
tcttcag 367

<210> SEQ ID NO 226
<211> LENGTH: 122
<212> TYPE: PRT
<213> ORGANISM: Artificial Sequence
<220> FEATURE:

<223> OTHER INFORMATION: Synthetic

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ile Thr Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Thr Asn Thr Tyr Tyr Ala Asp Ser Val
    50                  55                  60

Lys Gly Arg Phe Thr Ile Ser Arg Asp Lys Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Leu His Asn Trp Lys Tyr Gly Thr Phe Asp Ile Trp
            100                 105                 110

Gly Gln Gly Thr Met Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct ctatcaccta tgcc 24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Ser Ile Thr Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtgtta gtggtactaa taca 24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Val Ser Gly Thr Asn Thr
1               5

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231
gcgaaagatc tcctacataa ctggaaatac gggacttttg atatc 45

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Ala Lys Asp Leu Leu His Asn Trp Lys Tyr Gly Thr Phe Asp Ile
1 5 10 15

<210> SEQ ID NO 233
<211> LENGTH: 322
<212> TYPE: DNA
<213> ORGANISM: Artificial Sequence
<220> FEATURE:
<223> OTHER INFORMATION: Synthetic

<400> SEQUENCE: 233
gaaatagtga tgacgcagtc tccagccacc ctgtctgtgt ctccagggga aagagccacc 60
ctctcctgca gggccagtca gagtgttgac agcaacttag tctggtacca acaaaaacct 120
ggccaggttc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataagt ggccgctcac tttcggcgga 300
gggaccaagg tggagatcaa ac 322

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Asp Ser Asn
20 25 30

Leu Val Trp Tyr Gln Gln Lys Pro Gly Gln Val Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Lys Trp Pro Leu
85 90 95

Thr Phe Gly Gly Gly Thr Lys Val Glu Ile Lys
100 105

<210> SEQ ID NO 235

<211> LENGTH: 18
<212> TYPE: DNA
<213> ORGANISM: Artificial Sequence
<220> FEATURE:
<223> OTHER INFORMATION: Synthetic

<400> SEQUENCE: 235
cagagtgttg acagcaac 18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Val Asp Ser Asn
1 5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 ggtgcatcc 9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Gly Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
cagcagtata ataagtggcc gctcact 27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Tyr Asn Lys Trp Pro Leu Thr
1 5

<210> SEQ ID NO 241
<211> LENGTH: 367
<212> TYPE: DNA
<213> ORGANISM: Artificial Sequence
<220> FEATURE:

<223> OTHER INFORMATION: Synthetic

<400> SEQUENCE: 241

```
gaggttcagc tgttggagtc tgggggaggc ttggtacagc cggggggggtc cctgagactc      60

tcctgtgcag cctctggatt cacctctatc acctatgcca tgagctgggt ccgccaggct     120

ccagggaagg ggctggagtg ggtctcagct attagtgtta gtggtactaa tacatactac     180

gcagactccg tgaagggccg gttcaccatc tccagagaca agtccaagaa catgctgtat     240

ctgcaaatga acagcctgag agccgaggac acggccgtgt attactgtgc gaaagatctc     300

ctacataact ggaaatacgg gacttttgat atctggggcc aagggacaat ggtcaccgtc     360

tcttcag                                                               367
```

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ile Thr Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Thr Asn Thr Tyr Tyr Ala Asp Ser Val
    50                  55                  60

Lys Gly Arg Phe Thr Ile Ser Arg Asp Lys Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Leu His Asn Trp Lys Tyr Gly Thr Phe Asp Ile Trp
            100                 105                 110

Gly Gln Gly Thr Met Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggattcacct ctatcaccta tgcc                                             24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Ser Ile Thr Tyr Ala
1               5
```

<210> SEQ ID NO 245

<211> LENGTH: 24
<212> TYPE: DNA
<213> ORGANISM: Artificial Sequence
<220> FEATURE:
<223> OTHER INFORMATION: Synthetic

<400> SEQUENCE: 245
attagtgtta gtggtactaa taca 24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Val Ser Gly Thr Asn Thr
1 5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
gcgaaagatc tcctacataa ctggaaatac gggacttttg atatc 45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Lys Asp Leu Leu His Asn Trp Lys Tyr Gly Thr Phe Asp Ile
1 5 10 15

<210> SEQ ID NO 249
<211> LENGTH: 325
<212> TYPE: DNA
<213> ORGANISM: Artificial Sequence
<220> FEATURE:
<223> OTHER INFORMATION: Synthetic

<400> SEQUENCE: 249
gaaatagtga tgacgcagtc tccagccacc ctgtctgtgt ctccagggga aagagccacc 60
ctctcctgca gggccagtca gagtgttagc agcaacttag cctggaacca gcagaaacct 120
ggccaggctc ccaggctcct catctatggt gcatccacca gggccacggg tatcccagcc 180
aggttcagtg gcagtgggtc tgggacagag ttcactctca ccatcagcag cctgcagtct 240
gaagattttg cagtttatta ctgtcagcag tataacaact ggcccatgta cacttttggc 300
caggggacca agctggagat caaac 325

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Asn Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Met
                85                  90                  95

Tyr Thr Phe Gly Gln Gly Thr Lys Leu Glu Ile Lys
            100                 105


<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251

cagagtgtta gcagcaac                                                   18


<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Ser Val Ser Ser Asn
1               5


<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253

ggtgcatcc                                                              9


<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Gly Ala Ser
1


<210> SEQ ID NO 255
<211> LENGTH: 30
<212> TYPE: DNA
<213> ORGANISM: Artificial Sequence
<220> FEATURE:
<223> OTHER INFORMATION: Synthetic
```

<400> SEQUENCE: 255
cagcagtata acaactggcc catgtacact 30

<210> SEQ ID NO 256
<211> LENGTH: 10
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Asn Trp Pro Met Tyr Thr
1 5 10

<210> SEQ ID NO 257
<211> LENGTH: 361
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctgggaggtc cctgagactc 60
tcctgtgaag cctctggatt caccttcagt agttctggca tgcactgggt ccgccaggct 120
ccaggcaagg ggctgcagtg ggtggctgtt atatcatatg atggaaataa taaattttat 180
gaagactccg tgaagggccg attgaccatt tccagagaca attccaacaa cactctgtgg 240
ctgcaaatga acagcctgag agttgaagac acggctgttt attactgtgc gaaatcagga 300
ggtagagtgg gagccgcctt tgcctactgg ggccagggaa ccctggtcac cgtctcctca 360
g 361

<210> SEQ ID NO 258
<211> LENGTH: 120
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Ser Ser Ser
20 25 30

Gly Met His Trp Val Arg Gln Ala Pro Gly Lys Gly Leu Gln Trp Val
35 40 45

Ala Val Ile Ser Tyr Asp Gly Asn Asn Lys Phe Tyr Glu Asp Ser Val
50 55 60

Lys Gly Arg Leu Thr Ile Ser Arg Asp Asn Ser Asn Asn Thr Leu Trp
65 70 75 80

Leu Gln Met Asn Ser Leu Arg Val Glu Asp Thr Ala Val Tyr Tyr Cys
85 90 95

Ala Lys Ser Gly Gly Arg Val Gly Ala Ala Phe Ala Tyr Trp Gly Gln
100 105 110

Gly Thr Leu Val Thr Val Ser Ser
115 120

<210> SEQ ID NO 259
<211> LENGTH: 24

<212> TYPE: DNA
<213> ORGANISM: Artificial Sequence
<220> FEATURE:
<223> OTHER INFORMATION: Synthetic

<400> SEQUENCE: 259
ggattcacct tcagtagttc tggc 24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Ser Ser Gly
1 5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atatcatatg atggaaataa taaa 24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Tyr Asp Gly Asn Asn Lys
1 5

<210> SEQ ID NO 263
<211> LENGTH: 39
<212> TYPE: DNA
<213> ORGANISM: Artificial Sequence
<220> FEATURE:
<223> OTHER INFORMATION: Synthetic

<400> SEQUENCE: 263
gcgaaatcag gaggtagagt gggagccgcc tttgcctac 39

<210> SEQ ID NO 264
<211> LENGTH: 13
<212> TYPE: PRT
<213> ORGANISM: Artificial Sequence
<220> FEATURE:
<223> OTHER INFORMATION: Synthetic

<400> SEQUENCE: 264

Ala Lys Ser Gly Gly Arg Val Gly Ala Ala Phe Ala Tyr
1 5 10

<210> SEQ ID NO 265
<211> LENGTH: 337
<212> TYPE: DNA
<213> ORGANISM: Artificial Sequence
<220> FEATURE:
<223> OTHER INFORMATION: Synthetic

<400> SEQUENCE: 265

```
gatattgtga acactcagtc tccactctct ctgcccgtca cccctggaga gccggcctcc     60
atctcctgca ggtctagtca gagcctcctg tatggtaatg gatacaacta tttggattgg    120
tacctgcaga agccagggca ctctccacag ctcctgatct atttgggttc taatcggggc    180
tccggggtcc ctgacaggtt cagtggcagt ggatcaggca cagattttac actgaagatc    240
agcagagtgg aggctgaaga tgttggcatt tattactgca tgcaaactct acaaactcca    300
ttcactttcg gccctgggac caaaatgtat atcaaac                             337
```

<210> SEQ ID NO 266
<211> LENGTH: 112
<212> TYPE: PRT
<213> ORGANISM: Artificial Sequence
<220> FEATURE:
<223> OTHER INFORMATION: Synthetic

<400> SEQUENCE: 266

```
Asp Ile Val Asn Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Gly
            20                  25                  30

Asn Gly Tyr Asn Tyr Leu Asp Trp Tyr Leu Gln Lys Pro Gly His Ser
        35                  40                  45

Pro Gln Leu Leu Ile Tyr Leu Gly Ser Asn Arg Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Thr
                85                  90                  95

Leu Gln Thr Pro Phe Thr Phe Gly Pro Gly Thr Lys Met Tyr Ile Lys
            100                 105                 110
```

<210> SEQ ID NO 267
<211> LENGTH: 33
<212> TYPE: DNA
<213> ORGANISM: Artificial Sequence
<220> FEATURE:
<223> OTHER INFORMATION: Synthetic

<400> SEQUENCE: 267

```
cagagcctcc tgtatggtaa tggatacaac tat                                  33
```

<210> SEQ ID NO 268
<211> LENGTH: 11
<212> TYPE: PRT
<213> ORGANISM: Artificial Sequence
<220> FEATURE:
<223> OTHER INFORMATION: Synthetic

<400> SEQUENCE: 268

```
Gln Ser Leu Leu Tyr Gly Asn Gly Tyr Asn Tyr
1               5                   10
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 ttgggttct 9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Leu Gly Ser
1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
atgcaaactc tacaaactcc attcact 27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Met Gln Thr Leu Gln Thr Pro Phe Thr
1 5

<210> SEQ ID NO 273
<211> LENGTH: 376
<212> TYPE: DNA
<213> ORGANISM: Artificial Sequence
<220> FEATURE:
<223> OTHER INFORMATION: Synthetic

<400> SEQUENCE: 273
gaggtgcagc tgttggagtc tgggggaggc ttggtacagc ctggggggtc cctgagactc 60
tcctgtgcag gctctggaat cacctttagc agctatgcca tgagctgggt ccgccaggct 120
ccagggaagg ggctggagtg ggtctcagct attagtggta atggtggtac cacaaactac 180
gcagactccg tgaagggccg gttcaccatc tccagagaca actccaagaa cacgctgtat 240
ctgcaaatga acagcctgag agccgaggac acggccgtat attactgtgc gaaagaaaga 300
atccttacca gcagctggac gaggtacggt attatggacg tctggggcca agggaccacg 360
gtcaccgtct cctcag 376

<210> SEQ ID NO 274
<211> LENGTH: 125
<212> TYPE: PRT
<213> ORGANISM: Artificial Sequence
<220> FEATURE:
<223> OTHER INFORMATION: Synthetic

<400> SEQUENCE: 274

Glu Val Gln Leu Leu Glu Ser Gly Gly Gly Leu Val Gln Pro Gly Gly
1 5 10 15

```
Ser Leu Arg Leu Ser Cys Ala Gly Ser Gly Ile Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Arg Ile Leu Thr Ser Ser Trp Thr Arg Tyr Gly Ile Met
            100                 105                 110

Asp Val Trp Gly Gln Gly Thr Thr Val Thr Val Ser Ser
        115                 120                 125


<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

ggaatcacct ttagcagcta tgcc                                            24


<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Ile Thr Phe Ser Ser Tyr Ala
1               5


<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277

attagtggta atggtggtac caca                                            24


<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ser Gly Asn Gly Gly Thr Thr
1               5


<210> SEQ ID NO 279
<211> LENGTH: 54
<212> TYPE: DNA
<213> ORGANISM: Artificial Sequence
<220> FEATURE:
<223> OTHER INFORMATION: Synthetic
```

<400> SEQUENCE: 279
gcgaaagaaa gaatccttac cagcagctgg acgaggtacg gtattatgga cgtc 54

<210> SEQ ID NO 280
<211> LENGTH: 18
<212> TYPE: PRT
<213> ORGANISM: Artificial Sequence
<220> FEATURE:
<223> OTHER INFORMATION: Synthetic

<400> SEQUENCE: 280

Ala Lys Glu Arg Ile Leu Thr Ser Ser Trp Thr Arg Tyr Gly Ile Met
1 5 10 15

Asp Val

<210> SEQ ID NO 281
<211> LENGTH: 322
<212> TYPE: DNA
<213> ORGANISM: Artificial Sequence
<220> FEATURE:
<223> OTHER INFORMATION: Synthetic

<400> SEQUENCE: 281
gaaatagtga tgacgcagtc tccagccacc ctgtctatgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataact ggcctctcac tttcggcgga 300
gggaccaagt tagagatcaa ac 322

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Glu Ile Val Met Thr Gln Ser Pro Ala Thr Leu Ser Met Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Leu
85 90 95

Thr Phe Gly Gly Gly Thr Lys Leu Glu Ile Lys
100 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagagtgtta gcagcaac 18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Ser Val Ser Ser Asn
1 5

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 ggtgcatcc 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Gly Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
cagcagtata ataactggcc tctcact 27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Asn Asn Trp Pro Leu Thr
1 5

<210> SEQ ID NO 289
<211> LENGTH: 358
<212> TYPE: DNA
<213> ORGANISM: Artificial Sequence
<220> FEATURE:
<223> OTHER INFORMATION: Synthetic

<400> SEQUENCE: 289
caggtgcaac tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaaacac caactacaac 180
ccgtccctca agagtcgagt caccatatca gtagacacgt ccaagaacca gttctccctg 240
aaactgaact ctgtgaccgc cgcggacacg gctgtgtatt actgtgcgag aagagaggct 300
acagtaactc catactttga ctactggggc cagggaaccc tggtcaccgt ctcctcag 358

<210> SEQ ID NO 290
<211> LENGTH: 119
<212> TYPE: PRT
<213> ORGANISM: Artificial Sequence
<220> FEATURE:
<223> OTHER INFORMATION: Synthetic

<400> SEQUENCE: 290

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Arg Glu Ala Thr Val Thr Pro Tyr Phe Asp Tyr Trp Gly Gln Gly
            100                 105                 110

Thr Leu Val Thr Val Ser Ser
        115
```

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggtgggtcct tcagtggtta ctac 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

```
Gly Gly Ser Gly Ser Gly Tyr Tyr
1               5
```

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293

```
atcaatcata gtggaaacac c                                               21


<210> SEQ ID NO 294
<211> LENGTH: 7
<212> TYPE: PRT
<213> ORGANISM: Artificial Sequence
<220> FEATURE:
<223> OTHER INFORMATION: Synthetic

<400> SEQUENCE: 294

Ile Asn His Ser Gly Asn Thr
1               5


<210> SEQ ID NO 295
<211> LENGTH: 39
<212> TYPE: DNA
<213> ORGANISM: Artificial Sequence
<220> FEATURE:
<223> OTHER INFORMATION: Synthetic

<400> SEQUENCE: 295

gcgagaagag aggctacagt aactccatac tttgactac                            39


<210> SEQ ID NO 296
<211> LENGTH: 13
<212> TYPE: PRT
<213> ORGANISM: Artificial Sequence
<220> FEATURE:
<223> OTHER INFORMATION: Synthetic

<400> SEQUENCE: 296

Ala Arg Arg Glu Ala Thr Val Thr Pro Tyr Phe Asp Tyr
1               5                   10


<210> SEQ ID NO 297
<211> LENGTH: 322
<212> TYPE: DNA
<213> ORGANISM: Artificial Sequence
<220> FEATURE:
<223> OTHER INFORMATION: Synthetic

<400> SEQUENCE: 297

gacatccagt tgacccagtc tccatccttc ctgtctgcat ctgtaggaga cagagtcacc      60

atcacttgct gggccagtca gggcattagc agttatttag cctggtatca gcaaaaacca     120

gggaaagccc ctaagctcct gatctatgct gcatccactt tgcaaagtgg ggtcccatca     180

aggttcagcg gcagtggatc tgggacagaa ttcactctca caatcagcag cctgcagcct     240

gaagattttg caacttatta ctgtcaacag cttaatagtt atccgctcac tttcggcgga     300

gggaccaagg tggagatcaa ac                                              322


<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30
```

```
Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105


<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299

cagggcatta gcagttat                                                    18


<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Ile Ser Ser Tyr
1               5


<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301

gctgcatcc                                                               9


<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
1


<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303

caacagctta atagttatcc gctcact                                          27


<210> SEQ ID NO 304
```

<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Leu Asn Ser Tyr Pro Leu Thr
1               5

<210> SEQ ID NO 305
<211> LENGTH: 355
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc gtggtccagc ctgggaggtc cctgagactc     60
tcctgtgtag tctctggatt caacttcagt aggaatggca tacactgggt ccgccaggct    120
ccaggcaagg ggctggaatg ggtggcagtt atatcatatg atggaagaaa taaattttat    180
gtagagtccg tgaagggccg attcaccatc tccagagaca attccaagaa cacgctgtat    240
ctgcaaatga acagtctgag agttgaggac acggctgtat attactgtgc gaaatcctca    300
attggagggt tttttgaata ctggggccag ggaaccctgg tcaccgtctc ctcag         355

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Glu Ser Gly Gly Gly Val Val Gln Pro Gly Arg
1               5                   10                  15

Ser Leu Arg Leu Ser Cys Val Val Ser Gly Phe Asn Phe Ser Arg Asn
            20                  25                  30

Gly Ile His Trp Val Arg Gln Ala Pro Gly Lys Gly Leu Glu Trp Val
        35                  40                  45

Ala Val Ile Ser Tyr Asp Gly Arg Asn Lys Phe Tyr Val Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Ser Ser Ile Gly Gly Phe Phe Glu Tyr Trp Gly Gln Gly Thr
            100                 105                 110

Leu Val Thr Val Ser Ser
        115

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcaact tcagtaggaa tggc                                            24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Asn Phe Ser Arg Asn Gly
1 5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atatcatatg atggaagaaa taaa 24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Tyr Asp Gly Arg Asn Lys
1 5

<210> SEQ ID NO 311
<211> LENGTH: 33
<212> TYPE: DNA
<213> ORGANISM: Artificial Sequence
<220> FEATURE:
<223> OTHER INFORMATION: Synthetic

<400> SEQUENCE: 311
gcgaaatcct caattggagg gttttttgaa tac 33

<210> SEQ ID NO 312
<211> LENGTH: 11
<212> TYPE: PRT
<213> ORGANISM: Artificial Sequence
<220> FEATURE:
<223> OTHER INFORMATION: Synthetic

<400> SEQUENCE: 312

Ala Lys Ser Ser Ile Gly Gly Phe Phe Glu Tyr
1 5 10

<210> SEQ ID NO 313
<211> LENGTH: 337
<212> TYPE: DNA
<213> ORGANISM: Artificial Sequence
<220> FEATURE:
<223> OTHER INFORMATION: Synthetic

<400> SEQUENCE: 313
gatattgtga tgactcagtc tccactctcc ctgcccgtca ctcctggaga gccggcctcc 60
atctcctgca ggtctagtca gagcctcctg catagtaatg gatacaacta tttggattgg 120
tacctgcaga agccaggaca gtctccacaa ctcatgatct atttgggttc tcatcgggcc 180

```
tccggggtcc ctgacaggtt cagtggcagt ggatcaggca cagattttac actgaaaatc    240

agcagagtgg aggctgagga tgttggagtc tattactgca ttcaagttca acaaactccg    300

atcaccttcg gccaagggac acggctggag attaaac                             337


<210> SEQ ID NO 314
<211> LENGTH: 112
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Met Ile Tyr Leu Gly Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ile Gln Val
                85                  90                  95

Gln Gln Thr Pro Ile Thr Phe Gly Gln Gly Thr Arg Leu Glu Ile Lys
            100                 105                 110


<210> SEQ ID NO 315
<211> LENGTH: 33
<212> TYPE: DNA
<213> ORGANISM: Artificial Sequence
<220> FEATURE:
<223> OTHER INFORMATION: Synthetic

<400> SEQUENCE: 315

cagagcctcc tgcatagtaa tggatacaac tat                                  33


<210> SEQ ID NO 316
<211> LENGTH: 11
<212> TYPE: PRT
<213> ORGANISM: Artificial Sequence
<220> FEATURE:
<223> OTHER INFORMATION: Synthetic

<400> SEQUENCE: 316

Gln Ser Leu Leu His Ser Asn Gly Tyr Asn Tyr
1               5                   10


<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317

ttgggttct                                                              9


<210> SEQ ID NO 318
<211> LENGTH: 3
<212> TYPE: PRT
<213> ORGANISM: Artificial Sequence
```

<220> FEATURE:
<223> OTHER INFORMATION: Synthetic

<400> SEQUENCE: 318

Leu Gly Ser
1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
attcaagttc aacaaactcc gatcacc 27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Ile Gln Val Gln Gln Thr Pro Ile Thr
1 5

<210> SEQ ID NO 321
<211> LENGTH: 337
<212> TYPE: DNA
<213> ORGANISM: Artificial Sequence
<220> FEATURE:
<223> OTHER INFORMATION: Synthetic

<400> SEQUENCE: 321
gatattgtga tgactcagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt acaagatttc taaccggttc 180
tctggggtcc cagacagatt cagtggcagt ggggcaggga cagatttcac actgaaaatc 240
agcagggtgg aagctgagga tgtcggggtt tatttctgca tgcaagctac acaatttccg 300
tacacttttg gccaggggac caagctggag atcaaag 337

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

```
Ser Arg Val Glu Ala Glu Asp Val Gly Val Tyr Phe Cys Met Gln Ala
                85                  90                  95

Thr Gln Phe Pro Tyr Thr Phe Gly Gln Gly Thr Lys Leu Glu Ile Lys
            100                 105                 110


<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323

caaagcctcg tacacagtga tggaaacacc tac                                  33


<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

Gln Ser Leu Val His Ser Asp Gly Asn Thr Tyr
1               5                   10


<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325

aagatttct                                                              9


<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Ile Ser
1


<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327

atgcaagcta cacaatttcc gtacact                                          27


<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328
```

Met Gln Ala Thr Gln Phe Pro Tyr Thr
1               5

<210> SEQ ID NO 329
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa = Gly
<220> FEATURE:
<221> NAME/KEY: VARIANT
<222> LOCATION: (2)..(2)
<223> OTHER INFORMATION: Xaa = Phe
<220> FEATURE:
<221> NAME/KEY: VARIANT
<222> LOCATION: (3)..(3)
<223> OTHER INFORMATION: Xaa = Thr
<220> FEATURE:
<221> NAME/KEY: VARIANT
<222> LOCATION: (4)..(4)
<223> OTHER INFORMATION: Xaa = Phe
<220> FEATURE:
<221> NAME/KEY: VARIANT
<222> LOCATION: (5)..(5)
<223> OTHER INFORMATION: Xaa = Ser
<220> FEATURE:
<221> NAME/KEY: VARIANT
<222> LOCATION: (6)..(6)
<223> OTHER INFORMATION: Xaa = Ala or Ser
<220> FEATURE:
<221> NAME/KEY: VARIANT
<222> LOCATION: (7)..(7)
<223> OTHER INFORMATION: Xaa = Phe or Tyr
<220> FEATURE:
<221> NAME/KEY: VARIANT
<222> LOCATION: (8)..(8)
<223> OTHER INFORMATION: Xaa = Gly or Ala

<400> SEQUENCE: 329

Xaa Xaa Xaa Xaa Xaa Xaa Xaa Xaa
1               5

<210> SEQ ID NO 330
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa = Ile
<220> FEATURE:
<221> NAME/KEY: VARIANT
<222> LOCATION: (2)..(2)
<223> OTHER INFORMATION: Xaa = Gly or Ser
<220> FEATURE:
<221> NAME/KEY: VARIANT
<222> LOCATION: (3)..(3)
<223> OTHER INFORMATION: Xaa = Tyr or Gly
<220> FEATURE:
<221> NAME/KEY: VARIANT
<222> LOCATION: (4)..(4)
<223> OTHER INFORMATION: Xaa = Ser or Asp
<220> FEATURE:
<221> NAME/KEY: VARIANT
<222> LOCATION: (5)..(5)
<223> OTHER INFORMATION: Xaa = Gly
<220> FEATURE:
<221> NAME/KEY: VARIANT
<222> LOCATION: (6)..(6)
<223> OTHER INFORMATION: Xaa = Gly
<220> FEATURE:
<221> NAME/KEY: VARIANT
<222> LOCATION: (7)..(7)
<223> OTHER INFORMATION: Xaa = Ser or Asn
<220> FEATURE:
<221> NAME/KEY: VARIANT
<222> LOCATION: (8)..(8)
<223> OTHER INFORMATION: Xaa = Ala or Glu

<400> SEQUENCE: 330

Xaa Xaa Xaa Xaa Xaa Xaa Xaa Xaa
1               5

<210> SEQ ID NO 331
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa = Ser or Ala
<220> FEATURE:
<221> NAME/KEY: VARIANT
<222> LOCATION: (2)..(2)
<223> OTHER INFORMATION: Xaa = Thr or Lys
<220> FEATURE:
<221> NAME/KEY: VARIANT
<222> LOCATION: (3)..(3)
<223> OTHER INFORMATION: Xaa = Asp or Ile
<220> FEATURE:
<221> NAME/KEY: VARIANT
<222> LOCATION: (4)..(4)
<223> OTHER INFORMATION: Xaa = Gly or Ser
<220> FEATURE:
<221> NAME/KEY: VARIANT
<222> LOCATION: (5)..(5)
<223> OTHER INFORMATION: Xaa = Ala or His
<220> FEATURE:
<221> NAME/KEY: VARIANT
<222> LOCATION: (6)..(6)
<223> OTHER INFORMATION: Xaa = Trp or Tyr
<220> FEATURE:
<221> NAME/KEY: VARIANT
<222> LOCATION: (7)..(7)
<223> OTHER INFORMATION: Xaa = Lys or Asp
<220> FEATURE:
<221> NAME/KEY: VARIANT
<222> LOCATION: (8)..(8)
<223> OTHER INFORMATION: Xaa = Met or Ile
<220> FEATURE:
<221> NAME/KEY: VARIANT
<222> LOCATION: (9)..(9)
<223> OTHER INFORMATION: Xaa = Ser or Leu
<220> FEATURE:
<221> NAME/KEY: VARIANT
<222> LOCATION: (10)..(10)
<223> OTHER INFORMATION: Xaa = Gly or Ser
<220> FEATURE:
<221> NAME/KEY: VARIANT
<222> LOCATION: (11)..(11)
<223> OTHER INFORMATION: Xaa = Leu or Gly
<220> FEATURE:
<221> NAME/KEY: VARIANT
<222> LOCATION: (12)..(12)
<223> OTHER INFORMATION: Xaa = Asp or Met
<220> FEATURE:
<221> NAME/KEY: VARIANT
<222> LOCATION: (13)..(13)
<223> OTHER INFORMATION: Xaa = Val or Asp
<220> FEATURE:
<221> NAME/KEY: VARIANT
<222> LOCATION: (14)..(14)
<223> OTHER INFORMATION: Xaa = Val or absent

<400> SEQUENCE: 331

Xaa Xaa Xaa Xaa Xaa Xaa Xaa Xaa Xaa Xaa Xaa Xaa Xaa Xaa
1 5 10

<210> SEQ ID NO 332
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa = Gln
<220> FEATURE:
<221> NAME/KEY: VARIANT
<222> LOCATION: (2)..(2)
<223> OTHER INFORMATION: Xaa = Asp or Gly
<220> FEATURE:
<221> NAME/KEY: VARIANT
<222> LOCATION: (3)..(3)
<223> OTHER INFORMATION: Xaa = Ile
<220> FEATURE:
<221> NAME/KEY: VARIANT
<222> LOCATION: (4)..(4)
<223> OTHER INFORMATION: Xaa = Ser
<220> FEATURE:
<221> NAME/KEY: VARIANT
<222> LOCATION: (5)..(5)
<223> OTHER INFORMATION: Xaa = Asp or Asn
<220> FEATURE:
<221> NAME/KEY: VARIANT
<222> LOCATION: (6)..(6)
<223> OTHER INFORMATION: Xaa = Tyr or Trp

<400> SEQUENCE: 332

Xaa Xaa Xaa Xaa Xaa Xaa
1 5

<210> SEQ ID NO 333
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa = Thr or Ala
<220> FEATURE:
<221> NAME/KEY: VARIANT
<222> LOCATION: (2)..(2)
<223> OTHER INFORMATION: Xaa = Thr or Ala
<220> FEATURE:
<221> NAME/KEY: VARIANT
<222> LOCATION: (3)..(3)
<223> OTHER INFORMATION: Xaa = Ser

<400> SEQUENCE: 333

Xaa Xaa Xaa
1

<210> SEQ ID NO 334
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Xaa = Gln
<220> FEATURE:
<221> NAME/KEY: VARIANT
<222> LOCATION: (2)..(2)
<223> OTHER INFORMATION: Xaa = Lys or Gln
<220> FEATURE:
<221> NAME/KEY: VARIANT
<222> LOCATION: (3)..(3)
<223> OTHER INFORMATION: Xaa = Ala or Tyr
<220> FEATURE:
<221> NAME/KEY: VARIANT
<222> LOCATION: (4)..(4)
<223> OTHER INFORMATION: Xaa = Asp or Asn
<220> FEATURE:
<221> NAME/KEY: VARIANT
<222> LOCATION: (5)..(5)
<223> OTHER INFORMATION: Xaa = Ser
<220> FEATURE:
<221> NAME/KEY: VARIANT
<222> LOCATION: (6)..(6)
<223> OTHER INFORMATION: Xaa = Ala or Phe
<220> FEATURE:
<221> NAME/KEY: VARIANT
<222> LOCATION: (7)..(7)
<223> OTHER INFORMATION: Xaa = Pro
<220> FEATURE:
<221> NAME/KEY: VARIANT
<222> LOCATION: (8)..(8)
<223> OTHER INFORMATION: Xaa = Leu
<220> FEATURE:
<221> NAME/KEY: VARIANT
<222> LOCATION: (9)..(9)
<223> OTHER INFORMATION: Xaa = Thr

<400> SEQUENCE: 334

Xaa Xaa Xaa Xaa Xaa Xaa Xaa Xaa Xaa
1               5

<210> SEQ ID NO 335
<211> LENGTH: 330
<212> TYPE: PRT
<213> ORGANISM: Artificial Sequence
<220> FEATURE:
<223> OTHER INFORMATION: Synthetic

<400> SEQUENCE: 335

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 336
<211> LENGTH: 327
<212> TYPE: PRT
<213> ORGANISM: Artificial Sequence
<220> FEATURE:
<223> OTHER INFORMATION: Synthetic

<400> SEQUENCE: 336

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 337
<211> LENGTH: 327
<212> TYPE: PRT
<213> ORGANISM: Artificial Sequence
<220> FEATURE:
<223> OTHER INFORMATION: Synthetic

<400> SEQUENCE: 337

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 338
<211> LENGTH: 1128
<212> TYPE: DNA
<213> ORGANISM: Homo sapiens

<400> SEQUENCE: 338

```
atgcaaaaac tgcaactctg tgtttatatt tacctgttta tgctgattgt tgctggtcca      60

gtggatctaa atgagaacag tgagcaaaaa gaaaatgtgg aaaaagaggg gctgtgtaat     120

gcatgtactt ggagacaaaa cactaaatct tcaagaatag aagccattaa gatacaaatc     180

ctcagtaaac ttcgtctgga aacagctcct aacatcagca aagatgttat aagacaactt     240

ttacccaaag ctcctccact ccgggaactg attgatcagt atgatgtcca gagggatgac     300

agcagcgatg gctctttgga agatgacgat tatcacgcta caacggaaac aatcattacc     360

atgcctacag agtctgattt tctaatgcaa gtggatggaa aacccaaatg ttgcttcttt     420

aaatttagct ctaaaataca atacaataaa gtagtaaagg cccaactatg gatatatttg     480

agacccgtcg agactcctac aacagtgttt gtgcaaatcc tgagactcat caaacctatg     540

aaagacggta caaggtatac tggaatccga tctctgaaac ttgacatgaa cccaggcact     600

ggtatttggc agagcattga tgtgaagaca gtgttgcaaa attggctcaa acaacctgaa     660

tccaacttag gcattgaaat aaaagcttta gatgagaatg gtcatgatct tgctgtaacc     720

ttcccaggac caggagaaga tgggctgaat ccgtttttag aggtcaaggt aacagacaca     780

ccaaaaagat ccagaaggga ttttggtctt gactgtgatg agcactcaac agaatcacga     840

tgctgtcgtt accctctaac tgtggatttt gaagcttttg gatgggattg gattatcgct     900

cctaaaagat ataaggccaa ttactgctct ggagagtgtg aatttgtatt tttacaaaaa     960

tatcctcata ctcatctggt acaccaagca aaccccagag gttcagcagg cccttgctgt    1020

actcccacaa agatgtctcc aattaatatg ctatatttta atggcaaaga acaaataata    1080

tatgggaaaa ttccagcgat ggtagtagac cgctgtgggt gctcatga                1128
```

<210> SEQ ID NO 339
<211> LENGTH: 375
<212> TYPE: PRT
<213> ORGANISM: Homo sapiens

<400> SEQUENCE: 339

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
```

```
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375


<210> SEQ ID NO 340
<211> LENGTH: 109
<212> TYPE: PRT
<213> ORGANISM: Homo sapiens

<400> SEQUENCE: 340

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30
```

```
Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105


<210> SEQ ID NO 341
<211> LENGTH: 1224
<212> TYPE: DNA
<213> ORGANISM: Homo sapiens

<400> SEQUENCE: 341

atggtgctcg cggccccgct gctgctgggc ttcctgctcc tcgccctgga gctgcggccc     60

cggggggagg cggccgaggg ccccgcggcg gcggcggcgg cggcggcggc ggcggcagcg    120

gcgggggtcg ggggggagcg ctccagccgg ccagccccgt ccgtggcgcc cgagccggac    180

ggctgccccg tgtgcgtttg gcggcagcac agccgcgagc tgcgcctaga gagcatcaag    240

tcgcagatct tgagcaaact gcggctcaag gaggcgccca acatcagccg cgaggtggtg    300

aagcagctgc tgcccaaggc gccgccgctg cagcagatcc tggacctaca cgacttccag    360

ggcgacgcgc tgcagcccga ggacttcctg gaggaggacg agtaccacgc caccaccgag    420

accgtcatta gcatggccca ggagacggac ccagcagtac agacagatgg cagccctctc    480

tgctgccatt ttcacttcag ccccaaggtg atgttcacaa aggtactgaa ggcccagctg    540

tgggtgtacc tacggcctgt accccgccca gccacagtct acctgcagat cttgcgacta    600

aaacccctaa ctggggaagg gaccgcaggg ggagggggcg gaggccggcg tcacatccgt    660

atccgctcac tgaagattga gctgcactca cgctcaggcc attggcagag catcgacttc    720

aagcaagtgc tacacagctg gttccgccag ccacagagca actggggcat cgagatcaac    780

gcctttgatc ccagtggcac agacctggct gtcacctccc tggggccggg agccgagggg    840

ctgcatccat tcatggagct tcgagtccta gagaacacaa aacgttcccg gcggaacctg    900

ggtctggact gcgacgagca ctcaagcgag tcccgctgct gccgatatcc cctcacagtg    960

gactttgagg ctttcggctg ggactggatc atcgcaccta agcgctacaa ggccaactac   1020

tgctccggcc agtgcgagta catgttcatg caaaaatatc cgcataccca tttggtgcag   1080

caggccaatc caagaggctc tgctgggccc tgttgtaccc ccaccaagat gtccccaatc   1140

aacatgctct acttcaatga caagcagcag attatctacg gcaagatccc tggcatggtg   1200

gtggatcgct gtggctgctc ttaa                                          1224


<210> SEQ ID NO 342
<211> LENGTH: 407
<212> TYPE: PRT
<213> ORGANISM: Homo sapiens

<400> SEQUENCE: 342

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30
```

```
Ala Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
    290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
        355                 360                 365

Gly Pro Cys Cys Thr Pro Thr Lys Met Ser Pro Ile Asn Met Leu Tyr
    370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405
```

<210> SEQ ID NO 343
<211> LENGTH: 109
<212> TYPE: PRT
<213> ORGANISM: Homo sapiens

<400> SEQUENCE: 343

```
Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105
```

<210> SEQ ID NO 344
<211> LENGTH: 1503
<212> TYPE: DNA
<213> ORGANISM: Homo sapiens

<400> SEQUENCE: 344

```
atgagactcc ccaaactcct cactttcttg ctttggtacc tggcttggct ggacctggaa     60

ttcatctgca ctgtgttggg tgcccctgac ttgggccaga gaccccaggg gaccaggcca    120

ggattggcca aagcagaggc caaggagagg ccccccctgg cccggaacgt cttcaggcca    180

gggggtcaca gctatggtgg gggggccacc aatgccaatg ccagggcaaa gggaggcacc    240

gggcagacag gaggcctgac acagcccaag aaggatgaac ccaaaaagct gccccccaga    300

ccgggcggcc ctgaacccaa gccaggacac cctccccaaa caaggcaggc tacagcccgg    360

actgtgaccc caaaaggaca gcttcccgga ggcaaggcac ccccaaaagc aggatctgtc    420

cccagctcct tcctgctgaa gaaggccagg gagcccgggc ccccacgaga gcccaaggag    480

ccgtttcgcc caccccccat cacaccccac gagtacatgc tctcgctgta caggacgctg    540

tccgatgctg acagaaaggg aggcaacagc agcgtgaagt tggaggctgg cctggccaac    600

accatcacca gctttattga caaagggcaa gatgaccgag gtcccgtggt caggaagcag    660

aggtacgtgt ttgacattag tgccctggag aaggatgggc tgctgggggc cgagctgcgg    720

atcttgcgga agaagccctc ggacacggcc aagccagcgg cccccggagg cgggcgggct    780

gcccagctga agctgtccag ctgccccagc ggccggcagc cggcctcctt gctggatgtg    840

cgctccgtgc caggcctgga cggatctggc tgggaggtgt tcgacatctg gaagctcttc    900

cgaaacttta agaactcggc ccagctgtgc ctggagctgg aggcctggga acggggcagg    960

gccgtggacc tccgtggcct gggcttcgac cgcgccgccc ggcaggtcca cgagaaggcc   1020

ctgttcctgg tgtttggccg caccaagaaa cgggacctgt tctttaatga gattaaggcc   1080

cgctctggcc aggacgataa gaccgtgtat gagtacctgt tcagccagcg gcgaaaacgg   1140

cgggccccac tggccactcg ccagggcaag cgacccagca agaaccttaa ggctcgctgc   1200

agtcggaagg cactgcatgt caacttcaag gacatgggct gggacgactg gatcatcgca   1260

ccccttgagt acgaggcttt ccactgcgag gggctgtgcg agttcccatt gcgctcccac   1320

ctggagccca cgaatcatgc agtcatccag accctgatga actccatgga ccccgagtcc   1380

acaccaccca cctgctgtgt gcccacgcgg ctgagtccca tcagcatcct cttcattgac   1440

tctgccaaca acgtggtgta taagcagtat gaggacatgg tcgtggagtc gtgtggctgc   1500
```

```
agg                                                                  1503

<210> SEQ ID NO 345
<211> LENGTH: 501
<212> TYPE: PRT
<213> ORGANISM: Homo sapiens

<400> SEQUENCE: 345

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365
```

```
Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500


<210> SEQ ID NO 346
<211> LENGTH: 120
<212> TYPE: PRT
<213> ORGANISM: Homo sapiens

<400> SEQUENCE: 346

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120


<210> SEQ ID NO 347
<211> LENGTH: 107
<212> TYPE: PRT
<213> ORGANISM: Artificial Sequence
<220> FEATURE:
<223> OTHER INFORMATION: Synthetic

<400> SEQUENCE: 347

Gln Ala Lys His Lys Gln Arg Lys Arg Leu Lys Ser Ser Cys Arg Tyr
1               5                   10                  15

Pro Leu Thr Val Asp Phe Glu Ala Phe Gly Trp Asp Trp Ile Ile Ala
            20                  25                  30

Pro Lys Arg Tyr Lys Ala Asn Tyr Cys Ser Gly Glu Cys Glu Phe Val
        35                  40                  45
```

```
Phe Leu Gln Lys Tyr Pro His Thr His Leu Val His Gln Ala Asn Pro
    50                  55                  60

Arg Gly Ser Ala Gly Pro Cys Cys Thr Pro Thr Lys Met Ser Pro Ile
65                  70                  75                  80

Asn Met Leu Tyr Phe Asn Gly Lys Glu Gln Ile Ile Tyr Gly Lys Ile
                85                  90                  95

Pro Ala Met Val Val Asp Arg Cys Gly Cys Ser
            100                 105


<210> SEQ ID NO 348
<211> LENGTH: 109
<212> TYPE: PRT
<213> ORGANISM: Artificial Sequence
<220> FEATURE:
<223> OTHER INFORMATION: Synthetic

<400> SEQUENCE: 348

Ala Leu Asp Thr Asn Tyr Cys Phe Ser Ser Thr Glu Lys Asn Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105


<210> SEQ ID NO 349
<211> LENGTH: 111
<212> TYPE: PRT
<213> ORGANISM: Artificial Sequence
<220> FEATURE:
<223> OTHER INFORMATION: Synthetic

<400> SEQUENCE: 349

Asp Phe Gly Leu Asp Cys Asp Glu His Ser Thr Glu Ser Arg Cys Cys
1               5                   10                  15

Lys Arg His Pro Leu Tyr Val Asp Phe Ser Asp Val Gly Trp Asn Asp
            20                  25                  30

Trp Ile Val Ala Pro Pro Gly Tyr His Ala Phe Tyr Cys Ser Gly Glu
        35                  40                  45

Cys Glu Phe Val Phe Leu Gln Lys Tyr Pro His Thr His Leu Val His
    50                  55                  60

Gln Ala Asn Pro Arg Gly Ser Ala Gly Pro Cys Cys Thr Pro Thr Lys
65                  70                  75                  80

Met Ser Pro Ile Asn Met Leu Tyr Phe Asn Gly Lys Glu Gln Ile Ile
                85                  90                  95

Tyr Gly Lys Ile Pro Ala Met Val Val Asp Arg Cys Gly Cys Ser
            100                 105                 110


<210> SEQ ID NO 350
<211> LENGTH: 110
<212> TYPE: PRT
<213> ORGANISM: Artificial Sequence
```

<220> FEATURE:
<223> OTHER INFORMATION: Synthetic

<400> SEQUENCE: 350

Asp Phe Gly Leu Asp Cys Asp Glu His Ser Thr Glu Ser Arg Cys Cys
1 5 10 15

Val Arg Gln Leu Tyr Ile Asp Phe Arg Lys Asp Leu Gly Trp Lys Trp
20 25 30

Ile His Glu Pro Lys Gly Tyr His Ala Asn Phe Cys Ser Gly Glu Cys
35 40 45

Glu Phe Val Phe Leu Gln Lys Tyr Pro His Thr His Leu Val His Gln
50 55 60

Ala Asn Pro Arg Gly Ser Ala Gly Pro Cys Cys Thr Pro Thr Lys Met
65 70 75 80

Ser Pro Ile Asn Met Leu Tyr Phe Asn Gly Lys Glu Gln Ile Ile Tyr
85 90 95

Gly Lys Ile Pro Ala Met Val Val Asp Arg Cys Gly Cys Ser
100 105 110

<210> SEQ ID NO 351
<211> LENGTH: 114
<212> TYPE: PRT
<213> ORGANISM: Artificial Sequence
<220> FEATURE:
<223> OTHER INFORMATION: Synthetic

<400> SEQUENCE: 351

Asp Phe Gly Leu Asp Cys Asp Glu His Ser Thr Glu Ser Arg Cys Cys
1 5 10 15

Arg Tyr Pro Leu Thr Val Asp Phe Glu Ala Phe Gly Trp Asp Trp Ile
20 25 30

Ile Ala Pro Lys Arg Tyr Lys Ala Asn Tyr Cys Ser Gly Glu Cys Pro
35 40 45

Phe Pro Leu Ala Asp His Leu Asn Ser Thr Asn His Ala Ile Val Gln
50 55 60

Thr Leu Val Asn Ser Val Asn Ser Lys Ile Pro Lys Ala Cys Cys Thr
65 70 75 80

Pro Thr Lys Met Ser Pro Ile Asn Met Leu Tyr Phe Asn Gly Lys Glu
85 90 95

Gln Ile Ile Tyr Gly Lys Ile Pro Ala Met Val Val Asp Arg Cys Gly
100 105 110

Cys Ser

<210> SEQ ID NO 352
<211> LENGTH: 112
<212> TYPE: PRT
<213> ORGANISM: Artificial Sequence
<220> FEATURE:
<223> OTHER INFORMATION: Synthetic

<400> SEQUENCE: 352

Asp Phe Gly Leu Asp Cys Asp Glu His Ser Thr Glu Ser Arg Cys Cys
1 5 10 15

Arg Tyr Pro Leu Thr Val Asp Phe Glu Ala Phe Gly Trp Asp Trp Ile
20 25 30

Ile Ala Pro Lys Arg Tyr Lys Ala Asn Tyr Cys Ser Gly Glu Cys Pro
35 40 45

Tyr Ile Trp Ser Leu Asp Thr Gln Tyr Ser Lys Val Leu Ala Leu Tyr

```
    50                  55                  60

Asn Gln His Asn Pro Gly Ala Ser Ala Ala Pro Cys Cys Thr Pro Thr
65                  70                  75                  80

Lys Met Ser Pro Ile Asn Met Leu Tyr Phe Asn Gly Lys Glu Gln Ile
                85                  90                  95

Ile Tyr Gly Lys Ile Pro Ala Met Val Val Asp Arg Cys Gly Cys Ser
            100                 105                 110


<210> SEQ ID NO 353
<211> LENGTH: 109
<212> TYPE: PRT
<213> ORGANISM: Artificial Sequence
<220> FEATURE:
<223> OTHER INFORMATION: Synthetic

<400> SEQUENCE: 353

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Ser Val Asn Ser Lys Ile Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105


<210> SEQ ID NO 354
<211> LENGTH: 109
<212> TYPE: PRT
<213> ORGANISM: Artificial Sequence
<220> FEATURE:
<223> OTHER INFORMATION: Synthetic

<400> SEQUENCE: 354

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Gly Ala Ser Ala Ala Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105


<210> SEQ ID NO 355
<211> LENGTH: 109
<212> TYPE: PRT
<213> ORGANISM: Artificial Sequence
<220> FEATURE:
```

<223> OTHER INFORMATION: Synthetic

<400> SEQUENCE: 355

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Val Pro Thr Glu Leu Ser
65                  70                  75                  80

Ala Ile Ser Met Leu Tyr Leu Asp Glu Asn Glu Lys Val Val Leu Lys
                85                  90                  95

Asn Tyr Gln Asp Met Val Val Glu Gly Cys Gly Cys Ser
            100                 105
```

<210> SEQ ID NO 356
<211> LENGTH: 108
<212> TYPE: PRT
<213> ORGANISM: Artificial Sequence
<220> FEATURE:
<223> OTHER INFORMATION: Synthetic

<400> SEQUENCE: 356

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Val Pro Gln Ala Leu Glu
65                  70                  75                  80

Pro Leu Pro Ile Val Tyr Tyr Val Gly Arg Lys Pro Lys Val Glu Gln
                85                  90                  95

Leu Ser Asn Met Ile Val Arg Ser Cys Gly Cys Ser
            100                 105
```

<210> SEQ ID NO 357
<211> LENGTH: 109
<212> TYPE: PRT
<213> ORGANISM: Artificial Sequence
<220> FEATURE:
<223> OTHER INFORMATION: Synthetic

<400> SEQUENCE: 357

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
```

```
65                  70                  75                  80

Pro Ile Asn Met Leu Tyr Phe Asn Gly Lys Glu Lys Val Val Leu Lys
                85                  90                  95

Asn Tyr Gln Asp Met Val Val Glu Gly Cys Gly Cys Ser
            100                 105
```

<210> SEQ ID NO 358
<211> LENGTH: 108
<212> TYPE: PRT
<213> ORGANISM: Artificial Sequence
<220> FEATURE:
<223> OTHER INFORMATION: Synthetic

<400> SEQUENCE: 358

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Lys Pro Lys Val Glu Gln
                85                  90                  95

Leu Ser Asn Met Ile Val Arg Ser Cys Gly Cys Ser
            100                 105
```

<210> SEQ ID NO 359
<211> LENGTH: 360
<212> TYPE: DNA
<213> ORGANISM: Artificial Sequence
<220> FEATURE:
<223> OTHER INFORMATION: Synthetic

<400> SEQUENCE: 359

```
gaggtgcagg tgttggagtc tgggggagac ttggtacagc ctggggggtc cctgagactc     60

tcctgtgcag cctctggatt cacctttagt gcctatgcca tgacctgggt ccgccaggct    120

ccagggaagg ggctggagtg ggtctcagct attagtggta gtggtggtag cgcatactac    180

gcagactccg tgaagggccg gttcaccatc tccagagaca attccaagaa cacggtatat    240

ctgcagatga acagcctgag agccgaggac acggccgtat attactgtgc gaaagatggg    300

gcctggaaaa tgtccggttt ggacgtctgg ggccaaggga ccacggtcat cgtctcctca    360
```

<210> SEQ ID NO 360
<211> LENGTH: 120
<212> TYPE: PRT
<213> ORGANISM: Artificial Sequence
<220> FEATURE:
<223> OTHER INFORMATION: Synthetic

<400> SEQUENCE: 360

```
Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45
```

```
Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser
        115                 120


<210> SEQ ID NO 361
<211> LENGTH: 24
<212> TYPE: DNA
<213> ORGANISM: Artificial Sequence
<220> FEATURE:
<223> OTHER INFORMATION: Synthetic

<400> SEQUENCE: 361

ggattcacct ttagtgccta tgcc                                            24


<210> SEQ ID NO 362
<211> LENGTH: 8
<212> TYPE: PRT
<213> ORGANISM: Artificial Sequence
<220> FEATURE:
<223> OTHER INFORMATION: Synthetic

<400> SEQUENCE: 362

Gly Phe Thr Phe Ser Ala Tyr Ala
1               5


<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363

attagtggta gtggtggtag cgca                                            24


<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Ile Ser Gly Ser Gly Gly Ser Ala
1               5


<210> SEQ ID NO 365
<211> LENGTH: 39
<212> TYPE: DNA
<213> ORGANISM: Artificial Sequence
<220> FEATURE:
<223> OTHER INFORMATION: Synthetic

<400> SEQUENCE: 365

gcgaaagatg gggcctggaa aatgtccggt ttggacgtc                            39
```

<210> SEQ ID NO 366
<211> LENGTH: 13
<212> TYPE: PRT
<213> ORGANISM: Artificial Sequence
<220> FEATURE:
<223> OTHER INFORMATION: Synthetic

<400> SEQUENCE: 366

```
Ala Lys Asp Gly Ala Trp Lys Met Ser Gly Leu Asp Val
1               5                   10
```

<210> SEQ ID NO 367
<211> LENGTH: 321
<212> TYPE: DNA
<213> ORGANISM: Artificial Sequence
<220> FEATURE:
<223> OTHER INFORMATION: Synthetic

<400> SEQUENCE: 367

```
gacatccaga tgacccagtc tccagcctcc ctgtctgcat ctgttggaga cagagtcacc     60

atcacttgtc gggcgagtca ggacattagc gattatttag cctggtatca gcagaaacca    120

gggaaaattc ctaggctcct gatctatact acatccactt tgcaatcagg ggtcccatct    180

cggttccgtg gcagtgggtc tgggacagat ttcactctca ccatcagcag cctgcagcct    240

gaagatgttg caacttatta ctgtcagaag tatgacagtg ccccgctcac tttcggcgga    300

gggaccaagg tggagatcaa a                                              321
```

<210> SEQ ID NO 368
<211> LENGTH: 107
<212> TYPE: PRT
<213> ORGANISM: Artificial Sequence
<220> FEATURE:
<223> OTHER INFORMATION: Synthetic

<400> SEQUENCE: 368

```
Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105
```

<210> SEQ ID NO 369
<211> LENGTH: 18
<212> TYPE: DNA
<213> ORGANISM: Artificial Sequence
<220> FEATURE:
<223> OTHER INFORMATION: Synthetic

<400> SEQUENCE: 369

```
caggacatta gcgattat                                                   18
```

<210> SEQ ID NO 370

<211> LENGTH: 6
<212> TYPE: PRT
<213> ORGANISM: Artificial Sequence
<220> FEATURE:
<223> OTHER INFORMATION: Synthetic

<400> SEQUENCE: 370

Gln Asp Ile Ser Asp Tyr
1               5

<210> SEQ ID NO 371
<211> LENGTH: 9
<212> TYPE: DNA
<213> ORGANISM: Artificial Sequence
<220> FEATURE:
<223> OTHER INFORMATION: Synthetic

<400> SEQUENCE: 371 actacatcc 9

<210> SEQ ID NO 372
<211> LENGTH: 3
<212> TYPE: PRT
<213> ORGANISM: Artificial Sequence
<220> FEATURE:
<223> OTHER INFORMATION: Synthetic

<400> SEQUENCE: 372

Thr Thr Ser
1

<210> SEQ ID NO 373
<211> LENGTH: 27
<212> TYPE: DNA
<213> ORGANISM: Artificial Sequence
<220> FEATURE:
<223> OTHER INFORMATION: Synthetic

<400> SEQUENCE: 373
cagaagtatg acagtgcccc gctcact 27

<210> SEQ ID NO 374
<211> LENGTH: 9
<212> TYPE: PRT
<213> ORGANISM: Artificial Sequence
<220> FEATURE:
<223> OTHER INFORMATION: Synthetic

<400> SEQUENCE: 374

Gln Lys Tyr Asp Ser Ala Pro Leu Thr
1               5

<210> SEQ ID NO 375
<211> LENGTH: 363
<212> TYPE: DNA
<213> ORGANISM: Artificial Sequence
<220> FEATURE:
<223> OTHER INFORMATION: Synthetic

<400> SEQUENCE: 375
caggtgcagc tggtggagtc tgggggaggc gtggtccagc ctgggaagtc cctgcgactc 60
tcctgtgcag cgtctggatt caccttcagt agttttggca tgcattgggt ccgccaggct 120
ccaggcaagg ggctggagtg ggtggcagtt attgggtatg atggaggtaa tgaatactat 180
gccgactccg tgaagggccg attcaccatc tccagagaca attccaagaa cacgctgaat 240
ctgcaaatga gcagcctgag agccgaagac acggctgtgt attattgttc gactataagt 300
cattacgata ttttgagcgg tatggacgtc tggggccgag ggaccacggt caccgtctcc 360
tca 363

<210> SEQ ID NO 376
<211> LENGTH: 121
<212> TYPE: PRT
<213> ORGANISM: Artificial Sequence
<220> FEATURE:
<223> OTHER INFORMATION: Synthetic

<400> SEQUENCE: 376

Gln Val Gln Leu Val Glu Ser Gly Gly Gly Val Val Gln Pro Gly Lys
1 5 10 15

Ser Leu Arg Leu Ser Cys Ala Ala Ser Gly Phe Thr Phe Ser Ser Phe
20 25 30

Gly Met His Trp Val Arg Gln Ala Pro Gly Lys Gly Leu Glu Trp Val
35 40 45

Ala Val Ile Gly Tyr Asp Gly Gly Asn Glu Tyr Tyr Ala Asp Ser Val
50 55 60

Lys Gly Arg Phe Thr Ile Ser Arg Asp Asn Ser Lys Asn Thr Leu Asn
65 70 75 80

Leu Gln Met Ser Ser Leu Arg Ala Glu Asp Thr Ala Val Tyr Tyr Cys
85 90 95

Ser Thr Ile Ser His Tyr Asp Ile Leu Ser Gly Met Asp Val Trp Gly
100 105 110

Arg Gly Thr Thr Val Thr Val Ser Ser
115 120

<210> SEQ ID NO 377
<211> LENGTH: 24
<212> TYPE: DNA
<213> ORGANISM: Artificial Sequence
<220> FEATURE:
<223> OTHER INFORMATION: Synthetic

<400> SEQUENCE: 377
ggattcacct tcagtagttt tggc 24

<210> SEQ ID NO 378
<211> LENGTH: 8
<212> TYPE: PRT
<213> ORGANISM: Artificial Sequence
<220> FEATURE:
<223> OTHER INFORMATION: Synthetic

<400> SEQUENCE: 378

Gly Phe Thr Phe Ser Ser Phe Gly
1 5

<210> SEQ ID NO 379
<211> LENGTH: 24
<212> TYPE: DNA
<213> ORGANISM: Artificial Sequence
<220> FEATURE:
<223> OTHER INFORMATION: Synthetic

<400> SEQUENCE: 379
attgggtatg atggaggtaa tgaa 24

<210> SEQ ID NO 380

<211> LENGTH: 8
<212> TYPE: PRT
<213> ORGANISM: Artificial Sequence
<220> FEATURE:
<223> OTHER INFORMATION: Synthetic

<400> SEQUENCE: 380

Ile Gly Tyr Asp Gly Gly Asn Glu
1 5

<210> SEQ ID NO 381
<211> LENGTH: 42
<212> TYPE: DNA
<213> ORGANISM: Artificial Sequence
<220> FEATURE:
<223> OTHER INFORMATION: Synthetic

<400> SEQUENCE: 381
tcgactataa gtcattacga tattttgagc ggtatggacg tc 42

<210> SEQ ID NO 382
<211> LENGTH: 14
<212> TYPE: PRT
<213> ORGANISM: Artificial Sequence
<220> FEATURE:
<223> OTHER INFORMATION: Synthetic

<400> SEQUENCE: 382

Ser Thr Ile Ser His Tyr Asp Ile Leu Ser Gly Met Asp Val
1 5 10

<210> SEQ ID NO 383
<211> LENGTH: 324
<212> TYPE: DNA
<213> ORGANISM: Artificial Sequence
<220> FEATURE:
<223> OTHER INFORMATION: Synthetic

<400> SEQUENCE: 383
gacatccaga tgacccagtc tccatcttcc gtgtctgcat ctgtaggaga cagagtcacc 60
atcacttgtc gggcgagtca gggtattagc aactggttag cctggtatca gcagaaacca 120
gggaaagccc ctaagctcct gatctttgct gcatccagtt tgcaaagtgg ggtcccatca 180
cggttcagcg gcagtgcatc tgggacagat ttcactctca ccatcaacag cctgcagcct 240
gaagattttg caacttacta ttgtcaacag gctaacagtt tcccgctcac tttcggcgga 300
gggaccaagg tggagatcaa acga 324

<210> SEQ ID NO 384
<211> LENGTH: 108
<212> TYPE: PRT
<213> ORGANISM: Artificial Sequence
<220> FEATURE:
<223> OTHER INFORMATION: Synthetic

<400> SEQUENCE: 384

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Asn Trp
20 25 30

Leu Ala Trp Tyr Gln Gln Lys Pro Gly Lys Ala Pro Lys Leu Leu Ile
35 40 45

Phe Ala Ala Ser Ser Leu Gln Ser Gly Val Pro Ser Arg Phe Ser Gly
50 55 60

Ser Ala Ser Gly Thr Asp Phe Thr Leu Thr Ile Asn Ser Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys Arg
100 105

<210> SEQ ID NO 385
<211> LENGTH: 18
<212> TYPE: DNA
<213> ORGANISM: Artificial Sequence
<220> FEATURE:
<223> OTHER INFORMATION: Synthetic

<400> SEQUENCE: 385
cagggtatta gcaactgg 18

<210> SEQ ID NO 386
<211> LENGTH: 6
<212> TYPE: PRT
<213> ORGANISM: Artificial Sequence
<220> FEATURE:
<223> OTHER INFORMATION: Synthetic

<400> SEQUENCE: 386

Gln Gly Ile Ser Asn Trp
1 5

<210> SEQ ID NO 387
<211> LENGTH: 9
<212> TYPE: DNA
<213> ORGANISM: Artificial Sequence
<220> FEATURE:
<223> OTHER INFORMATION: Synthetic

<400> SEQUENCE: 387 gctgcatcc 9

<210> SEQ ID NO 388
<211> LENGTH: 3
<212> TYPE: PRT
<213> ORGANISM: Artificial Sequence
<220> FEATURE:
<223> OTHER INFORMATION: Synthetic

<400> SEQUENCE: 388

Ala Ala Ser
1

<210> SEQ ID NO 389
<211> LENGTH: 27
<212> TYPE: DNA
<213> ORGANISM: Artificial Sequence
<220> FEATURE:
<223> OTHER INFORMATION: Synthetic

<400> SEQUENCE: 389
caacaggcta acagtttccc gctcact 27

<210> SEQ ID NO 390
<211> LENGTH: 9
<212> TYPE: PRT
<213> ORGANISM: Artificial Sequence
<220> FEATURE:
<223> OTHER INFORMATION: Synthetic

<400> SEQUENCE: 390

Gln Gln Ala Asn Ser Phe Pro Leu Thr
1 5

<210> SEQ ID NO 391
<211> LENGTH: 340
<212> TYPE: PRT
<213> ORGANISM: Artificial Sequence
<220> FEATURE:
<223> OTHER INFORMATION: Synthetic

<400> SEQUENCE: 391

Glu Ala Glu Thr Arg Glu Cys Ile Tyr Tyr Asn Ala Asn Trp Glu Leu
1 5 10 15

Glu Arg Thr Asn Gln Ser Gly Leu Glu Arg Cys Glu Gly Glu Gln Asp
20 25 30

Lys Arg Leu His Cys Tyr Ala Ser Trp Ala Asn Ser Ser Gly Thr Ile
35 40 45

Glu Leu Val Lys Lys Gly Cys Trp Leu Asp Asp Phe Asn Cys Tyr Asp
50 55 60

Arg Gln Glu Cys Val Ala Thr Glu Glu Asn Pro Gln Val Tyr Phe Cys
65 70 75 80

Cys Cys Glu Gly Asn Phe Cys Asn Glu Arg Phe Thr His Leu Pro Glu
85 90 95

Ala Gly Gly Pro Glu Val Thr Tyr Glu Pro Pro Pro Thr Ala Pro Ser
100 105 110

Gly Asp Lys Thr His Thr Cys Pro Pro Cys Pro Ala Pro Glu Leu Leu
115 120 125

Gly Gly Pro Ser Val Phe Leu Phe Pro Pro Lys Pro Lys Asp Thr Leu
130 135 140

Met Ile Ser Arg Thr Pro Glu Val Thr Cys Val Val Val Asp Val Ser
145 150 155 160

His Glu Asp Pro Glu Val Lys Phe Asn Trp Tyr Val Asp Gly Val Glu
165 170 175

Val His Asn Ala Lys Thr Lys Pro Arg Glu Glu Gln Tyr Asn Ser Thr
180 185 190

Tyr Arg Val Val Ser Val Leu Thr Val Leu His Gln Asp Trp Leu Asn
195 200 205

Gly Lys Glu Tyr Lys Cys Lys Val Ser Asn Lys Ala Leu Pro Ala Pro
210 215 220

Ile Glu Lys Thr Ile Ser Lys Ala Lys Gly Gln Pro Arg Glu Pro Gln
225 230 235 240

Val Tyr Thr Leu Pro Pro Ser Arg Asp Glu Leu Thr Lys Asn Gln Val
245 250 255

Ser Leu Thr Cys Leu Val Lys Gly Phe Tyr Pro Ser Asp Ile Ala Val
260 265 270

Glu Trp Glu Ser Asn Gly Gln Pro Glu Asn Asn Tyr Lys Thr Thr Pro
275 280 285

Pro Val Leu Asp Ser Asp Gly Ser Phe Phe Leu Tyr Ser Lys Leu Thr
290 295 300

Val Asp Lys Ser Arg Trp Gln Gln Gly Asn Val Phe Ser Cys Ser Val
305 310 315 320

Met His Glu Ala Leu His Asn His Tyr Thr Gln Lys Ser Leu Ser Leu
325 330 335

Ser Pro Gly Lys
340

<210> SEQ ID NO 392
<211> LENGTH: 366
<212> TYPE: DNA
<213> ORGANISM: Artificial Sequence
<220> FEATURE:
<223> OTHER INFORMATION: Synthetic

<400> SEQUENCE: 392
caggtacagc tgcagcagtc aggtccagga ctgctgaagc cctcgcagac cctctcactc 60
acctgtgcca tctccgggga cagtgtctct agcaacagtg ctgcttggag ttggatcagg 120
cagtccccat cgagaggcct tgagtggctg ggaaggacat attacagggc caactggttt 180
aatgattatg cactttctgt gaaaagtcga ataaccatca acccagtcac atccacgaac 240
cacttctccc tgcagctgca ctctgtgact cccgaggaca cggctgtgta ttactgtgca 300
agagaagggg ctctgggata ctactttgac tcctggggcc agggaaccct ggtcaccgtc 360
tcctca 366

<210> SEQ ID NO 393
<211> LENGTH: 122
<212> TYPE: PRT
<213> ORGANISM: Artificial Sequence
<220> FEATURE:
<223> OTHER INFORMATION: Synthetic

<400> SEQUENCE: 393

Gln Val Gln Leu Gln Gln Ser Gly Pro Gly Leu Leu Lys Pro Ser Gln
1 5 10 15

Thr Leu Ser Leu Thr Cys Ala Ile Ser Gly Asp Ser Val Ser Ser Asn
20 25 30

Ser Ala Ala Trp Ser Trp Ile Arg Gln Ser Pro Ser Arg Gly Leu Glu
35 40 45

Trp Leu Gly Arg Thr Tyr Tyr Arg Ala Asn Trp Phe Asn Asp Tyr Ala
50 55 60

Leu Ser Val Lys Ser Arg Ile Thr Ile Asn Pro Val Thr Ser Thr Asn
65 70 75 80

His Phe Ser Leu Gln Leu His Ser Val Thr Pro Glu Asp Thr Ala Val
85 90 95

Tyr Tyr Cys Ala Arg Glu Gly Ala Leu Gly Tyr Tyr Phe Asp Ser Trp
100 105 110

Gly Gln Gly Thr Leu Val Thr Val Ser Ser
115 120

<210> SEQ ID NO 394
<211> LENGTH: 30
<212> TYPE: DNA
<213> ORGANISM: Artificial Sequence
<220> FEATURE:
<223> OTHER INFORMATION: Synthetic

<400> SEQUENCE: 394
ggggacagtg tctctagcaa cagtgctgct 30

<210> SEQ ID NO 395
<211> LENGTH: 10
<212> TYPE: PRT
<213> ORGANISM: Artificial Sequence
<220> FEATURE:

<223> OTHER INFORMATION: Synthetic

<400> SEQUENCE: 395

Gly Asp Ser Val Ser Ser Asn Ser Ala Ala
1 5 10

<210> SEQ ID NO 396
<211> LENGTH: 27
<212> TYPE: DNA
<213> ORGANISM: Artificial Sequence
<220> FEATURE:
<223> OTHER INFORMATION: Synthetic

<400> SEQUENCE: 396
acatattaca gggccaactg gtttaat 27

<210> SEQ ID NO 397
<211> LENGTH: 9
<212> TYPE: PRT
<213> ORGANISM: Artificial Sequence
<220> FEATURE:
<223> OTHER INFORMATION: Synthetic

<400> SEQUENCE: 397

Thr Tyr Tyr Arg Ala Asn Trp Phe Asn
1 5

<210> SEQ ID NO 398
<211> LENGTH: 36
<212> TYPE: DNA
<213> ORGANISM: Artificial Sequence
<220> FEATURE:
<223> OTHER INFORMATION: Synthetic

<400> SEQUENCE: 398
gcaagagaag ggctctggg atactacttt gactcc 36

<210> SEQ ID NO 399
<211> LENGTH: 12
<212> TYPE: PRT
<213> ORGANISM: Artificial Sequence
<220> FEATURE:
<223> OTHER INFORMATION: Synthetic

<400> SEQUENCE: 399

Ala Arg Glu Gly Ala Leu Gly Tyr Tyr Phe Asp Ser
1 5 10

<210> SEQ ID NO 400
<211> LENGTH: 339
<212> TYPE: DNA
<213> ORGANISM: Artificial Sequence
<220> FEATURE:
<223> OTHER INFORMATION: Synthetic

<400> SEQUENCE: 400
gacatcgtga tgacccagtc tccagactcc ctggctgtgt ctctgggcga gagggccacc 60
atcaactgca agtccagtca aagtgtttta tacagctcca acaataagaa ttatttagct 120
tggtaccaac agaaaccagg gcagcctcct acactgctca tttactgggc atctacccgg 180
gaatccgggg tccctgaccg attcagtggc agcgggtctg ggacagattt cactctcacc 240
atcagcagcc tgcaggcgga agatgtggca atttattact gtcaccaata ttttattact 300
ccactcactt tcggcggagg gaccaaggtg gagatcaaa 339

<210> SEQ ID NO 401
<211> LENGTH: 113
<212> TYPE: PRT
<213> ORGANISM: Artificial Sequence
<220> FEATURE:
<223> OTHER INFORMATION: Synthetic

<400> SEQUENCE: 401

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Thr Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Phe Ile Thr Pro Leu Thr Phe Gly Gly Gly Thr Lys Val Glu Ile
            100                 105                 110

Lys
```

<210> SEQ ID NO 402
<211> LENGTH: 36
<212> TYPE: DNA
<213> ORGANISM: Artificial Sequence
<220> FEATURE:
<223> OTHER INFORMATION: Synthetic

<400> SEQUENCE: 402

```
caaagtgttt tatacagctc caacaataag aattat                              36
```

<210> SEQ ID NO 403
<211> LENGTH: 12
<212> TYPE: PRT
<213> ORGANISM: Artificial Sequence
<220> FEATURE:
<223> OTHER INFORMATION: Synthetic

<400> SEQUENCE: 403

```
Gln Ser Val Leu Tyr Ser Ser Asn Asn Lys Asn Tyr
1               5                   10
```

<210> SEQ ID NO 404
<211> LENGTH: 9
<212> TYPE: DNA
<213> ORGANISM: Artificial Sequence
<220> FEATURE:
<223> OTHER INFORMATION: Synthetic

<400> SEQUENCE: 404

```
tgggcatct                                                             9
```

<210> SEQ ID NO 405
<211> LENGTH: 3
<212> TYPE: PRT
<213> ORGANISM: Artificial Sequence
<220> FEATURE:
<223> OTHER INFORMATION: Synthetic

<400> SEQUENCE: 405

Trp Ala Ser
1

<210> SEQ ID NO 406
<211> LENGTH: 27
<212> TYPE: DNA
<213> ORGANISM: Artificial Sequence
<220> FEATURE:
<223> OTHER INFORMATION: Synthetic

<400> SEQUENCE: 406
caccaatatt ttattactcc actcact 27

<210> SEQ ID NO 407
<211> LENGTH: 9
<212> TYPE: PRT
<213> ORGANISM: Artificial Sequence
<220> FEATURE:
<223> OTHER INFORMATION: Synthetic

<400> SEQUENCE: 407

His Gln Tyr Phe Ile Thr Pro Leu Thr
1 5

<210> SEQ ID NO 408
<211> LENGTH: 378
<212> TYPE: DNA
<213> ORGANISM: Artificial Sequence
<220> FEATURE:
<223> OTHER INFORMATION: Synthetic

<400> SEQUENCE: 408
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatacaat 180
gcagactccg tgaagggccg attcaccatc tccagagaca attccaagaa cacggtgtat 240
ctgcaaatga acagcctgag agccgaggac acggctgtgt attactgtgc gagagcccgg 300
aattacgata ttttgactgg ttattataac ctcggtatgg acgtctgggg ccaagggacc 360
acggtcaccg tctcctca 378

<210> SEQ ID NO 409
<211> LENGTH: 126
<212> TYPE: PRT
<213> ORGANISM: Artificial Sequence
<220> FEATURE:
<223> OTHER INFORMATION: Synthetic

<400> SEQUENCE: 409

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Asn Ala Asp Ser Val
50 55 60

Lys Gly Arg Phe Thr Ile Ser Arg Asp Asn Ser Lys Asn Thr Val Tyr
65 70 75 80

Leu Gln Met Asn Ser Leu Arg Ala Glu Asp Thr Ala Val Tyr Tyr Cys

```
            85                  90                  95

Ala Arg Ala Arg Asn Tyr Asp Ile Leu Thr Gly Tyr Tyr Asn Leu Gly
            100                 105                 110

Met Asp Val Trp Gly Gln Gly Thr Thr Val Thr Val Ser Ser
        115                 120                 125


<210> SEQ ID NO 410
<211> LENGTH: 24
<212> TYPE: DNA
<213> ORGANISM: Artificial Sequence
<220> FEATURE:
<223> OTHER INFORMATION: Synthetic

<400> SEQUENCE: 410

ggattcacct tcagtagcta tggc                                            24


<210> SEQ ID NO 411
<211> LENGTH: 8
<212> TYPE: PRT
<213> ORGANISM: Artificial Sequence
<220> FEATURE:
<223> OTHER INFORMATION: Synthetic

<400> SEQUENCE: 411

Gly Phe Thr Phe Ser Ser Tyr Gly
1               5


<210> SEQ ID NO 412
<211> LENGTH: 24
<212> TYPE: DNA
<213> ORGANISM: Artificial Sequence
<220> FEATURE:
<223> OTHER INFORMATION: Synthetic

<400> SEQUENCE: 412

atatggtatg atggaagtaa taaa                                            24


<210> SEQ ID NO 413
<211> LENGTH: 8
<212> TYPE: PRT
<213> ORGANISM: Artificial Sequence
<220> FEATURE:
<223> OTHER INFORMATION: Synthetic

<400> SEQUENCE: 413

Ile Trp Tyr Asp Gly Ser Asn Lys
1               5


<210> SEQ ID NO 414
<211> LENGTH: 57
<212> TYPE: DNA
<213> ORGANISM: Artificial Sequence
<220> FEATURE:
<223> OTHER INFORMATION: Synthetic

<400> SEQUENCE: 414

gcgagagccc ggaattacga tattttgact ggttattata acctcggtat ggacgtc        57


<210> SEQ ID NO 415
<211> LENGTH: 23
<212> TYPE: PRT
<213> ORGANISM: Artificial Sequence
<220> FEATURE:
<223> OTHER INFORMATION: Synthetic

<400> SEQUENCE: 415
```

```
Ala Arg Ala Arg Asn Tyr Asp Ile Leu Thr Gly Tyr Tyr Asn Leu Gly
1               5                   10                  15

Met Asp Val Ser Pro Gly Lys
            20
```

<210> SEQ ID NO 416
<211> LENGTH: 321
<212> TYPE: DNA
<213> ORGANISM: Artificial Sequence
<220> FEATURE:
<223> OTHER INFORMATION: Synthetic

<400> SEQUENCE: 416

```
gacatccaga tgacccagtc tccatcctcc ctgtctgcat ctgtaggaga cagagtcacc     60

atcacttgcc gggcaagtca gggcattaga aatgatttag gctggtatca acagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag cataatagtt acccgtacac ttttggccag    300

gggaccaagc tggagatcaa a                                              321
```

<210> SEQ ID NO 417
<211> LENGTH: 107
<212> TYPE: PRT
<213> ORGANISM: Artificial Sequence
<220> FEATURE:
<223> OTHER INFORMATION: Synthetic

<400> SEQUENCE: 417

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105
```

<210> SEQ ID NO 418
<211> LENGTH: 18
<212> TYPE: DNA
<213> ORGANISM: Artificial Sequence
<220> FEATURE:
<223> OTHER INFORMATION: Synthetic

<400> SEQUENCE: 418

```
cagggcatta gaaatgat                                                   18
```

<210> SEQ ID NO 419
<211> LENGTH: 6
<212> TYPE: PRT
<213> ORGANISM: Artificial Sequence
<220> FEATURE:
<223> OTHER INFORMATION: Synthetic

<400> SEQUENCE: 419

Gln Gly Ile Arg Asn Asp
1 5

<210> SEQ ID NO 420
<211> LENGTH: 9
<212> TYPE: DNA
<213> ORGANISM: Artificial Sequence
<220> FEATURE:
<223> OTHER INFORMATION: Synthetic

<400> SEQUENCE: 420 gctgcatcc 9

<210> SEQ ID NO 421
<211> LENGTH: 3
<212> TYPE: PRT
<213> ORGANISM: Artificial Sequence
<220> FEATURE:
<223> OTHER INFORMATION: Synthetic

<400> SEQUENCE: 421

Ala Ala Ser
1

<210> SEQ ID NO 422
<211> LENGTH: 27
<212> TYPE: DNA
<213> ORGANISM: Artificial Sequence
<220> FEATURE:
<223> OTHER INFORMATION: Synthetic

<400> SEQUENCE: 422
ctacagcata atagttaccc gtacact 27

<210> SEQ ID NO 423
<211> LENGTH: 9
<212> TYPE: PRT
<213> ORGANISM: Artificial Sequence
<220> FEATURE:
<223> OTHER INFORMATION: Synthetic

<400> SEQUENCE: 423

Leu Gln His Asn Ser Tyr Pro Tyr Thr
1 5

<210> SEQ ID NO 424
<211> LENGTH: 375
<212> TYPE: DNA
<213> ORGANISM: Artificial Sequence
<220> FEATURE:
<223> OTHER INFORMATION: Synthetic

<400> SEQUENCE: 424
gaagtgcagc tggtggagtc tgggggaaac ttggtacagt ctggcaggtc cctgagactc 60
tcctgtacag cctctggatt cgcctttgat gattttgcca tgcactgggt ccggcaagtt 120
ccagggaagg gcctggagtg ggtctcaggt attagttgga atagtgatac catcggctat 180
gcggactctg tgaagggccg attcaccatt tccagagaca acgcccagaa ctccctgttt 240
ctgcaaatgg acagtctgag agctgaggac acggccttgt attactgtgt aaaagatatg 300
gttcggggac ttataggcta ctactactac ggtatggacg tctggggcca agggaccacg 360
gtcaccgtct cctca 375

<210> SEQ ID NO 425
<211> LENGTH: 125
<212> TYPE: PRT
<213> ORGANISM: Artificial Sequence
<220> FEATURE:
<223> OTHER INFORMATION: Synthetic

<400> SEQUENCE: 425

```
Glu Val Gln Leu Val Glu Ser Gly Gly Asn Leu Val Gln Ser Gly Arg
1               5                   10                  15

Ser Leu Arg Leu Ser Cys Thr Ala Ser Gly Phe Ala Phe Asp Asp Phe
            20                  25                  30

Ala Met His Trp Val Arg Gln Val Pro Gly Lys Gly Leu Glu Trp Val
        35                  40                  45

Ser Gly Ile Ser Trp Asn Ser Asp Thr Ile Gly Tyr Ala Asp Ser Val
    50                  55                  60

Lys Gly Arg Phe Thr Ile Ser Arg Asp Asn Ala Gln Asn Ser Leu Phe
65                  70                  75                  80

Leu Gln Met Asp Ser Leu Arg Ala Glu Asp Thr Ala Leu Tyr Tyr Cys
                85                  90                  95

Val Lys Asp Met Val Arg Gly Leu Ile Gly Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 426
<211> LENGTH: 24
<212> TYPE: DNA
<213> ORGANISM: Artificial Sequence
<220> FEATURE:
<223> OTHER INFORMATION: Synthetic

<400> SEQUENCE: 426

```
ggattcgcct ttgatgattt tgcc                                            24
```

<210> SEQ ID NO 427
<211> LENGTH: 8
<212> TYPE: PRT
<213> ORGANISM: Artificial Sequence
<220> FEATURE:
<223> OTHER INFORMATION: Synthetic

<400> SEQUENCE: 427

```
Gly Phe Ala Phe Asp Asp Phe Ala
1               5
```

<210> SEQ ID NO 428
<211> LENGTH: 24
<212> TYPE: DNA
<213> ORGANISM: Artificial Sequence
<220> FEATURE:
<223> OTHER INFORMATION: Synthetic

<400> SEQUENCE: 428

```
attagttgga atagtgatac catc                                            24
```

<210> SEQ ID NO 429
<211> LENGTH: 8
<212> TYPE: PRT
<213> ORGANISM: Artificial Sequence
<220> FEATURE:
<223> OTHER INFORMATION: Synthetic

<400> SEQUENCE: 429

Ile Ser Trp Asn Ser Asp Thr Ile
1               5

<210> SEQ ID NO 430
<211> LENGTH: 54
<212> TYPE: DNA
<213> ORGANISM: Artificial Sequence
<220> FEATURE:
<223> OTHER INFORMATION: Synthetic

<400> SEQUENCE: 430
gtaaaagata tggttcgggg acttataggc tactactact acggtatgga cgtc          54

<210> SEQ ID NO 431
<211> LENGTH: 18
<212> TYPE: PRT
<213> ORGANISM: Artificial Sequence
<220> FEATURE:
<223> OTHER INFORMATION: Synthetic

<400> SEQUENCE: 431

Val Lys Asp Met Val Arg Gly Leu Ile Gly Tyr Tyr Tyr Tyr Gly Met
1               5                   10                  15

Asp Val

<210> SEQ ID NO 432
<211> LENGTH: 321
<212> TYPE: DNA
<213> ORGANISM: Artificial Sequence
<220> FEATURE:
<223> OTHER INFORMATION: Synthetic

<400> SEQUENCE: 432
gaaatagtgt tgacgcagtc tccagccatc ctgtctttgt ctccagggga aagagccatc     60
ctctcctgca gggccagtca gagtatttac acctacttat cctggtacca acagacacct    120
ggccgggctc ccaggctcct catctatgag acatccagca gggccactgg catcccagcc    180
aggttcattg gcagtgggtc tgggacagac ttcactctca ccatcagtag cctagagcct    240
gaagattttg cattttatta ctgtcagcac cgtagcgact ggcctcccac ttttggccag    300
gggaccaagc tggagatcaa a                                              321

<210> SEQ ID NO 433
<211> LENGTH: 107
<212> TYPE: PRT
<213> ORGANISM: Artificial Sequence
<220> FEATURE:
<223> OTHER INFORMATION: Synthetic

<400> SEQUENCE: 433

Glu Ile Val Leu Thr Gln Ser Pro Ala Ile Leu Ser Leu Ser Pro Gly
1               5                   10                  15

Glu Arg Ala Ile Leu Ser Cys Arg Ala Ser Gln Ser Ile Tyr Thr Tyr
            20                  25                  30

Leu Ser Trp Tyr Gln Gln Thr Pro Gly Arg Ala Pro Arg Leu Leu Ile
        35                  40                  45

Tyr Glu Thr Ser Ser Arg Ala Thr Gly Ile Pro Ala Arg Phe Ile Gly
    50                  55                  60

Ser Gly Ser Gly Thr Asp Phe Thr Leu Thr Ile Ser Ser Leu Glu Pro
65                  70                  75                  80

```
Glu Asp Phe Ala Phe Tyr Tyr Cys Gln His Arg Ser Asp Trp Pro Pro
                85                  90                  95

Thr Phe Gly Gln Gly Thr Lys Leu Glu Ile Lys
            100                 105


<210> SEQ ID NO 434
<211> LENGTH: 18
<212> TYPE: DNA
<213> ORGANISM: Artificial Sequence
<220> FEATURE:
<223> OTHER INFORMATION: Synthetic

<400> SEQUENCE: 434

cagagtattt acacctac                                                     18


<210> SEQ ID NO 435
<211> LENGTH: 6
<212> TYPE: PRT
<213> ORGANISM: Artificial Sequence
<220> FEATURE:
<223> OTHER INFORMATION: Synthetic

<400> SEQUENCE: 435

Gln Ser Ile Tyr Thr Tyr
1               5


<210> SEQ ID NO 436
<211> LENGTH: 9
<212> TYPE: DNA
<213> ORGANISM: Artificial Sequence
<220> FEATURE:
<223> OTHER INFORMATION: Synthetic

<400> SEQUENCE: 436

gagacatcc                                                                9


<210> SEQ ID NO 437
<211> LENGTH: 3
<212> TYPE: PRT
<213> ORGANISM: Artificial Sequence
<220> FEATURE:
<223> OTHER INFORMATION: Synthetic

<400> SEQUENCE: 437

Glu Thr Ser
1


<210> SEQ ID NO 438
<211> LENGTH: 27
<212> TYPE: DNA
<213> ORGANISM: Artificial Sequence
<220> FEATURE:
<223> OTHER INFORMATION: Synthetic

<400> SEQUENCE: 438

cagcaccgta gcgactggcc tcccact                                           27


<210> SEQ ID NO 439
<211> LENGTH: 9
<212> TYPE: PRT
<213> ORGANISM: Artificial Sequence
<220> FEATURE:
<223> OTHER INFORMATION: Synthetic

<400> SEQUENCE: 439
```

Gln His Arg Ser Asp Trp Pro Pro Thr
1 5

<210> SEQ ID NO 440
<211> LENGTH: 351
<212> TYPE: DNA
<213> ORGANISM: Artificial Sequence
<220> FEATURE:
<223> OTHER INFORMATION: Synthetic

<400> SEQUENCE: 440
caggtgcagc tggtggagtc ggggggaggc gtggtccagc ctgggaggtc cctgagactc 60
tcctgtgtag cgtctggatt caccgtcagt agttatggca ttcactgggt ccgccaggct 120
ccaggcaagg gactggagtg ggtgtcagtt atatggtatg atggaagaaa taaagactat 180
gcagactccg tgaagggccg attcaccatc tccagagaca attccaagaa cacggtgtat 240
ttggaaatga aaggcctgag agccgaggac acggctcttt attattgtgc gagagacaaa 300
actggggatt ttgactcctg gggccaggga accctggtca ccgtctcctc a 351

<210> SEQ ID NO 441
<211> LENGTH: 117
<212> TYPE: PRT
<213> ORGANISM: Artificial Sequence
<220> FEATURE:
<223> OTHER INFORMATION: Synthetic

<400> SEQUENCE: 441

Gln Val Gln Leu Val Glu Ser Gly Gly Gly Val Val Gln Pro Gly Arg
1 5 10 15

Ser Leu Arg Leu Ser Cys Val Ala Ser Gly Phe Thr Val Ser Ser Tyr
20 25 30

Gly Ile His Trp Val Arg Gln Ala Pro Gly Lys Gly Leu Glu Trp Val
35 40 45

Ser Val Ile Trp Tyr Asp Gly Arg Asn Lys Asp Tyr Ala Asp Ser Val
50 55 60

Lys Gly Arg Phe Thr Ile Ser Arg Asp Asn Ser Lys Asn Thr Val Tyr
65 70 75 80

Leu Glu Met Lys Gly Leu Arg Ala Glu Asp Thr Ala Leu Tyr Tyr Cys
85 90 95

Ala Arg Asp Lys Thr Gly Asp Phe Asp Ser Trp Gly Gln Gly Thr Leu
100 105 110

Val Thr Val Ser Ser
115

<210> SEQ ID NO 442
<211> LENGTH: 24
<212> TYPE: DNA
<213> ORGANISM: Artificial Sequence
<220> FEATURE:
<223> OTHER INFORMATION: Synthetic

<400> SEQUENCE: 442
ggattcaccg tcagtagtta tggc 24

<210> SEQ ID NO 443
<211> LENGTH: 8
<212> TYPE: PRT
<213> ORGANISM: Artificial Sequence
<220> FEATURE:
<223> OTHER INFORMATION: Synthetic

<400> SEQUENCE: 443

Gly Phe Thr Val Ser Ser Tyr Gly
1               5

<210> SEQ ID NO 444
<211> LENGTH: 24
<212> TYPE: DNA
<213> ORGANISM: Artificial Sequence
<220> FEATURE:
<223> OTHER INFORMATION: Synthetic

<400> SEQUENCE: 444
atatggtatg atggaagaaa taaa 24

<210> SEQ ID NO 445
<211> LENGTH: 8
<212> TYPE: PRT
<213> ORGANISM: Artificial Sequence
<220> FEATURE:
<223> OTHER INFORMATION: Synthetic

<400> SEQUENCE: 445

Ile Trp Tyr Asp Gly Arg Asn Lys
1               5

<210> SEQ ID NO 446
<211> LENGTH: 30
<212> TYPE: DNA
<213> ORGANISM: Artificial Sequence
<220> FEATURE:
<223> OTHER INFORMATION: Synthetic

<400> SEQUENCE: 446
gcgagagaca aaactgggga ttttgactcc 30

<210> SEQ ID NO 447
<211> LENGTH: 10
<212> TYPE: PRT
<213> ORGANISM: Artificial Sequence
<220> FEATURE:
<223> OTHER INFORMATION: Synthetic

<400> SEQUENCE: 447

Ala Arg Asp Lys Thr Gly Asp Phe Asp Ser
1               5                   10

<210> SEQ ID NO 448
<211> LENGTH: 321
<212> TYPE: DNA
<213> ORGANISM: Artificial Sequence
<220> FEATURE:
<223> OTHER INFORMATION: Synthetic

<400> SEQUENCE: 448
gacatccaga tgacccagtc tccatcctcc ctgtctgcat ctgtaggtga cagagtcacc 60
atcacttgcc gggcaagtca gaacattaac agctttttaa gttggtatca gcagaaacca 120
ggaaaagccc ctaagttcct gatctatgat gcttccagta tacaaagtgg ggccccatcg 180
aggttcagtg gcagtggatc tgggacagat ttcactctca ccatcagtag tctgcaacct 240
gaagattttg caacttacta ctgtcaacag agttacagtt ccccgttcac ttttggccag 300
gggaccaagc tggagatcaa a 321

<210> SEQ ID NO 449

<211> LENGTH: 111
<212> TYPE: PRT
<213> ORGANISM: Artificial Sequence
<220> FEATURE:
<223> OTHER INFORMATION: Synthetic

<400> SEQUENCE: 449

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Asn Ser Phe
20 25 30

Leu Ser Trp Tyr Gln Gln Lys Pro Gly Lys Ala Pro Lys Phe Leu Ile
35 40 45

Tyr Asp Ala Ser Ser Ile Gln Ser Gly Ala Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ser Pro Phe
85 90 95

Thr Phe Gly Gln Gly Thr Lys Leu Glu Ile Lys Ser Pro Gly Lys
100 105 110

<210> SEQ ID NO 450
<211> LENGTH: 18
<212> TYPE: DNA
<213> ORGANISM: Artificial Sequence
<220> FEATURE:
<223> OTHER INFORMATION: Synthetic

<400> SEQUENCE: 450
cagaacatta acagcttt 18

<210> SEQ ID NO 451
<211> LENGTH: 6
<212> TYPE: PRT
<213> ORGANISM: Artificial Sequence
<220> FEATURE:
<223> OTHER INFORMATION: Synthetic

<400> SEQUENCE: 451

Gln Asn Ile Asn Ser Phe
1 5

<210> SEQ ID NO 452
<211> LENGTH: 9
<212> TYPE: DNA
<213> ORGANISM: Artificial Sequence
<220> FEATURE:
<223> OTHER INFORMATION: Synthetic

<400> SEQUENCE: 452 gatgcttcc 9

<210> SEQ ID NO 453
<211> LENGTH: 3
<212> TYPE: PRT
<213> ORGANISM: Artificial Sequence
<220> FEATURE:
<223> OTHER INFORMATION: Synthetic

<400> SEQUENCE: 453

Asp Ala Ser
1

<210> SEQ ID NO 454
<211> LENGTH: 27
<212> TYPE: DNA
<213> ORGANISM: Artificial Sequence
<220> FEATURE:
<223> OTHER INFORMATION: Synthetic

<400> SEQUENCE: 454
caacagagtt acagttcccc gttcact 27

<210> SEQ ID NO 455
<211> LENGTH: 9
<212> TYPE: PRT
<213> ORGANISM: Artificial Sequence
<220> FEATURE:
<223> OTHER INFORMATION: Synthetic

<400> SEQUENCE: 455

Gln Gln Ser Tyr Ser Ser Pro Phe Thr
1 5

<210> SEQ ID NO 456
<211> LENGTH: 375
<212> TYPE: DNA
<213> ORGANISM: Artificial Sequence
<220> FEATURE:
<223> OTHER INFORMATION: Synthetic

<400> SEQUENCE: 456
gaagtgcagc tggtggagtc tgggggaggc ttggtacagc ctggcaggtc cctgagactc 60
tcctgtaaag cctctggatt cgcctttgat gatttcgcca tgcactgggt ccggcaagct 120
ccagggaagg gcctggagtg ggtctcaggt attgtttgga acagtggtga cataggctat 180
gcggactctg tgaagggccg attcaccatc tccagagaca acgccaagaa ctccctgtat 240
ctgcaactga atagtctgag aactgaggac acggccttgt atttctgtgt aaaagatatg 300
gttcggggac ttatgggctt caactattac ggtatggacg tctggggcca agggaccacg 360
gtcaccgtct cctca 375

<210> SEQ ID NO 457
<211> LENGTH: 125
<212> TYPE: PRT
<213> ORGANISM: Artificial Sequence
<220> FEATURE:
<223> OTHER INFORMATION: Synthetic

<400> SEQUENCE: 457

Glu Val Gln Leu Val Glu Ser Gly Gly Gly Leu Val Gln Pro Gly Arg
1 5 10 15

Ser Leu Arg Leu Ser Cys Lys Ala Ser Gly Phe Ala Phe Asp Asp Phe
20 25 30

Ala Met His Trp Val Arg Gln Ala Pro Gly Lys Gly Leu Glu Trp Val
35 40 45

Ser Gly Ile Val Trp Asn Ser Gly Asp Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Leu Asn Ser Leu Arg Thr Glu Asp Thr Ala Leu Tyr Phe Cys
85 90 95

Val Lys Asp Met Val Arg Gly Leu Met Gly Phe Asn Tyr Tyr Gly Met
100 105 110

Asp Val Trp Gly Gln Gly Thr Thr Val Thr Val Ser Ser
115 120 125

<210> SEQ ID NO 458
<211> LENGTH: 24
<212> TYPE: DNA
<213> ORGANISM: Artificial Sequence
<220> FEATURE:
<223> OTHER INFORMATION: Synthetic

<400> SEQUENCE: 458
ggattcgcct ttgatgattt cgcc 24

<210> SEQ ID NO 459
<211> LENGTH: 8
<212> TYPE: PRT
<213> ORGANISM: Artificial Sequence
<220> FEATURE:
<223> OTHER INFORMATION: Synthetic

<400> SEQUENCE: 459

Gly Phe Ala Phe Asp Asp Phe Ala
1 5

<210> SEQ ID NO 460
<211> LENGTH: 24
<212> TYPE: DNA
<213> ORGANISM: Artificial Sequence
<220> FEATURE:
<223> OTHER INFORMATION: Synthetic

<400> SEQUENCE: 460
attgtttgga acagtggtga cata 24

<210> SEQ ID NO 461
<211> LENGTH: 8
<212> TYPE: PRT
<213> ORGANISM: Artificial Sequence
<220> FEATURE:
<223> OTHER INFORMATION: Synthetic

<400> SEQUENCE: 461

Ile Val Trp Asn Ser Gly Asp Ile
1 5

<210> SEQ ID NO 462
<211> LENGTH: 54
<212> TYPE: DNA
<213> ORGANISM: Artificial Sequence
<220> FEATURE:
<223> OTHER INFORMATION: Synthetic

<400> SEQUENCE: 462
gtaaaagata tggttcgggg acttatgggc ttcaactatt acggtatgga cgtc 54

<210> SEQ ID NO 463
<211> LENGTH: 18
<212> TYPE: PRT
<213> ORGANISM: Artificial Sequence
<220> FEATURE:
<223> OTHER INFORMATION: Synthetic

<400> SEQUENCE: 463

Val Lys Asp Met Val Arg Gly Leu Met Gly Phe Asn Tyr Tyr Gly Met
1 5 10 15

Asp Val

<210> SEQ ID NO 464
<211> LENGTH: 321
<212> TYPE: DNA
<213> ORGANISM: Artificial Sequence
<220> FEATURE:
<223> OTHER INFORMATION: Synthetic

<400> SEQUENCE: 464
gaaattgtgt tgacgcagtc tccagccacc ctgtctttgt ctccagggga aagagccacc 60
ctctcctgca gggccagtca aactattagt acttatttag tctggtaccg acagagacct 120
ggccaggctc ccagtctcct catttatgat gcatccaaca gggccactga catcccagcc 180
aggttcagtg gcagtgggtc tgggacagac ttcactctca ccatcagcag ccttgagcct 240
gaagattttg cagtttatta ctgtcagcag cgtagcaact ggccgatcac cttcggccaa 300
gggacacgac tggagattaa a 321

<210> SEQ ID NO 465
<211> LENGTH: 107
<212> TYPE: PRT
<213> ORGANISM: Artificial Sequence
<220> FEATURE:
<223> OTHER INFORMATION: Synthetic

<400> SEQUENCE: 465

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Thr Ile Ser Thr Tyr
20 25 30

Leu Val Trp Tyr Arg Gln Arg Pro Gly Gln Ala Pro Ser Leu Leu Ile
35 40 45

Tyr Asp Ala Ser Asn Arg Ala Thr Asp Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Ile
85 90 95

Thr Phe Gly Gln Gly Thr Arg Leu Glu Ile Lys
100 105

<210> SEQ ID NO 466
<211> LENGTH: 18
<212> TYPE: DNA
<213> ORGANISM: Artificial Sequence
<220> FEATURE:
<223> OTHER INFORMATION: Synthetic

<400> SEQUENCE: 466
caaactatta gtacttat 18

<210> SEQ ID NO 467
<211> LENGTH: 6
<212> TYPE: PRT
<213> ORGANISM: Artificial Sequence
<220> FEATURE:
<223> OTHER INFORMATION: Synthetic

<400> SEQUENCE: 467

Gln Thr Ile Ser Thr Tyr
1 5

<210> SEQ ID NO 468
<211> LENGTH: 9
<212> TYPE: DNA
<213> ORGANISM: Artificial Sequence
<220> FEATURE:
<223> OTHER INFORMATION: Synthetic

<400> SEQUENCE: 468 gatgcatcc 9

<210> SEQ ID NO 469
<211> LENGTH: 3
<212> TYPE: PRT
<213> ORGANISM: Artificial Sequence
<220> FEATURE:
<223> OTHER INFORMATION: Synthetic

<400> SEQUENCE: 469

Asp Ala Ser
1

<210> SEQ ID NO 470
<211> LENGTH: 27
<212> TYPE: DNA
<213> ORGANISM: Artificial Sequence
<220> FEATURE:
<223> OTHER INFORMATION: Synthetic

<400> SEQUENCE: 470
cagcagcgta gcaactggcc gatcacc 27

<210> SEQ ID NO 471
<211> LENGTH: 9
<212> TYPE: PRT
<213> ORGANISM: Artificial Sequence
<220> FEATURE:
<223> OTHER INFORMATION: Synthetic

<400> SEQUENCE: 471

Gln Gln Arg Ser Asn Trp Pro Ile Thr
1 5

<210> SEQ ID NO 472
<211> LENGTH: 369
<212> TYPE: DNA
<213> ORGANISM: Artificial Sequence
<220> FEATURE:
<223> OTHER INFORMATION: Synthetic

<400> SEQUENCE: 472
gaagtgcagc tggtggagtc tgggggaggc ttggtacagc ctggcaggtc cctgacactc 60
tcctgtgcag tctctggatt cacctttgat gatcatgcca tgcactgggt ccggcaagct 120
ccagggaagg gcctggagtg ggtctcaggt attagttgga atagtgtaag tataggctat 180
gcggactctg tgaagggccg attcacgatc tccagagaca acgccaagac ctccctctat 240
ctgcaaatga acagtctgag agttgacgac acggccttat attactgtgt gcaagattta 300
aacgatattt tgactggtta tcccctcttt gacttttggg gccagggaac cctggtcacc 360
gtctcctca 369

<210> SEQ ID NO 473
<211> LENGTH: 123
<212> TYPE: PRT

<213> ORGANISM: Artificial Sequence
<220> FEATURE:
<223> OTHER INFORMATION: Synthetic

<400> SEQUENCE: 473

```
Glu Val Gln Leu Val Glu Ser Gly Gly Gly Leu Val Gln Pro Gly Arg
1               5                   10                  15

Ser Leu Thr Leu Ser Cys Ala Val Ser Gly Phe Thr Phe Asp Asp His
            20                  25                  30

Ala Met His Trp Val Arg Gln Ala Pro Gly Lys Gly Leu Glu Trp Val
        35                  40                  45

Ser Gly Ile Ser Trp Asn Ser Val Ser Ile Gly Tyr Ala Asp Ser Val
    50                  55                  60

Lys Gly Arg Phe Thr Ile Ser Arg Asp Asn Ala Lys Thr Ser Leu Tyr
65                  70                  75                  80

Leu Gln Met Asn Ser Leu Arg Val Asp Asp Thr Ala Leu Tyr Tyr Cys
                85                  90                  95

Val Gln Asp Leu Asn Asp Ile Leu Thr Gly Tyr Pro Leu Phe Asp Phe
            100                 105                 110

Trp Gly Gln Gly Thr Leu Val Thr Val Ser Ser
        115                 120
```

<210> SEQ ID NO 474
<211> LENGTH: 24
<212> TYPE: DNA
<213> ORGANISM: Artificial Sequence
<220> FEATURE:
<223> OTHER INFORMATION: Synthetic

<400> SEQUENCE: 474
ggattcacct ttgatgatca tgcc 24

<210> SEQ ID NO 475
<211> LENGTH: 8
<212> TYPE: PRT
<213> ORGANISM: Artificial Sequence
<220> FEATURE:
<223> OTHER INFORMATION: Synthetic

<400> SEQUENCE: 475

```
Gly Phe Thr Phe Asp Asp His Ala
1               5
```

<210> SEQ ID NO 476
<211> LENGTH: 24
<212> TYPE: DNA
<213> ORGANISM: Artificial Sequence
<220> FEATURE:
<223> OTHER INFORMATION: Synthetic

<400> SEQUENCE: 476
attagttgga atagtgtaag tata 24

<210> SEQ ID NO 477
<211> LENGTH: 8
<212> TYPE: PRT
<213> ORGANISM: Artificial Sequence
<220> FEATURE:
<223> OTHER INFORMATION: Synthetic

<400> SEQUENCE: 477

```
Ile Ser Trp Asn Ser Val Ser Ile
1               5
```

<210> SEQ ID NO 478
<211> LENGTH: 48
<212> TYPE: DNA
<213> ORGANISM: Artificial Sequence
<220> FEATURE:
<223> OTHER INFORMATION: Synthetic

<400> SEQUENCE: 478
gtgcaagatt taaacgatat tttgactggt tatcccctct ttgacttt 48

<210> SEQ ID NO 479
<211> LENGTH: 16
<212> TYPE: PRT
<213> ORGANISM: Artificial Sequence
<220> FEATURE:
<223> OTHER INFORMATION: Synthetic

<400> SEQUENCE: 479

Val Gln Asp Leu Asn Asp Ile Leu Thr Gly Tyr Pro Leu Phe Asp Phe
1 5 10 15

<210> SEQ ID NO 480
<211> LENGTH: 324
<212> TYPE: DNA
<213> ORGANISM: Artificial Sequence
<220> FEATURE:
<223> OTHER INFORMATION: Synthetic

<400> SEQUENCE: 480
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccgtca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 481
<211> LENGTH: 108
<212> TYPE: PRT
<213> ORGANISM: Artificial Sequence
<220> FEATURE:
<223> OTHER INFORMATION: Synthetic

<400> SEQUENCE: 481

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys
100 105

<210> SEQ ID NO 482
<211> LENGTH: 18
<212> TYPE: DNA
<213> ORGANISM: Artificial Sequence
<220> FEATURE:
<223> OTHER INFORMATION: Synthetic

<400> SEQUENCE: 482
cagagcatta gcagctat 18

<210> SEQ ID NO 483
<211> LENGTH: 10
<212> TYPE: PRT
<213> ORGANISM: Artificial Sequence
<220> FEATURE:
<223> OTHER INFORMATION: Synthetic

<400> SEQUENCE: 483

Gln Ser Ile Ser Ser Tyr Ser Pro Gly Lys
1 5 10

<210> SEQ ID NO 484
<211> LENGTH: 9
<212> TYPE: DNA
<213> ORGANISM: Artificial Sequence
<220> FEATURE:
<223> OTHER INFORMATION: Synthetic

<400> SEQUENCE: 484 gctgcatcc 9

<210> SEQ ID NO 485
<211> LENGTH: 3
<212> TYPE: PRT
<213> ORGANISM: Artificial Sequence
<220> FEATURE:
<223> OTHER INFORMATION: Synthetic

<400> SEQUENCE: 485

Ala Ala Ser
1

<210> SEQ ID NO 486
<211> LENGTH: 30
<212> TYPE: DNA
<213> ORGANISM: Artificial Sequence
<220> FEATURE:
<223> OTHER INFORMATION: Synthetic

<400> SEQUENCE: 486
caacagagtt acagtacccc tccgatcacc 30

<210> SEQ ID NO 487
<211> LENGTH: 10
<212> TYPE: PRT
<213> ORGANISM: Artificial Sequence
<220> FEATURE:
<223> OTHER INFORMATION: Synthetic

<400> SEQUENCE: 487

Gln Gln Ser Tyr Ser Thr Pro Pro Ile Thr
1 5 10

<210> SEQ ID NO 488
<211> LENGTH: 369
<212> TYPE: DNA

```
<213> ORGANISM: Artificial Sequence
<220> FEATURE:
<223> OTHER INFORMATION: Synthetic

<400> SEQUENCE: 488

gaagtgcagc tggtggagtc tgggggaggc ttggtacagg ctggcaggtc cctaagactc     60

tcctgtgaag cctctggatt cacctttgat gattatggca tgcactgggt ccggcaaggt    120

ccagggaagg gcctggagtg ggtctcaggt attagttgga atagtggtaa catagactat    180

gcggactctg tgaagggccg attcaccatc tccagagaca acgccaagac ctccctgtat    240

ctgcaaatga acagtctgaa aactgacgac acggccttgt atttctgtgc aaaagatgct    300

gtggggttta actggaacta ctttctcttt gactactggg gccagggaac cctggtcacc    360

gtctcctca                                                            369


<210> SEQ ID NO 489
<211> LENGTH: 123
<212> TYPE: PRT
<213> ORGANISM: Artificial Sequence
<220> FEATURE:
<223> OTHER INFORMATION: Synthetic

<400> SEQUENCE: 489

Glu Val Gln Leu Val Glu Ser Gly Gly Gly Leu Val Gln Ala Gly Arg
1               5                   10                  15

Ser Leu Arg Leu Ser Cys Glu Ala Ser Gly Phe Thr Phe Asp Asp Tyr
            20                  25                  30

Gly Met His Trp Val Arg Gln Gly Pro Gly Lys Gly Leu Glu Trp Val
        35                  40                  45

Ser Gly Ile Ser Trp Asn Ser Gly Asn Ile Asp Tyr Ala Asp Ser Val
    50                  55                  60

Lys Gly Arg Phe Thr Ile Ser Arg Asp Asn Ala Lys Thr Ser Leu Tyr
65                  70                  75                  80

Leu Gln Met Asn Ser Leu Lys Thr Asp Asp Thr Ala Leu Tyr Phe Cys
                85                  90                  95

Ala Lys Asp Ala Val Gly Phe Asn Trp Asn Tyr Phe Leu Phe Asp Tyr
            100                 105                 110

Trp Gly Gln Gly Thr Leu Val Thr Val Ser Ser
        115                 120


<210> SEQ ID NO 490
<211> LENGTH: 24
<212> TYPE: DNA
<213> ORGANISM: Artificial Sequence
<220> FEATURE:
<223> OTHER INFORMATION: Synthetic

<400> SEQUENCE: 490

ggattcacct ttgatgatta tggc                                            24


<210> SEQ ID NO 491
<211> LENGTH: 8
<212> TYPE: PRT
<213> ORGANISM: Artificial Sequence
<220> FEATURE:
<223> OTHER INFORMATION: Synthetic

<400> SEQUENCE: 491

Gly Phe Thr Phe Asp Asp Tyr Gly
1               5
```

<210> SEQ ID NO 492
<211> LENGTH: 24
<212> TYPE: DNA
<213> ORGANISM: Artificial Sequence
<220> FEATURE:
<223> OTHER INFORMATION: Synthetic

<400> SEQUENCE: 492
attagttgga atagtggtaa cata 24

<210> SEQ ID NO 493
<211> LENGTH: 8
<212> TYPE: PRT
<213> ORGANISM: Artificial Sequence
<220> FEATURE:
<223> OTHER INFORMATION: Synthetic

<400> SEQUENCE: 493

Ile Ser Trp Asn Ser Gly Asn Ile
1 5

<210> SEQ ID NO 494
<211> LENGTH: 48
<212> TYPE: DNA
<213> ORGANISM: Artificial Sequence
<220> FEATURE:
<223> OTHER INFORMATION: Synthetic

<400> SEQUENCE: 494
gcaaaagatg ctgtggggtt taactggaac tactttctct ttgactac 48

<210> SEQ ID NO 495
<211> LENGTH: 16
<212> TYPE: PRT
<213> ORGANISM: Artificial Sequence
<220> FEATURE:
<223> OTHER INFORMATION: Synthetic

<400> SEQUENCE: 495

Ala Lys Asp Ala Val Gly Phe Asn Trp Asn Tyr Phe Leu Phe Asp Tyr
1 5 10 15

<210> SEQ ID NO 496
<211> LENGTH: 351
<212> TYPE: DNA
<213> ORGANISM: Artificial Sequence
<220> FEATURE:
<223> OTHER INFORMATION: Synthetic

<400> SEQUENCE: 496
caggtgcagc tggtggagtc tgggggaggc gtggtccagc ctgggaggtc cctgagactc 60
acctgtgtag cgtctggatt caccgtcagt agttatggaa tgcactgggt ccgccaggcc 120
ccaggcaagg ggctggagtg ggtggcagtt atgttttatg atgaaagtaa aaaatattat 180
gcagactccg tgaagggccg attcaccatc tccagagaca attccaagaa cacgctgtat 240
ctgcaaatga acagcctgag agtcgaggac acggctgtgt attactgtgc gagagatgaa 300
cagctcgact ttgaatactg gggccaggga accctggtca ccgtctcctc a 351

<210> SEQ ID NO 497
<211> LENGTH: 117
<212> TYPE: PRT
<213> ORGANISM: Artificial Sequence
<220> FEATURE:
<223> OTHER INFORMATION: Synthetic

<400> SEQUENCE: 497

Gln Val Gln Leu Val Glu Ser Gly Gly Gly Val Val Gln Pro Gly Arg
1               5                   10                  15

Ser Leu Arg Leu Thr Cys Val Ala Ser Gly Phe Thr Val Ser Ser Tyr
            20                  25                  30

Gly Met His Trp Val Arg Gln Ala Pro Gly Lys Gly Leu Glu Trp Val
        35                  40                  45

Ala Val Met Phe Tyr Asp Glu Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Glu Gln Leu Asp Phe Glu Tyr Trp Gly Gln Gly Thr Leu
            100                 105                 110

Val Thr Val Ser Ser
        115

<210> SEQ ID NO 498
<211> LENGTH: 24
<212> TYPE: DNA
<213> ORGANISM: Artificial Sequence
<220> FEATURE:
<223> OTHER INFORMATION: Synthetic

<400> SEQUENCE: 498
ggattcaccg tcagtagtta tgga                                            24

<210> SEQ ID NO 499
<211> LENGTH: 8
<212> TYPE: PRT
<213> ORGANISM: Artificial Sequence
<220> FEATURE:
<223> OTHER INFORMATION: Synthetic

<400> SEQUENCE: 499

Gly Phe Thr Val Ser Ser Tyr Gly
1               5

<210> SEQ ID NO 500
<211> LENGTH: 24
<212> TYPE: DNA
<213> ORGANISM: Artificial Sequence
<220> FEATURE:
<223> OTHER INFORMATION: Synthetic

<400> SEQUENCE: 500
atgttttatg atgaaagtaa aaaa                                            24

<210> SEQ ID NO 501
<211> LENGTH: 8
<212> TYPE: PRT
<213> ORGANISM: Artificial Sequence
<220> FEATURE:
<223> OTHER INFORMATION: Synthetic

<400> SEQUENCE: 501

Met Phe Tyr Asp Glu Ser Lys Lys
1               5

<210> SEQ ID NO 502

<211> LENGTH: 30
<212> TYPE: DNA
<213> ORGANISM: Artificial Sequence
<220> FEATURE:
<223> OTHER INFORMATION: Synthetic

<400> SEQUENCE: 502
gcgagagatg aacagctcga ctttgaatac 30

<210> SEQ ID NO 503
<211> LENGTH: 10
<212> TYPE: PRT
<213> ORGANISM: Artificial Sequence
<220> FEATURE:
<223> OTHER INFORMATION: Synthetic

<400> SEQUENCE: 503

Ala Arg Asp Glu Gln Leu Asp Phe Glu Tyr
1 5 10

<210> SEQ ID NO 504
<211> LENGTH: 369
<212> TYPE: DNA
<213> ORGANISM: Artificial Sequence
<220> FEATURE:
<223> OTHER INFORMATION: Synthetic

<400> SEQUENCE: 504
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attagttgga atagtggtag cataggctat 180
gcggactctg tgaagggccg attcaccatc tccagagaca acgccaagaa ctccctgtat 240
ctgcaaatga acagtctgag agctgaggac acggccttgt attactgtgc aaaagatata 300
atggggaact gggactactt ctacggtatg gacgtctggg gccaagggac cacggtcacc 360
gtctcctca 369

<210> SEQ ID NO 505
<211> LENGTH: 123
<212> TYPE: PRT
<213> ORGANISM: Artificial Sequence
<220> FEATURE:
<223> OTHER INFORMATION: Synthetic

<400> SEQUENCE: 505

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Ile Met Gly Asn Trp Asp Tyr Phe Tyr Gly Met Asp Val
100 105 110

Trp Gly Gln Gly Thr Thr Val Thr Val Ser Ser 115 120

<210> SEQ ID NO 506
<211> LENGTH: 24
<212> TYPE: DNA
<213> ORGANISM: Artificial Sequence
<220> FEATURE:
<223> OTHER INFORMATION: Synthetic

<400> SEQUENCE: 506
ggattcacct ttgatgatta tgcc 24

<210> SEQ ID NO 507
<211> LENGTH: 8
<212> TYPE: PRT
<213> ORGANISM: Artificial Sequence
<220> FEATURE:
<223> OTHER INFORMATION: Synthetic

<400> SEQUENCE: 507

Gly Phe Thr Phe Asp Asp Tyr Ala
1 5

<210> SEQ ID NO 508
<211> LENGTH: 24
<212> TYPE: DNA
<213> ORGANISM: Artificial Sequence
<220> FEATURE:
<223> OTHER INFORMATION: Synthetic

<400> SEQUENCE: 508
attagttgga atagtggtag cata 24

<210> SEQ ID NO 509
<211> LENGTH: 8
<212> TYPE: PRT
<213> ORGANISM: Artificial Sequence
<220> FEATURE:
<223> OTHER INFORMATION: Synthetic

<400> SEQUENCE: 509

Ile Ser Trp Asn Ser Gly Ser Ile
1 5

<210> SEQ ID NO 510
<211> LENGTH: 48
<212> TYPE: DNA
<213> ORGANISM: Artificial Sequence
<220> FEATURE:
<223> OTHER INFORMATION: Synthetic

<400> SEQUENCE: 510
gcaaaagata taatggggaa ctgggactac ttctacggta tggacgtc 48

<210> SEQ ID NO 511
<211> LENGTH: 16
<212> TYPE: PRT
<213> ORGANISM: Artificial Sequence
<220> FEATURE:
<223> OTHER INFORMATION: Synthetic

<400> SEQUENCE: 511

Ala Lys Asp Ile Met Gly Asn Trp Asp Tyr Phe Tyr Gly Met Asp Val
1 5 10 15

<210> SEQ ID NO 512

<211> LENGTH: 369
<212> TYPE: DNA
<213> ORGANISM: Artificial Sequence
<220> FEATURE:
<223> OTHER INFORMATION: Synthetic

<400> SEQUENCE: 512
gaagtgcagc tggtggagtc tgggggaggc ttggtacagc ctggcaggtc cctgagactc 60
tcctgtgcag cctctggatt cacctttgat gataatgcca tgcactgggt ccggcaacct 120
ccagggaagg gcctggagtg ggtctcaggt attagttgga atagtggaag cataggctat 180
gcggactctg tgaagggccg attcaccatc tccagagaca acgccaagaa ctccctgtat 240
ctgcaaatga acagtctgag agctgaggac acggccttgt attactgtgc aaaagatata 300
aacgatattt tgactggtta tcctcttttt gattactggg gccagggaac cctggtcacc 360
gtctcctca 369

<210> SEQ ID NO 513
<211> LENGTH: 123
<212> TYPE: PRT
<213> ORGANISM: Artificial Sequence
<220> FEATURE:
<223> OTHER INFORMATION: Synthetic

<400> SEQUENCE: 513

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Asn
            20                  25                  30

Ala Met His Trp Val Arg Gln Pro Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Asn Asp Ile Leu Thr Gly Tyr Pro Leu Phe Asp Tyr
            100                 105                 110

Trp Gly Gln Gly Thr Leu Val Thr Val Ser Ser
        115                 120

<210> SEQ ID NO 514
<211> LENGTH: 24
<212> TYPE: DNA
<213> ORGANISM: Artificial Sequence
<220> FEATURE:
<223> OTHER INFORMATION: Synthetic

<400> SEQUENCE: 514
ggattcacct ttgatgataa tgcc 24

<210> SEQ ID NO 515
<211> LENGTH: 8
<212> TYPE: PRT
<213> ORGANISM: Artificial Sequence
<220> FEATURE:
<223> OTHER INFORMATION: Synthetic

<400> SEQUENCE: 515

Gly Phe Thr Phe Asp Asp Asn Ala 1 5

<210> SEQ ID NO 516
<211> LENGTH: 24
<212> TYPE: DNA
<213> ORGANISM: Artificial Sequence
<220> FEATURE:
<223> OTHER INFORMATION: Synthetic

<400> SEQUENCE: 516
attagttgga atagtggaag cata 24

<210> SEQ ID NO 517
<211> LENGTH: 12
<212> TYPE: PRT
<213> ORGANISM: Artificial Sequence
<220> FEATURE:
<223> OTHER INFORMATION: Synthetic

<400> SEQUENCE: 517

Ile Ser Trp Asn Ser Gly Ser Ile Ser Pro Gly Lys
1 5 10

<210> SEQ ID NO 518
<211> LENGTH: 48
<212> TYPE: DNA
<213> ORGANISM: Artificial Sequence
<220> FEATURE:
<223> OTHER INFORMATION: Synthetic

<400> SEQUENCE: 518
gcaaaagata taaacgatat tttgactggt tatcctcttt ttgattac 48

<210> SEQ ID NO 519
<211> LENGTH: 16
<212> TYPE: PRT
<213> ORGANISM: Artificial Sequence
<220> FEATURE:
<223> OTHER INFORMATION: Synthetic

<400> SEQUENCE: 519

Ala Lys Asp Ile Asn Asp Ile Leu Thr Gly Tyr Pro Leu Phe Asp Tyr
1 5 10 15

<210> SEQ ID NO 520
<211> LENGTH: 378
<212> TYPE: DNA
<213> ORGANISM: Artificial Sequence
<220> FEATURE:
<223> OTHER INFORMATION: Synthetic

<400> SEQUENCE: 520
gaagtgcagc tggtggagtc tgggggaggc gtggtacagc ctggggggtc cctgagactc 60
tcctgtgcag cctctacatt cacctttgat gattttgcca tgcactgggt ccgtcaagct 120
ccagggaagg gtctggagtg ggtctctctt attactgggg atggtggtag cacatactat 180
gcagaccctg tgaagggccg attcaccatc tccagagaca acagcaaaaa ctccctgtat 240
ctgcaaatga acagtctgag aactgaggac accgccttgt attactgtgt aaaagattgg 300
tggatagcag ctcgtccgga ctactactac tacggtatgg acgtctgggg ccaagggacc 360
acggtcaccg tctcctca 378

<210> SEQ ID NO 521
<211> LENGTH: 126

<212> TYPE: PRT
<213> ORGANISM: Artificial Sequence
<220> FEATURE:
<223> OTHER INFORMATION: Synthetic

<400> SEQUENCE: 521

```
Glu Val Gln Leu Val Glu Ser Gly Gly Gly Val Val Gln Pro Gly Gly
1               5                   10                  15

Ser Leu Arg Leu Ser Cys Ala Ala Ser Thr Phe Thr Phe Asp Asp Phe
            20                  25                  30

Ala Met His Trp Val Arg Gln Ala Pro Gly Lys Gly Leu Glu Trp Val
        35                  40                  45

Ser Leu Ile Thr Gly Asp Gly Gly Ser Thr Tyr Tyr Ala Asp Pro Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Val Lys Asp Trp Trp Ile Ala Ala Arg Pro Asp Tyr Tyr Tyr Tyr Gly
            100                 105                 110

Met Asp Val Trp Gly Gln Gly Thr Thr Val Thr Val Ser Ser
        115                 120                 125
```

<210> SEQ ID NO 522
<211> LENGTH: 24
<212> TYPE: DNA
<213> ORGANISM: Artificial Sequence
<220> FEATURE:
<223> OTHER INFORMATION: Synthetic

<400> SEQUENCE: 522

```
acattcacct ttgatgattt tgcc                                              24
```

<210> SEQ ID NO 523
<211> LENGTH: 8
<212> TYPE: PRT
<213> ORGANISM: Artificial Sequence
<220> FEATURE:
<223> OTHER INFORMATION: Synthetic

<400> SEQUENCE: 523

```
Thr Phe Thr Phe Asp Asp Phe Ala
1               5
```

<210> SEQ ID NO 524
<211> LENGTH: 24
<212> TYPE: DNA
<213> ORGANISM: Artificial Sequence
<220> FEATURE:
<223> OTHER INFORMATION: Synthetic

<400> SEQUENCE: 524

```
attactgggg atggtggtag caca                                              24
```

<210> SEQ ID NO 525
<211> LENGTH: 8
<212> TYPE: PRT
<213> ORGANISM: Artificial Sequence
<220> FEATURE:
<223> OTHER INFORMATION: Synthetic

<400> SEQUENCE: 525

```
Ile Thr Gly Asp Gly Gly Ser Thr
```

1 5

<210> SEQ ID NO 526
<211> LENGTH: 57
<212> TYPE: DNA
<213> ORGANISM: Artificial Sequence
<220> FEATURE:
<223> OTHER INFORMATION: Synthetic

<400> SEQUENCE: 526
gtaaaagatt ggtggatagc agctcgtccg gactactact actacggtat ggacgtc 57

<210> SEQ ID NO 527
<211> LENGTH: 19
<212> TYPE: PRT
<213> ORGANISM: Artificial Sequence
<220> FEATURE:
<223> OTHER INFORMATION: Synthetic

<400> SEQUENCE: 527

Val Lys Asp Trp Trp Ile Ala Ala Arg Pro Asp Tyr Tyr Tyr Tyr Gly
1 5 10 15

Met Asp Val

<210> SEQ ID NO 528
<211> LENGTH: 378
<212> TYPE: DNA
<213> ORGANISM: Artificial Sequence
<220> FEATURE:
<223> OTHER INFORMATION: Synthetic

<400> SEQUENCE: 528
caggtgcagc tgcaggagtc gggcccagga ctggtgaagc cctcggagac cctgtccatc 60
acctgcactg tctctggtgg ctccttcagt agtcacttct ggacctggat ccggcagccc 120
ccaggaaagg gactggaatg gattggatat ctccattata gtgggggcac cagctacaac 180
ccctccctca agagtcgagt catcatatca gtggacacgt ccaagaacca gttctccctg 240
aaactgaact ctgtgaccgc tgcggacacg gccgtgtatt actgtgcgag agctagatcg 300
gggattactt ttgggggact tatcgtccct ggttcttttg atatctgggg ccaagggaca 360
atggtcaccg tctcttca 378

<210> SEQ ID NO 529
<211> LENGTH: 126
<212> TYPE: PRT
<213> ORGANISM: Artificial Sequence
<220> FEATURE:
<223> OTHER INFORMATION: Synthetic

<400> SEQUENCE: 529

Gln Val Gln Leu Gln Glu Ser Gly Pro Gly Leu Val Lys Pro Ser Glu
1 5 10 15

Thr Leu Ser Ile Thr Cys Thr Val Ser Gly Gly Ser Phe Ser Ser His
20 25 30

Phe Trp Thr Trp Ile Arg Gln Pro Pro Gly Lys Gly Leu Glu Trp Ile
35 40 45

Gly Tyr Leu His Tyr Ser Gly Gly Thr Ser Tyr Asn Pro Ser Leu Lys
50 55 60

Ser Arg Val Ile Ile Ser Val Asp Thr Ser Lys Asn Gln Phe Ser Leu
65 70 75 80

Lys Leu Asn Ser Val Thr Ala Ala Asp Thr Ala Val Tyr Tyr Cys Ala

```
            85                  90                  95

Arg Ala Arg Ser Gly Ile Thr Phe Gly Gly Leu Ile Val Pro Gly Ser
            100                 105                 110

Phe Asp Ile Trp Gly Gln Gly Thr Met Val Thr Val Ser Ser
        115                 120                 125


<210> SEQ ID NO 530
<211> LENGTH: 24
<212> TYPE: DNA
<213> ORGANISM: Artificial Sequence
<220> FEATURE:
<223> OTHER INFORMATION: Synthetic

<400> SEQUENCE: 530

ggtggctcct tcagtagtca cttc                                            24


<210> SEQ ID NO 531
<211> LENGTH: 8
<212> TYPE: PRT
<213> ORGANISM: Artificial Sequence
<220> FEATURE:
<223> OTHER INFORMATION: Synthetic

<400> SEQUENCE: 531

Gly Gly Ser Phe Ser Ser His Phe
1               5


<210> SEQ ID NO 532
<211> LENGTH: 21
<212> TYPE: DNA
<213> ORGANISM: Artificial Sequence
<220> FEATURE:
<223> OTHER INFORMATION: Synthetic

<400> SEQUENCE: 532

ctccattata gtgggggcac c                                               21


<210> SEQ ID NO 533
<211> LENGTH: 7
<212> TYPE: PRT
<213> ORGANISM: Artificial Sequence
<220> FEATURE:
<223> OTHER INFORMATION: Synthetic

<400> SEQUENCE: 533

Leu His Tyr Ser Gly Gly Thr
1               5


<210> SEQ ID NO 534
<211> LENGTH: 60
<212> TYPE: DNA
<213> ORGANISM: Artificial Sequence
<220> FEATURE:
<223> OTHER INFORMATION: Synthetic

<400> SEQUENCE: 534

gcgagagcta gatcggggat tacttttggg ggacttatcg tccctggttc ttttgatatc     60


<210> SEQ ID NO 535
<211> LENGTH: 20
<212> TYPE: PRT
<213> ORGANISM: Artificial Sequence
<220> FEATURE:
<223> OTHER INFORMATION: Synthetic

<400> SEQUENCE: 535
```

```
Ala Arg Ala Arg Ser Gly Ile Thr Phe Gly Gly Leu Ile Val Pro Gly
1               5                   10                  15

Ser Phe Asp Ile
            20


<210> SEQ ID NO 536
<211> LENGTH: 324
<212> TYPE: DNA
<213> ORGANISM: Artificial Sequence
<220> FEATURE:
<223> OTHER INFORMATION: Synthetic

<400> SEQUENCE: 536

gaaatagttt tgacacagag tcccggcaca ctgtcactct ctcccgggga aagagccacc     60

ttgtcatgta gagcaagtca gtcagtctct agctcttatc tcgcctggta ccagcagaag    120

ccgggacagg cccctagact gctgatctac ggggcaagtt ccagggccac cggaatcccc    180

gaccggttca gtggaagcgg aagcggaacc gattttactt tgacgatttc tagactggag    240

ccagaggatt tcgccgttta ctattgtcaa cagtacggaa gcagcccgtg gacgtttggc    300

cagggcacga aggtagaaat caag                                           324


<210> SEQ ID NO 537
<211> LENGTH: 108
<212> TYPE: PRT
<213> ORGANISM: Artificial Sequence
<220> FEATURE:
<223> OTHER INFORMATION: Synthetic

<400> SEQUENCE: 537

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 538
<211> LENGTH: 21
<212> TYPE: DNA
<213> ORGANISM: Artificial Sequence
<220> FEATURE:
<223> OTHER INFORMATION: Synthetic

<400> SEQUENCE: 538

cagtcagtct ctagctctta t                                               21


<210> SEQ ID NO 539
<211> LENGTH: 7
<212> TYPE: PRT
<213> ORGANISM: Artificial Sequence
<220> FEATURE:
<223> OTHER INFORMATION: Synthetic
```

<400> SEQUENCE: 539

Gln Ser Val Ser Ser Ser Tyr
1               5

<210> SEQ ID NO 540
<211> LENGTH: 9
<212> TYPE: DNA
<213> ORGANISM: Artificial Sequence
<220> FEATURE:
<223> OTHER INFORMATION: Synthetic

<400> SEQUENCE: 540 ggggcaagt 9

<210> SEQ ID NO 541
<211> LENGTH: 3
<212> TYPE: PRT
<213> ORGANISM: Artificial Sequence
<220> FEATURE:
<223> OTHER INFORMATION: Synthetic

<400> SEQUENCE: 541

Gly Ala Ser
1

<210> SEQ ID NO 542
<211> LENGTH: 27
<212> TYPE: DNA
<213> ORGANISM: Artificial Sequence
<220> FEATURE:
<223> OTHER INFORMATION: Synthetic

<400> SEQUENCE: 542
caacagtacg gaagcagccc gtggacg 27

<210> SEQ ID NO 543
<211> LENGTH: 9
<212> TYPE: PRT
<213> ORGANISM: Artificial Sequence
<220> FEATURE:
<223> OTHER INFORMATION: Synthetic

<400> SEQUENCE: 543

Gln Gln Tyr Gly Ser Ser Pro Trp Thr
1               5

<210> SEQ ID NO 544
<211> LENGTH: 378
<212> TYPE: DNA
<213> ORGANISM: Artificial Sequence
<220> FEATURE:
<223> OTHER INFORMATION: Synthetic

<400> SEQUENCE: 544
caggtgcagc tgcaggagtc gggcccagga ctggtgaagc cttcggagac cctgtccctc 60
atttgttctg tctctggtgg ctccttcagt agtcacttct ggagttggat ccggcagccc 120
ccagggaagg gactggagtg gattgggtat gtcctttaca gtgggggcac caattacaac 180
ccctccctca agagtcgagt caccatatca gtagacacgt ccaagaatca gttcttcctg 240
aaactgagct ctgtgaccgc tgcggacacg gccgattatt actgtgcgag agctatatcg 300
gggattacgt ttgggggaat tatcgtccct ggttcttttg atatctgggg ccaagggaca 360
atggtcaccg tctcttca 378

<210> SEQ ID NO 545
<211> LENGTH: 126
<212> TYPE: PRT
<213> ORGANISM: Artificial Sequence
<220> FEATURE:
<223> OTHER INFORMATION: Synthetic

<400> SEQUENCE: 545

```
Gln Val Gln Leu Gln Glu Ser Gly Pro Gly Leu Val Lys Pro Ser Glu
1               5                   10                  15

Thr Leu Ser Leu Ile Cys Ser Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Val Leu Tyr Ser Gly Gly Thr Asn Tyr Asn Pro Ser Leu Lys
    50                  55                  60

Ser Arg Val Thr Ile Ser Val Asp Thr Ser Lys Asn Gln Phe Phe Leu
65                  70                  75                  80

Lys Leu Ser Ser Val Thr Ala Ala Asp Thr Ala Asp Tyr Tyr Cys Ala
                85                  90                  95

Arg Ala Ile Ser Gly Ile Thr Phe Gly Gly Ile Ile Val Pro Gly Ser
            100                 105                 110

Phe Asp Ile Trp Gly Gln Gly Thr Met Val Thr Val Ser Ser
        115                 120                 125
```

<210> SEQ ID NO 546
<211> LENGTH: 24
<212> TYPE: DNA
<213> ORGANISM: Artificial Sequence
<220> FEATURE:
<223> OTHER INFORMATION: Synthetic

<400> SEQUENCE: 546

```
ggtggctcct tcagtagtca cttc                                            24
```

<210> SEQ ID NO 547
<211> LENGTH: 8
<212> TYPE: PRT
<213> ORGANISM: Artificial Sequence
<220> FEATURE:
<223> OTHER INFORMATION: Synthetic

<400> SEQUENCE: 547

```
Gly Gly Ser Phe Ser Ser His Phe
1               5
```

<210> SEQ ID NO 548
<211> LENGTH: 21
<212> TYPE: DNA
<213> ORGANISM: Artificial Sequence
<220> FEATURE:
<223> OTHER INFORMATION: Synthetic

<400> SEQUENCE: 548

```
gtcctttaca gtgggggcac c                                               21
```

<210> SEQ ID NO 549
<211> LENGTH: 7
<212> TYPE: PRT
<213> ORGANISM: Artificial Sequence
<220> FEATURE:
<223> OTHER INFORMATION: Synthetic

<400> SEQUENCE: 549

```
Val Leu Tyr Ser Gly Gly Thr
1               5
```

<210> SEQ ID NO 550
<211> LENGTH: 60
<212> TYPE: DNA
<213> ORGANISM: Artificial Sequence
<220> FEATURE:
<223> OTHER INFORMATION: Synthetic

<400> SEQUENCE: 550

```
gcgagagcta tatcggggat tacgtttggg ggaattatcg tccctggttc ttttgatatc     60
```

<210> SEQ ID NO 551
<211> LENGTH: 24
<212> TYPE: PRT
<213> ORGANISM: Artificial Sequence
<220> FEATURE:
<223> OTHER INFORMATION: Synthetic

<400> SEQUENCE: 551

```
Ala Arg Ala Ile Ser Gly Ile Thr Phe Gly Gly Ile Ile Val Pro Gly
1               5                   10                  15

Ser Phe Asp Ile Ser Pro Gly Lys
            20
```

<210> SEQ ID NO 552
<211> LENGTH: 378
<212> TYPE: DNA
<213> ORGANISM: Artificial Sequence
<220> FEATURE:
<223> OTHER INFORMATION: Synthetic

<400> SEQUENCE: 552

```
caggtgcagc tgcaggagtc gggcccagga ctggtgaagc cctcggagac cctgtccctc     60

acctgcactg tctctggtgg ctccttcagt agtcacttct ggagctggat ccggcagccc    120

ccagggaagg gactggagtg gattggatat atcttataca ctgggggcac cagcttcaac    180

ccctccctca agagtcgagt ctccatgtca gtgggcacgt ccaagaacca gttctccctg    240

aaattgagct ctgtgaccgc tgcggacacg gccgtatatt actgtgcgag agctagatcg    300

gggataacgt ttacgggtat tatcgtccct ggctcttttg atatctgggg ccaagggaca    360

atggtcaccg tctcttca                                                  378
```

<210> SEQ ID NO 553
<211> LENGTH: 126
<212> TYPE: PRT
<213> ORGANISM: Artificial Sequence
<220> FEATURE:
<223> OTHER INFORMATION: Synthetic

<400> SEQUENCE: 553

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60
```

```
Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser
        115                 120                 125


<210> SEQ ID NO 554
<211> LENGTH: 24
<212> TYPE: DNA
<213> ORGANISM: Artificial Sequence
<220> FEATURE:
<223> OTHER INFORMATION: Synthetic

<400> SEQUENCE: 554

ggtggctcct tcagtagtca cttc                                            24


<210> SEQ ID NO 555
<211> LENGTH: 8
<212> TYPE: PRT
<213> ORGANISM: Artificial Sequence
<220> FEATURE:
<223> OTHER INFORMATION: Synthetic

<400> SEQUENCE: 555

Gly Gly Ser Phe Ser Ser His Phe
1               5


<210> SEQ ID NO 556
<211> LENGTH: 21
<212> TYPE: DNA
<213> ORGANISM: Artificial Sequence
<220> FEATURE:
<223> OTHER INFORMATION: Synthetic

<400> SEQUENCE: 556

atcttataca ctgggggcac c                                               21


<210> SEQ ID NO 557
<211> LENGTH: 7
<212> TYPE: PRT
<213> ORGANISM: Artificial Sequence
<220> FEATURE:
<223> OTHER INFORMATION: Synthetic

<400> SEQUENCE: 557

Ile Leu Tyr Thr Gly Gly Thr
1               5


<210> SEQ ID NO 558
<211> LENGTH: 60
<212> TYPE: DNA
<213> ORGANISM: Artificial Sequence
<220> FEATURE:
<223> OTHER INFORMATION: Synthetic

<400> SEQUENCE: 558

gcgagagcta gatcggggat aacgtttacg ggtattatcg tccctggctc ttttgatatc     60


<210> SEQ ID NO 559
<211> LENGTH: 20
<212> TYPE: PRT
```

<213> ORGANISM: Artificial Sequence
<220> FEATURE:
<223> OTHER INFORMATION: Synthetic

<400> SEQUENCE: 559

Ala Arg Ala Arg Ser Gly Ile Thr Phe Thr Gly Ile Ile Val Pro Gly
1 5 10 15

Ser Phe Asp Ile
20

<210> SEQ ID NO 560
<211> LENGTH: 378
<212> TYPE: DNA
<213> ORGANISM: Artificial Sequence
<220> FEATURE:
<223> OTHER INFORMATION: Synthetic

<400> SEQUENCE: 560
caggtgcagc tgcaggagtc gggcccagga ctggtgaagc cttcggagac cctgtccctc 60
acttgttctg tctctggtgg ctccttcagt agtcacttct ggagctggat ccggcagccc 120
ccagggaagg gactggagtg gattggatat atccattaca gtgggggcac caattacaac 180
ccctccctca agagtcgagt caccatatca gtagacacgt ccaagaacca gttctccctt 240
aaactgactt ctgtgaccgc tgcggacacg gccgattatt actgtgcgag agctatatcg 300
gggattacgt ttgggggaat gatcgtccct ggttcttttg atgtctgggg cgaagggaca 360
atggtcaccg tctcttca 378

<210> SEQ ID NO 561
<211> LENGTH: 126
<212> TYPE: PRT
<213> ORGANISM: Artificial Sequence
<220> FEATURE:
<223> OTHER INFORMATION: Synthetic

<400> SEQUENCE: 561

Gln Val Gln Leu Gln Glu Ser Gly Pro Gly Leu Val Lys Pro Ser Glu
1 5 10 15

Thr Leu Ser Leu Thr Cys Ser Val Ser Gly Gly Ser Phe Ser Ser His
20 25 30

Phe Trp Ser Trp Ile Arg Gln Pro Pro Gly Lys Gly Leu Glu Trp Ile
35 40 45

Gly Tyr Ile His Tyr Ser Gly Gly Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Thr Ser Val Thr Ala Ala Asp Thr Ala Asp Tyr Tyr Cys Ala
85 90 95

Arg Ala Ile Ser Gly Ile Thr Phe Gly Gly Met Ile Val Pro Gly Ser
100 105 110

Phe Asp Val Trp Gly Glu Gly Thr Met Val Thr Val Ser Ser
115 120 125

<210> SEQ ID NO 562
<211> LENGTH: 24
<212> TYPE: DNA
<213> ORGANISM: Artificial Sequence
<220> FEATURE:
<223> OTHER INFORMATION: Synthetic

<400> SEQUENCE: 562
ggtggctcct tcagtagtca cttc 24

<210> SEQ ID NO 563
<211> LENGTH: 8
<212> TYPE: PRT
<213> ORGANISM: Artificial Sequence
<220> FEATURE:
<223> OTHER INFORMATION: Synthetic

<400> SEQUENCE: 563

Gly Gly Ser Phe Ser Ser His Phe
1 5

<210> SEQ ID NO 564
<211> LENGTH: 21
<212> TYPE: DNA
<213> ORGANISM: Artificial Sequence
<220> FEATURE:
<223> OTHER INFORMATION: Synthetic

<400> SEQUENCE: 564
atccattaca gtgggggcac c 21

<210> SEQ ID NO 565
<211> LENGTH: 7
<212> TYPE: PRT
<213> ORGANISM: Artificial Sequence
<220> FEATURE:
<223> OTHER INFORMATION: Synthetic

<400> SEQUENCE: 565

Ile His Tyr Ser Gly Gly Thr
1 5

<210> SEQ ID NO 566
<211> LENGTH: 60
<212> TYPE: DNA
<213> ORGANISM: Artificial Sequence
<220> FEATURE:
<223> OTHER INFORMATION: Synthetic

<400> SEQUENCE: 566
gcgagagcta tatcggggat tacgtttggg ggaatgatcg tccctggttc ttttgatgtc 60

<210> SEQ ID NO 567
<211> LENGTH: 20
<212> TYPE: PRT
<213> ORGANISM: Artificial Sequence
<220> FEATURE:
<223> OTHER INFORMATION: Synthetic

<400> SEQUENCE: 567

Ala Arg Ala Ile Ser Gly Ile Thr Phe Gly Gly Met Ile Val Pro Gly
1 5 10 15

Ser Phe Asp Val
20

<210> SEQ ID NO 568
<211> LENGTH: 378
<212> TYPE: DNA
<213> ORGANISM: Artificial Sequence
<220> FEATURE:
<223> OTHER INFORMATION: Synthetic

<400> SEQUENCE: 568

```
caggtgcagc tgcaggagtc gggcccagga ctggtgaagc cttcggagac cctgtccctc     60

acctgcactg tctctggtgg caccttcagt agtcacttct ggagctggat ccggcagccc    120

ccaggaaagg gactggagtg gattggatat atcttttaca ctgggggcac caaccacaac    180

ccctccctca agagtcgagt caccatatca atagacacgt ccaagaacca gttctccctg    240

aaactgacct ctgtgaccgc tgcggacacg gccgtgtatt actgtgcgag agctagatcg    300

gggattacgt ttgggggagt tatcgtccct ggttcttttg atatctgggg ccaagggaca    360

atggtcaccg tctcttca                                                  378
```

<210> SEQ ID NO 569
<211> LENGTH: 126
<212> TYPE: PRT
<213> ORGANISM: Artificial Sequence
<220> FEATURE:
<223> OTHER INFORMATION: Synthetic

<400> SEQUENCE: 569

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Thr Phe Ser Ser His
            20                  25                  30

Phe Trp Ser Trp Ile Arg Gln Pro Pro Gly Lys Gly Leu Glu Trp Ile
        35                  40                  45

Gly Tyr Ile Phe Tyr Thr Gly Gly Thr Asn His Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Ala Arg Ser Gly Ile Thr Phe Gly Gly Val Ile Val Pro Gly Ser
            100                 105                 110

Phe Asp Ile Trp Gly Gln Gly Thr Met Val Thr Val Ser Ser
        115                 120                 125
```

<210> SEQ ID NO 570
<211> LENGTH: 24
<212> TYPE: DNA
<213> ORGANISM: Artificial Sequence
<220> FEATURE:
<223> OTHER INFORMATION: Synthetic

<400> SEQUENCE: 570

```
ggtggcacct tcagtagtca cttc                                            24
```

<210> SEQ ID NO 571
<211> LENGTH: 8
<212> TYPE: PRT
<213> ORGANISM: Artificial Sequence
<220> FEATURE:
<223> OTHER INFORMATION: Synthetic

<400> SEQUENCE: 571

```
Gly Gly Thr Phe Ser Ser His Phe
1               5
```

<210> SEQ ID NO 572
<211> LENGTH: 21
<212> TYPE: DNA
<213> ORGANISM: Artificial Sequence
<220> FEATURE:

<223> OTHER INFORMATION: Synthetic

<400> SEQUENCE: 572
atcttttaca ctgggggcac c 21

<210> SEQ ID NO 573
<211> LENGTH: 7
<212> TYPE: PRT
<213> ORGANISM: Artificial Sequence
<220> FEATURE:
<223> OTHER INFORMATION: Synthetic

<400> SEQUENCE: 573

Ile Phe Tyr Thr Gly Gly Thr
1 5

<210> SEQ ID NO 574
<211> LENGTH: 60
<212> TYPE: DNA
<213> ORGANISM: Artificial Sequence
<220> FEATURE:
<223> OTHER INFORMATION: Synthetic

<400> SEQUENCE: 574
gcgagagcta gatcggggat tacgtttggg ggagttatcg tccctggttc ttttgatatc 60

<210> SEQ ID NO 575
<211> LENGTH: 20
<212> TYPE: PRT
<213> ORGANISM: Artificial Sequence
<220> FEATURE:
<223> OTHER INFORMATION: Synthetic

<400> SEQUENCE: 575

Ala Arg Ala Arg Ser Gly Ile Thr Phe Gly Gly Val Ile Val Pro Gly
1 5 10 15

Ser Phe Asp Ile
20

<210> SEQ ID NO 576
<211> LENGTH: 378
<212> TYPE: DNA
<213> ORGANISM: Artificial Sequence
<220> FEATURE:
<223> OTHER INFORMATION: Synthetic

<400> SEQUENCE: 576
caggtgcagc tgcaggagtc gggcccagga ctggtgaaac cttcggagac cctgtccctc 60
acctgcactg tctctggtgg ctccttcagc agtcacttct ggaactggat ccggcagtcc 120
ccagggaggg gactggaatg gattggatat atctattaca gtgggggcac caactataac 180
ccctccttca agagtcgagt caccatgtca gtagacacgt ccaagaacca gttctccctg 240
aaactgagct ctgtgaccgc tgcggacacg gccgtgtttt actgtgcgag agctagatcg 300
gggataacgt ttgggggagt tctcgtccct ggttcttttg atatttgggg ccaagggaca 360
atggtcaccg tctcttca 378

<210> SEQ ID NO 577
<211> LENGTH: 126
<212> TYPE: PRT
<213> ORGANISM: Artificial Sequence
<220> FEATURE:
<223> OTHER INFORMATION: Synthetic

<400> SEQUENCE: 577

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Asn Trp Ile Arg Gln Ser Pro Gly Arg Gly Leu Glu Trp Ile
        35                  40                  45

Gly Tyr Ile Tyr Tyr Ser Gly Gly Thr Asn Tyr Asn Pro Ser Phe Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Phe Tyr Cys Ala
                85                  90                  95

Arg Ala Arg Ser Gly Ile Thr Phe Gly Gly Val Leu Val Pro Gly Ser
            100                 105                 110

Phe Asp Ile Trp Gly Gln Gly Thr Met Val Thr Val Ser Ser
        115                 120                 125

<210> SEQ ID NO 578
<211> LENGTH: 24
<212> TYPE: DNA
<213> ORGANISM: Artificial Sequence
<220> FEATURE:
<223> OTHER INFORMATION: Synthetic

<400> SEQUENCE: 578
ggtggctcct tcagcagtca cttc                                              24

<210> SEQ ID NO 579
<211> LENGTH: 8
<212> TYPE: PRT
<213> ORGANISM: Artificial Sequence
<220> FEATURE:
<223> OTHER INFORMATION: Synthetic

<400> SEQUENCE: 579

Gly Gly Ser Phe Ser Ser His Phe
1               5

<210> SEQ ID NO 580
<211> LENGTH: 21
<212> TYPE: DNA
<213> ORGANISM: Artificial Sequence
<220> FEATURE:
<223> OTHER INFORMATION: Synthetic

<400> SEQUENCE: 580
atctattaca gtgggggcac c                                                 21

<210> SEQ ID NO 581
<211> LENGTH: 7
<212> TYPE: PRT
<213> ORGANISM: Artificial Sequence
<220> FEATURE:
<223> OTHER INFORMATION: Synthetic

<400> SEQUENCE: 581

Ile Tyr Tyr Ser Gly Gly Thr
1               5

<210> SEQ ID NO 582
<211> LENGTH: 60

<212> TYPE: DNA
<213> ORGANISM: Artificial Sequence
<220> FEATURE:
<223> OTHER INFORMATION: Synthetic

<400> SEQUENCE: 582
gcgagagcta gatcggggat aacgtttggg ggagttctcg tccctggttc ttttgatatt 60

<210> SEQ ID NO 583
<211> LENGTH: 20
<212> TYPE: PRT
<213> ORGANISM: Artificial Sequence
<220> FEATURE:
<223> OTHER INFORMATION: Synthetic

<400> SEQUENCE: 583

Ala Arg Ala Arg Ser Gly Ile Thr Phe Gly Gly Val Leu Val Pro Gly
1 5 10 15

Ser Phe Asp Ile
20

<210> SEQ ID NO 584
<211> LENGTH: 378
<212> TYPE: DNA
<213> ORGANISM: Artificial Sequence
<220> FEATURE:
<223> OTHER INFORMATION: Synthetic

<400> SEQUENCE: 584
caggtgcagc tgcaggagtc gggcccagga ctggtgaagc cttcggagac cctgtccctc 60
acctgcactg tctctggtgg ctccttcagt agtcacttct ggagctggat ccggcagccc 120
ccaggaaagg gactggagtg gattgggtat atctattaca gtgggggcac ccactacaac 180
ccctccctcg agagtcgagt caccatatca gtagacacgt ccaagaacca gttctccctg 240
aaactgaact ctgtgaccgc tgcggacacg gccgtttatt actgtgcgag agctagatcg 300
gggattactt ttgggggact tatcgtccct ggttcttttg atatctgggg ccaagggaca 360
atggtcaccg tctcttca 378

<210> SEQ ID NO 585
<211> LENGTH: 130
<212> TYPE: PRT
<213> ORGANISM: Artificial Sequence
<220> FEATURE:
<223> OTHER INFORMATION: Synthetic

<400> SEQUENCE: 585

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Phe Ser Ser His
20 25 30

Phe Trp Ser Trp Ile Arg Gln Pro Pro Gly Lys Gly Leu Glu Trp Ile
35 40 45

Gly Tyr Ile Tyr Tyr Ser Gly Gly Thr His Tyr Asn Pro Ser Leu Glu
50 55 60

Ser Arg Val Thr Ile Ser Val Asp Thr Ser Lys Asn Gln Phe Ser Leu
65 70 75 80

Lys Leu Asn Ser Val Thr Ala Ala Asp Thr Ala Val Tyr Tyr Cys Ala
85 90 95

Arg Ala Arg Ser Gly Ile Thr Phe Gly Gly Leu Ile Val Pro Gly Ser
100 105 110

```
Phe Asp Ile Trp Gly Gln Gly Thr Met Val Thr Val Ser Ser Ser Pro
        115                 120                 125

Gly Lys
    130


<210> SEQ ID NO 586
<211> LENGTH: 24
<212> TYPE: DNA
<213> ORGANISM: Artificial Sequence
<220> FEATURE:
<223> OTHER INFORMATION: Synthetic

<400> SEQUENCE: 586

ggtggctcct tcagtagtca cttc                                            24


<210> SEQ ID NO 587
<211> LENGTH: 8
<212> TYPE: PRT
<213> ORGANISM: Artificial Sequence
<220> FEATURE:
<223> OTHER INFORMATION: Synthetic

<400> SEQUENCE: 587

Gly Gly Ser Phe Ser Ser His Phe
1               5


<210> SEQ ID NO 588
<211> LENGTH: 21
<212> TYPE: DNA
<213> ORGANISM: Artificial Sequence
<220> FEATURE:
<223> OTHER INFORMATION: Synthetic

<400> SEQUENCE: 588

atctattaca gtgggggcac c                                               21


<210> SEQ ID NO 589
<211> LENGTH: 7
<212> TYPE: PRT
<213> ORGANISM: Artificial Sequence
<220> FEATURE:
<223> OTHER INFORMATION: Synthetic

<400> SEQUENCE: 589

Ile Tyr Tyr Ser Gly Gly Thr
1               5


<210> SEQ ID NO 590
<211> LENGTH: 60
<212> TYPE: DNA
<213> ORGANISM: Artificial Sequence
<220> FEATURE:
<223> OTHER INFORMATION: Synthetic

<400> SEQUENCE: 590

gcgagagcta gatcggggat tacttttggg ggacttatcg tccctggttc ttttgatatc     60


<210> SEQ ID NO 591
<211> LENGTH: 20
<212> TYPE: PRT
<213> ORGANISM: Artificial Sequence
<220> FEATURE:
<223> OTHER INFORMATION: Synthetic

<400> SEQUENCE: 591
```

```
Ala Arg Ala Arg Ser Gly Ile Thr Phe Gly Gly Leu Ile Val Pro Gly
1               5                   10                  15

Ser Phe Asp Ile
            20
```

<210> SEQ ID NO 592
<211> LENGTH: 375
<212> TYPE: DNA
<213> ORGANISM: Artificial Sequence
<220> FEATURE:
<223> OTHER INFORMATION: Synthetic

<400> SEQUENCE: 592

```
cgggtgcaac tggtgcagtc tgggtctgag gtgaagaagc ctggggcctc agtgaaggtc     60

tcctgcaggg cttctggata catcttcacc agttatgata tcaattgggt gcgacaggcc    120

actggacaag ggcttgagtg gatgggatgg atgaacccta ataatggtaa cacagcctat    180

acacagaagt tccagggcag agtcaccatg accaggaaca cctccataag cacagcctac    240

atggagctga gcagcctgag atctgaggac acggccgtgt attactgtgc gagaaaggga    300

ttactatggt tcgggaagtt attagggtac ggtatggacg tctggggcca agggaccacg    360

gtcaccgtct cctca                                                     375
```

<210> SEQ ID NO 593
<211> LENGTH: 125
<212> TYPE: PRT
<213> ORGANISM: Artificial Sequence
<220> FEATURE:
<223> OTHER INFORMATION: Synthetic

<400> SEQUENCE: 593

```
Arg Val Gln Leu Val Gln Ser Gly Ser Glu Val Lys Lys Pro Gly Ala
1               5                   10                  15

Ser Val Lys Val Ser Cys Arg Ala Ser Gly Tyr Ile Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Asn Gly Asn Thr Ala Tyr Thr Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Gly Leu Leu Trp Phe Gly Lys Leu Leu Gly Tyr Gly Met
            100                 105                 110

Asp Val Trp Gly Gln Gly Thr Thr Val Thr Val Ser Ser
        115                 120                 125
```

<210> SEQ ID NO 594
<211> LENGTH: 24
<212> TYPE: DNA
<213> ORGANISM: Artificial Sequence
<220> FEATURE:
<223> OTHER INFORMATION: Synthetic

<400> SEQUENCE: 594

```
ggatacatct tcaccagtta tgat                                            24
```

<210> SEQ ID NO 595
<211> LENGTH: 8

<212> TYPE: PRT
<213> ORGANISM: Artificial Sequence
<220> FEATURE:
<223> OTHER INFORMATION: Synthetic

<400> SEQUENCE: 595

Gly Tyr Ile Phe Thr Ser Tyr Asp
1 5

<210> SEQ ID NO 596
<211> LENGTH: 24
<212> TYPE: DNA
<213> ORGANISM: Artificial Sequence
<220> FEATURE:
<223> OTHER INFORMATION: Synthetic

<400> SEQUENCE: 596
atgaacccta ataatggtaa caca 24

<210> SEQ ID NO 597
<211> LENGTH: 8
<212> TYPE: PRT
<213> ORGANISM: Artificial Sequence
<220> FEATURE:
<223> OTHER INFORMATION: Synthetic

<400> SEQUENCE: 597

Met Asn Pro Asn Asn Gly Asn Thr
1 5

<210> SEQ ID NO 598
<211> LENGTH: 54
<212> TYPE: DNA
<213> ORGANISM: Artificial Sequence
<220> FEATURE:
<223> OTHER INFORMATION: Synthetic

<400> SEQUENCE: 598
gcgagaaagg gattactatg gttcgggaag ttattagggt acggtatgga cgtc 54

<210> SEQ ID NO 599
<211> LENGTH: 18
<212> TYPE: PRT
<213> ORGANISM: Artificial Sequence
<220> FEATURE:
<223> OTHER INFORMATION: Synthetic

<400> SEQUENCE: 599

Ala Arg Lys Gly Leu Leu Trp Phe Gly Lys Leu Leu Gly Tyr Gly Met
1 5 10 15

Asp Val

<210> SEQ ID NO 600
<211> LENGTH: 324
<212> TYPE: DNA
<213> ORGANISM: Artificial Sequence
<220> FEATURE:
<223> OTHER INFORMATION: Synthetic

<400> SEQUENCE: 600
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240

```
cctgaagatt ttgcagtgta ttactgtcag cagtatggta gctcaccttg gacgttcggc     300

caagggacca aggtggaaat caaa                                            324


<210> SEQ ID NO 601
<211> LENGTH: 108
<212> TYPE: PRT
<213> ORGANISM: Artificial Sequence
<220> FEATURE:
<223> OTHER INFORMATION: Synthetic

<400> SEQUENCE: 601

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 602
<211> LENGTH: 21
<212> TYPE: DNA
<213> ORGANISM: Artificial Sequence
<220> FEATURE:
<223> OTHER INFORMATION: Synthetic

<400> SEQUENCE: 602

cagagtgtta gcagcagcta c                                                21


<210> SEQ ID NO 603
<211> LENGTH: 7
<212> TYPE: PRT
<213> ORGANISM: Artificial Sequence
<220> FEATURE:
<223> OTHER INFORMATION: Synthetic

<400> SEQUENCE: 603

Gln Ser Val Ser Ser Ser Tyr
1               5


<210> SEQ ID NO 604
<211> LENGTH: 9
<212> TYPE: DNA
<213> ORGANISM: Artificial Sequence
<220> FEATURE:
<223> OTHER INFORMATION: Synthetic

<400> SEQUENCE: 604

ggtgcatcc                                                               9


<210> SEQ ID NO 605
<211> LENGTH: 3
<212> TYPE: PRT
<213> ORGANISM: Artificial Sequence
<220> FEATURE:
```

```
<223> OTHER INFORMATION: Synthetic

<400> SEQUENCE: 605

Gly Ala Ser
1


<210> SEQ ID NO 606
<211> LENGTH: 27
<212> TYPE: DNA
<213> ORGANISM: Artificial Sequence
<220> FEATURE:
<223> OTHER INFORMATION: Synthetic

<400> SEQUENCE: 606

cagcagtatg gtagctcacc ttggacg                                          27


<210> SEQ ID NO 607
<211> LENGTH: 9
<212> TYPE: PRT
<213> ORGANISM: Artificial Sequence
<220> FEATURE:
<223> OTHER INFORMATION: Synthetic

<400> SEQUENCE: 607

Gln Gln Tyr Gly Ser Ser Pro Trp Thr
1               5


<210> SEQ ID NO 608
<211> LENGTH: 120
<212> TYPE: PRT
<213> ORGANISM: Artificial Sequence
<220> FEATURE:
<223> OTHER INFORMATION: Synthetic

<400> SEQUENCE: 608

Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser
        115                 120


<210> SEQ ID NO 609
<211> LENGTH: 8
<212> TYPE: PRT
<213> ORGANISM: Artificial Sequence
<220> FEATURE:
<223> OTHER INFORMATION: Synthetic

<400> SEQUENCE: 609

Gly Phe Thr Phe Ser Ala Tyr Ala
1               5
```

<210> SEQ ID NO 610
<211> LENGTH: 8
<212> TYPE: PRT
<213> ORGANISM: Artificial Sequence
<220> FEATURE:
<223> OTHER INFORMATION: Synthetic

<400> SEQUENCE: 610

Ile Ser Gly Ser Gly Gly Ser Ala
1               5

<210> SEQ ID NO 611
<211> LENGTH: 13
<212> TYPE: PRT
<213> ORGANISM: Artificial Sequence
<220> FEATURE:
<223> OTHER INFORMATION: Synthetic

<400> SEQUENCE: 611

Ala Lys Asp Gly Ala Trp Lys Met Ser Gly Leu Asp Val
1               5                   10

<210> SEQ ID NO 612
<211> LENGTH: 107
<212> TYPE: PRT
<213> ORGANISM: Artificial Sequence
<220> FEATURE:
<223> OTHER INFORMATION: Synthetic

<400> SEQUENCE: 612

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105

<210> SEQ ID NO 613
<211> LENGTH: 6
<212> TYPE: PRT
<213> ORGANISM: Artificial Sequence
<220> FEATURE:
<223> OTHER INFORMATION: Synthetic

<400> SEQUENCE: 613

Gln Asp Ile Ser Asp Tyr
1               5

<210> SEQ ID NO 614
<211> LENGTH: 3
<212> TYPE: PRT
<213> ORGANISM: Artificial Sequence
<220> FEATURE:
<223> OTHER INFORMATION: Synthetic

<400> SEQUENCE: 614

```
Thr Thr Ser
1


<210> SEQ ID NO 615
<211> LENGTH: 9
<212> TYPE: PRT
<213> ORGANISM: Artificial Sequence
<220> FEATURE:
<223> OTHER INFORMATION: Synthetic

<400> SEQUENCE: 615

Gln Lys Tyr Asp Ser Ala Pro Leu Thr
1               5


<210> SEQ ID NO 616
<211> LENGTH: 109
<212> TYPE: PRT
<213> ORGANISM: Homo sapiens

<400> SEQUENCE: 616

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105


<210> SEQ ID NO 617
<211> LENGTH: 426
<212> TYPE: PRT
<213> ORGANISM: Homo sapiens

<400> SEQUENCE: 617

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
```

```
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425


<210> SEQ ID NO 618
<211> LENGTH: 340
<212> TYPE: PRT
<213> ORGANISM: Artificial Sequence
<220> FEATURE:
<223> OTHER INFORMATION: Synthetic

<400> SEQUENCE: 618

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Ala Asn Ser Ser Gly Thr Ile
        35                  40                  45

Glu Leu Val Lys Lys Gly Cys Trp Leu Asp Asp Phe Asn Cys Tyr Asp
    50                  55                  60

Arg Gln Glu Cys Val Ala Thr Glu Glu Asn Pro Gln Val Tyr Phe Cys
```

```
65                  70                  75                  80

Cys Cys Glu Gly Asn Phe Cys Asn Glu Arg Phe Thr His Leu Pro Glu
                85                  90                  95

Ala Gly Gly Pro Glu Val Thr Tyr Glu Pro Pro Pro Thr Ala Pro Ser
            100                 105                 110

Gly Asp Lys Thr His Thr Cys Pro Pro Cys Pro Ala Pro Glu Leu Leu
        115                 120                 125

Gly Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340


<210> SEQ ID NO 619
<211> LENGTH: 411
<212> TYPE: PRT
<213> ORGANISM: Homo sapiens

<400> SEQUENCE: 619

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Gln Pro Pro Pro Pro Pro Pro Gly Ser Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95
```

```
Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Ser Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
            340                 345                 350

Ala Val Val Asn Gln Tyr Arg Met Arg Gly Leu Asn Pro Gly Thr Val
        355                 360                 365

Asn Ser Cys Cys Ile Pro Thr Lys Leu Ser Thr Met Ser Met Leu Tyr
    370                 375                 380

Phe Asp Asp Glu Tyr Asn Ile Val Lys Arg Asp Val Pro Asn Met Ile
385                 390                 395                 400

Val Glu Glu Cys Gly Cys Ala Ser Pro Gly Lys
                405                 410
```

<210> SEQ ID NO 620
<211> LENGTH: 122
<212> TYPE: PRT
<213> ORGANISM: Homo sapiens

<400> SEQUENCE: 620

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Tyr Thr Phe Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Tyr Asn Trp Asn Tyr Gly Ala Phe Asp Ile Trp
            100                 105                 110

Gly Gln Gly Thr Met Val Thr Val Ser Ser
        115                 120


<210> SEQ ID NO 621
<211> LENGTH: 107
<212> TYPE: PRT
<213> ORGANISM: Homo sapiens

<400> SEQUENCE: 621

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105


<210> SEQ ID NO 622
<211> LENGTH: 115
<212> TYPE: PRT
<213> ORGANISM: Artificial Sequence
<220> FEATURE:
<223> OTHER INFORMATION: Synthetic 12A5-5HC polypeptide
<220> FEATURE:
<221> NAME/KEY: MOD_RES
<222> LOCATION: (50)..(50)
<223> OTHER INFORMATION: Any naturally occurring amino acid
<220> FEATURE:
<221> NAME/KEY: MOD_RES
<222> LOCATION: (50)..(50)
<223> OTHER INFORMATION: Xaa = Any naturally occurring amino acid

<400> SEQUENCE: 622

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Asn Trp Val Arg Gln Ala Pro Gly Lys Gly Leu Glu Trp Val
        35                  40                  45

Ala Xaa Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
```

```
            100                 105                 110

Val Ser Ser
        115


<210> SEQ ID NO 623
<211> LENGTH: 107
<212> TYPE: PRT
<213> ORGANISM: Artificial Sequence
<220> FEATURE:
<223> OTHER INFORMATION: Synthetic 12A5-5LC polypeptide

<400> SEQUENCE: 623

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Trp Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105


<210> SEQ ID NO 624
<211> LENGTH: 124
<212> TYPE: PRT
<213> ORGANISM: Artificial Sequence
<220> FEATURE:
<223> OTHER INFORMATION: Antibody Fragment

<400> SEQUENCE: 624

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Phe Met His Trp Val Arg Gln Ala Pro Gly Gln Gly Leu Glu Trp Ile
        35                  40                  45

Gly Asn Ile Tyr Pro Tyr Asn Ser Val Ser Asn Tyr Asn Gln Arg Phe
    50                  55                  60

Lys Ala Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Tyr Tyr Tyr Gly Thr Gly Pro Ala Asp Trp Tyr Tyr Asp
            100                 105                 110

Val Trp Gly Gln Gly Thr Leu Val Thr Val Ser Ser
        115                 120


<210> SEQ ID NO 625
<211> LENGTH: 107
<212> TYPE: PRT
<213> ORGANISM: Artificial Sequence
<220> FEATURE:
<223> OTHER INFORMATION: Antibody Fragment

<400> SEQUENCE: 625
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Lys Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Ser Asp Glu Phe Pro Leu
                85                  90                  95

Thr Phe Gly Gln Gly Thr Lys Leu Glu Ile Lys
            100                 105


<210> SEQ ID NO 626
<211> LENGTH: 117
<212> TYPE: PRT
<213> ORGANISM: Homo sapiens

<400> SEQUENCE: 626

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Glu Asn Trp Gly Phe Asp Pro Trp Gly Gln Gly Thr Leu
            100                 105                 110

Val Thr Val Ser Ser
        115


<210> SEQ ID NO 627
<211> LENGTH: 105
<212> TYPE: PRT
<213> ORGANISM: Homo sapiens

<400> SEQUENCE: 627

Ser Tyr Glu Leu Thr Gln Pro Pro Ser Val Ser Val Ser Pro Gly Gln
1               5                   10                  15

Thr Ala Thr Ile Thr Cys Ser Gly His Ala Leu Gly Asp Lys Phe Val
            20                  25                  30

Ser Trp Tyr Gln Gln Gly Ser Gly Gln Ser Pro Val Leu Val Ile Tyr
        35                  40                  45

Asp Asp Thr Gln Arg Pro Ser Gly Ile Pro Gly Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Ser Phe Val Phe
                85                  90                  95
```

```
Gly Gly Gly Thr Lys Val Thr Val Leu
            100                 105


<210> SEQ ID NO 628
<211> LENGTH: 120
<212> TYPE: PRT
<213> ORGANISM: Homo sapiens

<400> SEQUENCE: 628

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Thr Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Met Gly Gly Tyr Asp Arg Tyr Tyr Phe Asp Tyr Trp Gly Gln
            100                 105                 110

Gly Thr Leu Val Thr Val Ser Ser
        115                 120


<210> SEQ ID NO 629
<211> LENGTH: 113
<212> TYPE: PRT
<213> ORGANISM: Homo sapiens

<400> SEQUENCE: 629

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Asn Thr Pro Leu Thr Phe Gly Gly Gly Thr Lys Val Glu Ile
            100                 105                 110

Lys


<210> SEQ ID NO 630
<211> LENGTH: 113
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is an unknown amino acid
<220> FEATURE:
<221> NAME/KEY: MISC_FEATURE
<222> LOCATION: (113)..(113)
```

<223> OTHER INFORMATION: Xaa is an unknown amino acid

<400> SEQUENCE: 630

Xaa Val Lys Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Asp Thr Asn Phe Ile Glu Ser Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Val Arg Phe Ala Tyr Trp Gly Gln Gly Thr Thr Val Thr Val Ser
            100                 105                 110

Xaa

<210> SEQ ID NO 631
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 631

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Met Val
            100                 105                 110

<210> SEQ ID NO 632
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 632

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105


<210> SEQ ID NO 633
<211> LENGTH: 116
<212> TYPE: PRT
<213> ORGANISM: Artificial Sequence
<220> FEATURE:
<223> OTHER INFORMATION: Mouse CDRs and human VH & J segment

<400> SEQUENCE: 633

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Ser Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Tyr Ala Met Asn Tyr Trp Gly Gln Gly Thr Leu Val
            100                 105                 110

Thr Val Ser Ser
        115


<210> SEQ ID NO 634
<211> LENGTH: 107
<212> TYPE: PRT
<213> ORGANISM: Artificial Sequence
<220> FEATURE:
<223> OTHER INFORMATION: Mouse CDRs and human VH & J segment

<400> SEQUENCE: 634

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105


<210> SEQ ID NO 635
<211> LENGTH: 124
<212> TYPE: PRT
```

<213> ORGANISM: Artificial Sequence
<220> FEATURE:
<223> OTHER INFORMATION: Synthetic construct

<400> SEQUENCE: 635

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Lys Val
            20                  25                  30

Gly Ser Ser Val Ser Trp Ile Arg Gln Pro Pro Gly Lys Gly Leu Glu
        35                  40                  45

Trp Ile Gly His Ile Tyr Trp Asp Asp Asp Lys Arg Leu Asn Pro Ser
    50                  55                  60

Leu Arg Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ala Ile Thr Thr Val Ile Gly Gly Gly Thr Phe Asp
            100                 105                 110

Leu Trp Gly Gln Gly Thr Leu Val Thr Val Ser Ser
        115                 120
```

<210> SEQ ID NO 636
<211> LENGTH: 106
<212> TYPE: PRT
<213> ORGANISM: Artificial Sequence
<220> FEATURE:
<223> OTHER INFORMATION: Synthetic construct

<400> SEQUENCE: 636

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Leu Asn Pro Leu Thr
                85                  90                  95

Phe Gly Gly Gly Thr Lys Val Glu Ile Lys
            100                 105
```

<210> SEQ ID NO 637
<211> LENGTH: 124
<212> TYPE: PRT
<213> ORGANISM: Artificial Sequence
<220> FEATURE:
<223> OTHER INFORMATION: Synthetic construct

<400> SEQUENCE: 637

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Arg Lys Val
            20                  25                  30

Gly Arg Ser Val Ser Trp Ile Arg Gln Pro Pro Gly Lys Ala Leu Glu
        35                  40                  45
```

```
Trp Leu Ala His Ile Tyr Trp Asp Asp Asp Lys Arg Tyr Asn Pro Ser
    50                  55                  60

Leu Arg Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ala Ile Thr Thr Val Ile Gly Gly Gly Thr Phe Asp
            100                 105                 110

Tyr Trp Gly Gln Gly Thr Thr Val Thr Val Ser Ser
        115                 120


<210> SEQ ID NO 638
<211> LENGTH: 106
<212> TYPE: PRT
<213> ORGANISM: Artificial Sequence
<220> FEATURE:
<223> OTHER INFORMATION: Synthetic construct

<400> SEQUENCE: 638

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Tyr Arg Asn Pro Leu Thr
                85                  90                  95

Phe Gly Gly Gly Thr Lys Val Glu Ile Lys
            100                 105


<210> SEQ ID NO 639
<211> LENGTH: 113
<212> TYPE: PRT
<213> ORGANISM: Artificial Sequence
<220> FEATURE:
<223> OTHER INFORMATION: Synthetic construct

<400> SEQUENCE: 639

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Val Trp Val
        35                  40                  45

Ser Ala Ile Thr Ser Ser Gly Gly Ser Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser
```

<210> SEQ ID NO 640
<211> LENGTH: 112
<212> TYPE: PRT
<213> ORGANISM: Artificial Sequence
<220> FEATURE:
<223> OTHER INFORMATION: Synthetic construct

<400> SEQUENCE: 640

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His His Ser Gly Tyr His
                85                  90                  95

Phe Thr Phe Gly Gly Gly Thr Lys Val Glu Ile Lys Ser Pro Gly Lys
            100                 105                 110
```

<210> SEQ ID NO 641
<211> LENGTH: 439
<212> TYPE: PRT
<213> ORGANISM: Artificial Sequence
<220> FEATURE:
<223> OTHER INFORMATION: Full length landogrozumab heavy chain

<400> SEQUENCE: 641

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Pro Met Ser Trp Val Arg Gln Ala Pro Gly Lys Gly Leu Val Trp Val
        35                  40                  45

Ser Ala Ile Thr Ser Ser Gly Gly Ser Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
```

```
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly
        435
```

<210> SEQ ID NO 642
<211> LENGTH: 215
<212> TYPE: PRT
<213> ORGANISM: Artificial Sequence
<220> FEATURE:
<223> OTHER INFORMATION: Full length landogrozumab light chain

<400> SEQUENCE: 642

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Val Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His His Ser Gly Tyr His
                85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
```

```
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 643
<211> LENGTH: 7
<212> TYPE: PRT
<213> ORGANISM: Artificial Sequence
<220> FEATURE:
<223> OTHER INFORMATION: HCVR1

<400> SEQUENCE: 643

Gly Leu Thr Phe Ser Arg Tyr
1               5


<210> SEQ ID NO 644
<211> LENGTH: 6
<212> TYPE: PRT
<213> ORGANISM: Artificial Sequence
<220> FEATURE:
<223> OTHER INFORMATION: HCVR2

<400> SEQUENCE: 644

Thr Ser Ser Gly Gly Ser
1               5


<210> SEQ ID NO 645
<211> LENGTH: 4
<212> TYPE: PRT
<213> ORGANISM: Artificial Sequence
<220> FEATURE:
<223> OTHER INFORMATION: HCVR3

<400> SEQUENCE: 645

Leu Pro Asp Tyr
1


<210> SEQ ID NO 646
<211> LENGTH: 9
<212> TYPE: PRT
<213> ORGANISM: Artificial Sequence
<220> FEATURE:
<223> OTHER INFORMATION: LCVR1

<400> SEQUENCE: 646

Ser Ser Val Ser Ser Ser Tyr Leu His
1               5


<210> SEQ ID NO 647
<211> LENGTH: 7
<212> TYPE: PRT
<213> ORGANISM: Artificial Sequence
<220> FEATURE:
<223> OTHER INFORMATION: LCVR2
```

```
<400> SEQUENCE: 647

Ser Thr Ser Asn Leu Val Ala
1               5


<210> SEQ ID NO 648
<211> LENGTH: 9
<212> TYPE: PRT
<213> ORGANISM: Artificial Sequence
<220> FEATURE:
<223> OTHER INFORMATION: LCVR3

<400> SEQUENCE: 648

Gln His His Ser Gly Tyr His Phe Thr
1               5
```

METHODS FOR ALTERING BODY COMPOSITION BY ADMINISTERING A GDF8 INHIBITOR AND AN ACTIVIN A INHIBITOR

CROSS REFERENCES TO RELATED APPLICATIONS

This application claims the benefit of U.S. Provisional Application No. 62/637,017, filed 1 Mar. 2018, the entire contents of which are incorporated herein by reference.

SEQUENCE LISTING

This application includes a Sequence Listing in electronic format entitled "Sequence-Listing-40848-091USU1", which was created on 26 Feb. 2019 and which has a size of 288 kilobytes (KB) (295,202 bytes). The contents of txt fie "Sequence-Listing-40848-091USU1" are incorporated by reference herein.

FIELD OF THE INVENTION

The present invention relates to compositions and methods for altering body composition in a subject. The compositions and methods also reduce fat mass in a subject. The compositions and methods also increase muscle volume and/or lean body mass in the subject. More specifically, the invention relates to compositions that comprise a GDF8 inhibitor and an Activin A inhibitor and the use of such compositions to treat diseases and disorders characterized by increased fat mass, and/or decreased muscle volume or decreased lean body mass.

BACKGROUND

Growth and differentiation factor-8 (GDF8, also known as myostatin), is a secreted ligand belonging to the transforming growth factor-β (TGF-β) superfamily of growth factors. GDF8 plays a central role in the development and maintenance of skeletal muscle, acting as a negative regulator of myogenesis and skeletal muscle mass. Myostatin mutations (including knockout) translate into phenotypes that are predominantly increased muscle mass, but can be made up of variations in muscling (more muscle fibers), muscle fiber composition (greater cross-sectional area of muscle fibers), increased protein/DNA ratio, and other.

Antibodies to GDF8 and therapeutic methods are disclosed in, e.g., U.S. Pat. No. 8,840,894. Anti-GDF8 antibodies are also mentioned in, e.g., U.S. Pat. Nos. 6,096,506; 7,320,789; 7,261,893; 7,807,159; 7,888,486; 7,635,760; 7,632,499; in US Patent Appl. Publ. Nos. 2006/0263354; 2007/0178095; 2008/0299126; 2010/0166764; 2009/0148436; and International Patent Appl. Publ. Nos. WO2004/037861; WO2007/047112; WO 2010/070094.

Activins belong to the transforming growth factor-beta (TGF-β) superfamily and exert a broad range of biological effects on cell proliferation, differentiation, metabolism, homeostasis, and apoptosis, as well as immune response and tissue repair. Activin A is a disulfide-linked homodimer (two beta-A chains) that binds to and activates heteromeric complexes of a type I (Act RI-A and Act RI-B) and a type II (Act RII-A and Act RII-B) serine-threonine kinase receptor.

Antibodies to Activin A and uses thereof are disclosed in, e.g., U.S. Pat. Nos. 8,309,082; 9,718,881; and International Patent Appl. Publ. No. WO2008/031061.

Compositions comprising an anti-GDF8 antibody and an anti-Activin A antibody and therapeutic methods are disclosed in, e.g., U.S. Pat. No. 8,871,209.

Obesity is a global problem for over a third of the world population. In the United States of America, the average obesity rate is over 20%. The costs of obesity-related illness are staggering, amounting to $190.2 billion, roughly 21% of annual medical costs in the U.S. Obesity is an epidemic disease characterized by chronic low-grade inflammation associated with dysfunctional (elevated) fat mass. In Framingham Heart Study participants, abdominal adiposity was associated with incident cardiovascular disease (CVD) after adjustments for clinical risk factors and overall adiposity. Britton JACC 2013 62; 921. Abdominal visceral fat accumulation was positively associated with the progression of coronary noncalcified plaque. Imai Atherosclerosis 2012. Because high fat mass is associated with such serious conditions as congestive heart failure, high blood pressure/hypertension, pulmonary embolism, osteoarthritis, lymphedema, gastro-esophageal reflux disease, chronic renal failure, cancer, fatty-liver disease, and even depression, there remains a need for therapies that reduce total fat and/or android fat mass in subjects.

BRIEF SUMMARY OF THE INVENTION

In one aspect, the invention is directed to a method for altering body composition in a subject, i.e., increase muscle mass and decreasing fat mass, comprising administering a first composition comprising an effective amount of a GDF8 inhibitor and a second composition comprising an effective amount of an Activin A inhibitor to the subject. In another aspect, the invention is directed to a method for inducing a reduction in fat mass in a subject comprising administering an effective amount of a composition comprising a GDF8 inhibitor and an Activin A inhibitor to the subject.

In another aspect, the invention is directed to a method for treating a disease or disorder characterized by or associated with increased fat mass, the method comprising administering to a subject in need thereof a first composition comprising an effective amount of a GDF8 inhibitor and a second composition comprising an effective amount of an Activin A inhibitor. In another aspect, the invention is directed to a method for treating a disease or disorder characterized by or associated with increased fat mass, the method comprising administering to a subject in need thereof an effective amount of a composition comprising a GDF8 inhibitor and an Activin A inhibitor. In one aspect, the invention is directed to a method for altering body composition in a subject, i.e., increase muscle mass and decreasing fat mass, comprising administering an effective amount of a GDF8 inhibitor and an effective amount of an Activin A inhibitor to the subject, wherein there is an insignificant change in total body mass. Thus, in one aspect of the invention, a subject administered an effective amount of a GDF8 inhibitor and an effective amount of an Activin A inhibitor will experience an increase in muscle mass concurrently with a decrease in fat mass, leading to a minimal and/or insignificant change in total body mass.

In one aspect, the invention is directed to a use of a GDF8 inhibitor and/or an Activin A inhibitor in the preparation of a medicament for achieving a reduction in fat mass in a subject. In another aspect, the invention is directed to a use of a GDF8 inhibitor and/or an Activin A inhibitor in the preparation of a medicament for treating a disease or disorder associated with increased fat mass in a subject.

In some embodiments, a GDF8 inhibitor is provided for use in a method for treating a disease or disorder characterized by increased fat mass, wherein the method comprises administrating to a subject the GDF8 inhibitor and an Activin A inhibitor.

In some embodiments, an Activin A inhibitor is provided for use in a method for treating a disease or disorder characterized by increased fat mass, wherein the method comprises administrating to a subject the Activin A inhibitor and a GDF8 inhibitor.

In some embodiments, a non-therapeutic method is provided for decreasing fat mass in a subject, the method comprising administering to the subject an Activin A inhibitor and a GDF8 inhibitor.

In one embodiment of a method according to the invention, the effective amount of a GDF8 inhibitor comprises a dosing regimen selected from the group consisting of at least 0.1 mg/kg to about 10 gm/kg, 1 mg/kg to about 1 gm/kg, and 10 mg/kg to 100 mg/kg. In a further embodiment of a method according to the invention, the effective amount of a GDF8 inhibitor comprises a dosing regimen selected from the group consisting of a single dose of about 0.01 to about 20 mg/kg body weight, about 0.1 to about 10 mg/kg body weight, and about 0.1 to about 5 mg/kg body weight.

In another embodiment of a method according to the invention, the effective amount of an Activin A inhibitor comprises a dosing regimen selected from the group consisting of at least 0.1 mg/kg to about 10 gm/kg, 1 mg/kg to about 1 gm/kg, and 10 mg/kg to 100 mg/kg. In a further embodiment of a method according to the invention, the effective amount of an Activin A inhibitor comprises a dosing regimen selected from the group consisting of a single dose of about 0.01 to about 20 mg/kg body weight, about 0.1 to about 10 mg/kg body weight, and about 0.1 to about 5 mg/kg body weight.

In one embodiment of a method according to the invention, the effective amount of a GDF8 inhibitor is 6 mg/kg body weight and the effective amount of an Activin A inhibitor is 3 mg/kg body weight. In one embodiment of a method according to the invention, the effective amount of a GDF8 inhibitor is 6 mg/kg body weight and the effective amount of an Activin A inhibitor is 10 mg/kg body weight.

In one embodiment of a method according to the invention, the first composition is formulated for intravenous, subcutaneous, or oral administration. In another embodiment of a method according to the invention, the second composition is formulated for intravenous, subcutaneous, or oral administration. In certain embodiments of a method according to the invention, the first and second compositions are administered concurrently or sequentially to the subject.

In one embodiment of a method according to the invention, the first and second compositions are combined into a third composition prior to administration. In a further embodiment, the third composition is formulated for intravenous, subcutaneous, or oral administration.

In one embodiment, a method according to the invention further comprises measuring total fat mass in the subject before administration. In another embodiment, a method according to the invention further comprises measuring total fat mass in the subject after administration, and administering the first and second composition until the subject has a reduction in total fat mass of at least 2% to 8%, 2.5% to 6%, 3% to 4%, or at least 2.0%, at least 2.5%, at least 3.0%, or at least 3.5%, or more.

In one embodiment, a method according to the invention further comprises measuring android fat mass in the subject before administration. In another embodiment, a method according to the invention further comprises measuring android fat mass in the subject after administration, and administering the first and second composition until the subject has a reduction in android fat mass of at least 2% to 8%, 2.5% to 6%, 3% to 4%, or at least 2.0%, at least 2.5%, at least 3.0%, or at least 3.5%, or more.

In one embodiment, a method according to the invention further comprises measuring subcutaneous adipose tissue volume in the subject before administration. In another embodiment, a method according to the invention further comprises measuring subcutaneous adipose tissue volume in the subject after administration, and administering the first and second composition until the subject has a reduction in android fat mass of at least 2% to 8%, 2.5% to 6%, 3% to 4%, or at least 2.0%, at least 2.5%, at least 3.0%, or at least 3.5%, or more.

In some embodiments, a method is provided comprising administering to a subject in need thereof an effective amount of a GDF8 inhibitor and an effective amount of a Activin A inhibitor, wherein the GDF8 inhibitor and the Activin A inhibitor are co-administered within 48 hours or less, 24 hours or less, 12 hours or less, 6 hours or less, 3 hours or less, or 1 hour or less.

In some embodiments, a method is provided comprising administering to a subject in need thereof an effective amount of a GDF8 inhibitor and an effective amount of a Activin A inhibitor, wherein the subject exhibits a decrease in total fat mass, android fat mass, and/or subcutaneous adipose tissue volume.

In some embodiments, a method is provided comprising administering to a subject in need thereof an effective amount of a GDF8 inhibitor and an effective amount of a Activin A inhibitor, wherein the subject exhibits a decrease in total fat mass, android fat mass, and/or subcutaneous adipose tissue volume after 4 weeks or more, or 8 weeks or more, following administration.

In some embodiments, a method is provided comprising administering to a subject in need thereof an effective amount of a GDF8 inhibitor and an effective amount of a Activin A inhibitor, wherein the subject exhibits a decrease in total fat mass, android fat mass, and/or subcutaneous adipose tissue volume, wherein the subject does not exhibit reduced thigh intramuscular adipose tissue volume.

In some embodiments, a method is provided comprising administering to a subject in need thereof an effective amount of a GDF8 inhibitor and an effective amount of a Activin A inhibitor, wherein the subject exhibits a decrease in total fat mass, android fat mass, and/or subcutaneous adipose tissue volume, wherein the subject does not exhibit reduced thigh intramuscular adipose tissue volume after 4 weeks or more, or 8 weeks or more, following administration.

In some embodiments, a kit is provided comprising a first container containing a effective amount of a GDF8 inhibitor and a second container containing an effective amount of a specific Activin A inhibitor.

In some embodiments, the GDF8 inhibitor is an isolated antibody or an antigen-binding fragment thereof that specifically binds to GDF8.

In one embodiment of a method according to the invention, the GDF8 inhibitor is an antibody or an antigen-binding fragment thereof that specifically binds to GDF8. In another embodiment, the antibody or antigen-binding fragment that specifically binds GDF8 comprises the heavy chain complementarity determining regions (HCDRs) of a heavy chain variable region (HCVR) comprising SEQ ID NO:360, and the light chain complementarity determining regions (LCDRs) of a light chain variable region (LCVR) comprising SEQ ID NO:368. In still another embodiment, the antibody or antigen-binding fragment that specifically binds GDF8 comprises three HCDRs comprising SEQ ID NO:362, SEQ ID NO:364, and SEQ ID NO:366, and three LCDRs comprising SEQ ID NO:370, SEQ ID NO:372, and SEQ ID NO:374.

In some embodiments, the Activin A inhibitor is an isolated antibody or an antigen-binding fragment thereof that specifically binds to Activin A.

In one embodiment of a method according to the invention, the Activin A inhibitor is an antibody or antigen-binding fragment thereof that specifically binds Activin A. In another embodiment, the antibody or antigen-binding fragment that specifically binds Activin A comprises the heavy chain complementarity determining regions (HCDRs) of a heavy chain variable region (HCVR) comprising SEQ ID NO:553, and the light chain complementarity determining regions (LCDRs) of a light chain variable region (LCVR) comprising SEQ ID NO:537. In still another embodiment, the antibody or antigen-binding fragment that specifically binds Activin A comprises three HCDRs comprising SEQ ID NO:555, SEQ ID NO:557, and SEQ ID NO:559, and three LCDRs comprising SEQ ID NO:539, SEQ ID NO:541, and SEQ ID NO:543.

In one embodiment of a method according to the invention, the effective dose of the Activin A inhibitor is selected from the group comprising between 100% to 200% of the effective dose of the GDF8 inhibitor, between 100% and 250% of the effective dose of the GDF8 inhibitor, between 100% and 300% of the effective dose of the GDF8 inhibitor, and between 100% and 400% by weight of the effective dose of the GDF8 inhibitor.

In another embodiment of a method according to the invention, the weight ratio of the effective dose of the Activin A inhibitor to effective dose of the GDF8 inhibitor is from 10:1 to 1:10, 8:1 to 1:8, 6:1 to 1:6, 3:1 to 1:3, or about 2:1 to 1:2. In another embodiment of a method according to the invention, the weight ratio of the effective dose of the Activin A inhibitor is about 1.5 to 2.0 times as large by weight as the amount the GDF8 inhibitor.

In one embodiment of a method according to the invention, the GDF8 inhibitor is a bispecific antibody or antigen-binding fragment thereof that specifically binds GDF8 and also specifically binds Activin A. In another embodiment, the Activin A inhibitor is a bispecific antibody or antigen-binding fragment thereof that specifically binds Activin A and also specifically binds GDF8.

In one embodiment of a method according to the invention, the reduction of fat mass in the subject is a reduction in total fat mass as measured by DXA (Dual-energy X-ray absorptiometry). In another embodiment of a method according to the invention, the reduction of fat mass in the subject is a reduction in android fat mass as measured by DXA (Dual-energy X-ray absorptiometry).

In one embodiment of a method according to the invention, the reduction of fat mass in the subject is a reduction in subcutaneous adipose tissue volume as measured by MRI (Magnetic Resonance Imaging).

In one embodiment of a method according to the invention, the subject experiences an increase in muscle volume. The muscle volume may be thigh muscle tissue volume, for example, as measured by MRI. In some embodiments, the muscle volume may be thigh muscle tissue volume, for example, as measured by MRI. In some embodiments, the thigh muscle volume may be thigh muscle tissue volume including intramuscular adipose tissue and large vessels, or thigh muscle tissue volume excluding intramuscular adipose tissue and large vessels, for example, as measured by MRI.

In one embodiment of a method according to the invention, the subject experiences an increase in total lean mass. The total lean mass may be measured by DXA (dual x-ray absorptiometry.

In one embodiment of a method according to the invention, the subject experiences an increase in appendicular lean body mass. The appendicular lean body mass may be measured by DXA, and, for example, calculated by aLBM equation.

In one embodiment of a method according to the invention, the subject experiences a decrease in total fat mass, for example, as measured by DXA.

In one embodiment of a method according to the invention, the subject experiences a decrease in android fat mass, for example, as measured by DXA.

In one embodiment of a method according to the invention, the subject experiences a decrease in subcutaneous adipose tissue volume, for example, as measured by DXA.

In one embodiment of a method according to the invention, the subject experiences a decrease in sum of fat mass of arms and legs, for example, as measured by DXA.

In one embodiment of the invention, the subject does not exhibit a decrease in thigh intramuscular adipose tissue volume, for example, as measured by MRI.

In one embodiment of the invention, the subject does not exhibit a decrease in total bone mineral density (BMD) mass, for example, as measured by DXA.

In one embodiment of the invention, the subject does not exhibit a decrease in total bone mineral content (BMC) mass, for example, as measured by DXA.

In one embodiment of the invention, the subject exhibits an increase in total bone mineral content (BMC) mass, for example, as measured by DXA.

In another embodiment of a method according to the invention, the subject does not have a muscle wasting condition or disease.

In some embodiments, a kit is provided for use in altering body composition, decreasing fat mass, increasing lean mass, or treating a disease or disorder characterized by or associated with increased fat mass, the kit comprising a first container comprising a composition comprising an effective amount of a GDF8 inhibitor and a second container comprising a second composition comprising an effective amount of an Activin A inhibitor.

In some embodiments, a GDF8 inhibitor is provided for use in manufacture of a first composition for use as a medicament in a kit for altering body composition, decreasing fat mass, increasing lean mass, or treating a disease or disorder characterized by or associated with increased fat mass, the kit further comprising a second composition comprising an Activin A inhibitor.

In some embodiments, an Activin A inhibitor is provided for use in manufacture of a first composition for use as a medicament in a kit for altering body composition, decreasing fat mass, increasing lean mass, or treating a disease or disorder characterized by or associated with increased fat mass, the kit further comprising a second composition comprising a GDF8 inhibitor.

In some embodiments, a GDF8 inhibitor is provided for use in manufacture of a first composition for use in a kit for altering body composition, decreasing fat mass, or increasing lean mass in a subject, the kit further comprising a second composition comprising an Activin A inhibitor.

In some embodiments, an Activin A inhibitor is provided for use in manufacture of a first composition for use in a kit for altering body composition, decreasing fat mass, or increasing lean mass in a subject, the kit further comprising a second composition comprising a GDF8 inhibitor.

In some embodiments, a first composition comprising a GDF8 inhibitor is provided for use in altering body composition, decreasing fat mass, increasing lean mass, or treating a disease or disorder characterized by or associated with increased fat mass or decreased lean mass in a subject, wherein the subject has received a second composition comprising an Activin A inhibitor.

In some embodiments, a first composition comprising an Activin A inhibitor is provided for use in altering body composition, decreasing fat mass, increasing lean mass, or treating a disease or disorder characterized by or associated with increased fat mass or decreased lean mass in a subject, wherein the subject has received a second composition comprising a GDF8 inhibitor.

In some embodiments, a first composition comprising a GDF8 inhibitor is provided for use in method for altering body composition, decreasing fat mass, increasing lean mass, or treating a disease or disorder characterized by or associated with increased fat mass or decreased lean mass, the method further comprising administering a second composition comprising an Activin A inhibitor.

In some embodiments, a first composition comprising an Activin A inhibitor is provided for use in method for altering body composition, decreasing fat mass, increasing lean mass, or treating a disease or disorder characterized by or associated with increased fat mass or decreased lean mass, the method further comprising administering a second composition comprising an GDF8 inhibitor.

In some embodiments, a composition is provided comprising an Activin A inhibitor and a GDF8 inhibitor for use in altering body composition, decreasing fat mass, increasing lean mass, or treating or preventing a disease or disorder characterized by or associated with increased fat mass or decreased lean mass.

Other embodiments of the present invention will become apparent from a review of the ensuing detailed description.

BRIEF DESCRIPTION OF THE FIGURES

FIG. 2A shows Table 1 with the ascending dose panels used in the study of 48 healthy post-menopausal women according to Example 2. A single intravenous dose of anti-GDF8 antibody REGN1033 and/or anti-Activin A antibody REGN2477 was utilized. In the primary analyses, the placebo and high dose combination groups were pooled across panels, yielding 12 subjects on placebo and 12 on the high dose combination, as shown by boxed regions in the table.

DETAILED DESCRIPTION

Figure 1:
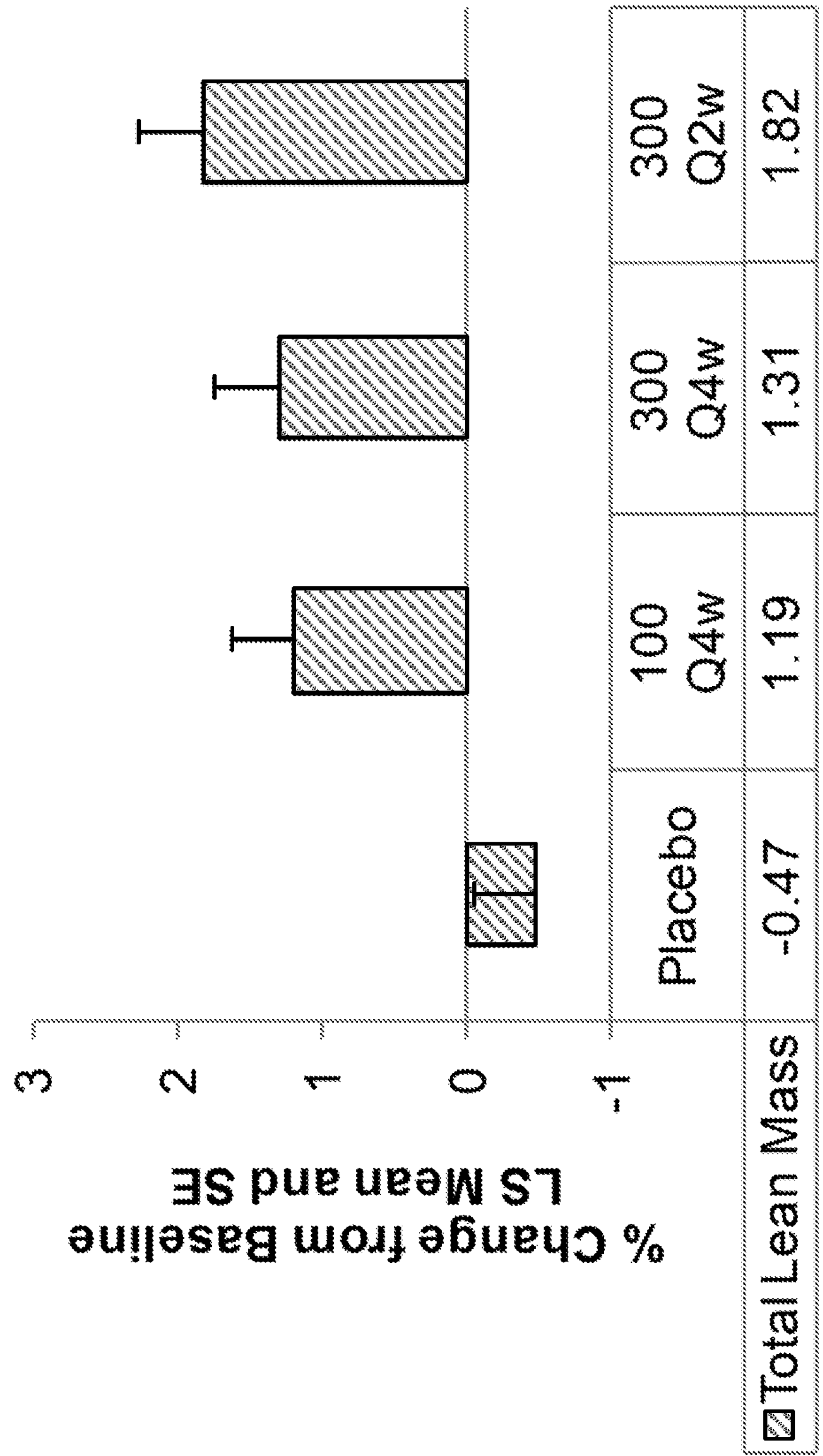
FIG. 1 shows a bar graph depicting results of clinical studies in sarcopenia patients 70 years of age or older receiving anti-GDF8 antibody REGN1033 alone after 12 weeks as the percent change from baseline of total lean mass in LS mean and SE compared to placebo. Patients receiving REGN1033 exhibited significantly increased total lean body mass at 12 weeks at each of three dosing regimens when compared to placebo (n=65). Patients receiving 100 mg anti-GDF8 antibody REGN1033 Q4W S.C. exhibited a difference vs. placebo of 1.66% total lean mass (n=62, P=0.0077). Patients receiving 300 mg anti-GDF8 Q4W SC exhibited a difference vs. placebo of 1.78% total lean mass (n=64, P=0.0043). Patients receiving 300 mg Q2W SC exhibited a difference vs. placebo of 2.29% total lean mass (n=59, P=0.0004).

Before the present invention is described, it is to be understood that this invention is not limited to particular compositions, methods, and experimental conditions described, as such compositions, methods, and conditions may vary. It is also to be understood that the terminology used herein is for the purpose of describing particular embodiments only, and is not intended to be limiting, since the scope of the present invention will be limited only by the appended claims. Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference in their entirety.

Antibodies and Antigen-Binding Fragments of Antibodies

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies (or antigen-binding portion thereof) may be identical to the human germline sequences, or may be naturally or artificially modified. An amino acid consensus sequence may be defined based on a side-by-side analysis of two or more CDRs.

Antibodies may be referred to herein according to the following nomenclature: Fc prefix (e.g. "H1M," "H2aM," "H4H"), followed by a numerical identifier (e.g. "10446"), followed by a "P," "P2" or "N" suffix. Thus, according to this nomenclature, an antibody may be referred to herein as, e.g., "H4H10446P2". The H1M, H2M and H4H prefixes on the antibody designations used herein indicate the particular Fc region isotype of the antibody. For example, an "H2aM" antibody has a mouse IgG2a Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG2a Fc can be converted to an antibody with a human IgG4, etc.), but in any event, the variable domains (including the CDRs) will remain the same, and the binding properties are expected to be identical or substantially similar regardless of the nature of the Fc domain.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody used in the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody used in the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

Full antibody molecules and antigen-binding fragments may be monospecific or multispecific (e.g., bispecific). A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment described herein using routine techniques available in the art.

The antibodies used in the compositions and methods of the invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., *Proc. Natl. Acad. Sci.* (*USA*) 95:652-656 (1998)).

The antibodies described herein may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibody molecules described herein may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Recombinant antibodies may be used in an additional embodiment of the compositions and methods of the invention.

An "isolated antibody," as used herein, means an antibody that has been identified and separated and/or recovered from at least one component of its natural environment. For example, an antibody that has been separated or removed from at least one component of an organism, tissue or cell in which the antibody naturally exists or is naturally produced is an "isolated antibody" for purposes of the invention. An isolated antibody also includes an antibody in situ within a recombinant cell, as well as an antibody that has been subjected to at least one purification or isolation step.

According to certain embodiments, an isolated antibody may be substantially free of other cellular material and/or chemicals. Isolated antibodies may be used in an additional embodiment of the compositions and methods of the invention.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% w/w of a protein sample, usually about 95%, and preferably over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide analog or variant" as used herein refers to a polypeptide that is comprised of a segment of at least 25 amino acids that has substantial identity to a portion of an amino acid sequence and that has at least one of the following properties: (1) specific binding to GDF8 under suitable binding conditions, or (2) ability to block the biological activity of GDF8. Typically, polypeptide analogs or variants comprise a conservative amino acid substitution (or insertion or deletion) with respect to the naturally occurring sequence. Analogs typically are at least 20 amino acids long, at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton 1984 W. H. Freeman and Company, New York; Introduction to Protein Structure (Branden & Tooze, eds., 1991, Garland Publishing, NY); and Thornton et at. 1991 Nature 354:105, which are each incorporated herein by reference.

Non-peptide analogs are commonly used in the pharmaceutical industry as drugs with properties analogous to those of the template peptide. These types of non-peptide compound are termed "peptide mimetics" or "peptidomimetics" (see, for example, Fauchere (1986) J. Adv. Drug Res. 15:29; and Evans et al. (1987) J. Med. Chem. 30:1229, which are incorporated herein by reference. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al. (1992) Ann. Rev. Biochem. 61:387, incorporated herein by reference), for example, by adding internal cysteine residues capable of forming intramolecular disulfide bridges which cyclize the peptide.

As applied to polypeptides, the term "substantial identity" or "substantially identical" means that two peptide sequences, when optimally aligned, such as by the programs GAP or BESTFIT using default gap weights, share at least about 80% sequence identity, at least about 90%, at least about 95%, at least about 98% or at least about 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000), supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215:403-410 and Altschul et al. (1997) Nucleic Acids Res. 25:3389 402, each of which is herein incorporated by reference.

The length of polypeptide sequences compared for homology will generally be at least about 16 amino acid residues, at least about 20 residues, at least about 24 residues, at least about 28 residues, or at least about 35 residues. When searching a database containing sequences from a large number of different organisms, it is preferable to compare amino acid sequences.

In some embodiments, the invention relates to a method for altering the body composition of a subject comprising administering a first composition comprising an effective amount of a GDF8 inhibitor and a second composition comprising an effective amount of an Activin A inhibitor to the subject.

In some embodiments, the invention relates to a method for inducing a reduction in fat mass in a subject comprising administering a first composition comprising an effective amount of a GDF8 inhibitor and a second composition comprising an effective amount of an Activin A inhibitor to the subject.

In some embodiments, the invention relates to a method for inducing an increase in muscle mass in a subject, the method comprising administering to a subject in need thereof a first composition comprising an effective amount of a GDF8 inhibitor and a second composition comprising an effective amount of an Activin A inhibitor.

In some embodiments, the invention relates to a method for altering the body composition of a subject comprising administering a composition comprising an effective amount of a GDF8 inhibitor and an effective amount of an Activin A inhibitor to the subject.

In some embodiments, the invention relates to a method for inducing a reduction in fat mass in a subject comprising administering a composition comprising an effective amount of a GDF8 inhibitor and an effective amount of an Activin A inhibitor to the subject.

In some embodiments, the invention relates to a method for inducing an increase in muscle mass in a subject, the method comprising administering to a subject in need thereof a composition comprising an effective amount of a GDF8 inhibitor and an effective amount of an Activin A inhibitor.

In some embodiments, the subject is a human subject. The human subject may be an adult human subject. The subject may be a male or female subject. The subject may be a healthy subject. The subject may be suffering from unwanted fat mass. The subject may be suffering from, or at risk of suffering from, a disease and disorder characterized by increased fat mass, and/or decreased muscle volume or decreased lean body mass. The subject may be a post-menopausal female subject. The subject may be a male subject or female subject 40 years of age or older, 50 years of age or older, 60 years of age or older, or 70 years of age or older.

In some embodiments, the invention relates to a method comprising administering a composition comprising a GDF8 inhibitor and a composition comprising an Activin A inhibitor to a subject in need thereof for treating or preventing diseases and disorders characterized by increased fat mass, and/or decreased muscle volume or decreased lean body mass.

In some embodiments according to the invention, the subject has at least one disease or disorder that may be associated with increased fat mass. In some embodiments, the disease or disorder may be selected from the group consisting of obesity, metabolic syndromes, nutritional disorders, high cholesterol, dyslipidemia, cardiovascular disease, cellulitis, cancer (including of the colon, esophagus, kidney, pancreas, gallbladder, breast, or endometrium), polycystic ovarian syndrome, gout, gallbladder disease, sleep apnea, respiratory disorder, asthma, osteoarthritis, cataract, congestive heart failure, enlarged heart, high blood pressure/hypertension, pulmonary embolism, lymphedema, gastro-esophageal reflux disease, hernia, chronic renal failure, urinary incontinence, connective tissue diseases, and fatty-liver disease. In another embodiment, the disease or disorder may be sarcopenia.

GDF8 Inhibitors

The present invention includes methods for altering body composition, inducing a reduction in fat mass, and increasing lean mass in a subject, and methods for treating a disease or disorder characterized by increased fat mass in a subject, comprising administering a composition comprising an effective amount of a GDF8 inhibitor to the subject.

The term "GDF8" (also referred to as "growth and differentiation factor-8" and "myostatin") means the protein having the amino acid sequence of SEQ ID NO:340 (mature protein). According to the present invention, GDF8-specific binding proteins specifically bind GDF8 but do not bind other ActRIIB ligands such as GDF3, BMP2, BMP4, BMP7, BMP9, BMP10, GDF11, Activin A, Activin B, Activin AB, Nodal, etc.

As used herein, a "GDF8 inhibitor" is any agent that binds to or interacts with human GDF8 and interferes with or inhibits the normal biological function of GDF8 in vitro or in vivo. Non-limiting examples of categories of GDF8 inhibitors include small molecule GDF8 antagonists, nucleic acid-based inhibitors of GDF8 expression or activity (e.g., siRNA or antisense), peptide-based molecules that specifically interact with GDF8 (e.g., peptibodies), receptor molecules that specifically interact with GDF8, GDF8-binding scaffold molecules, proteins comprising a ligand-binding portion of a receptor that specifically binds GDF8, and anti-GDF8 aptamers or portions thereof. In a preferred embodiment, a GDF8 inhibitor that can be used in the context of the present invention is an anti-GDF8 antibody or antigen-binding fragment thereof that specifically binds human GDF8. Anti-GDF8 antibodies include neutralizing and/or blocking antibodies. The inhibition caused by anti-GDF8 neutralizing and/or blocking antibodies need not be complete, as long as it is detectable using appropriate assays.

As used herein, the expression "anti-GDF8 antibody" also includes multispecific antigen-binding molecules (e.g., bispecific antibodies), wherein at least one binding domain (e.g., "binding arm") of the multispecific antigen-binding molecule specifically binds GDF8.

Exemplary anti-GDF8 antibodies that can be used in the compositions and methods of the invention include, e.g., the fully-human anti-GDF8 antibody H4H1657N2, also known as REGN1033, (e.g., an anti-GDF8 antibody comprising the heavy and light chain variable regions having amino acid sequences SEQ ID NO: 360 and SEQ ID NO: 368, respectively, as set forth in U.S. Pat. No. 8,840,894). Other GDF8 antagonists that can be used in the compositions and methods of the invention include anti-GDF8 antibodies (e.g., the antibody designated 2_112_1, e.g., having ATCC deposit designation PTA-6574, or e.g., 2_112_K, e.g., having HCVR/LCVR amino acid sequences SEQ ID NOs: 620 and 621) as set forth in US 2006/0263354 and U.S. Pat. No. 7,807,159; anti-GDF8 antibodies (e.g., 12A5-5, e.g., having HCVR/LCVR amino acid sequences of SEQ ID NO: 622 and 623) as set forth in U.S. Pat. No. 8,999,343 and US Publication No. 2013/0209489; anti-GDF8 antibodies (e.g., 10B3H8L5, e.g., having HCVR/LCVR amino acid sequences of SEQ ID NO:624 and 625, and 10B3H8L5-Fc-disabled) as set forth in US Publication No. 2013/0142788; anti-GDF8 antibodies (e.g., stamulumab/MYO-29, e.g., having HCVR/LCVR amino acid sequences of SEQ ID NOs: 626 and 627) as set forth in U.S. Pat. Nos. 8,940,874 and 7,261,893; anti-GDF8 antibodies (e.g., RK22/PF-0625616, e.g., having HCVR/LCVR amino acid sequences of SEQ ID NO: 628 and 629) as set forth in U.S. Pat. No. 8,415,459; anti-GDF8 antibodies (e.g., JA-16, e.g., having CDRs of HCVR amino acid sequence of SEQ ID NO: 630) as set forth in U.S. Pat. No. 7,731,961; anti-GDF8 antibodies (e.g., RK35, e.g., having HCVR/LCVR amino acid sequences of SEQ ID NO: 631 and 632) as set forth in U.S. Pat. No. 8,496,934 or 7,888,486, anti-GDF8 antibodies (e.g., OGD1.0.0, e.g., having HCVR/LCVR amino acid sequences of SEQ ID NO: 633 and 634) as set forth in U.S. Pat. No. 8,992,913; anti-GDF8 Fab molecules as set forth in European Patent No. 1 773 041 B1, and anti-GDF8 antibodies (e.g., C12, e.g., having HCVR/LCVR amino acid sequences of SEQ ID NOs: 635 and 636, C12-N93H, and/or 510C2 having HCVR/LCVR amino acid sequences of SEQ ID NOs: 637 and 638) as set forth in, e.g., U.S. Pat. Nos. 7,635,760 and 8,063,188, anti-GDF8 antibodies (e.g. 41C1E4/landogrozumab/LY2495655, e.g., having HCVR/LCVR amino acid sequences of SEQ ID NO: 639 and 640) as set forth in U.S. Pat. No. 7,632,499. In some embodiments, the anti-GDF8 antibody may have the full length heavy chain and full length light chain amino acid sequences of landogrozumab, e.g., SEQ ID Nos 641 and 642, respectively. In some embodiments, the anti-GDF8 antibody may comprise three heavy chain CDRs (HCDRs) and three light chain CDRs (LCDRs) of landogrozumab, for example, by Chothia definition, according to SEQ ID Nos: 643/644/645/646/647/648, respectively.

In one embodiment, an anti-GDF8 antibody or antigen-binding fragment thereof comprises a heavy chain variable region (HCVR) having an amino acid sequence selected from the group consisting of SEQ ID NO:2, 18, 34, 50, 66, 82, 98, 114, 130, 146, 162, 178, 194, 210, 226, 242, 258, 274, 290, 306, 360, and 376, or a substantially similar sequence thereof having at least 90%, at least 95%, at least 98% or at least 99% sequence identity.

In another embodiment, an anti-GDF8 antibody or antigen-binding fragment thereof comprises a light chain variable region (LCVR) amino acid sequence selected from the group consisting of SEQ ID NO:10, 26, 42, 58, 74, 90, 106, 122, 138, 154, 170, 186, 202, 218, 234, 250, 266, 282, 298, 314, 322, 368, and 384, or a substantially similar sequence thereof having at least 90%, at least 95%, at least 98% or at least 99% sequence identity.

In another embodiment, an anti-GDF8 antibody or antigen-binding fragment thereof comprises a HCVR amino acid sequence and a LCVR amino acid sequence, wherein the HCVR/LCVR sequence pair is selected from the group consisting of SEQ ID NO:2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, and 376/384.

In another embodiment, an anti-GDF8 antibody or antigen-binding fragment thereof comprises a HCVR amino acid sequence and a LCVR amino acid sequence, wherein the HCVR/LCVR sequence pair is selected from the group consisting of (HCVR/LCVR): 21-E5 (SEQ ID NO:34/42); 21-B9 (SEQ ID NO:18/26); 21-E9 (SEQ ID NO:98/106); 21-A2 (SEQ ID NO:2/10); 22-D3 (SEQ ID NO:50/58); 22-E6 (SEQ ID NO:66/74); 22-G10 (SEQ ID NO:82/90); 1A2 (SEQ ID NO:226/234); 20B12 (SEQ ID NO:274/282); 58C8 (SEQ ID NO:242/250); 19F2 (SEQ ID NO:258/266); 8D12-1 (SEQ ID NO:114/122); 4E3-7 (SEQ ID NO:194/202); 9B11-12 (SEQ ID NO:162/170); 4B9 (SEQ ID NO:226/234); 1H4-5 (SEQ ID NO:210/218); 9B4-3 (SEQ ID NO:178/186); 3E2-1 (SEQ ID NO:290/298); 4G3-25 (SEQ ID NO:306/314); 4B6-6 (SEQ ID NO:130/138); H4H1657N2 (SEQ ID NO:360/368); H4H1669P (SEQ ID NO:376/384).

In another embodiment, an anti-GDF8 antibody or antigen-binding fragment thereof comprises a heavy chain complementarity determining region 3 (HCDR3) domain and a light chain CDR3 (LCDR3) domain, wherein the HCDR3 domain has an amino acid sequence selected from the group consisting of SEQ ID NO:8, 24, 40, 56, 72, 88, 104, 120, 136, 152, 168, 184, 200, 216, 232, 248, 264, 280, 296, 312, 366, and 382, or a substantially similar sequence thereof having at least 90%, at least 95%, at least 98% or at least 99% sequence identity, and the LCDR3 domain has an amino acid sequence selected from the group consisting of SEQ ID NO:16, 32, 48, 64, 80, 96, 112, 128, 144, 160, 176, 192, 208, 224, 240, 256, 272, 288, 304, 320, 328, 374, and 390, or a substantially similar sequence thereof having at least 90%, at least 95%, at least 98% or at least 99% sequence identity. In another embodiment, an anti-GDF8 antibody or antigen-binding fragment thereof comprises an HCDR3/LCDR3 amino acid sequence pair selected from the group consisting of SEQ ID NO:8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 120/328, 366/374, and 382/390.

In another embodiment, an anti-GDF8 antibody or antigen-binding fragment thereof comprises heavy chain CDR1 (HCDR1) and CDR2 (HCDR2) domains and light chain CDR1 (LCDR1) and CDR2 (LCDR2) domains, wherein the HCDR1 domain has an amino acid sequence selected from the group consisting of SEQ ID NO:4, 20, 36, 52, 68, 84, 100, 116, 132, 148, 164, 180, 196, 212, 228, 244, 260, 276, 292, 308, 362, and 378, or a substantially similar sequence thereof having at least 90%, at least 95%, at least 98% or at least 99% sequence identity; the HCDR2 domain has an amino acid sequence selected from the group consisting of SEQ ID NO:6, 22, 38, 54, 70, 86, 102, 118, 134, 150, 166, 182, 198, 214, 230, 246, 262, 278, 294, 310, 364, and 380, or a substantially similar sequence thereof having at least 90%, at least 95%, at least 98% or at least 99% sequence identity; the LCDR1 domain has an amino acid sequence selected from the group consisting of SEQ ID NO:12, 28, 44, 60, 76, 92, 108, 124, 140, 156, 172, 188, 204, 220, 236, 252, 268, 284, 300, 316, 324, 370, and 386, or a substantially similar sequence thereof having at least 90%, at least 95%, at least 98% or at least 99% sequence identity and the LCDR2 domain has an amino acid sequence selected from the group consisting of SEQ ID NO:14, 30, 46, 62, 78, 94, 110, 126, 142, 158, 174, 190, 206, 222, 238, 254, 270, 286, 302, 318, 326, 372, and 388, or a substantially similar sequence thereof having at least 90%, at least 95%, at least 98% or at least 99% sequence identity. In another embodiment, the HCDR1, HCDR2 and HCDR3 domains have respective amino acid sequence combinations selected from the group consisting of SEQ ID NO:36/38/40, 116/118/120, 228/230/232, 362/364/366, and 378/380/382; and the LCDR1, LCDR2 and LCDR3 domains have respective amino acid sequence combinations selected from the group consisting of SEQ ID NO:44/46/48, 124/126/128, 236/238/240, 370/372/374, and 386/388/390.

In yet another embodiment, the heavy and light chain CDR domains of the anti-GDF8 antibody or antigen-binding fragment thereof (HCDR1/HCDR2/HCDR3/LCDR1/LCDR2/LCDR3) have amino acid sequence combinations selected from the group consisting of SEQ ID NO: 36/38/40/44/46/48 (e.g., 21-E5), 116/118/120/124/126/128 (e.g., 8D12), 228/230/232/236/238/240 (e.g., 1A2), 362/364/366/370/372/374 (e.g., H4H1657N2), and 378/380/382/386/388/390 (e.g., H4H1669P).

In another embodiment, an anti-GDF8 antibody or antigen-binding fragment thereof comprises heavy and light chain CDR domains contained within heavy and light chain variable region (HCVR/LCVR) amino acid sequence pairs selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, and 376/384.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In one embodiment, an anti-GDF8 antibody or antigen-binding fragment thereof comprises a HCVR having an amino acid sequence encoded by a nucleic acid sequence selected from the group consisting of SEQ ID NO:1, 17, 33, 49, 65, 81, 97, 113, 129, 145, 161, 177, 193, 209, 225, 241, 257, 273, 289, 305, 359, and 375, or a substantially similar sequence thereof having at least 90%, at least 95%, at least 98% or at least 99% sequence identity.

In another embodiment, an anti-GDF8 antibody or antigen-binding fragment thereof comprises a LCVR having an amino acid sequence encoded by a nucleic acid sequence selected from the group consisting of SEQ ID NO:9, 25, 41, 57, 73, 89, 105, 121, 137, 153, 169, 185, 201, 217, 233, 249, 265, 281, 297, 313, 321, 367, and 383, or a substantially similar sequence thereof having at least 90%, at least 95%, at least 98% or at least 99% sequence identity.

In another embodiment, an anti-GDF8 antibody or antigen-binding fragment thereof comprises a HCVR/LCVR pair having amino acid sequences encoded by a nucleic acid molecule pair selected from the group consisting of SEQ ID NO: 1/9, 17/25, 33/41, 49/57, 65/73, 81/89, 97/105, 113/121, 129/137, 145/153, 161/169, 177/185, 193/201, 209/217, 225/233, 241/249, 257/265, 273/281, 289/297, 305/313, 113/321, 359/367, and 375/383.

In another embodiment, an anti-GDF8 antibody or antigen-binding fragment thereof comprises a HCDR3 domain having an amino acid sequence encoded by a nucleic acid sequence selected from the group consisting of SEQ ID NO:7, 23, 39, 55, 71, 87, 103, 119, 135, 151, 167, 183, 199, 215, 231, 247, 263, 279, 295, 311, 365, and 381, or a substantially similar sequence thereof having at least 90%, at least 95%, at least 98% or at least 99% sequence identity, and a LCDR3 domain having an amino acid sequence encoded by a nucleic acid sequence selected from the group consisting of SEQ ID NO:15, 31, 47, 63, 79, 95, 111, 127, 143, 159, 175, 191, 207, 223, 239, 255, 271, 287, 303, 319, 327, 373, and 389, or a substantially similar sequence thereof having at least 90%, at least 95%, at least 98% or at least 99% sequence identity. In one embodiment, the HCDR3/LCDR3 domain pair has amino acid sequences encoded by a nucleic acid sequence pair selected from the group consisting of SEQ ID NO:7/15, 23/31, 39/47, 55/63, 71/79, 87/95, 103/111, 119/127, 135/143, 151/159, 167/175, 183/191, 199/207, 215/223, 231/239, 247/255, 263/271, 279/287, 295/303, 311/319, 119/327, 365/373, and 381/389.

In another embodiment, an anti-GDF8 antibody or antigen-binding fragment thereof comprises HCDR1 and HCDR2 domains, and LCDR1 and LCDR2 domains, wherein the HCDR1 domain has an amino acid sequence encoded by a nucleic acid sequence selected from the group consisting of SEQ ID NO:3, 19, 35, 51, 67, 83, 99, 115, 131, 147, 163, 179, 195, 211, 227, 243, 259, 275, 291, 307, 361, and 377, or a substantially similar sequence thereof having at least 90%, at least 95%, at least 98% or at least 99% sequence identity, the HCDR2 domain has an amino acid sequence encoded by a nucleic acid sequence selected from the group consisting of SEQ ID NO:5, 21, 37, 53, 69, 85, 101, 117, 133, 149, 165, 181, 197, 213, 229, 245, 261, 277, 293, 309, 363, and 379, or a substantially similar sequence thereof having at least 90%, at least 95%, at least 98% or at least 99% sequence identity, the LCDR1 domain has an amino acid sequence encoded by a nucleic acid sequence selected from the group consisting of SEQ ID NO:11, 27, 43, 59, 75, 91, 107, 123, 139, 155, 171, 187, 203, 219, 235, 251, 267, 283, 299, 315, 323, 369, and 385, or a substantially similar sequence thereof having at least 90%, at least 95%, at least 98% or at least 99% sequence identity, and the LCDR2 domain has an amino acid sequence encoded by a nucleic acid sequence selected from the group consisting of SEQ ID NO:13, 29, 45, 61, 77, 93, 109, 125, 141, 157, 173, 189, 205, 221, 237, 253, 269, 285, 301, 317, 325, 371, and 387.

In another embodiment, an anti-GDF8 antibody or antigen-binding fragment thereof comprises heavy and light chain CDR domains (HCDR1/HCDR2/HCDR3/LCDR1/LCDR2/LCDR3) having amino acid sequence combinations encoded by a nucleic acid sequence set of SEQ ID NO:35/37/39/43/45/47, 115/117/119/123/125/127, 227/229/231/235/237/239, 361/363/365/369/371/373, or 377/379/381/385/387/389.

In a preferred embodiment, the anti-GDF8 antibody or antigen-binding fragment thereof that specifically binds GDF8 comprises the HCDRs of a heavy chain variable region (HCVR) comprising SEQ ID NO:360 and the LCDRs of a light chain variable region (LCVR) comprising SEQ ID NO:368. In another embodiment, the anti-GDF8 antibody or antigen-binding fragment that specifically binds GDF8 comprises three HCDRs comprising SEQ ID NO:362, SEQ ID NO:364, and SEQ ID NO:366 and three LCDRs comprising SEQ ID NO:370, SEQ ID NO:372, and SEQ ID NO:374.

In another embodiment, an anti-GDF8 antibody or antigen-binding fragment thereof is a fully human or humanized antibody or antibody fragment that binds GDF8 with an affinity (expressed as a dissociation constant, "KD") of about 1 nM or less, as measured by surface plasmon resonance assay (for example, BIACORE™). In certain embodiments, the antibody of the invention exhibits a KD of about 700 pM or less; about 500 pM or less; about 320 pM or less; about 160 pM or less; about 100 pM or less; about 50 pM or less; about 10 pM or less; or about 5 pM or less.

In another embodiment, an anti-GDF8 antibody or antigen-binding fragment thereof is a fully human or humanized monoclonal antibody (mAb) that specifically binds and inhibits human GDF8 and exhibits an IC50 of less than or equal to about 10 nM; about 5 nM or less; about 3 nM or less; about 2 nM or less; about 1 nM or less; about 500 pM or less; or about 200 pM or less, as measured by GDF8 inducible luciferase assay.

In one embodiment, an anti-GDF8 antibody or antigen-binding fragment thereof has a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (Shield et al. (2002) JBC 277:26733). In other applications, modification of a galactosylation can be made in order to modify complement dependent cytotoxicity (CDC).

In another embodiment, an anti-GDF8 antibody or antigen-binding fragment thereof competes for specific binding to GDF8 with another antibody comprising a HCDR1/HCDR2/HCDR3/LCDR1/LCDR2/LCDR3 domain combination having amino acid sequences selected from the group consisting of SEQ ID NO:36/38/40/44/46/48, 116/118/120/124/126/128, 228/230/232/236/238/240, 362/364/366/370/372/374, or 378/380/382/386/388/390. In another embodiment, an anti-GDF8 antibody or antigen-binding fragment thereof competes for specific binding to GDF8 with another antibody comprising a HCVR/LCVR amino acid sequence pair of SEQ ID NO:2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, or 376/384.

In another embodiment, an anti-GDF8 antibody or antigen-binding fragment thereof recognizes the epitope on GDF8 that is recognized by another antibody comprising a HCDR1/HCDR2/HCDR3/LCDR1/LCDR2/LCDR3 domain combination having amino acid sequences selected from the group consisting of SEQ ID NO: 36/38/40/44/46/48, 116/118/120/124/126/128, 228/230/232/236/238/240, 362/364/366/370/372/374, or 378/380/382/386/388/390. In another embodiment, an anti-GDF8 antibody or antigen-binding fragment thereof recognizes the epitope on GDF8 that is recognized by another antibody comprising a HCVR/LCVR amino acid sequence pair of SEQ ID NO:2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, or 376/384.

Activin A Inhibitors

The present invention includes methods for altering body composition, inducing a reduction in fat mass, and/or increasing lean mass in a subject, and methods for treating a disease or disorder characterized by increased fat mass in a subject comprising administering a composition comprising an effective amount of an Activin A inhibitor to the subject.

As used herein, an "Activin A inhibitor" is any agent that binds to or interacts with human Activin A and interferes with or inhibits the normal biological function of Activin A in vitro or in vivo. Non-limiting examples of categories of Activin A inhibitors include small molecule Activin A antagonists, nucleic acid-based inhibitors of Activin A expression or activity (e.g., siRNA or antisense), peptide-based molecules that specifically interact with Activin A (e.g., peptibodies), receptor molecules that specifically interact with Activin A, Activin A-binding scaffold molecules, proteins comprising a ligand-binding portion of a receptor that specifically binds Activin A, and anti-Activin A aptamers or portions thereof. In a preferred embodiment, an Activin A inhibitor that can be used in the context of the present invention is an anti-Activin A antibody or antigen-binding fragment thereof that specifically binds human Activin A. Anti-Activin A antibodies include neutralizing and/or blocking antibodies. The inhibition caused by anti-Activin A neutralizing and/or blocking antibodies need not be complete, as long as it is detectable using appropriate assays.

Activins are homo- and hetero-dimeric molecules comprising βA and/or βB subunits. The βA subunit has the amino acid sequence of SEQ ID NO:617 and the βB subunit has the amino acid sequence of SEQ ID NO: 619. Activin A is a homodimer of two βA subunits; Activin B is a homodimer of two βB subunits; and Activin AB is a heterodimer of one βA subunit and one βB subunit. An anti-Activin A antibody or antigen-binding fragment thereof specifically binds the βA subunit. Since the βA subunit is found in both Activin A and Activin AB molecules, an "anti-Activin A antibody or antigen-binding fragment thereof" can specifically bind Activin A, as well as Activin AB (by virtue of its interaction with the βA subunit). Therefore, an anti-Activin A antibody or antigen-binding fragment thereof specifically binds Activin A, or Activin A and Activin AB, but does not bind other ActRIIB ligands, such as Activin B, GDF3, GDF8, BMP2, BMP4, BMP7, BMP9, BMP10, GDF11, Nodal, etc.

In some embodiments, an anti-Activin A antibody or antigen-binding fragment thereof is employed as set forth in U.S. Pat. No. 9,718,881. Exemplary anti-Activin A antibodies that can be used in the compositions and methods of the invention include, e.g., the fully-human anti-Activin antibody H4H10446P2, also known as REGN2477, (e.g., an anti-Activin A antibody comprising the heavy and light chain variable regions having amino acid sequences SEQ ID NO: 162 and SEQ ID NO: 146, respectively, as set forth in U.S. Pat. No. 9,718,881).

Table 2 sets forth heavy and light chain variable region amino acid sequence pairs of selected anti-Activin A antibodies and their corresponding antibody identifiers that can be used in the compositions and methods of the invention. The corresponding nucleic acid sequence identifiers are set forth in Table 3.

TABLE 2

| anti-Activin A Amino Acid Sequence Identifiers SEQ ID NOs: | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H4H10423P | 393 | 395 | 397 | 399 | 401 | 403 | 405 | 407 |
| H4H10424P | 409 | 411 | 413 | 415 | 417 | 419 | 421 | 423 |

TABLE 2-continued

| anti-Activin A Amino Acid Sequence Identifiers SEQ ID NOs: | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H4H10426P | 425 | 427 | 429 | 431 | 433 | 435 | 437 | 439 |
| H4H10429P | 441 | 443 | 445 | 447 | 449 | 451 | 453 | 455 |
| H4H10430P | 457 | 459 | 461 | 463 | 465 | 467 | 469 | 471 |
| H4H10432P2 | 473 | 475 | 477 | 479 | 481 | 483 | 485 | 487 |
| H4H10433P2 | 489 | 491 | 493 | 495 | 481 | 483 | 485 | 487 |
| H4H10436P2 | 497 | 499 | 501 | 503 | 481 | 483 | 485 | 487 |
| H4H10437P2 | 505 | 507 | 509 | 511 | 481 | 483 | 485 | 487 |
| H4H10438P2 | 513 | 515 | 517 | 519 | 481 | 483 | 485 | 487 |
| H4H10440P2 | 521 | 523 | 525 | 527 | 481 | 483 | 485 | 487 |
| H4H10442P2 | 529 | 531 | 533 | 535 | 537 | 539 | 541 | 543 |
| H4H10445P2 | 545 | 547 | 549 | 551 | 537 | 539 | 541 | 543 |
| H4H10446P2 | 553 | 555 | 557 | 559 | 537 | 539 | 541 | 543 |
| H4H10447P2 | 561 | 563 | 565 | 567 | 537 | 539 | 541 | 543 |
| H4H10448P2 | 569 | 571 | 573 | 575 | 537 | 539 | 541 | 543 |
| H4H10452P2 | 577 | 579 | 581 | 583 | 537 | 539 | 541 | 543 |
| H4H10468P2 | 585 | –587 | 589 | 591 | 537 | 539 | 541 | 543 |
| H2aM10965N | 593 | 595 | 597 | 599 | 601 | 603 | 605 | 607 |

TABLE 3

| anti-Activin A Nucleic Acid Sequence Identifiers SEQ ID NOs: | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H4H10423P | 392 | 394 | 396 | 398 | 400 | 402 | 404 | 406 |
| H4H10424P | 408 | 410 | 412 | 414 | 416 | 418 | 420 | 422 |
| H4H10426P | 424 | 426 | 428 | 430 | 432 | 434 | 436 | 438 |
| H4H10429P | 440 | 441 | 444 | 446 | 448 | 450 | 452 | 454 |
| H4H10430P | 456 | 458 | 460 | 462 | 464 | 466 | 468 | 470 |
| H4H10432P2 | 472 | 474 | 476 | 478 | 480 | 482 | 484 | 486 |
| H4H10433P2 | 488 | 490 | 492 | 494 | 480 | 482 | 484 | 486 |
| H4H10436P2 | 496 | 498 | 500 | 502 | 480 | 482 | 484 | 486 |
| H4H10437P2 | 504 | 506 | 508 | 510 | 480 | 482 | 484 | 486 |
| H4H10438P2 | 512 | 514 | 516 | 518 | 480 | 482 | 484 | 486 |
| H4H10440P2 | 520 | 522 | 524 | 526 | 480 | 482 | 484 | 486 |
| H4H10442P2 | 528 | 530 | 532 | 534 | 536 | 538 | 540 | 542 |
| H4H10445P2 | 544 | 546 | 548 | 550 | 536 | 538 | 540 | 542 |
| H4H10446P2 | 552 | 554 | 556 | 558 | 536 | 538 | 540 | 524 |
| H4H10447P2 | 560 | 562 | 564 | 566 | 536 | 538 | 540 | 542 |
| H4H10448P2 | 568 | 570 | 572 | 574 | 536 | 538 | 540 | 542 |
| H4H10452P2 | 576 | 578 | 580 | 582 | 536 | 538 | 540 | 542 |
| H4H10468P2 | 584 | 586 | 588 | 590 | 536 | 538 | 540 | 542 |
| H2aM10965N | 592 | 594 | 596 | 598 | 600 | 602 | 604 | 606 |

In one embodiment, an anti-Activin A antibody or antigen-binding fragment thereof comprises a heavy chain variable region (HCVR) having an amino acid sequence selected from the group consisting of SEQ ID NO: 393, 409, 425, 441, 457, 473, 489, 497, 505, 513, 521, 529, 545, 553, 561, 569, 577, 585, and 593, or a substantially similar sequence thereof having at least 90%, at least 95%, at least 98% or at least 99% sequence identity.

In another embodiment, an anti-Activin A antibody or antigen-binding fragment thereof comprises a light chain variable region (LCVR) having an amino acid sequence selected from the group consisting of SEQ ID NO: 401, 417, 433, 449, 465, 481, 537, and 601, or a substantially similar sequence thereof having at least 90%, at least 95%, at least 98% or at least 99% sequence identity.

In another embodiment, an anti-Activin A antibody or antigen-binding fragment thereof comprises a HCVR and LCVR (HCVR/LCVR) amino sequence pair selected from the group consisting of SEQ ID NO: 393/401, 409/417, 425/433, 441/449, 457/465, 473/481, 489/481, 497/481, 505/481, 513/481, 521/481, 529/537, 545/537, 553/537, 561/537, 569/537, 577/537, 585/537, and 593/601.

In another embodiment, an anti-Activin A antibody or antigen-binding fragment thereof comprises a heavy chain CDR3 (HCDR3) domain having an amino acid sequence selected from the group consisting of SEQ ID NO: 399, 415, 431, 447, 463, 479, 495, 503, 511, 519, 527, 535, 551, 559, 567, 575, 583, 591, and 599, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 407, 423, 439, 455, 471, 487, 543, and 607, or a substantially similar sequence thereof having at least 90%, at least 95%, at least 98% or at least 99% sequence identity.

In another embodiment, an anti-Activin A antibody or antigen-binding fragment thereof comprises a HCDR3/

LCDR3 amino acid sequence pair selected from the group consisting of SEQ ID NO: 399/407, 415/423, 431/439, 447/455, 463/471, 479/487, 495/487, 503/487, 511/487, 519/487, 527/487, 535/543, 551/543, 559/543, 567/543, 575/543, 583/543, 591/543, and 599/607.

In another embodiment, an anti-Activin A antibody or antigen-binding fragment thereof comprises a heavy chain CDR1 (HCDR1) domain having an amino acid sequence selected from the group consisting of SEQ ID NO: 395, 411, 427, 443, 459, 475, 491, 499, 507, 515, 523, 531, 547, 555, 563, 571, 579, 587, and 595, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 397, 413, 429, 445, 461, 477, 493, 501, 509, 517, 525, 533, 549, 557, 565, 573, 581, 589, and 597, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 403, 419, 435, 451, 467, 483, 539, and 603, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 405, 421, 437, 453, 469, 485, 541, and 605, or a substantially similar sequence thereof having at least 90%, at least 95%, at least 98% or at least 99% sequence identity.

In another embodiment, an anti-Activin A antibody or antigen-binding fragment thereof comprises HCDR1-HCDR2-HCDR3-LCDR1-LCDR2-LCDR3 domains, respectively, having the amino acid sequences selected from the group consisting of: SEQ ID NOs: 395-397-8-403-405-407; 411-413-415-419-421-423; 36-429-431-435-437-439; 443-445-447-451-453-455; 459-461-463-467-469-471; 475-477-479-483-485-487; 491-493-495-483-485-487; 499-501-503-483-485-487; 507-509-511-483-485-487; 515-517-519-483-485-487; 523-525-527-483-485-487; 531-533-535-539-541-543; 547-549-551-539-541-543; 555-557-559-539-541-543 (H4H10446P2); 563-565-567-539-541-543; 571-573-575-539-541-543; 579-581-583-539-541-543; 587-589-591-539-541-543; and 595-597-599-603-605-607.

In another embodiment, an anti-Activin A antibody or antigen-binding fragment thereof comprises the heavy and light chain CDR domains contained within heavy and light chain variable region (HCVR/LCVR) sequence pairs selected from the group consisting of SEQ ID NO: 393/401, 409/417, 425/433, 441/449, 457/465, 473/481, 489/481, 497/481, 505/481, 513/481, 521/481, 529/537, 545/537, 553/537, 561/537, 569/537, 577/537, 585/537, and 593/601.

In one embodiment, an anti-Activin A antibody or antigen-binding fragment thereof comprises a HCVR having an amino acid sequence encoded by a nucleic acid sequence selected from the group consisting of SEQ ID NO:392, 408, 424, 440, 456, 472, 488, 496, 504, 512, 520, 528, 544, 552, 560, 568, 576, 584, and 592, or a substantially similar sequence thereof having at least 90%, at least 95%, at least 98% or at least 99% sequence identity.

In another embodiment, an anti-Activin A antibody or antigen-binding fragment thereof comprises a LCVR having an amino acid sequence encoded by a nucleic acid sequence selected from the group consisting of SEQ ID NO: 400, 416, 432, 448, 464, 480, 536, and 600, or a substantially similar sequence thereof having at least 90%, at least 95%, at least 98% or at least 99% sequence identity.

In another embodiment, an anti-Activin A antibody or antigen-binding fragment thereof comprises a HCVR and a LCVR, wherein the HCVR/LCVR pair has amino acid sequences encoded by a nucleic acid sequence pair selected from the group consisting of SEQ ID NO: 392/400, 408/416, 424/432, 440/448, 456/464, 472/480, 488/480, 496/480, 504/480, 512/480, 520/480, 528/536, 544/536, 552/536, 560/536, 568/536, 576/536, 584/536, and 592/600.

In another embodiment, an anti-Activin A antibody or antigen-binding fragment thereof comprises a HCDR3 domain having an amino acid sequence encoded by a nucleic acid sequence selected from the group consisting of SEQ ID NO:398, 414, 430, 446, 462, 478, 498, 502, 510, 518, 526, 534, 550, 558, 566, 574, 582, 590, and 598, or a substantially similar sequence thereof having at least 90%, at least 95%, at least 98% or at least 99% sequence identity, and a LCDR3 domain having an amino acid sequence encoded by a nucleic acid sequence selected from the group consisting of SEQ ID NO:406, 422, 435, 454, 470, 486, 542, and 606, or a substantially similar sequence thereof having at least 90%, at least 95%, at least 98% or at least 99% sequence identity. In one embodiment, the HCDR3/LCDR3 domain set has amino acid sequences encoded by a nucleic acid sequence pair selected from the group consisting of SEQ ID NO:398/406, 414/422, 430/438, 446/454, 462/470, 478/486, 494/486, 502/486, 510/486, 518/486, 526/486, 534/542, 550/542, 558/542, 566/542, 574/542, 582/542, 590/542, and 598/606.

In another embodiment, an anti-Activin A antibody or antigen-binding fragment thereof comprises HCDR1 and HCDR2 domains, and LCDR1 and LCDR2 domains, wherein the HCDR1 domain has an amino acid sequence encoded by a nucleic acid sequence selected from the group consisting of SEQ ID NO:394, 410, 426, 442, 458, 474, 490, 498, 506, 514, 522, 530, 546, 554, 562, 570, 578, 586, and 594, or a substantially similar sequence thereof having at least 90%, at least 95%, at least 98% or at least 99% sequence identity, the HCDR2 domain has an amino acid sequence encoded by a nucleic acid sequence selected from the group consisting of SEQ ID NO:396, 412, 428, 444, 460, 476, 492, 500, 508, 516, 524, 532, 548, 556, 564, 572, 580, 588, and 596, or a substantially similar sequence thereof having at least 90%, at least 95%, at least 98% or at least 99% sequence identity, the LCDR1 domain has an amino acid sequence encoded by a nucleic acid sequence selected from the group consisting of SEQ ID NO:402, 418, 434, 450, 466, 482, 538, and 602, or a substantially similar sequence thereof having at least 90%, at least 95%, at least 98% or at least 99% sequence identity, and the LCDR2 domain has an amino acid sequence encoded by a nucleic acid sequence selected from the group consisting of SEQ ID NO:404, 420, 436, 452, 468, 484, 540, and 604, or a substantially similar sequence thereof having at least 90%, at least 95%, at least 98% or at least 99% sequence identity.

In another embodiment, an anti-Activin A antibody or antigen-binding fragment thereof comprises heavy and light chain CDR (HCDR1, HCDR2, HCDR3, LCDR1, LCDR2, LCDR3) domains having amino acid sequences encoded by a nucleic acid sequence set selected from the group consisting of SEQ ID NO: 394/396/398/402/404/406, 410/412/414/418/420/422, 426/428/430/434/436/438, 442/444/446/450/452/454, 458/460/462/466/468/470, 474/476/478/482/484/486, 490/492/494/482/484/486, 498/500/502/482/484/486, 506/508/510/482/484/486, 514/516/518/482/484/486, 522/524/526/482/484/486, 530/532/534/538/540/542, 546/548/550/538/540/542, 554/556/558/538/540/542, 562/564/566/

538/540/542, 570/572/574/538/540/542, 578/580/582/538/540/542, 586/588/590/538/540/542, and 594/596/598/602/604/606.

In one embodiment, the anti-Activin A antibody or antigen-binding fragment thereof comprises the HCVR and LCVR (HCVR/LCVR) amino sequence pair of SEQ ID NO: 553/537 and the anti-GDF8 antibody or antigen-binding fragment thereof comprises a HCVR and LCVR (HCVR/LCVR) amino sequence pair of SEQ ID NO: 360/368.

In another embodiment, the anti-Activin A antibody or antigen-binding fragment thereof comprises HCDR1-HCDR2-HCDR3-LCDR1-LCDR2-LCDR3 domains, respectively, having the amino acid sequences of: SEQ ID NOs: 555-557-559-539-541-543 (H4H10446P2), and the anti-GDF8 antibody or antigen-binding fragment thereof comprises HCDR1-HCDR2-HCDR3-LCDR1-LCDR2-LCDR3 domains, respectively, having the amino acid sequences of: SEQ ID NOs: 362/364/366/370/372/374 (e.g., H4H1657N2).

In another embodiment, an anti-Activin A antibody or antigen-binding fragment thereof has a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (Shield et al. (2002) JBC 277:26733). In other applications, modification of a galactosylation can be made in order to modify complement dependent cytotoxicity (CDC).

The fully-human anti-Activin A and/or anti-GDF8 antibodies described herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The compositions and methods of the invention use, in additional embodiments, antibodies and antigen-binding fragments thereof that are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences described herein, can easily produce numerous antibodies and antigen-binding fragments that comprise one or more individual germline back-mutations or combinations thereof. In certain embodiments, all of the framework and/or CDR residues within the VH and/or VL domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies and antigen-binding fragments used in the compositions and methods of the invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the invention.

The compositions and methods of the invention use, in additional embodiments, anti-GDF8 antibodies and/or anti-Activin A antibodies (or antigen-binding fragments thereof) comprising variants of any of the HCVR, LCVR, and/or CDR amino acid sequences described herein having one or more conservative substitutions. For example, anti-GDF8 antibodies and/or anti-Activin A antibodies used in the compositions and methods of the invention have, in some embodiments, HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences described herein.

Bispecific Antibodies

Bispecific antibodies (bsAbs) combine specificities of two antibodies and simultaneously bind different antigens or epitopes. Two or more antigen-recognizing elements are engineered into a single antibody. In one embodiment of the methods of the invention, the composition comprises an antibody comprising a GDF8-specific binding domain and an Activin A-specific binding domain. The term (antigen) "-specific binding domain," as used herein, includes polypeptides comprising or consisting of: (i) an antigen-binding fragment of an antibody molecule, (ii) a peptide that specifically interacts with a particular antigen (e.g., a peptibody), and/or (iii) a ligand-binding portion of a receptor that specifically binds a particular antigen. For example, included are bispecific antibodies with one arm comprising a first heavy chain variable region/light chain variable region (HCVR/LCVR) pair that specifically binds GDF8 and another arm comprising a second HCVR/LCVR pair that specifically binds Activin A.

Bispecific antibodies can be prepared according to known methods, including chemical cross-linking, hybrid hybridomas/quadromas, knobs into holes, CrossMab, dual-variable-domain immunoglobulin, recombinant engineering (tandem single chain variable fragments/diabodies), and dock and lock. Other exemplary bispecific formats that can be used in the context of the present invention include, without limitation, e.g., IgG-scFv fusions, dual variable domain (DVD)-Ig, common light chain, CrossFab, (SEED)body, leucine zipper, Duobody, IgG1/IgG2, dual acting Fab (DAF)-IgG, and Mab2 bispecific formats (see, e.g., Klein et al., mAbs 4:6, 1-11 (2012), and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates, which then self-assemble into multimeric complexes with defined composition, valency and geometry. (See, e.g., Kazane et al., J Am Chem Soc. 135 (1):340-346 (2013)).

Specific Binding

The term "specifically binds" or the like, as used herein, means that an antigen-specific binding protein, or an antigen-specific binding domain, forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another. Methods for determining whether two molecules specifically bind one another are well known in the art and include, for example, equilibrium dialysis, surface plasmon resonance, and the like. For example, an antigen-specific binding protein or an antigen-specific binding domain, as used in the context of the present invention, includes antibodies or antigen-binding fragments thereof that bind a particular antigen (e.g., GDF8, Activin A) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

Antibody binding (of antigen) can be quantitated in terms of $K_D$, a measurement of affinity. The lower the $K_D$ value, the higher the binding affinity of the antibody. The term "$K_D$", as used herein, is intended to refer to the equilibrium dissociation constant of a particular antibody-antigen interaction. Surface plasmon resonance can be used to measure ligand binding, for example, antibody-antigen interaction.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. For example, an antibody is said to specifically bind an antigen when the $K_D$ is less than or equal to $10^{-8}$ M, less than or equal to $10^{-9}$ M, or less than or equal to $10^{-10}$ M.

Preparation of Human Antibodies

Methods for generating monoclonal antibodies, including fully human monoclonal antibodies are known in the art. Any such known methods can be used in the context of the invention to make human antibodies that specifically bind to GDF8 and/or to Activin A.

Using VELOCIMMUNE™ technology or any other known method for generating monoclonal antibodies, high affinity chimeric antibodies to GDF8 and/or Activin A are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies used in the methods of the instant invention possess very high affinities, typically possessing $K_D$ of from about $10^{-12}$ through about $10^{-9}$ M, when measured by binding to antigen either immobilized on solid phase or in solution phase.

Pharmaceutical Compositions and Methods of Administration

The present invention includes methods for altering body composition of a subject. As used herein, the phrase "altering body composition" refers to a change in one or more of lean mass, fat mass, and/or bone mass in a subject. In some embodiments, body composition in a subject may be altered by administering an effective amount of a GDF8 inhibitor and an Activin A inhibitor to the subject. Lean mass may be, for example, thigh muscle volume, appendicular lean body mass, or total lean mass, etc. In some aspects, the thigh muscle volume may refer to thigh muscle tissue volume excluding intramuscular adipose tissue and large vessels. In some aspects, the thigh muscle volume may refer to thigh muscle tissue volume including intramuscular adipose tissue and large vessels. In some aspects, the appendicular lean body mass may be calculated by, for example, aLBM equation. In some aspects, the appendicular lean mass may be calculated by the sum of lean mass of arms and legs. Fat mass may be, for example, total fat mass, android fat mass, sum of intramuscular and perimuscular adipose tissue (IMAT), subcutaneous adipose tissue volume, sum of fat mass of arms and legs, thigh intramuscular adipose tissue, etc. Bone mass may be, for example, total bone mineral density (BMD) mass, total bone mineral content (BMC) mass, etc. In some embodiments, alteration of body composition comprises an increase in muscle mass and/or a reduction of fat mass. In some embodiments, alteration of body composition comprises an increase in muscle mass and a reduction of fat mass simultaneously. In some embodiments, alteration of body composition comprises an increase in muscle mass and a reduction of fat mass simultaneously, without reduction in bone mass. In some embodiments, alteration of body composition comprises an increase in bone mineral content mass. In some embodiments, alteration of body composition comprises a decrease in total fat mass, android fat mass, and/or subcutaneous fat mass. In some embodiments, alteration of body composition comprises a decrease in total fat mass, android fat mass, and/or subcutaneous fat mass, without a reduction in thigh intramuscular adipose tissue volume.

The present invention includes methods for altering body composition, for example, inducing a reduction in fat mass in a subject and methods for treating a disease or disorder characterized by increased fat mass, comprising administering a first composition comprising an effective amount of a GDF8 inhibitor and a second composition comprising an effective amount of an Activin A inhibitor to the subject. The first and second compositions can be administered concurrently or sequentially to the subject. The first and second compositions can also be combined into a third composition prior to administration. Thus, in certain embodiments, a composition comprising both a GDF8 inhibitor and an Activin A inhibitor can be administered to a subject. The GDF8 inhibitor in such a composition can, for example, be an anti-GDF8 antibody. The Activin A inhibitor in such a composition can, for example, be an anti-Activin A antibody.

The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the invention, provided that the active ingredient in the formulation is not inactivated by the formulation and the formulation is physiologically compatible and tolerable with the route of administration. See also Powell et al. "Compendium of excipients for parenteral formulations" PDA (1998) J Pharm Sci Technol 52:238-311.

Various delivery systems are known and can be used to administer the pharmaceutical compositions of the present invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical compositions of the present invention can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of active ingredient (e.g., anti-GDF8 antibody and/or anti-Activin A antibody) that can be administered to a subject is, generally, a therapeutically effective amount. The term "effective amount" is a concentration or amount of an active ingredient, for example, an antibody or antigen-binding fragment of an antibody, which results in achieving a particular stated purpose. The term "effective amount" is used interchangeably with the term "therapeutically effective amount" and signifies a concentration or amount of an active ingredient, for example, an antibody or antigen-binding fragment thereof, which is effective for achieving a stated therapeutic effect. The (therapeutically) effective amount may be determined empirically.

As used herein, the phrase "therapeutically effective amount" or "effective amount" means a dose of antigen-specific binding proteins and/or antigen-binding molecules (e.g., antibodies) that results in a detectable decrease in fat mass. The effective amount may also, in certain embodiments, result in an increase in one or more of the following parameters: body weight, muscle mass (e.g., tibialis anterior [TA] muscle mass, gastrocnemius [GA] muscle mass, quadriceps [Quad] muscle mass, appendicular lean body mass, etc.), muscle volume (e.g., thigh muscle volume), muscle strength/power, and/or muscle function, and glucose tolerance.

A "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a decrease in total fat mass of at least about 2% to 8%, at least 2.5% to 6%, at least 3% to 4%, or at least about 2.0%, at least about 2.5%, at least about 3.0%, or at least about 3.5%, or more. For example, a "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a decrease in total fat mass of at least about 3.5% or more.

In some embodiments, a "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a decrease in android fat mass of at least about 2% to 8%, at least 2.5% to 6%, at least 3% to 4%, or at least about 2.0%, at least about 2.5%, at least about 3.0%, or at least about 3.5%, or more. For example, a "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a decrease in android fat mass of at least about 3.5%.

In certain embodiments, the amount also results in an increase in TA or GA muscle mass of at least 2%, 5%, 10%, 15%, 20%, 25%, 30%, 40%, 50%, 60% or more, compared to control treated subjects.

In some embodiments, a "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a increase in thigh muscle volume of at least about 2% to 8%, 2.5% to 6%, 3% to 4%, or at least 2.0%, at least 2.5%, at least 3.0%, or at least 3.5%, or more In some embodiments, a "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a increase in total lean body mass of at least about 2% to 8%, 2.5% to 6%, 3% to 4%, or at least 2.0%, at least 2.5%, at least 3.0%, or at least 3.5%, or more In some embodiments, a "therapeutically effective amount" or "effective amount" of a GDF8 inhibitor (e.g., anti-GDF8 antibody) and/or an Activin A inhibitor (e.g., anti-Activin A antibody) includes, e.g., an amount of GDF8 inhibitor and/or Activin A inhibitor that, when administered to a subject, causes a increase in appendicular lean body mass of at least about 2% to 8%, 2.5% to 6%, 3% to 4%, or at least 2.0%, at least 2.5%, at least 3.0%, or at least 3.5%, or more.

In certain embodiments, the amount also results in an increase in TA or GA muscle mass of at least 2%, 3%, 5%, 10%, 15%, 20%, 25% or more, compared to control treated subjects.

In certain embodiments, a (therapeutically) effective amount of an anti-GDF8 antibody, anti-Activin A antibody, or bispecific antibody that specifically binds GDF8 and Activin A can be from about 0.05 mg to about 600 mg; e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the respective antibody. The dose may vary depending upon the age and the size of a subject to be administered, target disease, conditions, route of administration, and the like. Depending on the severity of the condition, the frequency and the duration of the treatment can be adjusted.

The amount of antibody (e.g., anti-GDF8 antibody, anti-Activin A antibody, or bispecific antibody that specifically binds GDF8 and Activin A) contained within the individual doses may be expressed in terms of milligrams of antibody per kilogram of patient body weight (i.e., mg/kg). For example, the anti-GDF8 antibody, anti-Activin A antibody, and/or anti-GDF8/anti-Activin A bispecific antibody in the first, second, or third composition administered per the methods of the invention may be administered to a patient at a dose of about 0.0001 to about 50 mg/kg of patient body weight (e.g. 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, etc.).

The effective amount of a GDF8 inhibitor (e.g., an anti-GDF8 antibody) may, in certain embodiments, comprises a dosing regimen selected from the group consisting of at least 0.1 mg/kg to about 10 gm/kg, 1 mg/kg to about 1 gm/kg, and 10 mg/kg to 100 mg/kg. The effective amount of an Activin A inhibitor (e.g., an anti-Activin A antibody) may, in certain embodiments, comprise a dosing regimen selected from the group consisting of at least 0.1 mg/kg to about 10 gm/kg, 1 mg/kg to about 1 gm/kg, and 10 mg/kg to 100 mg/kg.

The effective amount of a GDF8 inhibitor (e.g., an anti-GDF8 antibody) may, in additional embodiments, comprise a dosing regimen selected from a group consisting of a single dose of about 0.01 to about 20 mg/kg body weight, about 0.1 to about 10 mg/kg body weight, and about 0.1 to about 5 mg/kg body weight. The effective amount of an Activin A inhibitor (e.g., an anti-Activin A antibody) may, in additional embodiments, comprise a dosing regimen selected from a group consisting of a single dose of about 0.01 to about 20 mg/kg body weight, about 0.1 to about 10 mg/kg body weight, and about 0.1 to about 5 mg/kg body weight. In one specific aspect, the effective amount of an anti-GDF8 antibody is from about 2 mg/kg-10 mg/kg, 4 mg/kg-8 mg/kg, or about 6 mg/kg body weight of subject, and the effective amount of the anti-Activin A antibody is from 0.5 mg/kg-15 mg/kg, 2 mg/kg-12 mg/kg, about 3 mg/kg, or about 10 mg/kg body weight of a subject.

The first, second, and third compositions administered per methods of the invention may, in certain embodiments, comprise equal amounts of GDF8 inhibitor (e.g., anti-GDF8 antibody) and/or Activin A inhibitor (e.g., anti-Activin A antibody). Alternatively, the amount of GDF8 inhibitor (e.g., anti-GDF8 antibody) in the composition may be less than or greater than the amount of Activin A inhibitor (e.g., an anti-Activin A antibody). The effective amount of a GDF8 inhibitor (e.g., anti-GDF8 antibody) may be lower, when in combination with an Activin A inhibitor (e.g., an anti-Activin A antibody), than in a separate composition. The effective amount of an Activin A inhibitor (e.g., an anti-Activin A antibody) may be lower, when in combination with a GDF8 inhibitor (e.g., anti-GDF8 antibody), than in a separate composition. A person of ordinary skill in the art, using routine experimentation, will be able to determine the appropriate amounts of the individual components in the compositions necessary to produce a desired therapeutic effect.

Aspects of the Disclosure

The disclosure provides compositions, kits, and methods of using GDF8 inhibitors and Activin A inhibitors to reduce fat mass (induce a reduction in fat mass) in a subject. The disclosure also provides compositions, kits, and methods of using GDF8 inhibitors and Activin A inhibitors to treat diseases, disorders, and/or conditions associated with or characterized by increased fat mass in a subject. In preferred embodiments, the GDF8 inhibitor is an antibody or antigen-binding fragment thereof that specifically binds GDF8.

Therapeutic Methods

The present invention includes methods for altering body composition, for example, methods for inducing a reduction in fat mass in a subject, methods for increasing muscle mass in a subject, and methods for treating a disease or disorder characterized by increased fat mass, by specifically binding GDF8 and/or Activin A. For example, the present invention includes methods for inducing a reduction in fat mass in a subject, inducing an increase in muscle mass in a subject, and methods for treating a disease or disorder characterized by increased fat mass in a subject, by administering to the subject i) a composition comprising an anti-GDF8 antibody and a composition comprising an anti-Activin A antibody or ii) a composition comprising both an anti-GDF8 antibody and an anti-Activin A antibody or iii) a composition comprising a bispecific antibody comprising a first variable domain comprising a HCVR/LCVR pair that specifically binds GDF8 and a second variable domain comprising a HCVR/LCVR pair that specifically binds Activin A. Any of the GDF8 inhibitors and/or Activin A inhibitors disclosed or referred to herein can be used in the context of these aspects of the invention.

In methods comprising administering a GDF8 inhibitor and an Activin A inhibitor to a subject, the GDF8 inhibitor (for example, an anti-GDF8 antibody) and the Activin A inhibitor (for example, an anti-Activin A antibody) may be administered to the subject at the same or substantially the same time, e.g., in a single therapeutic dosage (third composition) or in two separate dosages (first and second compositions), which are administered simultaneously or within less than about 5 minutes of one another. Alternatively, the GDF8 inhibitor and the Activin A inhibitor (first and second compositions) may be administered to the subject sequentially, e.g., in separate therapeutic dosages separated in time from one another by more than about 5 minutes.

The reduction of fat mass in the subject of the methods according to the invention can be a reduction in total fat mass as measured by DXA (Dual-energy X-ray absorptiometry).

In another embodiment, the reduction of fat mass in the subject of the methods according to the invention is a reduction in android fat mass (i.e., visceral fat associated with the upper/central body) as measured by DXA (Dual-energy X-ray absorptiometry). In android obesity, the subject stores fat around his or her abdominal region. Android obesity can also be manifested in other areas of the upper trunk like the upper chest (front or back) nape area of the neck, and even the shoulders. Subjects who are android obese are at greater risk for obesity-related diseases/disorders like heart disease, and metabolic syndrome. The likelihood of developing gout, arterial-related diseases (due to high blood pressure) and many kinds of cancers are also linked to the central type of fat distribution in subjects who exhibit android obesity.

Body fat assessments are varied in precision and accuracy. Common anthropometric measures include: weight, waist circumference, and skinfold measurements using skin calipers. More complex methods include: bioelectrical impedance analysis (BIA), the BOD POD, and dual-energy X-ray absorptiometry (DEXA or DXA). DXA is especially accurate and valid, because it considers bone mineral content when estimating body fat and muscle. DEXA scans can evaluate different areas of fat distribution to determine the android/gynoid fat ratio, which is distinct from body mass index. DXA can measure total fat mass, total body muscle mass, visceral fat (fat around the organs) levels, intramuscular fat (fat between the muscles), total bone mineral density, and can even provide regional breakdowns. Finally, DXA can accurately assess the distribution of body fat associated with increased insulin resistance.

Avoidance of Side Effects

The present invention includes methods for altering body composition, for example, inducing a reduction in fat mass in a subject, and methods for treating a disease or disorder characterized by increased fat mass, comprising administering a GDF8 inhibitor and an Activin A inhibitor to the subject, without causing adverse side effects associated with the administration of molecules which bind multiple (e.g., 3 or more) ActRIIB ligands, for example, as set forth in U.S. Pat. No. 8,871,209. For example, the clinical molecule referred to as ACE-031 (Acceleron Pharma, Inc., Cambridge, Mass.) is a multimer consisting of the extracellular portion of ActRIIB fused to an IgG Fc domain (this molecule is also referred to herein as "ActRIIB-Fc"). ActRIIB-Fc binds GDF8 as well as other ActRIIB ligands such as, e.g., Activin A, Activin B, GDF11, BMP9, BMP10, and TGFβ, and is known to cause various adverse side effects when administered to human patients. For example, administration of ACE-031 to postmenopausal women in a Phase Ib ascending dose study was shown to cause undesired increases in hemoglobin and decreases in FSH levels. In addition, a Phase II study of ACE-031 in pediatric patients with muscular dystrophy was discontinued due to adverse effects including nose and gum bleeding. Dilated blood vessels are also observed in patients treated with ActRIIB-Fc. Effect of ACE-031 in boys with Duchenne muscular dystrophy (DMD) demonstrated trends for increased lean body mass and reduced fat mass but non-muscle-related adverse events contributed to a decision to discontinue the study. (Campbell, et al. 2017 Muscle Nerve 55: 458-464). Specifically inhibiting GDF8 and Activin A (e.g., by administering an anti-GDF8 antibody and an anti-Activin A antibody), while not inhibiting other ActRIIB ligands such as Activin B, GDF11, BMP9, BMP10, and TGFβ, results in an increase in a reduction in fat mass, without causing the adverse side effects associated with non-specific Activin-binding agents such as ActRIIB-Fc.

Administration Regimens

According to certain embodiments of the present invention, multiple doses of the compositions of the present invention (e.g., compositions comprising a GDF8 inhibitor and/or an Activin A inhibitor, for example, an anti-GDF8 antibody and/or an anti-Activin A antibody, or a bispecific antibody against GDF8 and Activin A), may be administered to a subject over a defined time course. The methods according to this aspect of the invention comprise sequentially administering to a subject multiple doses of the composition(s) of the present invention. As used herein, "sequentially administering" means that each dose of the compositions of the present invention are administered to the subject at a different point in time, e.g., on different days separated by a predetermined interval (e.g., hours, days, weeks or months). The present invention includes methods that comprise sequentially administering to the patient an initial dose of a first and/or a second composition; or a third composition; followed by one or more secondary doses of the first and/or second composition; or the third composition; and optionally followed by one or more tertiary doses of the first and/or second composition; or the third composition.

The terms "initial dose," "secondary doses," and "tertiary doses," refer to the temporal sequence of administration of the compositions of the present invention. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of active ingredient(s), e.g., anti-GDF8 antibody and/or anti-Activin A antibody, but will generally differ from one another in terms of frequency of administration. In certain embodiments, however, the amount of active ingredient(s) contained in the initial, secondary and/or tertiary doses will vary from one another (e.g., adjusted up or down as appropriate) during the course of treatment.

In one exemplary embodiment of the present invention, each secondary and/or tertiary dose is administered 1 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) days after the immediately preceding dose. The phrase "the immediately preceding dose," as used herein, means, in a sequence of multiple administrations, the dose(s) of the compositions of the present invention that are administered to a subject prior to the administration of the very next dose in the sequence, with no intervening doses.

The methods according to this aspect of the invention may comprise administering to a patient any number of secondary and/or tertiary doses of the compositions of the present invention. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 29 days after the immediately preceding dose. Similarly, in embodiments involving multiple tertiary doses, each tertiary dose may be administered at the same frequency as the other tertiary doses. For example, each tertiary dose may be administered to the patient 1 to 60 days after the immediately preceding dose. Alternatively, the frequency at which the secondary and/or tertiary doses are administered to a patient can vary over the course of the treatment regimen. The frequency of administration may also be adjusted during the course of treatment by a physician, depending on the needs of the individual patient following clinical examination.

In one embodiment, a subject may be subjected to preliminary DXA, then receive a composition comprising an anti-GDF8 antibody and an anti-Activin A antibody (or a composition comprising an anti-GDF8 antibody and a composition comprising an anti-Activin A antibody), then be subjected to follow-up DXA. If the fat mass is not measurably reduced in the follow-up DXA (in comparison with the preliminary DXA), the subject may receive the composition(s) again. Subsequent dosage amount and frequency of administration can, in an additional embodiment, be varied based on the results of the follow-up DXA.

Combination Therapies

The methods of the present invention, according to certain embodiments, comprise administering to the subject one or more additional therapeutic agents that may be advantageously combined with the composition comprising a GDF8 inhibitor and/or an Activin A inhibitor. As used herein, the expression "in combination with" means that the additional therapeutic agent(s) is/are administered before, after, or concurrently with a pharmaceutical composition comprising a GDF8 inhibitor and/or an Activin A inhibitor. The term "in combination with" also includes sequential or concomitant administration of a GDF8 inhibitor, an Activin A inhibitor, or both and a second therapeutic agent. The term "therapeutic agent" is also meant to include a specific therapy.

The additional therapeutic agent may be, e.g., another GDF8 antagonist/inhibitor, another Activin A antagonist/inhibitor, growth factor inhibitors, immunosuppressants, metabolic inhibitors, enzyme inhibitors, and cytotoxic/cytostatic agents, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a tumor necrosis factor (TNF) antagonist, an IL-8 antagonist, an IL-9 antagonist, an IL-17 antagonist, an IL-5 antagonist, an IgE antagonist, a CD48 antagonist, an IL-31 antagonist (including, e.g., as set forth in U.S. Pat. No. 7,531,637), a thymic stromal lymphopoietin (TSLP) antagonist (including, e.g., as set forth in US 2011/027468), interferon-gamma (IFNγ) antibiotics, topical corticosteroids, tacrolimus, pimecrolimus, cyclosporine, azathioprine, methotrexate, cromolyn sodium, proteinase inhibitors, systemic corticosteroids, systemic immunotherapy, anti-histamines, chemotherapy, light therapy, or combinations thereof.

In further embodiments, the invention features a composition, the additional therapeutic agent is selected from the group consisting of (1) 3-hydroxy-3-methylglutaryl-coenzyme A (HMG-CoA) reductase inhibitors, such as cerivastatin, atorvastatin, simvastatin, pitavastatin, rosuvastatin, fluvastatin, lovastatin, pravastatin, and the like; (2) inhibitors of cholesterol uptake and/or bile acid re-absorption; (3) niacin, which increases lipoprotein catabolism; (4) fibrates or amphipathic carboxylic acids, which reduce low-density lipoprotein (LDL) level, improve high-density lipoprotein (HDL) and TG levels, and reduce the number of non-fatal heart attacks; and (5) activators of the LXR transcription factor that plays a role in cholesterol elimination such as 22-hydroxycholesterol, or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

In still further embodiments, the second therapeutic agent is selected from one or more other inhibitors/antagonists of glucagon or an inhibitor/antagonist of the glucagon receptor, as well as inhibitors of other molecules, such as inhibitors of ANGPTL8 (for example, an anti-ANGPTL8 antibody), as well as inhibitors of other molecules, such as ANGPTL3 (for example, an anti-ANGPTL3 antibody), ANGPTL4, ANGPTL5, ANGPTL6, apolipoprotein C-III (also referred to as APOC3; see for example, inhibitors of APOC3 described in U.S. Pat. Nos. 8,530,439, 7,750,141, 7,598,227 and volanesorsen, also referred to as ISIS-APOCIIIRx) and proprotein convertase subtilisin/kexin type 9 (PCSK9), which are involved in lipid metabolism, in particular, cholesterol and/or triglyceride homeostasis. Inhibitors of these molecules include small molecules, antisense molecules and antibodies that specifically bind to these molecules and block their activity.

The additional therapeutic agent may, in further embodiments, be selected from the group consisting of analgesics, anti-inflammatory agents, including non-steroidal anti-inflammatory drugs (NSAIDS), such as Cox-2 inhibitors, and the like, so as to ameliorate and/or reduce the symptoms accompanying the underlying condition, if needed.

The additional therapeutic agent(s) may be administered prior to, concurrent with, or after the administration of the first and/or second; or third composition(s) described herein. For purposes of the present disclosure, such administration regimens may be considered the administration of an anti-GDF8 antibody and/or an anti-Activin A antibody "in combination with" a second therapeutically active component.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, molecular weight is average molecular weight, temperature is in degrees Centigrade, and pressure is at or near atmospheric.

Example 1. Anti-GDF8 Alone Increased Total Lean Mass up to 3% in Clinical Studies: Sarcopenia Phase 2 Data A randomized, double-blind, placebo-controlled interventional study phase 2 clinical trial was performed in patients 70 years and older including men and postmenopausal women having sarcopenia. Patients were treated 12 weeks with subcutaneous anti-GDF8 antibody REGN1033 (H4H1657N2) alone, at either 100 mg anti-GDF8 antibody, Q4W s.c. (n=62); 300 mg anti-GDF8 antibody Q4W s.c. (n=64), or 300 mg anti-GDF8 antibody Q2W s.c. (n=59), or placebo (n=65). As shown in FIG. 1 significant increase in total lean body mass compared to placebo was exhibited in patients after 12 weeks when using REGN1033 alone at each of the three doses, as shown in FIG. 1 and Table 4.

TABLE 4

Total Lean Mass % Change to Week 12 using anti-GDF8 REGN1033 alone

| | | Anti-GDF8 | | |
|---|---|---|---|---|
| | Placebo | 100 Q4W | 300 Q4W | 300 Q2W |
| N | 65 | 62 | 64 | 59 |
| Baseline Mean | 43.6 kg | 42.9 kg | 42.7 | 42.8 |
| Difference vs. placebo | — | 1.66% | 1.78% | 2.29% |
| P value | — | 0.0077 | 0.0043 | 0.0004 |

The effects on strength and function were varied. Anti-GDF8 was generally safe and well-tolerated (reactions, if any, were mild). Table 4 shows patients receiving REGN1033 in either 100 mg or 300 mg doses exhibited significantly increased Total lean mass as % change from placebo to week 12 data. Anti-GDF8 antibody REGN1033 alone increased total lean body mass up to 3% in the study. The 300 mg regimens also resulted in decreases in total and android fat mass.

Example 2. Combination of Anti-GDF8 and Anti-Activin A First In-Human Single Ascending Dose Study A randomized, double-blind placebo-controlled, ascending dose study was initiated to assess the tolerability and effects on body composition of a combination of an intravenous anti-GDF8 antibody and an anti-Activin A antibody vs. the individual components.

The primary objective of the study was to assess the safety and tolerability of an anti-Activin A antibody (e.g., H4H10446P2=REGN2477) alone and combined with an anti-GDF8 antibody (e.g., H4H1657N2=REGN1033) in healthy postmenopausal women aged 45 to 70 years of age.

Secondary objectives of the study included: an assessment of the effect of REGN2477 alone, REGN1033 alone, and REGN2477+REGN1033 in combination on thigh muscle volume as measured by Magnetic Resonance Imaging (MRI), and an assessment of the effects of REGN2477 alone, REGN1033 alone and REGN2477+REGN1033 in combination on total and regional body composition as measured by dual-energy X-ray absorptiometry (DXA)

Study Design

This study was a randomized, double-blind, placebo-controlled, ascending dose study to assess the safety, tolerability, and pharmacodynamics of intravenous REGN2477 (anti-Activin A) alone and in combination with REGN1033 (anti-GDF8) in healthy postmenopausal women.

A total of 48 subjects were randomized to 1 of the following 4 sequential ascending REGN2477 IV dose panels where 8 subjects were randomized in a 6:2 ratio into each of the first 3 Panels (Panels A, B, and C) and 24 subjects were randomized in a 1:1:1:1 ratio (6 subjects each) into Panel D.

Panel A: 4 subjects REGN1033 (6 mg/kg IV)+ REGN2477 low dose (1 mg/kg IV) or 2 subjects placebo

- Panel B: 4 subjects REGN1033 (6 mg/kg IV)+REGN2477 medium dose (3 mg/kg IV) or 2 subjects placebo
- Panel C: 4 subjects REGN1033 (6 mg/kg IV)+REGN2477 high dose (10 mg/kg IV) or 2 subjects placebo
- Panel D: REGN1033 (6 mg/kg IV+REGN2477 high dose (10 mg/kg IV) placebo, REGN2477 (10 mg/kg IV), or REGN1033 (6 mg/kg IV)

Figure 2B:
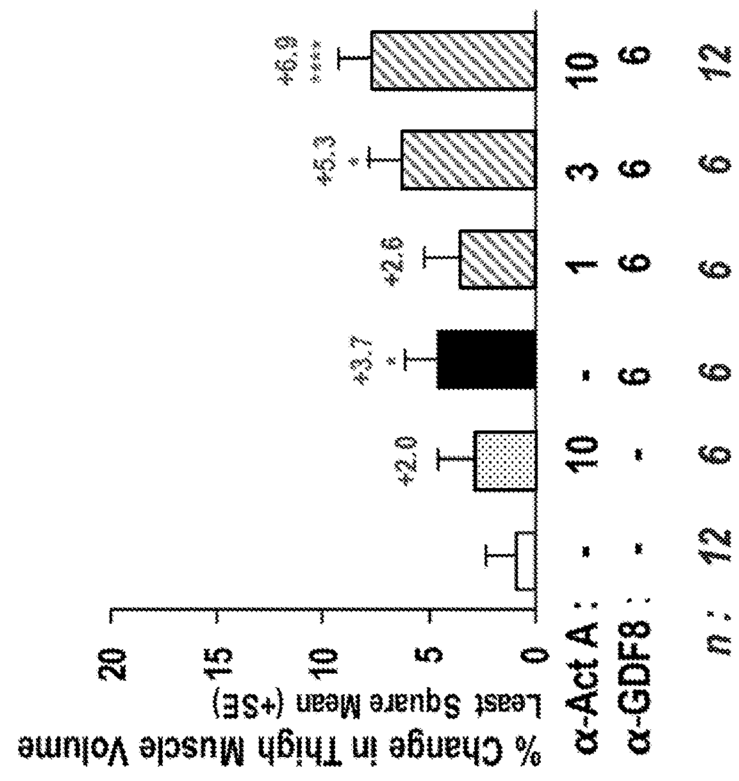
FIG. 2B shows a bar graph depicting thigh muscle volume (measured via MRI) % change at week 8 after a single I.V. dose of anti-Activin A antibody REGN2477 and/or anti-GDF8 antibody REGN1033 in healthy post-menopausal women. A significant increase in thigh muscle volume % change from placebo was exhibited by anti-GDF8 (6 mg/kg), anti-GDF8 (6 mg/kg)+mid dose anti-Activin A (3 mg/kg), and anti-GDF8 (6 mg/kg)+high dose anti-Activin A (10 mg/kg) groups. (*nominal $p<0.5$ vs. placebo, ****nominal $p<0.0001$ vs. placebo).

Subjects received a single intravenous dose of one or both of anti-GDF8 antibody REGN1033 and/or anti-Activin A antibody REGN2477. In the primary analyses, the placebo and high dose combination groups were pooled across panels, yielding 12 subjects on placebo and 12 on the high dose combination, as shown in FIG. 2A. The dosing schedule shown in FIG. 2A was used in studies shown in each of the subsequent FIGS. 2B to 17.

Subjects participated in a screening period of up to 28 days, followed by a baseline and treatment visit on day 1, and a follow-up period of 113 days.

Efficacy and Safety Analysis

The full analysis set (FAS) includes all randomized subjects; it is based on the treatment allocated (as randomized). Efficacy endpoints were analyzed using the FAS. The safety analysis set (SAF) includes all randomized subjects who received any study drug; it is based on the treatment received (as treated). Treatment compliance/administration and all clinical safety variables were analyzed using the SAF.

The efficacy variables included: Thigh muscle tissue volume, excluding and including intramuscular adipose tissue and large vessels as measured by Magnetic Resonance Imaging (MRI); Total lean mass as measured by dual X-ray absorptiometry (DXA); Appendicular lean body mass (calculated by a LBM equation) as measured by DXA; and Total fat mass as measured by DXA.

The demographics and baseline characteristics of the subjects were balanced across the treatment groups, as per the below Table 5:

Placebo subjects were pooled across panels. Missing efficacy data was not imputed. No adjustment for multiple testing is applied in this study.

Results

A total of 48 subjects were randomized, administered study drug and completed the study. One subject in the REGN2477+REGN1033 high dose group had an interrupted infusion of study drug due to an adverse event of 'Infusion site swelling'.

Efficacy

Figure 2C:
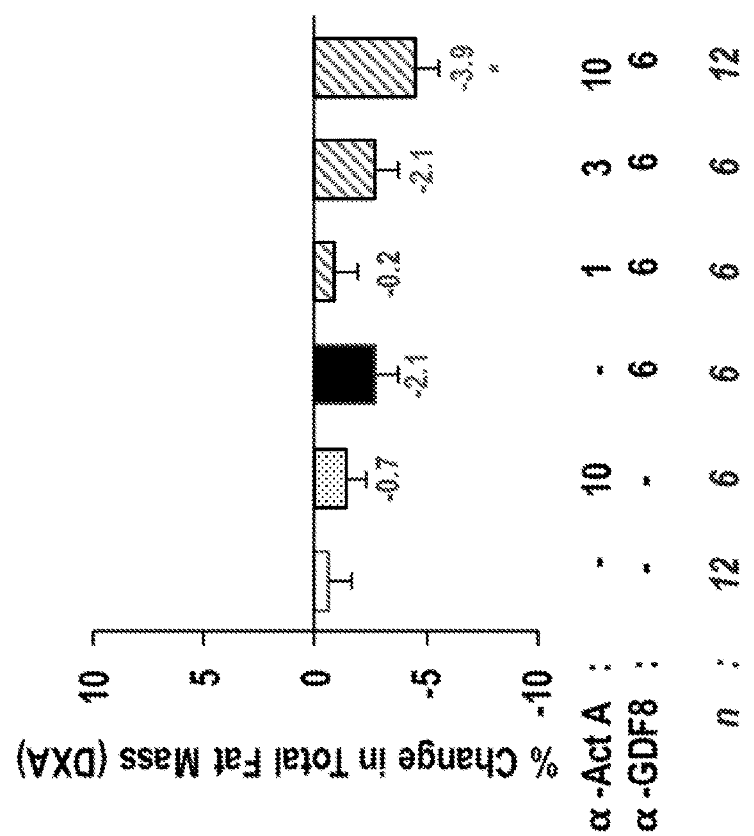
FIG. 2C shows a bar graph depicting total fat mass (measured via DXA) % change at week 8 after a single I.V. dose of anti-Activin A antibody REGN2477 and/or anti-GDF8 antibody REGN1033 in healthy post-menopausal women. The numbers show changes from placebo. A significant decrease in total fat mass % change was exhibited by the anti-GDF8 (6 mg/kg)+high dose anti-Activin A (10 mg/kg) group. (*nominal $p<0.05$ vs. placebo).

The blockade of both Activin A and GDF8 in combination increased thigh muscle volume and decreased fat mass at week 8, as shown in FIGS. 2B and 2C. The greatest effect was seen at the highest dose combination.

FIG. 2B shows a bar graph showing % change in thigh muscle volume by MRI at 8 weeks after a single dose in postmenopausal women. Numbers show changes from placebo. *indicates nominal p<0.05 vs. placebo; ****indicates nominal p<0.0001 vs. placebo. The single dose amounts as mg/kg of either anti-Activin A antibody and/or anti-GDF8 antibody are shown below the bar graph. Treatment with REGN2477+REGN1033 in medium and high dose combinations resulted in significantly increased thigh muscle volume (p<0.05; p<0.0001, respectively) in a dose-related manner compared with placebo. Subjects in high dose panel exhibited up to 7.73% as % change from baseline versus 0.88% with placebo at week 8.

FIG. 2C shows a bar graph showing % change in total fat mass by DXA at 8 weeks after a single dose in postmenopausal women. Numbers show changes from placebo. *indicates nominal p<0.05 vs. placebo; ****indicates nominal p<0.0001 vs. placebo. The single dose amounts as mg/kg of either anti-Activin A antibody and/or anti-GDF8 antibody are shown below the bar graph. Treatment with high dose REGN2477+REGN1033 combination resulted in significantly decreased total fat mass (p<0.05) compared with placebo.

TABLE 5

Baseline Characteristics were balanced across treatment groups

| | Placebo (N = 12) | Anti-GDF8 (N = 6) | Anti-Activin A (10 mg/kg) IV (N = 6) | Anti-GDF8 + anti-activin A (1 mg/kg) IV (N = 6) | Anti-GDF8 + anti-activin A (3 mg/kg) IV (N = 6) | Anti-GDF8 + anti-activin A (10 mg/kg) IV (N = 12) |
|---|---|---|---|---|---|---|
| Age (Years) | | | | | | |
| Median | 54 | 56 | 61 | 60 | 60 | 55.5 |
| Height (cm) | | | | | | |
| Median | 162.5 | 164.2 | 162.5 | 166.5 | 165 | 163.5 |
| Weight (kg) | | | | | | |
| Median | 68.35 | 70.5 | 69.6 | 61.35 | 67.05 | 70.4 |
| BMI ($kg/m^2$) | | | | | | |
| Median | 26.2 | 26.55 | 26.65 | 22.9 | 25.55 | 26.6 |

Statistical Methods

The percent change and change of efficacy variables from baseline to either week 4 or 8 in the full analysis set (FAS) were analyzed using analysis of covariance (ANCOVA) model with treatment group as fixed effect, and the baseline value as continuous covariate. Least-squares means at week 4 and week 8 for each treatment group with the corresponding standard error, confidence interval, and the p value for treatment comparisons were provided from this model.

Figure 3:
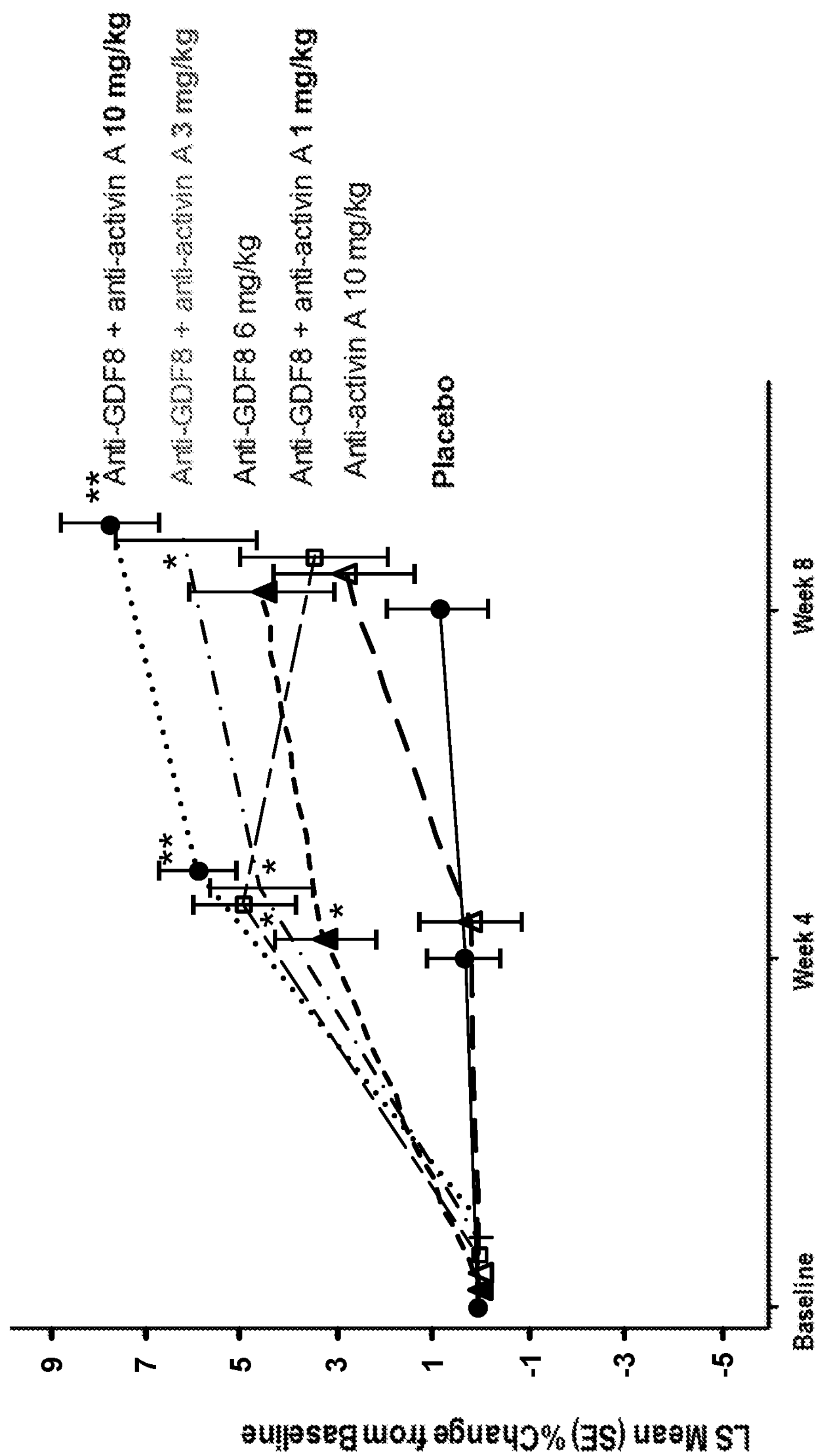
FIG. 3 shows a line graph depicting LS mean (SE) percent change from baseline in thigh muscle volume by MRI at weeks 0, 4, and 8 after a single I.V. dose of anti-Activin A antibody REGN2477 and/or anti-GDF8 antibody REGN1033 in healthy post-menopausal women. At 4 weeks after single I.V. dose, a significant increase in thigh muscle volume (measured by MRI excluding intramuscular adipose tissue) % change from placebo was exhibited by each of anti-GDF8 (6 mg/kg), anti-GDF8 (6 mg/kg)+low dose anti-Activin A (1 mg/kg), anti-GDF8 (6 mg/kg)+mid dose anti-Activin A (3 mg/kg), and anti-GDF8 (6 mg/kg)+high dose anti-Activin A (10 mg/kg) groups. At 8 weeks after single I.V. dose, a significant increase in thigh muscle volume % change from placebo was exhibited in anti-GDF8 (6 mg/kg)+mid dose anti-Activin A (3 mg/kg), and anti-GDF8 (6 mg/kg)+high dose anti-Activin A (10 mg/kg) groups. (*nominal $p<0.05$, nominal $p<0.001$). N values for each group are shown in FIG. 2**A.

As shown in FIG. 3, anti-Activin A antibody REGN2477 combined with anti-GDF8 antibody REGN1033 led to dose-dependent increases in thigh muscle volume. The thigh muscle volume results, as measured via MRI, excluding intermuscular adipose tissue and large vessels, are likewise summarized in Table 6, below. Treatment with mid- and high dose REGN2477+REGN1033 combination resulted in significantly increased thigh muscle volume (p<0.05) compared with placebo, as shown in Table 6.

TABLE 6

| Thigh Muscle Volume measured by MRI* | | | | | | | | |
|---|---|---|---|---|---|---|---|---|
| | | Placebo | anti-GDF8 | anti-activin A High Dose | anti-GDF8 + anti-activin A Low Dose | anti-GDF8 + anti-activin A Mid Dose | anti-GDF8 + anti-activin A High Dose |
| Week 4, % change | N | 12 | 6 | 6 | 6 | 6 | 12 |
| | mean | 0.4 | 3.3 | 0.3 | 4.9 | 4.6 | 5.9 |
| Week 8, % change | mean | 0.9 | 4.6 | 2.9 | 3.4 | 6.2 | 7.8 |
| | Δ LSM vs placebo (SE) | | 3.73 (1.819) | 1.97 (1.821) | 2.63 (1.824) | 5.31 (1.817) | 6.85 (1.484) |
| | Nominal p-value | | 0.0467 | 0.2846 | 0.1569 | 0.0056 | <0.0001 |

*excluding intermuscular adipose tissue and large vessels

As shown in Table 4, treatment with REGN2477+REGN1033 in medium and high dose combinations resulted in significantly increased thigh muscle volume in a dose-related manner compared with placebo.

Figure 4:
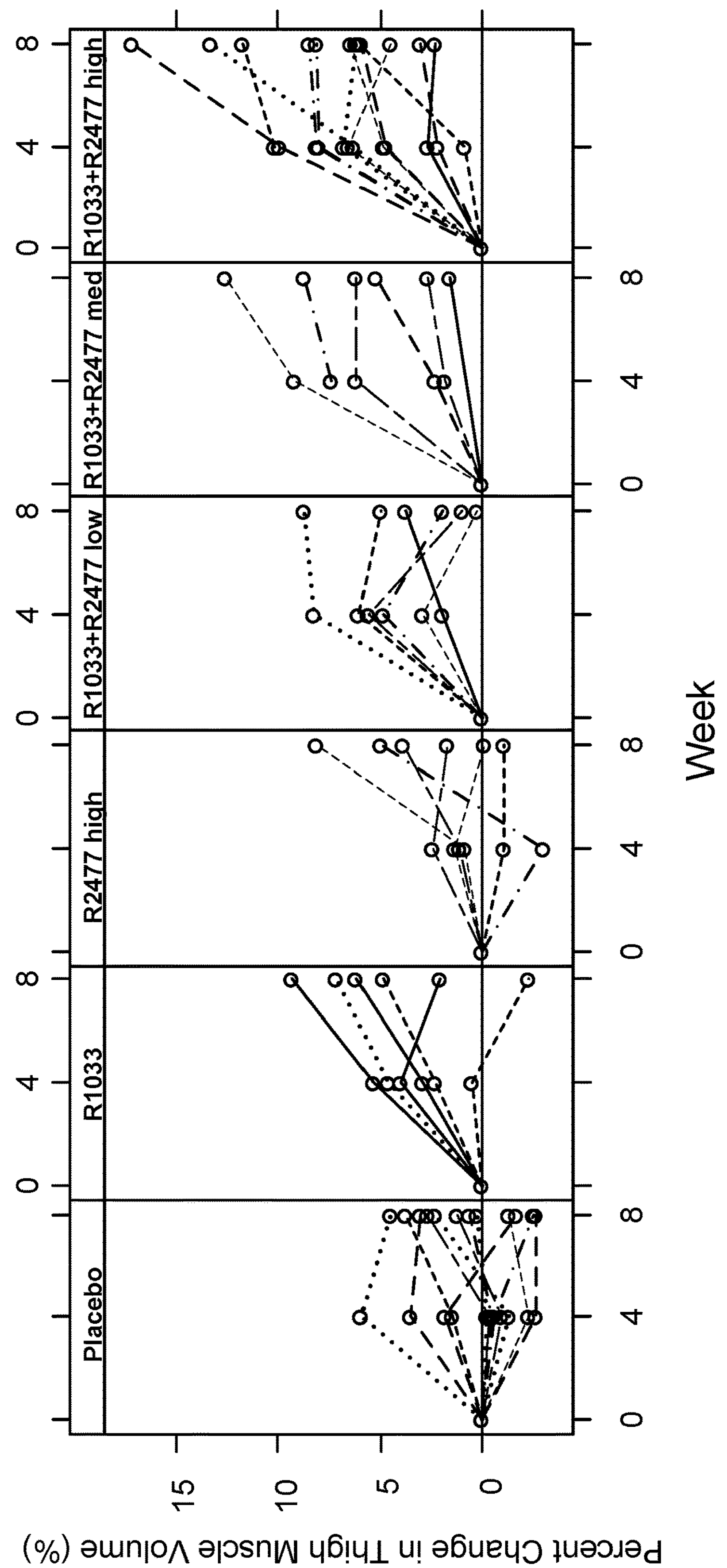
FIG. 4 show line graphs depicting individual data for percent change (from baseline) in thigh muscle volume by MRI at weeks 0, 4, and 8 after a single I.V. dose of anti-Activin A antibody REGN2477 and/or anti-GDF8 antibody REGN1033 in healthy post-menopausal women as % change from baseline in placebo, anti-GDF8 (6 mg/kg), high dose anti-Activin A (10 mg/kg), anti-GDF8 (6 mg/kg)+low dose anti-Activin A (1 mg/kg), anti-GDF8 (6 mg/kg)+mid dose anti-Activin A (3 mg/kg), and anti-GDF8 (6 mg/kg)+high dose anti-Activin A (10 mg/kg) groups for multiple individuals. Increases in thigh muscle volume were consistently observed in individual subjects following treatment with REGN2477+REGN1033 in combination. Within each treatment group, different lines indicate different individuals.

FIG. 4 shows that increases in thigh muscle volume were consistently observed in individual subjects following treatment with anti-Activin A+anti-GDF8 in combination. Within each treatment group, different lines indicate different individuals.

Figure 5:
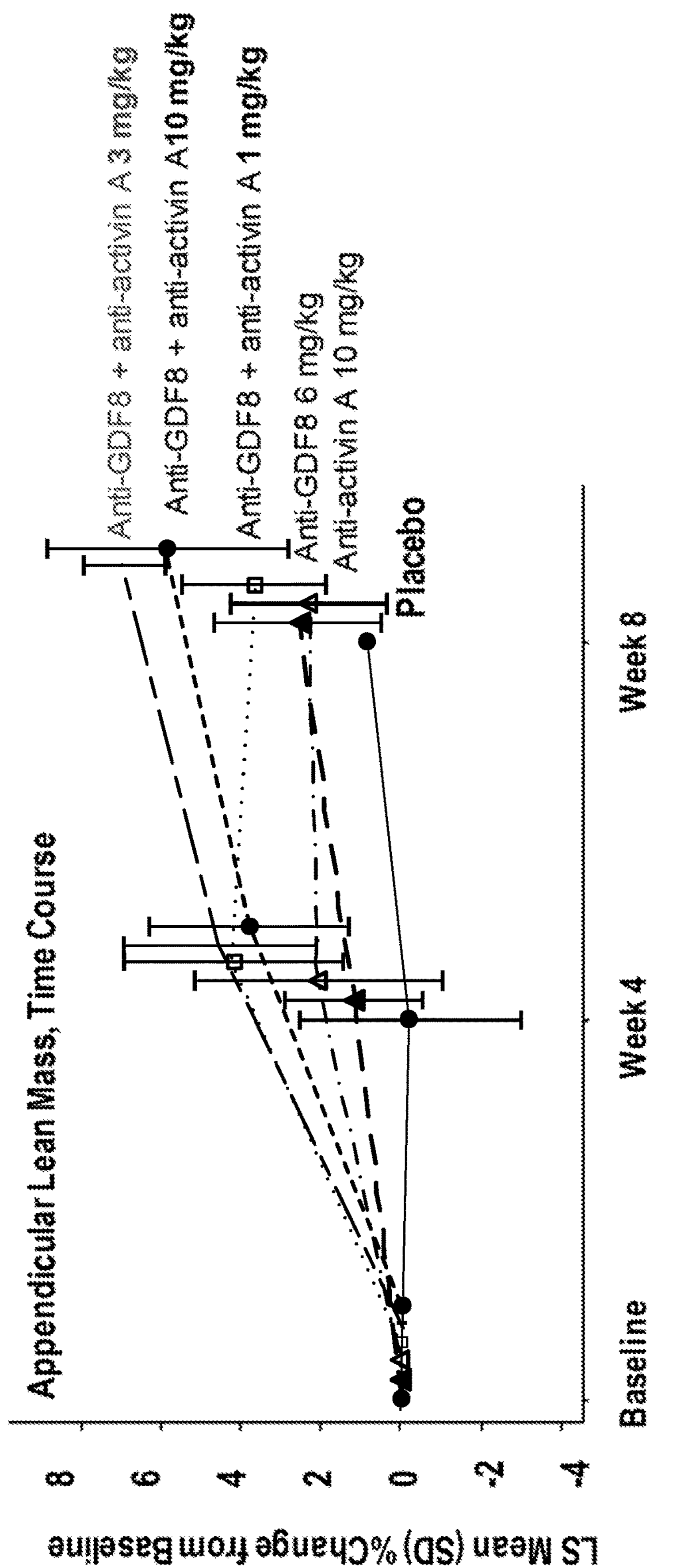
FIG. 5 shows a line graph depicting appendicular lean (body) mass (i.e., sum of lean tissue in the arms and legs) at weeks 0, 4, and 8 after a single I.V. dose of anti-Activin A antibody REGN2477 and/or anti-GDF8 antibody REGN1033 in healthy post-menopausal women as % percent change from baseline LS (least-squares) mean (SE) in six groups. N values for each group are shown in FIG. 2A. After 4 weeks and 8 weeks, each of the three combination dose groups, including anti-GDF8 (6 mg/kg)+low dose anti-Activin A (1 mg/kg), anti-GDF8 (6 mg/kg)+mid dose anti-Activin A (3 mg/kg), and anti-GDF8 (6 mg/kg)+high dose anti-Activin A (10 mg/kg) groups, exhibited significantly increased % change LS mean difference in appendicular lean mass compared to placebo (*nominal $p<0.05$, nominal $p<0.001$). N values for each group are shown in FIG. 2**A.

The pattern of effects on appendicular lean mass (the sum of lean mass of arms and legs) with anti-Activin A antibody REGN2477+anti-GDF8 antibody REGN1033 in combination was similar to that seen on thigh muscle volume, as shown in FIG. 5. The appendicular lean mass results, as measured via DXA, are likewise summarized in Table 7. The mid and high dosing combinations significantly increased appendicular lean mass compared to placebo, as shown in Table 7.

TABLE 7

| Appendicular Lean Mass by DXA | | | | | | | |
|---|---|---|---|---|---|---|---|
| | | Placebo | Anti-GDF8 | Anti-activin A High Dose | Anti-GDF8 + anti-activin A Low Dose | Anti-GDF8 + anti-activin A Mid Dose | Anti-GDF8 + anti-activin A High Dose |
| | N | 12 | 6 | 6 | 6 | 6 | 12 |
| Baseline, kg | Mean | 17.44 | 18.10 | 18.02 | 17.92 | 18.67 | 17.32 |
| Week 4, % Change | Mean | −0.2 | 1.2 | 2.1 | 4.2 | 4.6 | 3.8 |
| Week 8, % Change | Mean | 0.8 | 2.6 | 2.3 | 3.7 | 6.9 | 5.8 |
| | ΔLSM vs Placebo (SE) | | 1.90 (1.266) | 1.61 (1.265) | 2.96 (1.264) | 6.39 (1.275) | 4.97 (1.031) |
| | Nominal p-value | | 0.1418 | 0.2109 | 0.0242 | <0.0001 | <0.0001 |

Figure 6:
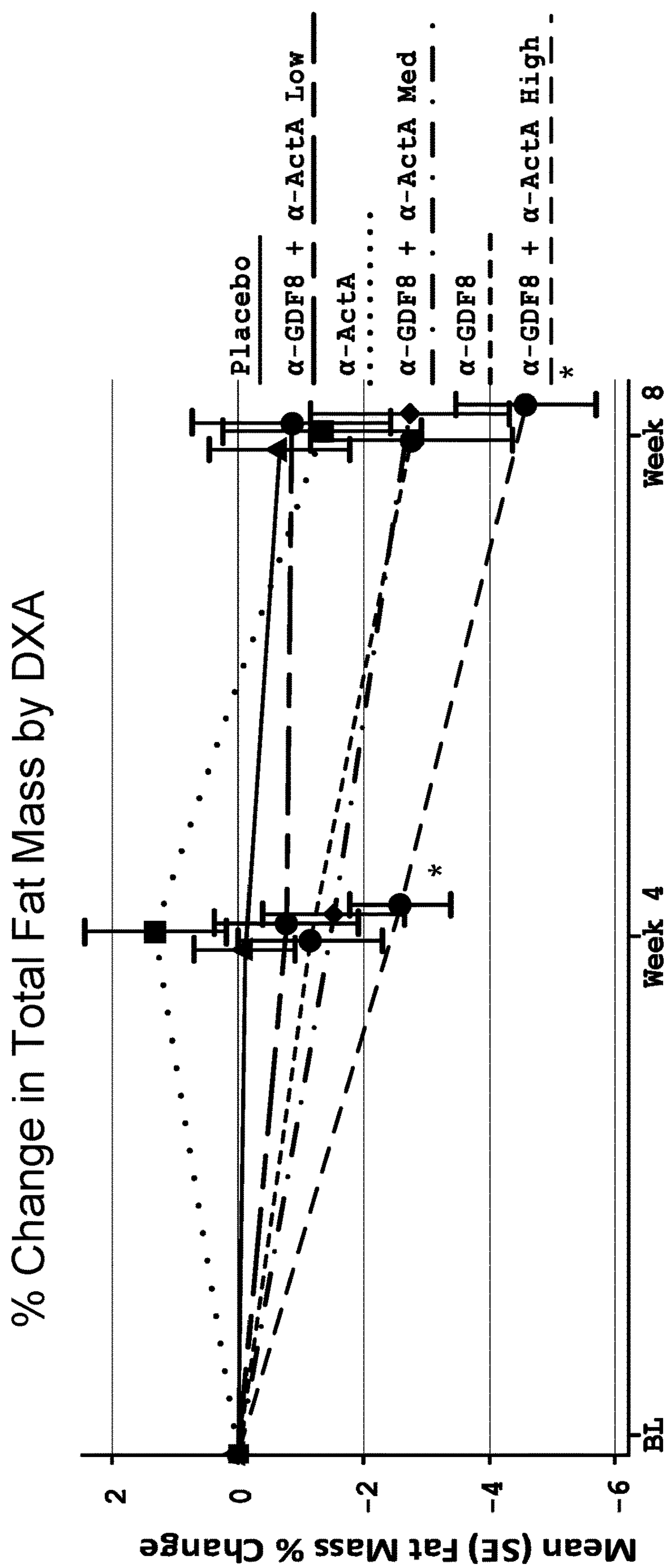
FIG. 6 shows a line graph depicting mean (SE=standard errors) total fat mass percent (as measured by DXA) change at weeks 0, 4, and 8 after a single I.V. dose of anti-Activin A antibody REGN2477 and/or anti-GDF8 antibody REGN1033 in healthy post-menopausal women in placebo, anti-GDF8 (6 mg/kg), high dose anti-Activin A (10 mg/kg), anti-GDF8 (6 mg/kg)+low dose anti-Activin A (1 mg/kg), anti-GDF8 (6 mg/kg)+mid dose anti-Activin A (3 mg/kg), and anti-GDF8 (6 mg/kg)+high dose anti-Activin A (10 mg/kg) groups. N values for each group are shown in FIG. 2A. The high dose group, (anti-GDF8 (6 mg/kg)+high dose anti-Activin A (10 mg/kg), exhibited a significant reduction in total fat mass as percent change LS Mean difference compared to placebo at week 4 and week 8 (*nominal $p<0.05$). Blockade of both Activin A and GDF8 led to reductions in total fat mass, as assessed by DXA.

As shown in FIG. 6, blockade of both Activin A and GDF8 led to reductions in total fat mass, as assessed by DXA. The high dose combination of anti-GDF8 antibody REGN1033 and anti-Activin A antibody REGN2477 significantly reduced total fat mass by DXA compared to placebo at week 8 (*p<0.05). The total fat mass results, as measured via DXA, are likewise summarized in Table 8, below.

TABLE 8

| Total Fat Mass by DXA | | | | | | |
|---|---|---|---|---|---|---|
| | Dose | anti-GDF8 High | anti-activin A High | anti-GDF8 + anti-activin A Low | anti-GDF8 + anti-activin A Mid | anti-GDF8 + anti-activin A High |
| Week 8, | N | 6 | 6 | 6 | 6 | 12 |
| % Change | ΔLSM vs Placebo (SE) | −2.11 (1.96) | −0.69 (1.93) | −0.2 (1.93) | −2.08 (1.93) | −3.92 (1.58)* |

*p < 0.05

Figure 7:
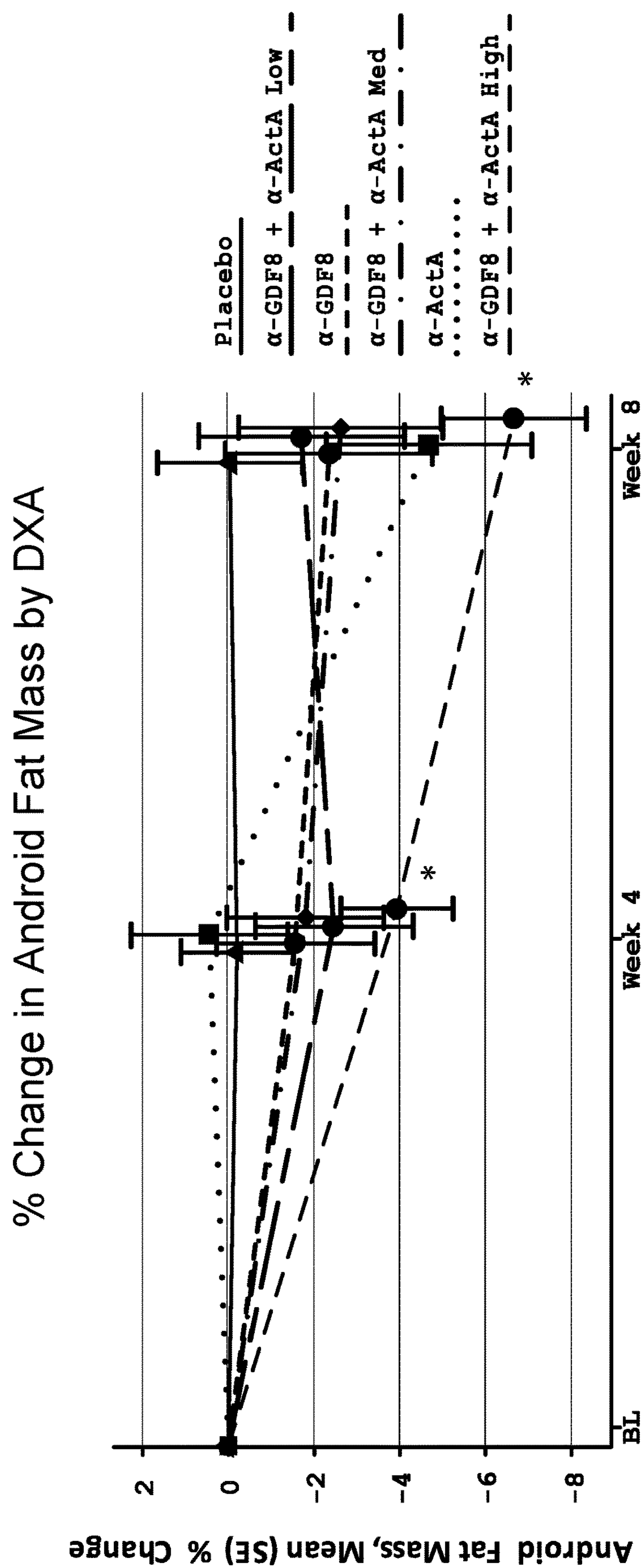
FIG. 7 shows a line graph depicting mean (SE) percent change in android fat mass at weeks 0, 4, and 8 after a single I.V. dose of anti-Activin A antibody REGN2477 and/or anti-GDF8 antibody REGN1033 in healthy post-menopausal women in six groups including placebo, anti-GDF8 (6 mg/kg), high dose (10 mg/kg) anti-Activin A, anti-GDF8 (6 mg/kg)+low dose (1 mg/kg) anti-Activin A, anti-GDF8 (6 mg/kg)+mid dose (3 mg/kg) anti-Activin A, and anti-GDF8 (6 mg/kg)+high dose (10 mg/kg) anti-Activin A groups. The high dose REGN1033+REGN2477 group exhibited significantly reduced percent change LS Mean difference in android fat mass by DXA compared to placebo at week 4 and week 8 (*nominal $p<0.05$). N values for each group are shown in FIG. 2A. Blockade of both Activin A and GDF8 was also associated with decreases in android fat mass, as assessed by DXA.

Blockade of Activin A and GDF8 was also found to be associated with decreases in android fat mass, as assessed by DXA, as shown in FIG. 7. The high dose combination of anti-GDF8 antibody REGN1033 and anti-Activin A antibody REGN2477 significantly reduced android fat mass by DXA compared to placebo at week 8 (*p<0.05).

Further efficacy results are shown in FIGS. 8 to 17 and summarized in the tables, below. REGN2477+REGN1033 high, medium and low doses are shown in FIG. 2A.

Figure 8:
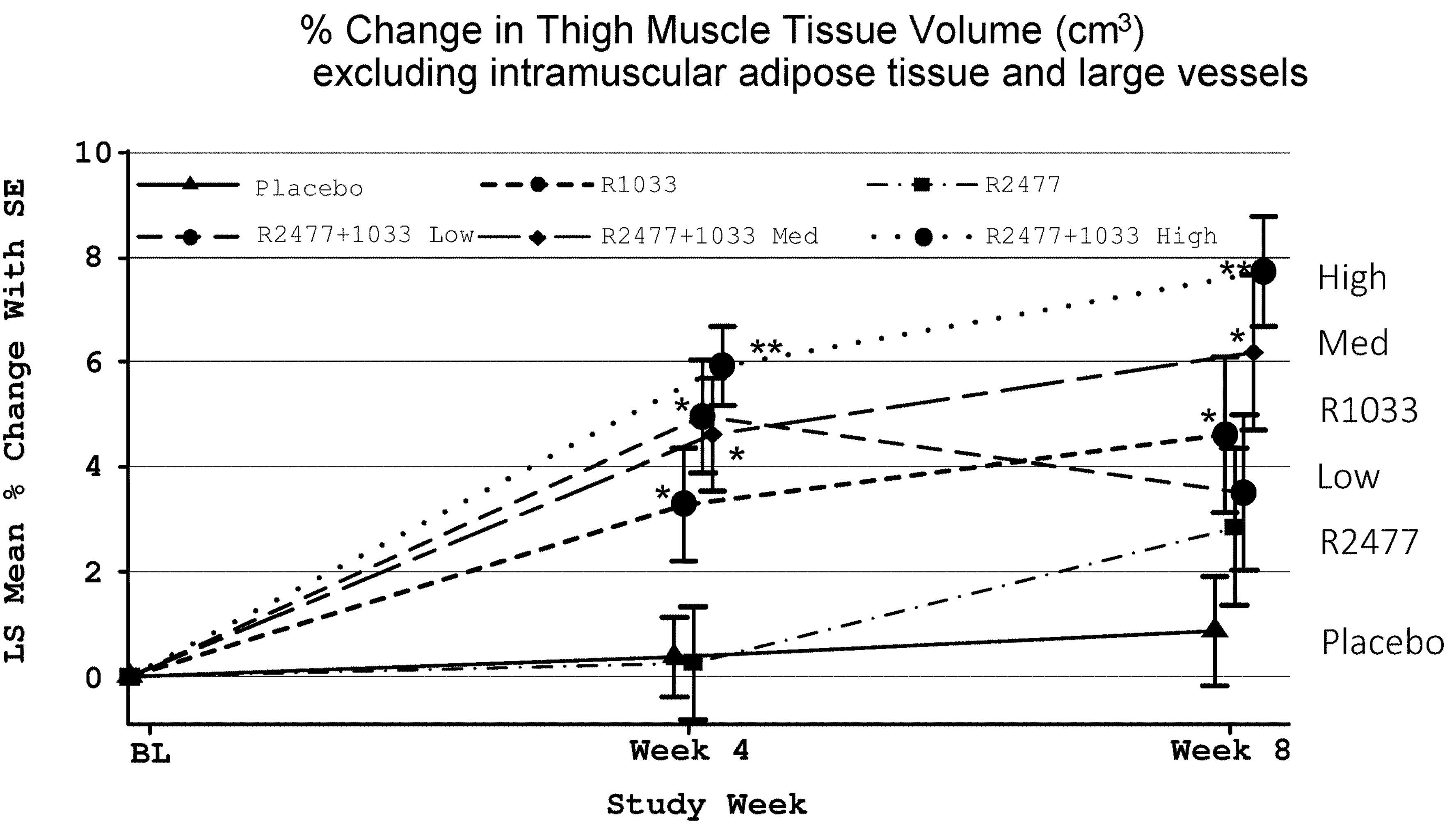
FIG. 8 shows a line graph depicting LS mean percent change with SE in thigh muscle volume (excluding intramuscular adipose tissue and large vessels) at weeks 0, 4, and 8 after a single I.V. dose of anti-Activin A antibody REGN2477 and/or anti-GDF8 antibody REGN1033 in healthy post-menopausal women in six groups including placebo, anti-GDF8 (6 mg/kg), high dose (10 mg/kg) anti-Activin A, anti-GDF8 (6 mg/kg)+low dose (1 mg/kg) anti-Activin A, anti-GDF8 (6 mg/kg)+mid dose (3 mg/kg) anti-Activin A, and anti-GDF8 (6 mg/kg)+high dose (10 mg/kg) anti-Activin A groups. N values for each group are shown in FIG. 2A. Compared with placebo, REGN2477+REGN1033 medium and high groups exhibited significantly increased mean % change in thigh muscle volume at 4 weeks and 8 weeks. (*nominal $p<0.05$, **nominal $p<0.001$).

Compared with placebo, REGN2477+REGN1033 medium (p<0.05) and high dose groups (p<0.001) exhibited significantly increased thigh muscle volume, excluding Intramuscular adipose tissue and large vessels (FIG. 8). Thigh muscle volume increased in the REGN2477+REGN1033 high dose group by 7.73% as compared with 0.88% in the placebo group (nominal p<0.001) at 8 weeks. Compared with placebo, REGN2477+REGN1033 at the medium dose and REGN1033 alone also significantly increased thigh muscle volume. Increases in thigh muscle volume were consistently observed in individual subjects treated with the combination in a dose responsive manner. (data not shown).

Figure 9:
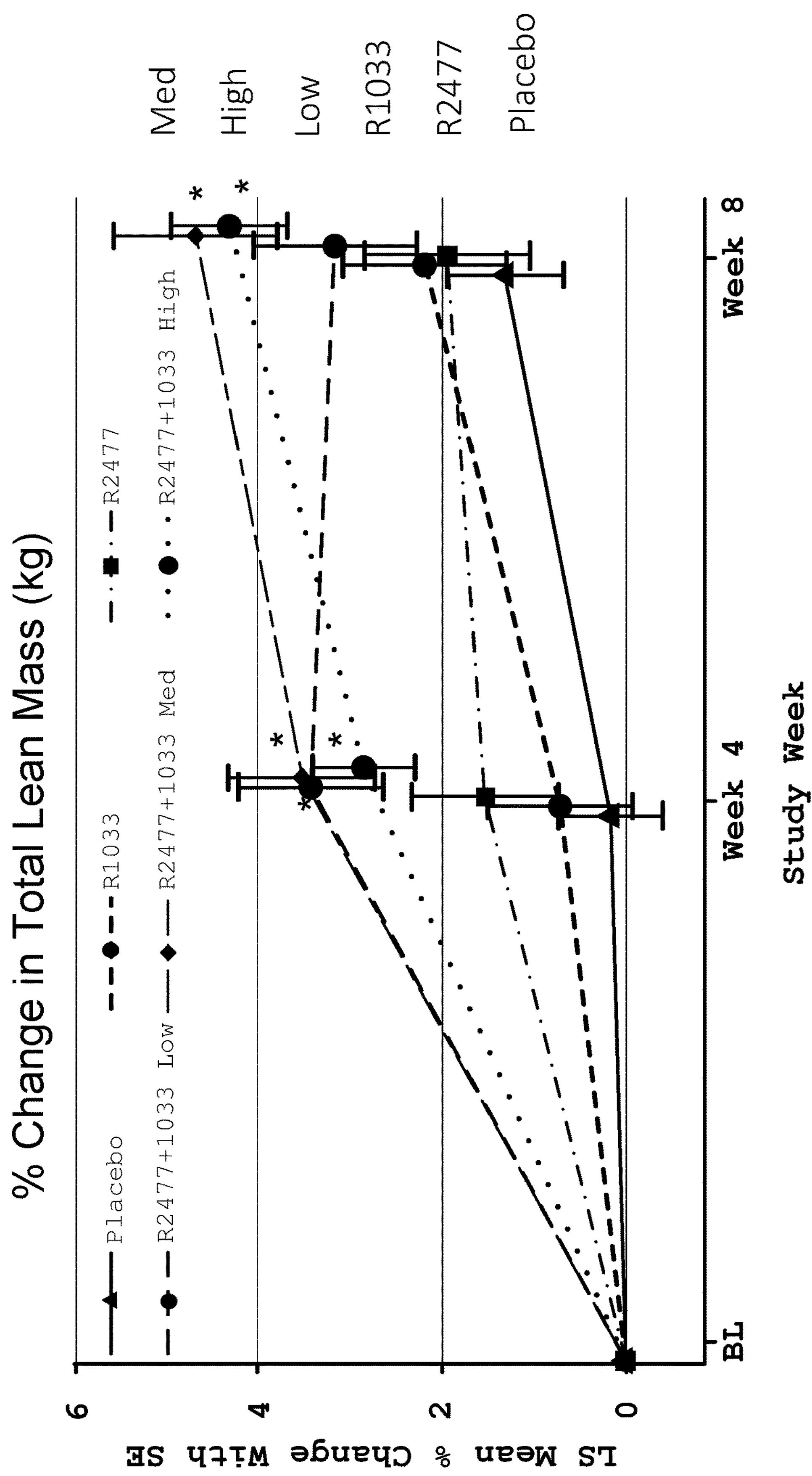
FIG. 9 shows a line graph depicting LS mean percent change with SE in total lean mass at weeks 0, 4, and 8 after a single I.V. dose of anti-Activin A antibody REGN2477 and/or anti-GDF8 antibody REGN1033 in healthy post-menopausal women for six groups including placebo, anti-GDF8 (6 mg/kg), high dose (10 mg/kg) anti-Activin A, anti-GDF8 (6 mg/kg)+low dose (1 mg/kg) anti-Activin A, anti-GDF8 (6 mg/kg)+mid dose (3 mg/kg) anti-Activin A, and anti-GDF8 (6 mg/kg)+high dose (10 mg/kg) anti-Activin A groups. N values for each group are shown in FIG. 2A. Compared with placebo, REGN2477+REGN1033 medium and high dose groups exhibited significantly increased % change in total lean mass compared to placebo at 4 weeks and 8 weeks. (*nominal $p<0.05$).

Compared with placebo, REGN2477+REGN1033 high dose group exhibited significantly increased total lean mass by DXA (p<0.05) (FIG. 9).

Figure 10:
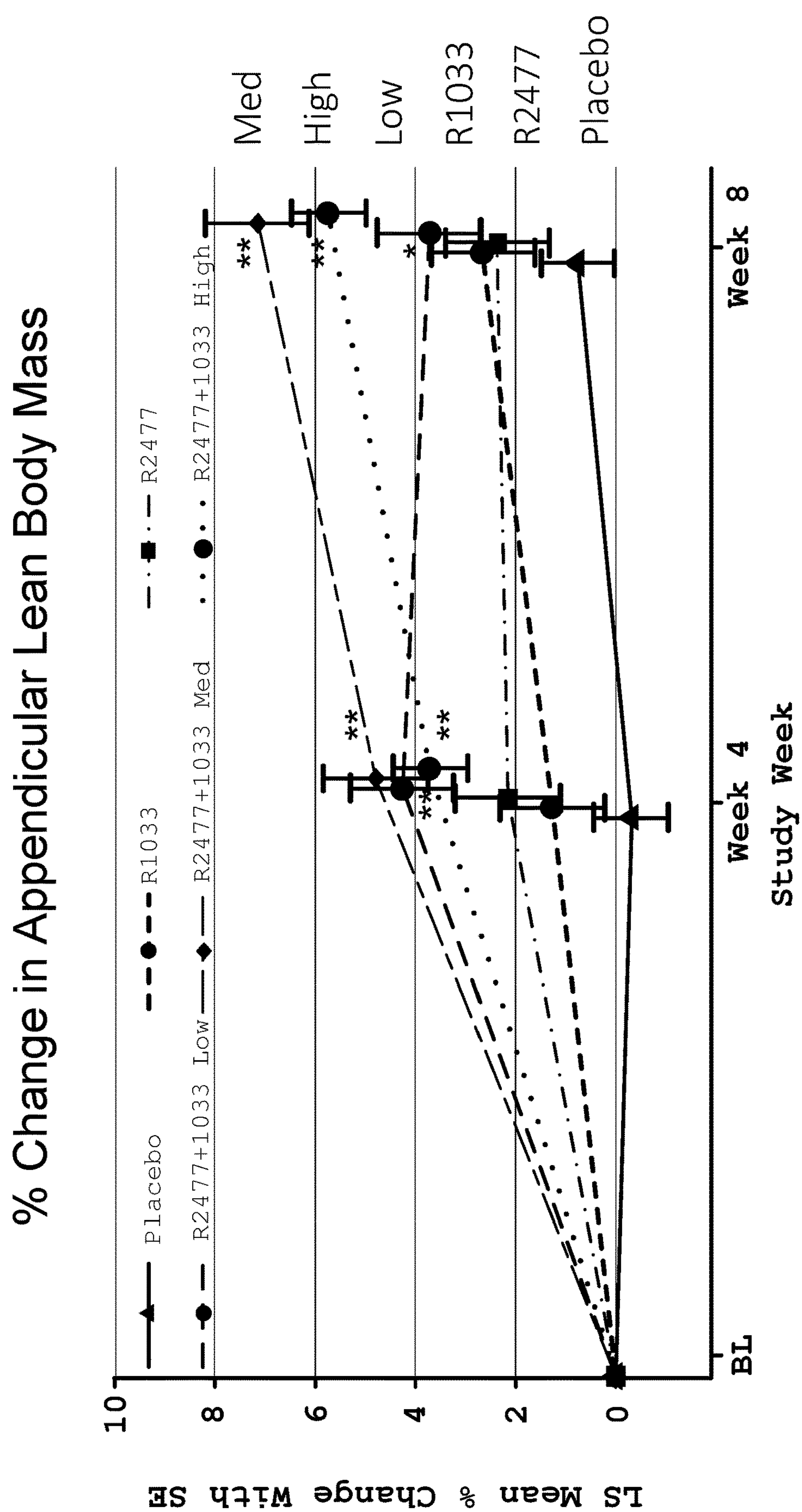
FIG. 10 shows a line graph depicting LS mean percent change with SE in appendicular lean body mass (calculated via aLBM equation), in kg, at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+mid dose (3 mg/kg) anti-Activin A, and anti-GDF8+high dose (10 mg/kg) anti-Activin A groups. N values for each group are shown in FIG. 2A. REGN2477+REGN1033 treatment resulted in significantly increased % change in appendicular lean body mass calculated by aLBM equation)(kg) at each low, medium and high dose groups at 4 weeks and 8 weeks compared with placebo (*$p<0.05$, **$p<0.001$).

Appendicular lean body mass (calculated via aLBM equation), was significantly increased in each of the combination REGN2477+REGN1033 treatment groups compared with placebo (low dose p<0.05, medium and high dose groups p<0.001)(FIG. 10). Appendicular lean body mass increased in the REGN2477+REGN1033 medium dose group by 7.15% from baseline as compared with 0.76% in the placebo group at 8 weeks. Similarly, appendicular lean body mass increased in the REGN2477+REGN1033 high dose group by 5.7% from baseline as compared with 0.76% in the placebo group.

Figure 11:
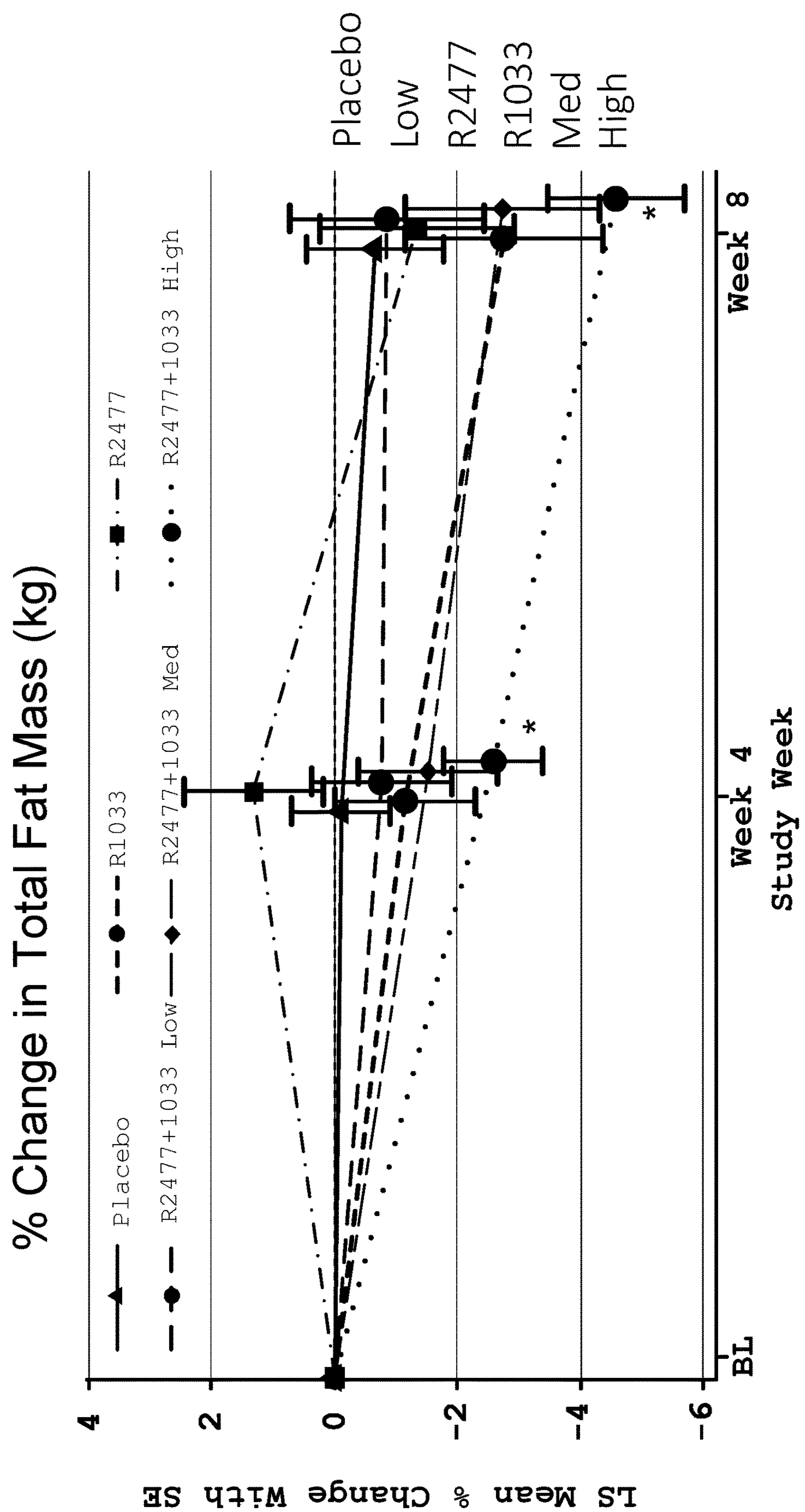
FIG. 11 shows a line graph depicting LS mean percent change with SE in total fat mass, in kg, at weeks 0, 4, and 8 after a single I.V. dose of anti-Activin A antibody REGN2477 and/or anti-GDF8 antibody REGN1033 in healthy post-menopausal women in six groups including placebo, anti-GDF8 (6 mg/kg), high dose (10 mg/kg) anti-Activin A, anti-GDF8+low dose (1 mg/kg) anti-Activin A, anti-GDF8 (6 mg/kg)+mid dose (3 mg/kg) anti-Activin A, and anti-GDF8 (6 mg/kg)+high dose (10 mg/kg) anti-Activin A groups. N values for each group are shown in FIG. 2A. The high dose combination REGN2477+REGN1033 treatment group exhibited significantly decreased % total fat mass: −3.92% (high dose group) compared with placebo −0.65% at 8 weeks. (*nominal $p<0.05$).

Total fat mass was significantly decreased in the high dose REGN2477+REGN1033 treatment group; total fat mass was decreased: 3.92% (high dose group) compared with placebo at 0.5% (nominal p<0.05) (FIG. 11).

Figure 12:
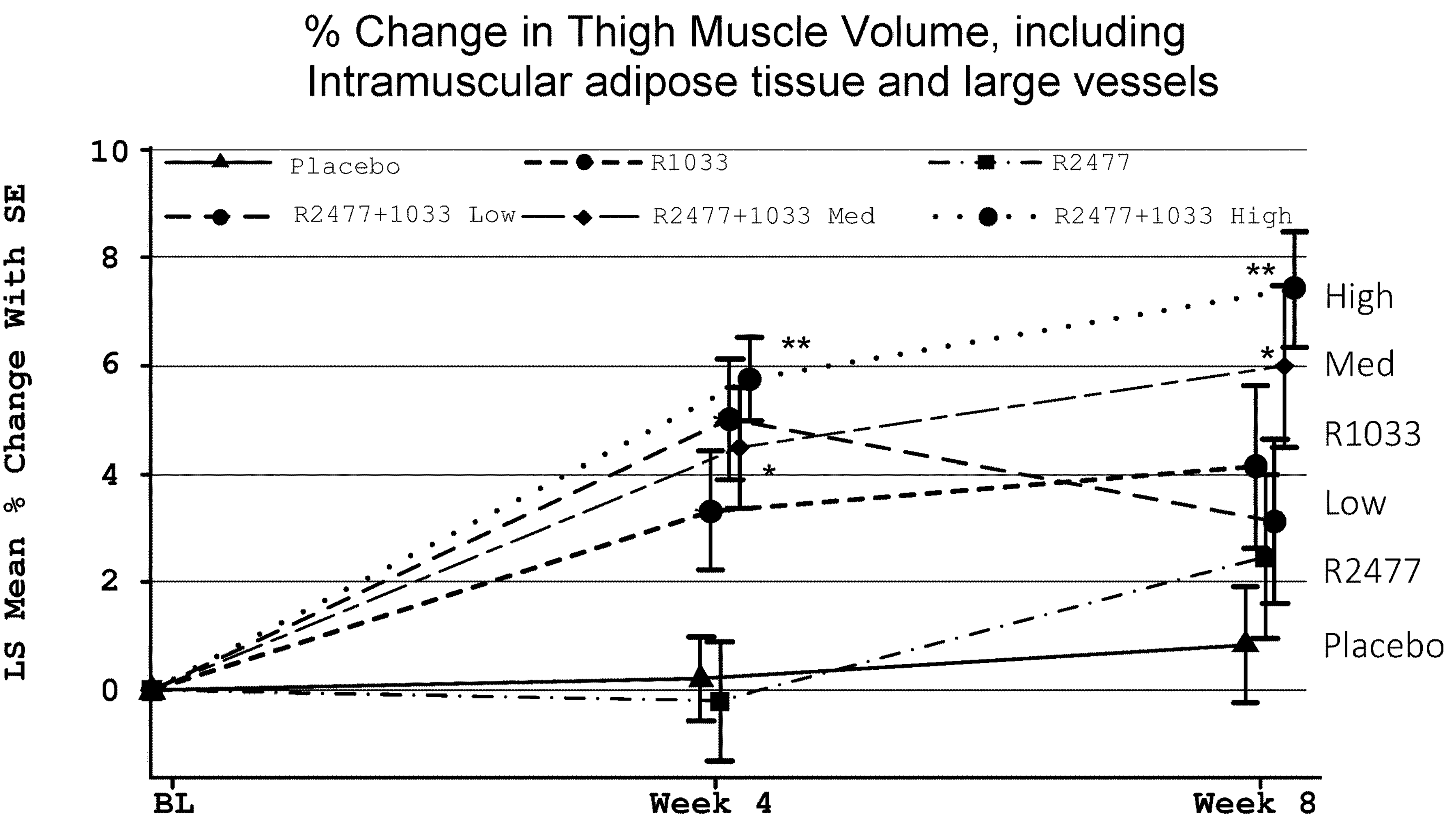
FIG. 12 shows a line graph depicting LS mean percent change with SE in thigh muscle volume, in $cm^3$, (including intramuscular adipose tissue and large vessels) at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+ mid dose (3 mg/kg) anti-Activin A, and anti-GDF8+high dose (10 mg/kg) anti-Activin A groups. N values for each group are shown in FIG. 2A. The high and medium dose REGN2477+REGN1033 treatment groups exhibited significantly increased % change in thigh muscle volume, including intramuscular adipose tissue and large vessels in medium and high treatment groups at 4 weeks and 8 weeks compared to placebo (*nominal $p<0.05$, **nominal $p<0.001$).

Compared to placebo, thigh muscle volume including intramuscular adipose tissue and large vessels was significantly increased in each of the medium and high dose REGN2477+REGN1033 groups and REGN1033 group at 4 weeks, and at 8 weeks (FIG. 12). Low dose REGN2477+REGN1033 also exhibited significant increase in thigh muscle volume including intramuscular adipose tissue and large vessels compared to placebo at 4 weeks.

Figure 13:
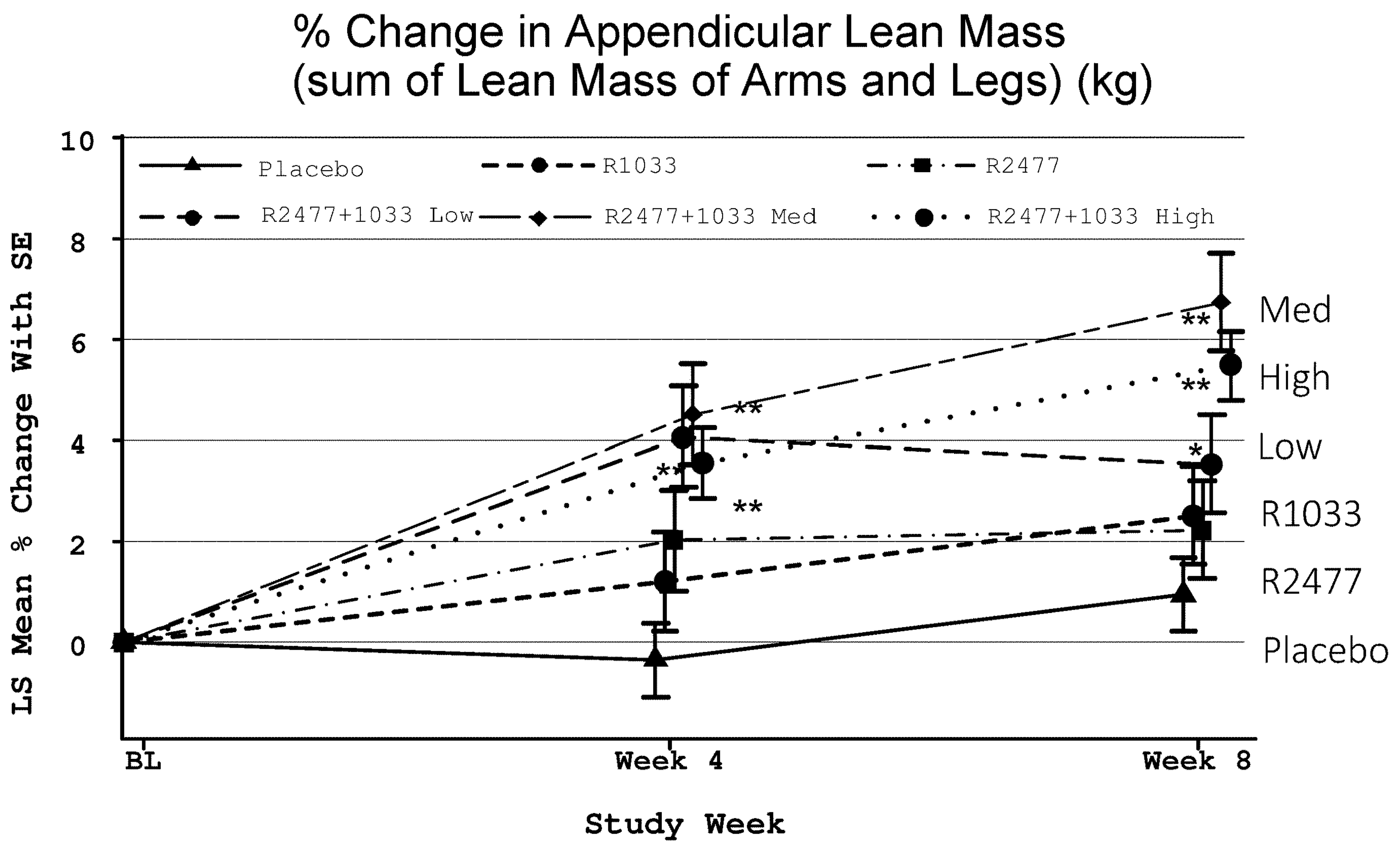
FIG. 13 shows a line graph depicting LS mean percent change with SE in appendicular lean mass (sum of lean mass of arms and legs), in kg, at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+mid dose (3 mg/kg) anti-Activin A, and anti-GDF8+high dose (10 mg/kg) anti-Activin A groups. N values for each group are shown in FIG. 2A. Appendicular lean mass was significantly increased as mean percent change from placebo in each REGN2477+ REGN1033 low, medium and high treatment groups at 4 and 8 weeks (*nominal $p<0.05$, *nominal *$p<0.001$).

Appendicular lean mass (sum of arms and legs) was significantly increased in each of combination REGN2477+REGN1033 treatment groups (p<0.05) at 4 and 8 weeks compared to placebo (FIG. 13).

Figure 14:
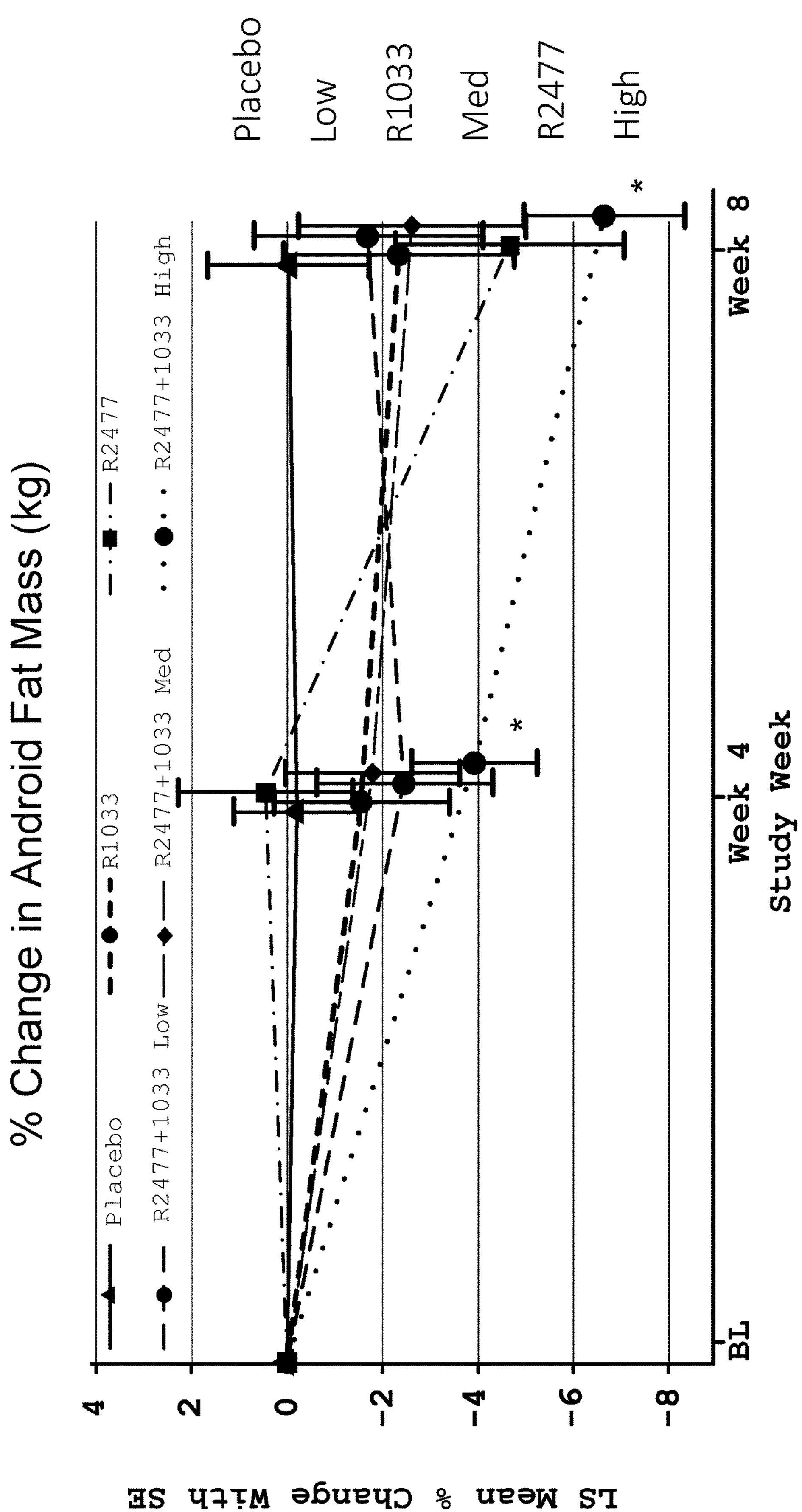
FIG. 14 shows a line graph depicting LS mean percent change with SE in android fat mass, in kg, at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+ mid dose (3 mg/kg) anti-Activin A, and anti-GDF8+high dose (10 mg/kg) anti-Activin A groups. N values for each group are shown in FIG. 2A. The high dose REGN1033+ REGN2477 group exhibited significantly reduced % change in android fat mass by DXA compared to placebo at week 4 and week 8 (*nominal $p<0.05$).

Android fat mass in the high dose REGN2477+REGN1033 treatment group was also significantly reduced (FIG. 14). Android fat mass was reduced 6.6% in the high dose REGN2477+REGN1033 group as compared to no reduction in the placebo.

Figure 15:
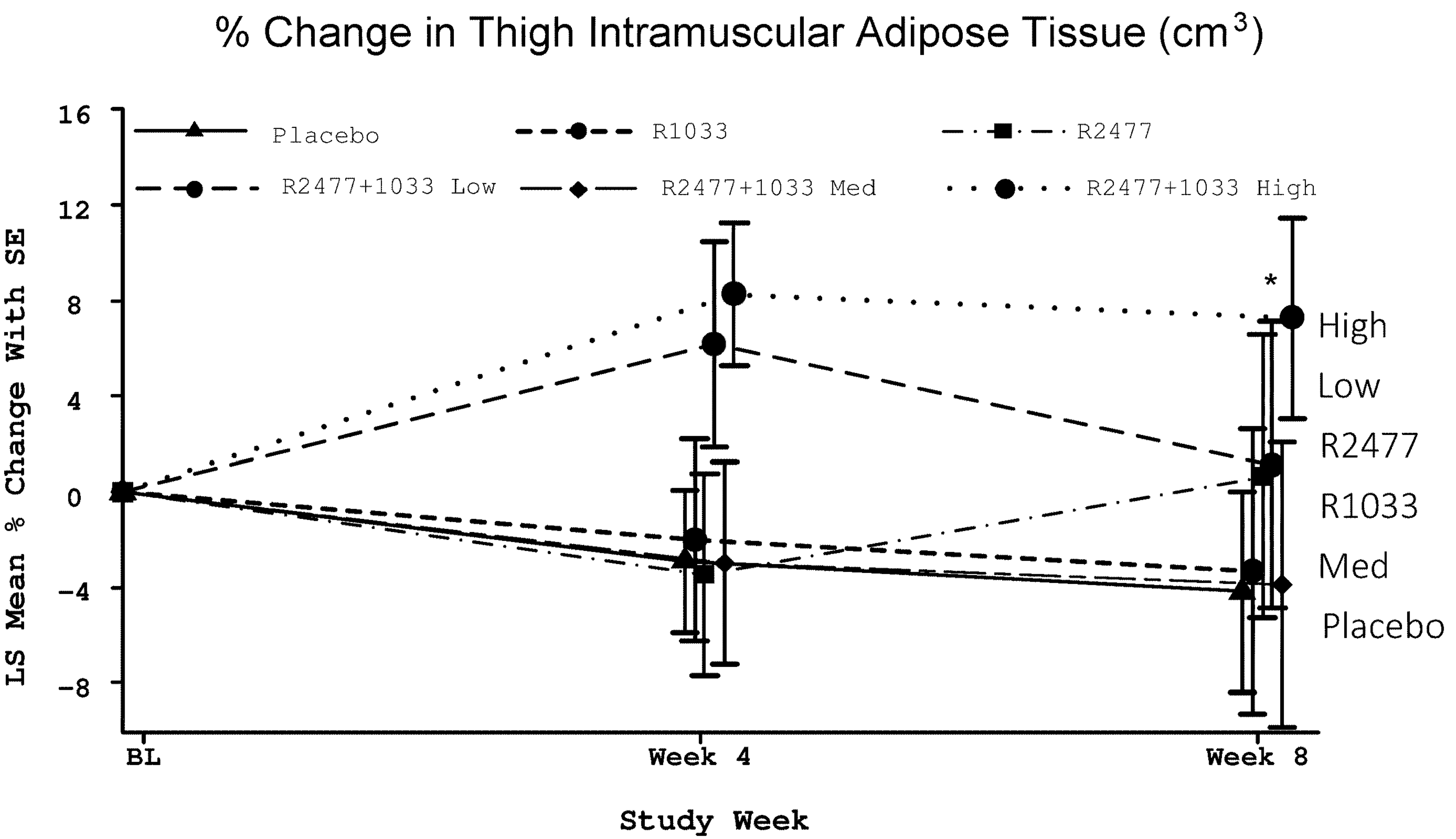
FIG. 15 shows a line graph depicting LS mean percent change with SE in thigh intramuscular adipose tissue volume, in $cm^3$, at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+mid dose (3 mg/kg) anti-Activin A, and anti-GDF8+high dose (10 mg/kg) anti-Activin A groups. N values for each group are shown in FIG. 2A. The high dose REGN1033+REGN2477 group exhibited increased thigh intramuscular adipose tissue volume as mean % change compared to placebo at 8 weeks. (*nominal $p<0.05$).
Figure 16:
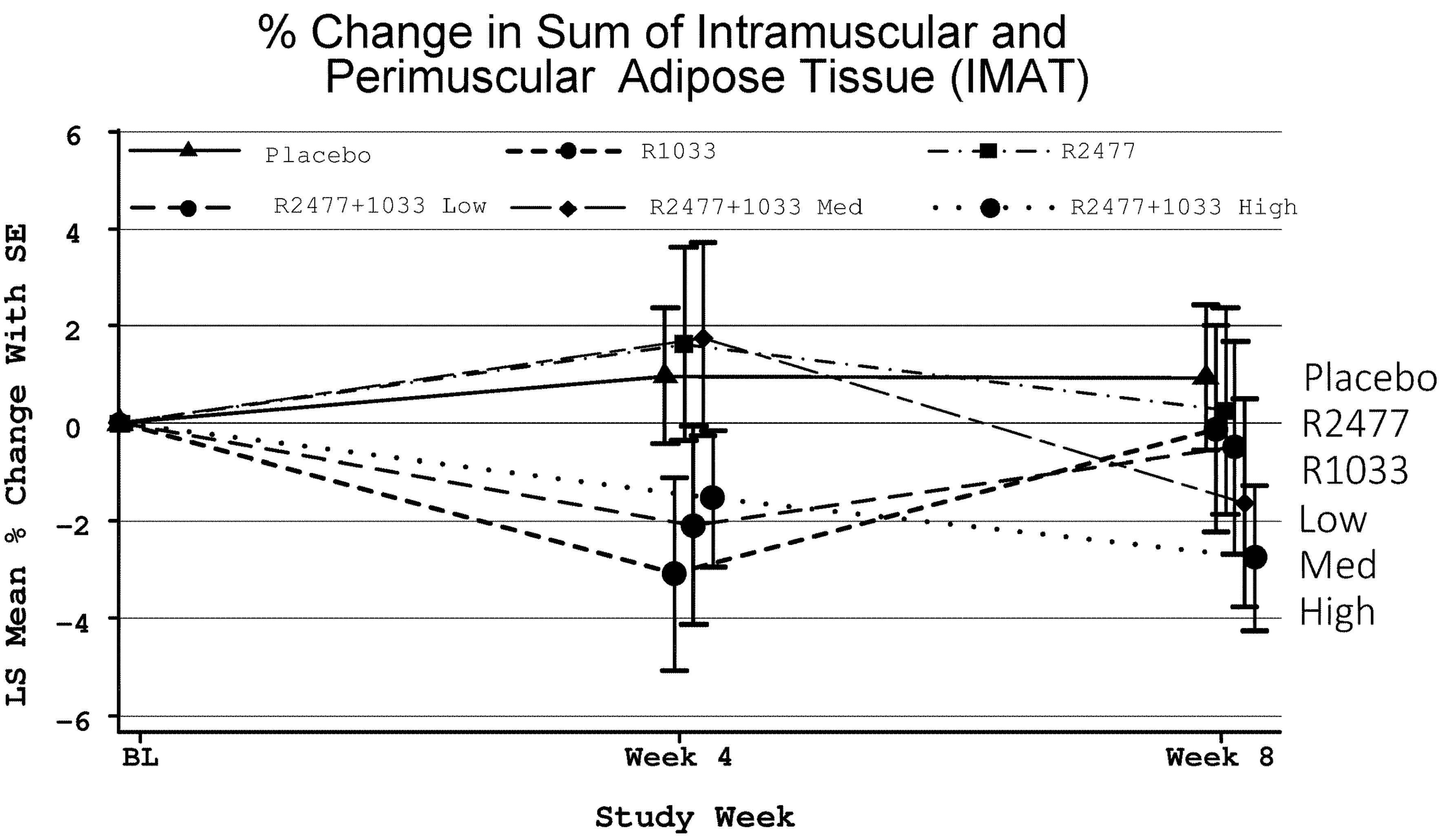
FIG. 16 shows a line graph depicting LS mean percent change with SE in sum of intramuscular and perimuscular adipose tissue (IMAT) at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+mid dose (3 mg/kg) anti-Activin A, and anti-GDF8+high dose (10 mg/kg) anti-Activin A groups. N values for each group are shown in FIG. 2A. The combination REGN1033+REGN2477 treatment groups were not significantly different than placebo in LS mean percent change with SE in sum of intramuscular and perimuscular adipose tissue (IMAT) at weeks 4 and 8.

Thigh intramuscular adipose tissue volume (cm3) was significantly increased in the high dose REGN2477+REGN1033 group (p<0.05) as compared to placebo at 8 weeks (FIG. 15).

Figure 17:
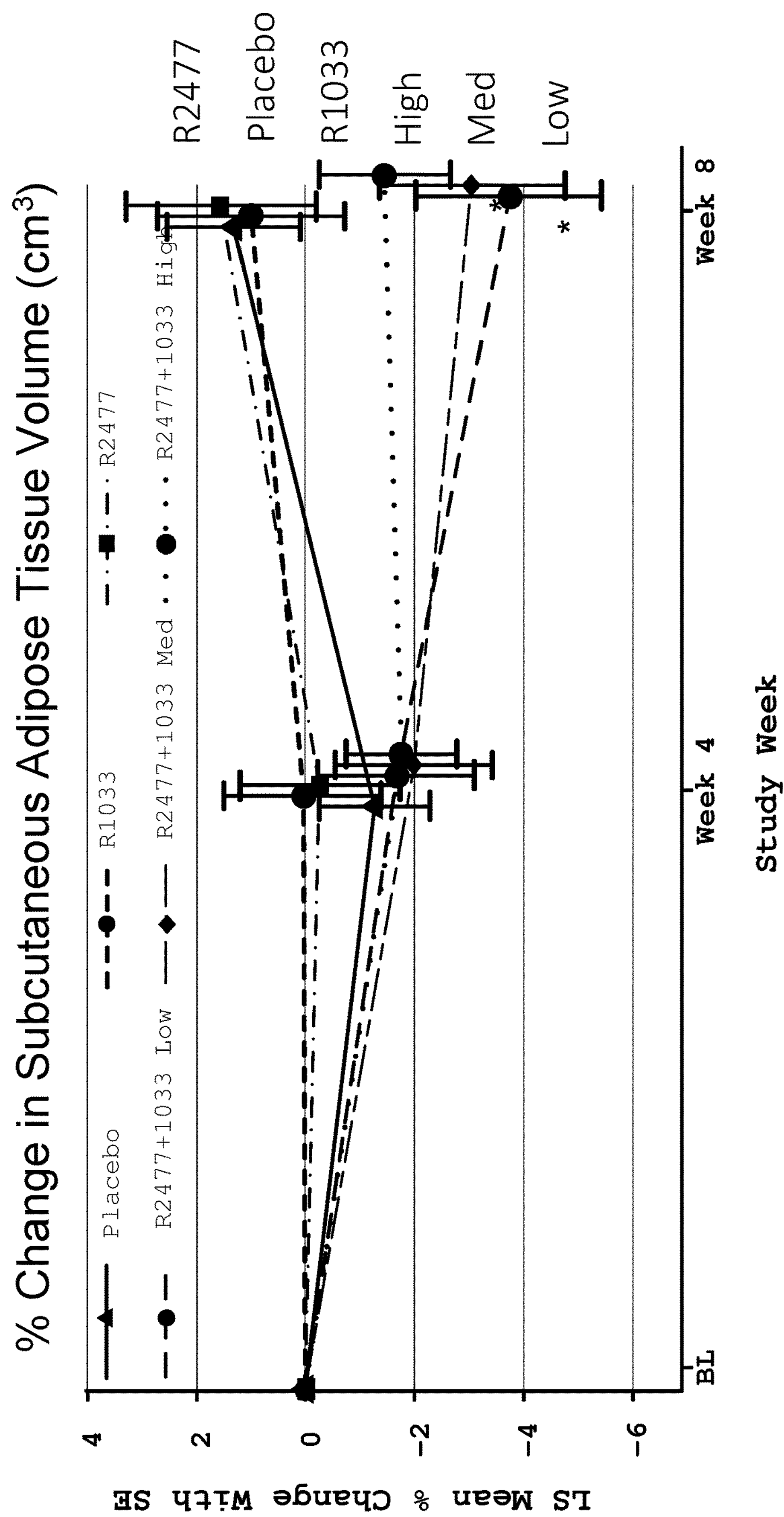
FIG. 17 shows a line graph depicting LS mean percent change with SE in subcutaneous adipose tissue volume, in $cm^3$, at weeks 0, 4, and 8 after a single I.V. dose of anti-Activin A antibody REGN2477 and/or anti-GDF8 antibody REGN1033 in healthy post-menopausal women in six groups including placebo, anti-GDF8, high dose (10 mg/kg) anti-Activin A, anti-GDF8+low dose (1 mg/kg) anti-Activin A, anti-GDF8+mid dose (3 mg/kg) anti-Activin A, and anti-GDF8+high dose (10 mg/kg) anti-Activin A groups. N values for each group are shown in FIG. 2A. The REGN1033+REGN2477 low and medium treatment groups exhibited significantly decreased % change in subcutaneous adipose tissue volume compared to placebo at 8 weeks (*nominal $p<0.05$).

Reductions in adipose tissue in the high dose group were observed in the sum of Intramuscular and Perimuscular Adipose Tissue (IMAT)(FIG. 16) and in the low and medium dose group of subcutaneous adipose tissue. (FIG. 17). In contrast, thigh intramuscular adipose tissue was increased in the high dose group to 8% as compared with placebo with a reduction of 4%. (FIG. 17).

REGN2477+REGN1033, in the high dose group, significantly increased all of the major measures of muscle volume and lean mass compared with placebo, at both Week 4 and Week 8; the effects at Week 4 were generally less pronounced than at Week 8 (Table 9). A summary of Percent Change in Key Body Composition Measures at Week 8 (Full Analysis Set, LS Means and SE presented) is shown in Table 9, below.

TABLE 9

| Summary of Change in Body Composition at Week 8 | | | | | | | | |
|---|---|---|---|---|---|---|---|---|
| Endpoint | | Placebo (n = 12) | R1033 (6 mg/kg) (n = 6) | R2477 (10 mg/kg) (n = 6) | Low R2477 (1 mg/kg) +R1033 (n = 6) | Medium R2477 (3 mg/kg) +R1033 (n = 6) | High R2477 (10 mg/kg) +R1033 (n = 12) |
| Thigh Muscle Volume | % Change from baseline | 0.88 (1.05) | 4.61 (1.49) | 2.85 (1.49) | 3.51 (1.49) | 6.19 (1.48) | 7.73 (1.05) |
| | Difference from placebo | | 3.73 (1.82)* | 1.97 (1.82) | 2.63 (1.82) | 5.31 (1.82)* | 6.85 (1.48)** |
| Total Lean Mass by DXA | % Change from baseline | 1.31 (0.64) | 2.18 (0.89) | 1.94 (0.90) | 3.16 (0.89) | 4.67 (0.89) | 4.31 (0.63) |
| | Difference from placebo | | 0.88 (1.10) | 0.63 (1.11) | 1.85 (1.10) | 3.37 (1.10)* | 3.00 (0.89)* |
| Appendicular Lean Body Mass | % Change from baseline | 0.76 (0.73) | 2.65 (1.03) | 2.37 (1.03) | 3.72 (1.03) | 7.15 (1.04) | 5.72 (0.73) |
| | Difference from placebo | | 1.90 (1.27) | 1.61 (1.26) | 2.96 (1.26)* | 6.39 (1.27)** | 4.97 (1.03)** |
| Total Fat Mass by DXA | % Change from baseline | −0.65 (1.12) | −2.76 (1.60) | −1.34 (1.58) | −0.85 (1.58) | −2.73 (1.58) | −4.57 (1.12) |
| | Difference from placebo | | −2.11 (1.96) | −0.69 (1.93) | −0.2 (1.93) | −2.08 (1.93) | −3.92 (1.58)* |

*p < 0.05;
**p < 0.001

In Table 9, above, changes from baseline and differences from placebo are Least-Squares (LS) means based on the ANCOVA model with baseline as a covariate and treatment as a fixed factor. Standard errors (SE) and p-values also taken from the ANCOVA. Nominal p-values are reported.

Bone mineral density (BMD) mass and bone mineral content (BMC) mass were measured by DXA, as shown in Table 10. At the high dose, R2477+R1033 increased Bone Mineral Content as measured by DXA, while total bone mineral density did not change (Table 10).

Sum of fat mass of arms and legs were measured as shown in Table 10. At the high dose, R2477+R1033 decreased sum of fat mass of arms and legs (p<0.05).

The data from the primary endpoint analysis is shown in Table 10, below.

TABLE 10

| Primary analysis of efficacy endpoints | | | | | | | |
|---|---|---|---|---|---|---|---|
| Parameter | Analysis Visit | Placebo (n = 12) | R1033 (n = 6) | R2477 (10 mg/kg) IV (n = 6) | R1033 + R2477 (1 mg/kg) IV (n = 6) | R1033 + R2477 (3 mg/kg) IV (n = 6) | R1033 + R2477 (10 mg/kg) IV (n = 12) |
| Thigh Muscle Tissue Volume (cm3), Excluding Intra-muscular Adipose Tissue and Large Vessels/% change | LS Mean (SE)Week 4 | 0.37 (0.76) | 3.27 (1.07) | 0.27 (1.08) | 4.96 (1.08) | 4.61 (1.07) | 5.92 (0.76) |
| | LS Mean Diff (SE)/ week 4 | | 2.9 (1.32)* | −0.11 (1.32) | 4.59 (1.32)* | 4.24 (1.31)* | 5.55 (1.07)** |
| | LS Mean (SE)/week 8 | 0.88 (1.05) | 4.61 (1.49) | 2.85 (1.49) | 3.51 (1.49) | 6.19 (1.48) | 7.73 (1.05) |
| | LS Mean Diff (SE)/ week 8 | | 3.73 (1.82)* | 1.97 (1.82) | 2.63 (1.82) | 5.31 (1.82)* | 6.85 (1.48)** |

TABLE 10-continued

| Primary analysis of efficacy endpoints | | | | | | | | |
|---|---|---|---|---|---|---|---|---|
| Parameter | Analysis Visit | Placebo (n = 12) | R1033 (n = 6) | R2477 (10 mg/kg) IV (n = 6) | R1033 + R2477 (1 mg/kg) IV (n = 6) | R1033 + R2477 (3 mg/kg) IV (n = 6) | R1033 + R2477 (10 mg/kg) IV (n = 12) |
| Change | LS Mean (SE)/week 4 | 1.64 (3.26) | 13.95 (4.61) | −0.14 (4.63) | 20.29 (4.63) | 18.77 (4.61) | 24.5 (3.26) |
| | LS Mean Diff (SE)/week 4 | | 12.32 (5.65)* | −1.78 (5.66) | 18.65 (5.67)* | 17.14 (5.64)* | 22.86 (4.61)** |
| | LS Mean (SE)/week 8 | 3.5 (4.13) | 20.42 (5.85) | 11.22 (5.87) | 14.55 (5.88) | 25.44 (5.85) | 31.95 (4.14) |
| | LS Mean Diff (SE)/ week 8 | | 16.91 (7.17)* | 7.71 (7.18) | 11.05 (7.19) | 21.94 (7.16)* | 28.45 (5.85)** |
| Thigh Muscle Volume (cm3), Including Intra-muscular Adipose Tissue and Large Vessels/% change | LS Mean (SE)/week 4 | 0.21 (0.78) | 3.32 (1.1) | −0.2 (1.11) | 5 (1.11) | 4.49 (1.1) | 5.76 (0.78) |
| | LS Mean Diff (SE)/ week 4 | | 3.1 (1.35)* | −0.41 (1.36) | 4.79 (1.35)* | 4.28 (1.35)* | 5.54 (1.1)** |
| | LS Mean (SE)/week 8 | 0.85 (1.06) | 4.14 (1.51) | 2.47 (1.52) | 3.14 (1.51) | 5.99 (1.5) | 7.41 (1.06) |
| | LS Mean Diff (SE)/ week 8 | | 3.29 (1.84) | 1.62 (1.85) | 2.29 (1.85) | 5.14 (1.84)* | 6.57 (1.5)** |
| change | LS Mean (SE)/week 4 | 0.99 (3.45) | 14.76 (4.89) | −2.61 (4.94) | 21.22 (4.91) | 19.35 (4.89) | 25.22 (3.45) |
| | LS Mean Diff (SE)/week 4 | | 13.77 (5.99)* | −3.6 (6.02) | 20.24 (6.01)* | 18.36 (5.98)* | 24.23 (4.88)** |
| | LS Mean (SE)/week 8 | 3.55 (4.42) | 19.54 (6.25) | 9.26 (6.32) | 13.64 (6.29) | 26.04 (6.25) | 32.27 (4.42) |
| | LS Mean Diff (SE)/week 8 | | 15.99 (7.66)* | 5.72 (7.7) | 10.09 (7.69) | 22.49 (7.65)* | 28.72 (6.25)** |
| Appendicular Lean Body Mass (Calculated by aLBM Equation) (kg)/% change | LS Mean (SE)/week 4 | −0.31 (0.74) | 1.26 (1.04) | 2.15 (1.04) | 4.26 (1.04) | 4.77 (1.05) | 3.7 (0.74) |
| | LS Mean Diff (SE)/ week 4 | | 1.57 (1.28) | 2.46 (1.28) | 4.57 (1.28)** | 5.08 (1.29)** | 4.01 (1.04)** |
| | LS Mean (SE)/week 8 | 0.76 (0.73) | 2.65 (1.03) | 2.37 (1.03) | 3.72 (1.03) | 7.15 (1.04) | 5.72 (0.73) |
| | LS Mean Diff (SE)/week 8 | | 1.9 (1.27) | 1.61 (1.26) | 2.96 (1.26)* | 6.39 (1.27)** | 4.97 (1.03)** |
| Change | LS Mean (SE)/week 4 | −0.05 (0.13) | 0.23 (0.18) | 0.35 (0.18) | 0.73 (0.18) | 0.84 (0.18) | 0.63 (0.13) |
| | LS Mean Diff (SE)/ week 4 | | 0.28 (0.22) | 0.4 (0.22) | 0.78 (0.22)* | 0.89 (0.22)** | 0.68 (0.18)** |
| | LS Mean (SE) | 0.11 (0.13) | 0.45 (0.19) | 0.41 (0.19) | 0.64 (0.18) | 1.28 (0.19) | 1.02 (0.13) |
| | LS Mean Diff (SE)/week 8 | | 0.33 (0.23) | 0.29 (0.23) | 0.53 (0.23)* | 1.16 (0.23)** | 0.91 (0.18)** |
| Total Lean Mass (kg)/ % change | LS Mean (SE)/week 4 | 0.16 (0.56) | 0.71 (0.79) | 1.53 (0.79) | 3.42 (0.79) | 3.52 (0.79) | 2.84 (0.56) |
| | LS Mean Diff (SE)/week 4 | | 0.55 (0.97) | 1.37 (0.98) | 3.26 (0.98)* | 3.36 (0.98)* | 2.69 (0.79)* |
| | LS Mean | 1.31 | 2.18 | 1.94 | 3.16 | 4.67 | 4.31 |

TABLE 10-continued

| Primary analysis of efficacy endpoints | | | | | | | |
|---|---|---|---|---|---|---|---|
| Parameter | Analysis Visit | Placebo (n = 12) | R1033 (n = 6) | R2477 (10 mg/kg) IV (n = 6) | R1033 + R2477 (1 mg/kg) IV (n = 6) | R1033 + R2477 (3 mg/kg) IV (n = 6) | R1033 + R2477 (10 mg/kg) IV (n = 12) |
| | (SE)/week 8 | (0.64) | (0.89) | (0.9) | (0.89) | (0.89) | (0.63) |
| | LS Mean Diff (SE)/week 8 | | 0.88 (1.1) | 0.63 (1.11) | 1.85 (1.1) | 3.37 (1.1)* | 3 (0.89)* |
| change | LS Mean (SE)/week 4 | 0.08 (0.23) | 0.25 (0.33) | 0.61 (0.33) | 1.42 (0.33) | 1.44 (0.33) | 1.14 (0.23) |
| | LS Mean Diff (SE)/week 4 | | 0.17 (0.41) | 0.54 (0.41) | 1.34 (0.41)* | 1.36 (0.41)* | 1.07 (0.33)* |
| | LS Mean (SE)/week 8 | 0.53 (0.27) | 0.86 (0.37) | 0.78 (0.37) | 1.27 (0.37) | 1.92 (0.37) | 1.8 (0.26) |
| | LS Mean Diff (SE)/week 8 | | 0.33 (0.46) | 0.25 (0.46) | 0.74 (0.46) | 1.39 (0.46)* | 1.26 (0.37)* |
| Appendicular Lean Mass (Sum of Lean Mass of Arms and Legs) (kg)/% change | LS Mean (SE)/week 4 | −0.35 (0.74) | 1.2 (1) | 2.02 (1) | 4.06 (1) | 4.51 (1) | 3.54 (0.71) |
| | LS Mean Diff (SE)/week 4 | | 1.56 (1.25) | 2.37 (1.24) | 4.42 (1.24)** | 4.87 (1.26)** | 3.89 (1.02)** |
| | LS Mean (SE)/week 8 | 0.95 (0.72) | 2.51 (0.97) | 2.22 (0.97) | 3.53 (0.97) | 6.74 (0.98) | 5.48 (0.69) |
| | LS Mean Diff (SE)/week 8 | | 1.56 (1.22) | 1.28 (1.21) | 2.58 (1.21)* | 5.79 (1.23)** | 4.53 (0.99)** |
| change | LS Mean (SE)/week 4 | −0.06 (0.14) | 0.23 (0.18) | 0.35 (0.18) | 0.73 (0.18) | 0.83 (0.19) | 0.64 (0.13) |
| | LS Mean Diff (SE)/week 4 | | 0.28 (0.23) | 0.41 (0.23) | 0.79 (0.23)* | 0.89 (0.23)** | 0.69 (0.19)** |
| | LS Mean (SE)/week 8 | 0.17 (0.14) | 0.44 (0.18) | 0.4 (0.18) | 0.64 (0.18) | 1.26 (0.18) | 1.02 (0.13) |
| | LS Mean Diff (SE)/week 8 | | 0.27 (0.23) | 0.23 (0.23) | 0.48 (0.23)* | 1.09 (0.23)** | 0.86 (0.19)** |
| Total Fat Mass (kg)/% change | LS Mean (SE)/week 4 | −0.11 (0.81) | −1.15 (1.15) | 1.32 (1.14) | −0.76 (1.14) | −1.52 (1.14) | −2.58 (0.8) |
| | LS Mean Diff (SE)/week 4 | | −1.04 (1.41) | 1.42 (1.39) | −0.65 (1.39) | −1.41 (1.39) | −2.47 (1.14)* |
| | LS Mean (SE)/week 8 | −0.65 (1.12) | −2.76 (1.6) | −1.34 (1.58) | −0.85 (1.58) | −2.73 (1.58) | −4.57 (1.12) |
| | LS Mean Diff (SE)/week 8 | | −2.11 (1.96) | −0.69 (1.93) | −0.2 (1.93) | −2.08 (1.93) | −3.92 (1.58)* |
| change | LS Mean (SE)/week 4 | 0.07 (0.21) | −0.18 (0.3) | 0.29 (0.29) | −0.29 (0.29) | −0.38 (0.29) | −0.6 (0.21) |
| | LS Mean Diff (SE)/week 4 | | −0.25 (0.36) | 0.23 (0.36) | −0.36 (0.36) | −0.45 (0.36) | −0.67 (0.29)* |
| | LS Mean (SE)/week 8 | −0.04 (0.28) | −0.54 (0.4) | −0.46 (0.4) | −0.34 (0.4) | −0.75 (0.4) | −1.16 (0.28) |
| | LS Mean Diff (SE)/week 8 | | −0.5 (0.49) | −0.42 (0.49) | −0.3 (0.49) | −0.71 (0.49) | −1.12 (0.4)* |
| Android Fat Mass (kg)/% change | LS Mean (SE)/week 4 | −0.21 (1.3) | −1.57 (1.85) | 0.44 (1.84) | −2.47 (1.84) | −1.8 (1.83) | −3.94 (1.3) |
| | LS Mean Diff (SE)/week 4 | | −1.35 (2.26) | 0.65 (2.25) | −2.25 (2.25) | −1.59 (2.25) | −3.73 (1.83)* |
| | LS Mean (SE) | −0.05 (1.69) | −2.35 (2.4) | −4.67 (2.39) | −1.71 (2.39) | −2.62 (2.38) | −6.65 (1.69) |

TABLE 10-continued

| Primary analysis of efficacy endpoints | | | | | | | |
|---|---|---|---|---|---|---|---|
| Parameter | Analysis Visit | Placebo (n = 12) | R1033 (n = 6) | R2477 (10 mg/kg) IV (n = 6) | R1033 + R2477 (1 mg/kg) IV (n = 6) | R1033 + R2477 (3 mg/kg) IV (n = 6) | R1033 + R2477 (10 mg/kg) IV (n = 12) |
| | LS Mean Diff (SE)/week 8 | | −2.31 (2.93) | −4.62 (2.92) | −1.66 (2.93) | −2.57 (2.92) | −6.61 (2.38)* |
| change | LS Mean (SE)/week 4 | 0.03 (0.03) | 0.01 (0.04) | 0 (0.04) | −0.05 (0.04) | −0.04 (0.04) | −0.07 (0.03) |
| | LS Mean Diff (SE)/week 4 | | −0.01 (0.05) | −0.02 (0.05) | −0.07 (0.05) | −0.06 (0.05) | −0.1 (0.04)* |
| | LS Mean (SE)/week 8 | 0.03 (0.04) | −0.01 (0.05) | −0.09 (0.05) | −0.03 (0.05) | −0.07 (0.05) | −0.13 (0.04) |
| | LS Mean Diff (SE)/week 8 | | −0.04 (0.06) | −0.11 (0.06) | −0.06 (0.06) | −0.1 (0.06) | −0.16 (0.05)* |
| Thigh Intra-muscular Adipose Tissue Volume (cm3)/% volume | LS Mean (SE)/week 4 | −2.9 (3) | −2 (4.24) | −3.44 (4.23) | 6.19 (4.28) | −2.99 (4.24) | 8.25 (2.98) |
| | LS Mean Diff (SE)/week 4 | | 0.9 (5.22) | −0.54 (5.17) | 9.09 (5.27) | −0.09 (5.17) | 11.15 (4.23)* |
| | LS Mean (SE)/week 8 | −4.19 (4.21) | −3.35 (5.96) | 0.65 (5.95) | 1.14 (6.02) | −3.88 (5.96) | 7.26 (4.19) |
| | LS Mean Diff (SE)/week 8 | | 0.84 (7.34) | 4.84 (7.26) | 5.33 (7.41) | 0.31 (7.27) | 11.45 (5.95) |
| change | LS Mean (SE)/week 4 | −0.09 (0.13) | −0.07 (0.18) | −0.2 (0.18) | 0.14 (0.18) | −0.12 (0.18) | 0.24 (0.13) |
| | LS Mean Diff (SE)/week 4 | | 0.02 (0.22) | −0.11 (0.22) | 0.23 (0.22) | −0.03 (0.22) | 0.33 (0.18) |
| | LS Mean (SE)/week 8 | −0.17 (0.17) | −0.13 (0.24) | −0.02 (0.24) | −0.08 (0.25) | −0.22 (0.24) | 0.2 (0.17) |
| | LS Mean Diff (SE)/week 8 | | 0.04 (0.3) | 0.15 (0.3) | 0.09 (0.3) | −0.05 (0.3) | 0.37 (0.24) |
| Sum of Intra-muscular and Peri-muscular Adipose Tissue (IMAT)/% change | LS Mean (SE)/week 4 | 0.98 (1.4) | −3.09 (1.98) | 1.63 (1.99) | −2.09 (2.03) | 1.75 (1.99) | −1.54 (1.4) |
| | LS Mean Diff (SE)/week 4 | | −4.07 (2.43) | 0.65 (2.43) | −3.07 (2.47) | 0.77 (2.43) | −2.52 (1.98) |
| | LS Mean (SE)/week 8 | 0.94 (1.49) | −0.12 (2.12) | 0.26 (2.13) | −0.5 (2.17) | −1.63 (2.12) | −2.76 (1.49) |
| | LS Mean Diff (SE)/week 8 | | −1.06 (2.6) | −0.68 (2.59) | −1.44 (2.64) | −2.57 (2.59) | −3.7 (2.11) |
| Change | LS Mean (SE)/week 4 | 1.05 (1.65) | −3.45 (2.34) | 2.29 (2.35) | −3.2 (2.4) | 1.93 (2.35) | −1.75 (1.65) |
| | LS Mean Diff (SE)/week 4 | | −4.5 (2.87) | 1.24 (2.87) | −4.25 (2.92) | 0.88 (2.87) | −2.8 (2.33) |
| | LS Mean (SE)/week 8 | 0.69 (1.8) | 0.28 (2.56) | 0.48 (2.57) | −1.73 (2.62) | −1.97 (2.57) | −3.04 (1.81) |
| | LS Mean Diff (SE)/week 8 | | −0.4 (3.14) | −0.21 (3.13) | −2.42 (3.19) | −2.66 (3.13) | −3.73 (2.55) |
| Sub-cutaneous Adipose Tissue Volume (cm3)/% change | LS Mean (SE)/week 4 | −1.27 (1.02) | 0.05 (1.45) | −0.26 (1.47) | −1.67 (1.44) | −1.98 (1.44) | −1.76 (1.02) |

TABLE 10-continued

| Primary analysis of efficacy endpoints | | | | | | | |
|---|---|---|---|---|---|---|---|
| Parameter | Analysis Visit | Placebo (n = 12) | R1033 (n = 6) | R2477 (10 mg/kg) IV (n = 6) | R1033 + R2477 (1 mg/kg) IV (n = 6) | R1033 + R2477 (3 mg/kg) IV (n = 6) | R1033 + R2477 (10 mg/kg) IV (n = 12) |
| | LS Mean Diff (SE)/week 4 | | 1.32 (1.78) | 1.01 (1.82) | −0.4 (1.76) | −0.71 (1.76) | −0.49 (1.44) |
| | LS Mean (SE)/week 8 | 1.31 (1.21) | 1.01 (1.71) | 1.56 (1.75) | −3.73 (1.71) | −3.04 (1.7) | −1.45 (1.21) |
| | LS Mean Diff (SE)/week 8 | | −0.31 (2.11) | 0.25 (2.15) | −5.04 (2.09)* | −4.36 (2.09)* | −2.77 (1.7) |
| change | LS Mean (SE)/week 4 | −3.94 (3.83) | 0.35 (5.42) | −0.74 (5.52) | −8.23 (5.39) | −3.02 (5.39) | −7.29 (3.82) |
| | LS Mean Diff (SE)/week 4 | | 4.29 (6.68) | 3.19 (6.8) | −4.3 (6.6) | 0.92 (6.6) | −3.35 (5.39) |
| | LS Mean (SE)/week 8 | 4.74 (4.74) | 5.7 (6.7) | 5.53 (6.83) | −17.58 (6.67) | −8.75 (6.66) | −5.55 (4.73) |
| | LS Mean Diff (SE)/week 8 | | 0.95 (8.26) | 0.79 (8.41) | −22.33 (8.16)* | −13.5 (8.17) | −10.3 (6.66) |
| Sum of Fat Mass of Arms and Legs (kg)/% change | LS Mean (SE)/week 4 | −0.8 (1.01) | −0.59 (1.44) | 1.89 (1.42) | 0.48 (1.42) | −2.87 (1.42) | −3.31 (1) |
| | LS Mean Diff (SE)/week 4 | | 0.21 (1.78) | 2.69 (1.74) | 1.28 (1.74) | −2.07 (1.74) | −2.51 (1.42) |
| | LS Mean (SE)/week 8 | −0.47 (1.34) | −2.44 (1.9) | 0.11 (1.87) | 0.27 (1.87) | −3.51 (1.87) | −5.2 (1.32) |
| | LS Mean Diff (SE)/week 8 | | −1.97 (2.35) | 0.58 (2.31) | 0.74 (2.3) | −3.04 (2.3) | −4.73 (1.88)* |
| change | LS Mean (SE)/week 4 | −0.09 (0.12) | −0.06 (0.17) | 0.21 (0.16) | 0.01 (0.16) | −0.33 (0.16) | −0.41 (0.11) |
| | LS Mean Diff (SE)/week 4 | | 0.02 (0.2) | 0.3 (0.2) | 0.09 (0.2) | −0.25 (0.2) | −0.33 (0.16) |
| | LS Mean (SE)/week 8 | −0.05 (0.15) | −0.26 (0.22) | −0.03 (0.21) | −0.07 (0.21) | −0.41 (0.21) | −0.62 (0.15) |
| | LS Mean Diff (SE)/week 8 | | −0.21 (0.27) | 0.02 (0.26) | −0.02 (0.26) | −0.37 (0.26) | −0.58 (0.22)* |
| Total Bone Mineral Density (BMD) Mass (g/cm2)/% change | LS Mean (SE)/week 4 | 0.05 (0.25) | −0.22 (0.36) | −0.48 (0.35) | −0.04 (0.36) | 0.47 (0.36) | 0.55 (0.25) |
| | LS Mean Diff (SE)/week 4 | | −0.27 (0.43) | −0.53 (0.43) | −0.09 (0.44) | 0.42 (0.44) | 0.5 (0.35) |
| | LS Mean (SE)/week 8 | −0.01 (0.28) | −0.47 (0.4) | −0.72 (0.4) | −0.08 (0.4) | −0.22 (0.41) | 0.16 (0.28) |
| | LS Mean Diff (SE)/week 8 | | −0.46 (0.49) | −0.71 (0.49) | −0.07 (0.5) | −0.21 (0.5) | 0.17 (0.4) |
| change | LS Mean (SE)/week 4 | 0 (0.003) | −0.002 (0.004) | −0.005 (0.004) | 0 (0.004) | 0.005 (0.004) | 0.006 (0.003) |
| | LS Mean Diff (SE)/week 4 | | 0 (0) | −0.01 (0) | 0 (0) | 0 (0) | 0.01 (0) |
| | LS Mean (SE)/week 8 | 0 (0.003) | −0.006 (0.004) | −0.008 (0.004) | 0 (0.004) | −0.002 (0.004) | 0.002 (0.003) |
| | LS Mean Diff (SE)/week 8 | | −0.01 (0.01) | −0.01 (0.01) | 0 (0.01) | 0 (0.01) | 0 (0) |
| Total Bone Mineral Content (BMC) Mass (kg)/% change | LS Mean (SE)/week 4 | 0.1 (0.28) | −0.16 (0.4) | −0.23 (0.4) | 0.25 (0.4) | −0.19 (0.4) | 0.62 (0.28) |

TABLE 10-continued

| Primary analysis of efficacy endpoints | | | | | | | |
|---|---|---|---|---|---|---|---|
| Parameter | Analysis Visit | Placebo (n = 12) | R1033 (n = 6) | R2477 (10 mg/kg) IV (n = 6) | R1033 + R2477 (1 mg/kg) IV (n = 6) | R1033 + R2477 (3 mg/kg) IV (n = 6) | R1033 + R2477 (10 mg/kg) IV (n = 12) |
| | LS Mean Diff (SE)/week 4 | | −0.26 (0.49) | −0.33 (0.49) | 0.15 (0.49) | −0.29 (0.49) | 0.52 (0.4) |
| | LS Mean (SE)/week 8 | −0.42 (0.26) | −0.27 (0.36) | −0.48 (0.36) | −0.08 (0.36) | −0.56 (0.36) | 0.65 (0.25) |
| | LS Mean Diff (SE)/week 8 | | 0.16 (0.45) | −0.05 (0.44) | 0.34 (0.44) | −0.14 (0.44) | 1.07 (0.36)* |
| change | LS Mean (SE)/week 4 | 0.002 (0.006) | −0.003 (0.009) | −0.005 (0.009) | 0.006 (0.009) | −0.003 (0.009) | 0.014 (0.006) |
| | LS Mean Diff (SE)/week 4 | | −0.01 (0.01) | −0.01 (0.01) | 0 (0.01) | −0.01 (0.01) | 0.01 (0.01) |
| | LS Mean (SE)/week 8 | −0.009 (0.006) | −0.007 (0.008) | −0.011 (0.008) | −0.001 (0.008) | −0.012 (0.008) | 0.014 (0.006) |
| | LS Mean Diff (SE)/week 8 | | 0 (0.01) | 0 (0.01) | 0.01 (0.01) | 0 (0.01) | 0.02 (0.01)* |
| T-score for Total Body/% change | LS Mean (SE)/week 4 | −18.26 (18.01) | −51.19 (25.74) | −2.95 (25.45) | −6.66 (25.7) | −39.76 (25.87) | −0.9 (17.96) |
| | LS Mean Diff (SE)/week 4 | | −32.93 (31.23) | 15.31 (31.1) | 11.6 (31.56) | −21.5 (31.73) | 17.37 (25.43) |
| | LS Mean (SE)/week 8 | −20.87 (17.94) | −58.54 (25.64) | 3.83 (25.35) | 5.16 (25.6) | 23.12 (25.77) | 8.49 (17.89) |
| | LS Mean Diff (SE)/week 8 | | −37.67 (31.11) | 24.71 (30.98) | 26.04 (31.44) | 44 (31.61) | 29.36 (25.33) |
| change | LS Mean (SE)/week 4 | 0.01 (0.03) | −0.03 (0.05) | −0.07 (0.05) | 0 (0.05) | 0.06 (0.05) | 0.08 (0.03) |
| | LS Mean Diff (SE)/week 4 | | −0.04 (0.06) | −0.07 (0.06) | −0.01 (0.06) | 0.06 (0.06) | 0.07 (0.05) |
| | LS Mean (SE)/week 8 | 0 (0.04) | −0.07 (0.05) | −0.1 (0.05) | −0.01 (0.05) | −0.03 (0.06) | 0.03 (0.04) |
| | LS Mean Diff (SE)/week 8 | | −0.07 (0.07) | −0.1 (0.07) | −0.01 (0.07) | −0.03 (0.07) | 0.03 (0.05) |

Note:

Least-squares (LS) means, standard errors (SE) and p-value taken from ANCOVA. The model includes baseline measurement as covariate and the treatment as fixed factor.

*indicated p-value < 0.05;

**indicated p-value < 0.001.

Compared with placebo, R2477+R1033 combination significantly increased thigh muscle volume and total lean mass in medium and high dose groups (FIGS. 8 and 9), significantly increased appendicular lean body mass in all dose groups (FIG. 10) and significantly decreased total fat mass as well as android fat mass in the high dose group (Table 10). R2477+R1033, in the high dose group, significantly increased all of the major measures of muscle volume and lean mass compared with placebo, at both Week 4 and Week 8; the effects at Week 4 were generally less pronounced than at Week 8 (Table 10). At Week 8, the high dose anti-Activin A R2477+anti-GDF8 R1033 group exhibited increased % change in total bone mineral content from placebo, as measured by DXA, while total bone mineral density did not change (Table 10).

Safety

All treatment emergent adverse events (TEAEs) were mild to moderate in severity except one severe TEAE of 'radius fracture' reported by a placebo subject. There were no serious adverse events, no deaths, and no discontinuations due to TEAEs. Headache was the most frequent TEAE in each of the treatment groups, occurring in 58.3% of all study subjects and in 50% of placebo subjects. Muscle spasms, nausea and mouth ulceration were the other frequent TEAEs in REGN2477+REGN1033 groups that occurred in 25% or more of subjects in the combination R2477+R1033 groups; these TEAEs occurred less frequently in the placebo group, but there does not appear to be any clear dose-response relationship. There were no clear signals of bleeding or diarrhea, adverse events that have been associated with blockade of activin receptors. One TEAE of a nosebleed (preferred term of epistaxis) occurred in a R2477+R1033 dose group—it resolved after 9 minutes.

Review of Potentially Clinically Significant Values (PCSVs) revealed no significant differences between REGN2477+REGN1033 and Placebo in Labs, Vital signs, and ECG that would indicate negative effects of REGN2477+REGN1033. Within laboratory, vital sign and ECG categories, there were 0-2 subjects with PCSVs in the combined REGN2477+REGN1033 dose groups (N of 24); however the percentage of subjects with PCSVs was equal to or lower than that found in the placebo group. There were no treatment-emergent PCSVs related to liver function tests.

CONCLUSIONS

In healthy postmenopausal women, single intravenous doses of REGN2477+REGN1033 increased thigh muscle volume, total lean mass, and appendicular lean body mass. One surprising finding was the uniformity of the thigh muscle changes: all of the individuals exposed to the combination exhibited an increase in thigh muscle volume, as shown in FIG. 4. In addition, single intravenous doses of REGN2477+REGN1033 decreased total fat, and in particular, android fat mass. Treatment with REGN1033 alone increased thigh muscle volume.

In general, REGN2477, REGN1033, and REGN2477+REGN1033 in this clinical study were considered to have an acceptable safety profile and were well tolerated. There were no serious adverse events.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for altering the body composition of a subject comprising administering a first composition comprising an effective amount of a growth differentiation factor 8 (GDF8) inhibitor and a second composition comprising an effective amount of an Activin A inhibitor to the subject, wherein the GDF8 inhibitor is an isolated antibody or an antigen-binding fragment thereof that specifically binds GDF8, wherein the antibody or antigen-binding fragment that specifically binds GDF8 comprises the heavy chain complementarity determining regions (HCDRs) of a heavy chain variable region (HCVR) comprising SEQ ID NO:360, and the light chain complementarity determining regions (LCDRs) of a light chain variable region (LCVR) comprising SEQ ID NO:368, wherein the Activin A inhibitor is an isolated antibody or antigen-binding fragment thereof that specifically binds Activin A, and wherein the antibody or antigen-binding fragment that specifically binds Activin A comprises the heavy chain complementarity determining regions (HCDRs) of a heavy chain variable region (HCVR) comprising SEQ ID NO:553, and the light chain complementarity determining regions (LCDRs) of a light chain variable region (LCVR) comprising SEQ ID NO: 537, and wherein a reduction in fat mass is induced in the subject.

2. The method of claim 1, wherein an increase in muscle mass is induced in the subject.

3. The method of claim 1, wherein the effective amount of a GDF8 inhibitor comprises a dosing regimen selected from the group consisting of at least 0.01 mg/kg to about 10 gm/kg, 1 mg/kg to about 1 gm/kg, and 10 mg/kg to 100 mg/kg.

4. The method of claim 3, wherein the effective amount of an Activin A inhibitor comprises a dosing regimen selected from the group consisting of at least 0.01 mg/kg to about 10 gm/kg, 1 mg/kg to about 1 gm/kg, and 10 mg/kg to 100 mg/kg.

5. The method of claim 1, wherein the effective amount of a GDF8 inhibitor comprises a dosing regimen selected from a group consisting of a single dose of about 0.01 to about 20 mg/kg body weight, about 0.1 to about 10 mg/kg body weight, and about 0.1 to about 5 mg/kg body weight.

6. The method of claim 5, wherein the effective amount of an Activin A inhibitor comprises a dosing regimen selected from a group consisting of a single dose of about 0.01 to about 20 mg/kg body weight, about 0.1 to about 10 mg/kg body weight, and about 0.1 to about 5 mg/kg body weight.

7. The method of claim 6, wherein the effective amount of the GDF8 inhibitor is 6 mg/kg body weight of the subject.

8. The method of claim 7, wherein the effective amount of the Activin A inhibitor is 3 mg/kg or 10 mg/kg body weight of the subject.

9. The method of claim 1, wherein the first composition is formulated for intravenous, subcutaneous, or oral administration.

10. The method of claim 1, wherein the second composition is formulated for intravenous, subcutaneous, or oral administration.

11. The method of claim 1, wherein the first and second compositions are combined into a third composition prior to administration.

12. The method of claim 11, wherein the third composition is formulated for intravenous, subcutaneous, or oral administration.

13. The method of claim 1, further comprising measuring total fat mass and/or android fat mass in the subject before administration.

14. The method of claim 13, further comprising measuring total fat mass and/or android fat mass in the subject after administration, and administering the composition until the subject has a reduction in total fat mass and/or android fat mass of at least about 2% to 8%, at least about 2.5% to 6%, at least about 3% to 4%, or at least about 3.5%.

15. The method of claim 1, wherein the antibody or antigen-binding fragment that specifically binds GDF8 comprises three HCDRs comprising SEQ ID NO:362, SEQ ID NO:364, and SEQ ID NO:366, and three LCDRs comprising SEQ ID NO:370, SEQ ID NO:372, and SEQ ID NO:374.

16. The method of claim 1, wherein the antibody or antigen-binding fragment that specifically binds Activin A comprises three HCDRs comprising SEQ ID NO:555, SEQ ID NO:557, and SEQ ID NO:559, and three LCDRs comprising SEQ ID NO:539, SEQ ID NO:541, and SEQ ID NO:543.

17. The method of any one of claim 1, wherein the Activin A inhibitor is in an amount selected from the group consisting of between 100% to 200% of the amount of the GDF8 inhibitor, between 100% and 250% of the amount of the GDF8 inhibitor, between 100% and 300% of the amount of the GDF8 inhibitor, and between 100% and 400% by weight of the amount of the GDF8 inhibitor.

18. The method of claim 17, wherein the amount of the Activin A inhibitor is about 1.5 to 2.0 times as large by weight as the amount of the GDF8 inhibitor.

19. The method of claim 1, wherein a reduction of fat mass in the subject is a reduction in total fat mass as measured by DXA (Dual-energy X-ray absorptiometry).

20. The method of claim 1, wherein a reduction of fat mass in the subject is a reduction in android fat mass as measured by DXA (Dual-energy X-ray absorptiometry).

21. The method of claim 1, wherein the subject experiences an increase in muscle volume after administration.

22. The method of claim 1, wherein the subject does not have a muscle wasting condition or disease.

23. A method for altering the body composition of a subject comprising administering a composition comprising an effective amount of a growth differentiation factor 8 (GDF8) inhibitor and an effective amount of an Activin A inhibitor to the subject, wherein the GDF8 inhibitor is an isolated antibody or an antigen-binding fragment thereof that specifically binds GDF8, wherein the antibody or antigen-binding fragment that specifically binds GDF8 comprises the heavy chain complementarity determining regions (HCDRs) of a heavy chain variable region (HCVR) comprising SEQ ID NO:360, and the light chain complementarity determining regions (LCDRs) of a light chain variable region (LCVR) comprising SEQ ID NO:368, wherein the Activin A inhibitor is an isolated antibody or antigen-binding fragment thereof that specifically binds Activin A, and wherein the antibody or antigen-binding fragment that specifically binds Activin A comprises the heavy chain complementarity determining regions (HCDRs) of a heavy chain variable region (HCVR) comprising SEQ ID NO:553, and the light chain complementarity determining regions (LCDRs) of a light chain variable region (LCVR) comprising SEQ ID NO: 537, and wherein a reduction in fat mass is induced in the subject.

24. The method of claim 23, wherein an increase in muscle mass is induced in the subject.

25. The method of claim 23, wherein the composition is formulated for intravenous, subcutaneous, or oral administration.

26. A method for treating a disease or disorder characterized by increased fat mass, wherein the method comprises administrating to a subject a growth differentiation factor 8 (GDF8) inhibitor and an Activin A inhibitor, wherein the GDF8 inhibitor is an isolated antibody or an antigen-binding fragment thereof that specifically binds GDF8, wherein the antibody or antigen-binding fragment that specifically binds GDF8 comprises the heavy chain complementarity determining regions (HCDRs) of a heavy chain variable region (HCVR) comprising SEQ ID NO:360, and the light chain complementarity determining regions (LCDRs) of a light chain variable region (LCVR) comprising SEQ ID NO:368, wherein the Activin A inhibitor is an isolated antibody or antigen-binding fragment thereof that specifically binds Activin A, and wherein the antibody or antigen-binding fragment that specifically binds Activin A comprises the heavy chain complementarity determining regions (HCDRs) of a heavy chain variable region (HCVR) comprising SEQ ID NO:553, and the light chain complementarity determining regions (LCDRs) of a light chain variable region (LCVR) comprising SEQ ID NO:537.

27. A non-therapeutic method for decreasing fat mass in a subject, the method comprising administering to the subject an Activin A inhibitor and a GDF8 inhibitor, wherein the GDF8 inhibitor, wherein the GDF8 inhibitor is an isolated antibody or an antigen-binding fragment thereof that specifically binds to GDF8, wherein the antibody or antigen-binding fragment that specifically binds GDF8 comprises the heavy chain complementarity determining regions (HCDRs) of a heavy chain variable region (HC VR) comprising SEQ ID NO:360, and the light chain complementarity determining regions (LCDRs) of a light chain variable region (LCVR) comprising SEQ ID NO:368, wherein the Activin A inhibitor is an isolated antibody or antigen-binding fragment thereof that specifically binds Activin A, and wherein the antibody or antigen-binding fragment that specifically binds Activin A comprises the heavy chain complementarity determining regions (HCDRs) of a heavy chain variable region (HCVR) comprising SEQ ID NO:553, and the light chain complementarity determining regions (LCDRs) of a light chain variable region (LCVR) comprising SEQ ID NO:537.

* * * * *